(12) United States Patent
Watanabe et al.

(10) Patent No.: US 10,323,024 B2
(45) Date of Patent: Jun. 18, 2019

(54) BIHETEROCYCLIC COMPOUND

(71) Applicant: SUMITOMO DAINIPPON PHARMA CO., LTD., Osaka-shi, Osaka (JP)

(72) Inventors: Hitoshi Watanabe, Toyonaka (JP); Yoshiaki Isobe, Takatsuki (JP); Hidenori Kimura, Tokyo (JP); Yuji Fujiwara, Ibaraki (JP)

(73) Assignee: SUMITOMO DAINIPPON PHARMA CO., LTD., Osaka-shi, Osaka (JP)

( * ) Notice: Subject to any disclaimer, the term of this patent is extended or adjusted under 35 U.S.C. 154(b) by 0 days.

(21) Appl. No.: 16/070,014

(22) PCT Filed: Jan. 12, 2017

(86) PCT No.: PCT/JP2017/000819
§ 371 (c)(1),
(2) Date: Jul. 13, 2018

(87) PCT Pub. No.: WO2017/122722
PCT Pub. Date: Jul. 20, 2017

(65) Prior Publication Data
US 2019/0016711 A1    Jan. 17, 2019

(30) Foreign Application Priority Data

Jan. 15, 2016 (JP) ................ 2016-006205
Sep. 6, 2016 (JP) ................ 2016-173510

(51) Int. Cl.
| | |
|---|---|
| *C07D 405/14* | (2006.01) |
| *C07D 405/04* | (2006.01) |
| *C07D 471/04* | (2006.01) |
| *A61P 25/28* | (2006.01) |
| *A61P 27/04* | (2006.01) |

(Continued)

(52) U.S. Cl.
CPC .......... *C07D 405/14* (2013.01); *A61K 31/352* (2013.01); *A61K 31/4192* (2013.01); *A61K 31/4709* (2013.01); *A61K 31/519* (2013.01); *A61P 25/28* (2018.01); *A61P 27/04* (2018.01); *C07D 311/22* (2013.01); *C07D 405/04* (2013.01); *C07D 471/04* (2013.01)

(58) Field of Classification Search
None
See application file for complete search history.

(56) References Cited

U.S. PATENT DOCUMENTS

| | | |
|---|---|---|
| 2003/0166711 A1 | 9/2003 | Kimura et al. |
| 2005/0119334 A1 | 6/2005 | Kumagai et al. |

(Continued)

FOREIGN PATENT DOCUMENTS

| | | |
|---|---|---|
| JP | 2006-335683 A | 12/2006 |
| JP | 2008-013530 A | 1/2008 |

(Continued)

OTHER PUBLICATIONS

S. Kaneko, et al., "A selective Sema3A inhibitor enhances regenerative responses and functional recovery of the injured spinal cord," Nature Medicine, vol. 12, No. 12, Dec. 2006, pp. 1380-1389.
A.L. Kolodkin, et al., "The semaphorin Genes Encode a Family of Transmembrane and Secreted Growth Cone Guidance Molecules," Cell, vol. 75, Dec. 31, 1993, pp. 1389-1399.
M. Omoto, et al., "The Semaphorin 3A Inhibitor SM-345431 Accelerates Peripheral Nerve Regeneration and Sensitivity in a Murine Corneal Transplantation Model," PLOS ONE, vol. 7, No. 11, Nov. 2012, e47716, pp. 1-9.

(Continued)

*Primary Examiner* — Kamal A Saeed
(74) *Attorney, Agent, or Firm* — Sughrue Mion, PLLC

(57) ABSTRACT

The present invention provides a compound of formula (1) and a pharmaceutical composition comprising the compound useful as a nerve regeneration promoter wherein $R^1$-L- is $R^1$—OC(O)—, or the like, $R^1$ is hydrogen atom, optionally-substituted $C_{1-6}$ alkyl group, optionally-substituted 3- to 8-membered cycloalkyl group, or the like, $R^2$ is hydrogen atom or the like, Ring A is formula (2) or formula (3) wherein $R^3$ is hydrogen atom, optionally-substituted $C_{1-6}$ alkyl group, or the like, the part of X, Y, and Z is X=Y—Z, X—Y=Z, or X—Y—Z, X is nitrogen atom, $NR^4$ ($R^4$ is hydrogen atom, optionally-substituted $C_{1-6}$ alkyl group, or the like), or the like, Y is carbon atom or the like, and Z is carbon atom, nitrogen atom or the like.

28 Claims, 2 Drawing Sheets

(51) Int. Cl.
   A61K 31/352    (2006.01)
   A61K 31/4192   (2006.01)
   A61K 31/4709   (2006.01)
   A61K 31/519    (2006.01)
   C07D 311/22    (2006.01)

(56) References Cited

U.S. PATENT DOCUMENTS

| 2007/0105948 | A1 | 5/2007 | Ikeda et al. |
| 2013/0137781 | A1 | 5/2013 | Maeda |
| 2013/0142848 | A1 | 6/2013 | Maeda et al. |
| 2014/0018416 | A1 | 1/2014 | Okano et al. |

FOREIGN PATENT DOCUMENTS

| JP | 2015-113324 A | 6/2015 |
| JP | 2016-037472 A | 3/2016 |
| WO | 03/062440 A1 | 7/2003 |
| WO | 2015/021226 A1 | 2/2015 |

OTHER PUBLICATIONS

K. Kikuchi, et al., "In Vitro and in Vivo Characterization of a Novel Semaphorin 3A Inhibitor, SM-216289 or Xanthofulvin*," Journal of Biological Chemistry, vol. 278, No. 44, Oct. 31, 2003, pp. 42985-42991.

M.R. Chin, et al., "Expedited Access to Vinaxanthone and Chemically Edited Derivatives Possessing Neuronal Regenerative Effects through Ynone Coupling Reactions," ACS Chemical Neuroscience, vol. 6, 2015, pp. 542-550.

A. Axelrod, et al., "Syntheses of Xanthofulvin and Vinaxanthone, Natural Products Enabling Spinal Cord Regeneration**," Angew. Chem. Int. Ed., vol. 52, 2013, pp. 3421-3424.

L. Zhang, et al., "Rewiring of regenerated axons by combining treadmill training with semaphorin3A inhibition," Molecular Brain, vol. 7, No. 14, 2014, pp. 1-17.

English translation of International Search Report dated Mar. 21, 2017 in International Application No. PCT/JP2017/000819.

English translation of International Preliminary Report on Patentability dated Jul. 17, 2018 in International Application No. PCT/JP2017/000819.

Y. Luo, et al., "Collapsin: A Protein in Brain That Induces the Collapse and Paralysis of Neuronal Growth Cones," Cell, vol. 75, Oct. 22, 1993, pp. 217-227.

S. Kaneko, et al., "A selective Sema3A inhibitor enhances regenerative responses and functional recovery of the injured spinal cord," Nature Medicine, vol. 12, No. 12, Dec. 2006, pp. 1381-1389.

BIHETEROCYCLIC COMPOUND

CROSS REFERENCE TO RELATED APPLICATIONS

This application is a National Stage of International Application No. PCT/JP2017/000819 filed Jan. 12, 2017, claiming priority based on Japanese Patent Application No. 2016-006205, filed Jan. 15, 2016, and Japanese Patent Application No. 2016-173510, filed Sep. 6, 2016.

TECHNICAL FIELD

The present invention relates bicyclic heterocyclyl compounds, and an inhibitor of semaphorin, a promotor of center/peripheral nerve regeneration, a medicament for preventing/treating nerve injury disease, a medicament for preventing/treating neurological disease associated with neurodegeneration or ischemic deficit, or a medicament for preventing/treating corneal disease, which comprises the bicyclic heterocyclyl compound as an active ingredient.

BACKGROUND ART

Semaphorins are endogenous proteins which are identified as a factor that can retract the nerve growth cone and suppress the axonal growth. Until now, about 20 kinds of molecular species thereof have been known. Amongst them, class type 3 subfamily gene cluster has been studied the most. The proteins that these genes encode are known to have in vitro potent activities for inhibiting neurite outgrowth and retracting growth cone. Amongst them, semaphorin 3A (Sema3A) (Non-Patent Literatures 1 and 2) has been studied the most, which can induce the growth cone retraction in cultural neuron, in a low concentration of 10 pM and in a short time.

Some substances inhibiting the Sema3A function have been already known, such as a certain group of xanthone compounds which are obtained from the culture of *Penicillium* sp. SPF-3059 strain (International Patent Organism Depositary, National Institute of Advanced Industrial Science and Technology, Accession number: FERM BP-7663) (Patent Literatures 1 and 2), and xanthone derivatives which are obtained by chemically-modifying the above xanthane compounds (Patent Literature 3).

And, it has been reported that the compounds can promote re-elongating the nerve fiber in spinal cord of a rat spinal cord injury model (Patent Literature 4 and Non-Patent Literature 3) and can promote regenerating the corneal sensory neuron of a mouse corneal graft model (Patent Literature 5 and Non-Patent Literature 4).

PRIOR ART

Patent Reference

[Patent Literature 1] WO 2002/09756
[Patent Literature 2] WO 2003/062243
[Patent Literature 3] WO 2003/062440
[Patent Literature 4] WO 2012/018069
[Patent Literature 5] WO 2012/115182

Non-Patent Reference

[Non-Patent Literature 1] Cell, 75, p 217 (1993)
[Non-Patent Literature 2] Cell, 75, p 1389 (1993)
[Non-Patent Literature 3] Nature Medicine, volume 3, Number 12, p 1398 (2006)
[Non-Patent Literature 4] PLOS ONE, volume 7, Issue 11, e47716 (2012)

SUMMARY OF INVENTION

Technical Problem

The purpose of the present invention may be to provide an inhibitor of semaphorin having a novel chemical structure, and a promotor of center/peripheral nerve regeneration, a medicament for preventing/treating nerve injury disease, a medicament for preventing/treating neurological disease associated with neurodegeneration or ischemic deficit, a medicament for preventing/treating corneal disease such as dry eye, or the like, which comprises the new inhibitor of semaphorin as an active ingredient.

Solution to Problem

The present inventors have extensively studied to reach the above object, and then have found that a compound of formula (1) or a pharmaceutically acceptable salt thereof (hereinafter, it may be referred to as "the present compound") has a semaphorin inhibitory activity, and thereby the present compound may be a useful medicament for treating or preventing neuropathic disease, neurodegenerative disease, neurological disease associated with ischemic deficit, and corneal disease. Based upon the new findings, the present invention has been completed.

The present invention can show as follows.

Term 1
A compound of formula (1):

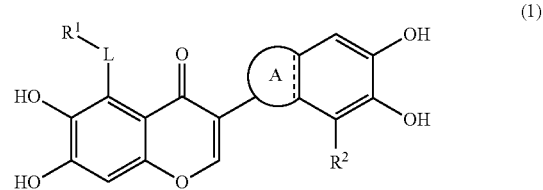

(1)

or a pharmaceutically acceptable salt thereof
wherein
$R^1$-L- is $R^1$—OC(O)— or $R^1$—NHC(O)—;
$R^1$ is
(i) hydrogen atom,
(ii) optionally-substituted $C_6$ alkyl group,
(iii) optionally-substituted $C_{2-6}$ alkenyl group,
(iv) optionally-substituted $C_{2-6}$ alkynyl group,
(v) optionally-substituted 3- to 8-membered cycloalkyl group,
(vi) optionally-substituted 4- to 8-membered cycloalkenyl group,
(vii) optionally-substituted 4- to 8-membered saturated aliphatic heterocyclyl group,
(viii) optionally-substituted 5- to 10-membered unsaturated aliphatic heterocyclyl group,
(ix) optionally-substituted 6- to 10-membered aryl group, or
(x) optionally-substituted 5- to 10-membered heteroaryl group;
$R^2$ is hydrogen atom, hydroxy group, or carboxyl group; and Ring A is a group of formula (2) or (3):

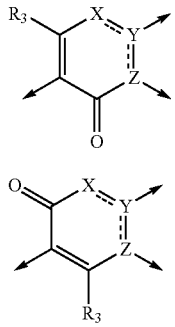

wherein $R^3$ is
(i) hydrogen atom,
(ii) optionally-substituted $C_{1-6}$ alkyl group,
(iii) optionally-substituted $C_{2-6}$ alkenyl group,
(iv) optionally-substituted $C_{2-6}$ alkynyl group,
(v) optionally-substituted 3- to 8-membered cycloalkyl group,
(vi) optionally-substituted 4- to 8-membered cycloalkenyl group,
(vii) optionally-substituted 4- to 8-membered saturated aliphatic heterocyclyl group,
(viii) optionally-substituted 5- to 10-membered unsaturated aliphatic heterocyclyl group,
(ix) optionally-substituted 6- to 10-membered aryl group, or
(x) optionally-substituted 5- to 10-membered heteroaryl group,
the part of X⋯Y⋯Z is X=Y—Z, X—Y=Z, or X—Y—Z,
X is nitrogen atom, $NR^4$, or oxygen atom, provided that X is not oxygen atom in the case of formula (2),
$R^4$ is
(i) hydrogen atom,
(ii) optionally-substituted $C_{1-6}$ alkyl group,
(iii) optionally-substituted $C_{2-6}$ alkenyl group,
(iv) optionally-substituted $C_{2-6}$ alkynyl group,
(v) optionally-substituted 3- to 8-membered cycloalkyl group,
(vi) optionally-substituted 4- to 8-membered cycloalkenyl group,
(vii) optionally-substituted 4- to 8-membered saturated aliphatic heterocyclyl group,
(viii) optionally-substituted 5- to 10-membered unsaturated aliphatic heterocyclyl group,
(ix) optionally-substituted 6- to 10-membered aryl group, or
(x) optionally-substituted 5- to 10-membered heteroaryl group,
Y is carbon atom or CH, and
Z is carbon atom, CH, or nitrogen atom, provided that the combination of X, Y, and Z should be any one of chemically-possible selections.

Term 2

The compound of Term 1 or a pharmaceutically acceptable salt thereof, which is represented by formula (1'):

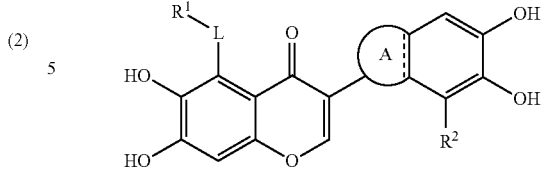

wherein
$R^1$-L- is $R^1$—OC(O)— or $R^1$—NHC(O)—;
$R^1$ is
(i) hydrogen atom,
(ii) optionally-substituted $C_{1-6}$ alkyl group,
(iii) optionally-substituted $C_{2-6}$ alkenyl group,
(iv) optionally-substituted $C_{2-6}$ alkynyl group,
(v) optionally-substituted 3- to 8-membered cycloalkyl group,
(vi) optionally-substituted 4- to 8-membered cycloalkenyl group,
(vii) optionally-substituted 4- to 8-membered saturated aliphatic heterocyclyl group,
(viii) optionally-substituted 5- to 10-membered unsaturated aliphatic heterocyclyl group,
(ix) optionally-substituted 6- to 10-membered aryl group, or
(x) optionally-substituted 5- to 10-membered heteroaryl group,
wherein the substituent(s) of the (ii) optionally-substituted $C_{1-6}$ alkyl group is one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, $C_{1-3}$ alkyl group, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and optionally-substituted 5- to 10-membered heteroaryl group (wherein the substituent(s) of said optionally-substituted 5- to 10-membered heteroaryl group is one or more substituents selected independently from the group consisting of amino group which may be substituted with one or two the same or different $C_{1-3}$ alkyl, $C_{1-3}$ alkyl group, hydroxy group, and carboxyl group), or
the (ii) optionally-substituted $C_{1-6}$ alkyl group may be any one of the following groups of formulae (4)-(6):
formula (4):

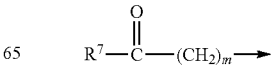

wherein m is 1, 2, 3, 4, or 5, $R^7$ is $C_{1-3}$ alkoxy group, amino acid group (which binds to C(O) at its N terminus), and peptide consisting of 2-3 amino acid residues (which binds to C(O) at its N terminus), formula (5):

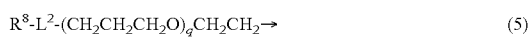

wherein q is 1, 2, 3, 4, or 5, $L^2$ is single bond or C(O), $R^8$ is hydroxy group, $C_{1-3}$ alkoxy group, amino group which may be substituted with one or two the same or different $C_{1-3}$ alkyl, amino acid group (which binds to $L^2$ at its N terminus), or peptide consisting of 2-3 amino acid residues (which binds to $L^2$ at its N terminus), formula (6):

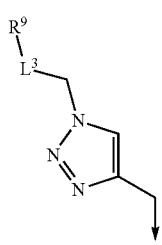

wherein $L^3$ is $CH_2$ or C(O), and $R^9$ is hydroxy group, $C_{1-3}$ alkoxy group, amino group which may be substituted with one or two the same or different $C_{1-3}$ alkyl, amino acid group (which binds to $L^3$ at its N terminus), or peptide consisting of 2-3 amino acid residues (which binds to $L^3$ at its N terminus), the substituent(s) of the (iii) optionally-substituted $C_{2-6}$ alkenyl group, and the (iv) optionally-substituted $C_{2-6}$ alkynyl group are independently one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and 5- to 10-membered heteroaryl group, the substituent(s) of the (v) optionally-substituted 3- to 8-membered cycloalkyl group, the (vi) optionally-substituted 4- to 8-membered cycloalkenyl group, the (vii) optionally-substituted 4- to 8-membered saturated aliphatic heterocyclyl group, the (viii) optionally-substituted 5- to 10-membered unsaturated aliphatic heterocyclyl group, the (ix) optionally-substituted 6- to 10-membered aryl group, and the (x) optionally-substituted 5- to 10-membered heteroaryl group are independently one or more substituents selected independently from the group consisting of hydroxy group, methoxy group, ethoxy group, amino group which may be substituted with one or two the same or different $C_{1-3}$ alkyl, and carboxyl group;

$R^2$ is hydrogen atom, hydroxy group, or carboxyl group; and

Ring A is a group of formula (2') or (3'):

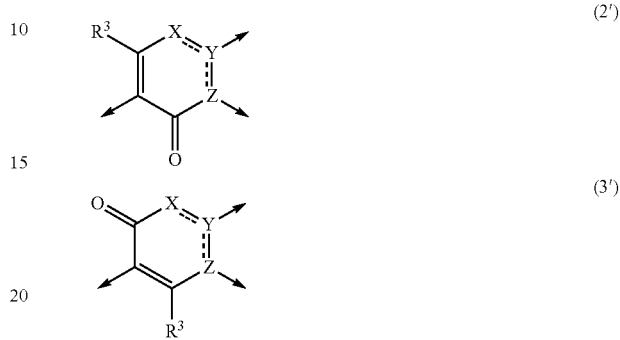

wherein $R^3$ is
(i) hydrogen atom,
(ii) optionally-substituted $C_{1-6}$ alkyl group,
(iii) optionally-substituted $C_{2-6}$ alkenyl group,
(iv) optionally-substituted $C_{2-6}$ alkynyl group,
(v) optionally-substituted 3- to 8-membered cycloalkyl group,
(vi) optionally-substituted 4- to 8-membered cycloalkenyl group,
(vii) optionally-substituted 4- to 8-membered saturated aliphatic heterocyclyl group,
(viii) optionally-substituted 5- to 10-membered unsaturated aliphatic heterocyclyl group,
(ix) optionally-substituted 6- to 10-membered aryl group, or
(x) optionally-substituted 5- to 10-membered heteroaryl group, wherein the substituent(s) of the (ii) optionally-substituted $C_{1-6}$ alkyl group, the (iii) optionally-substituted $C_{2-6}$ alkenyl group, the (iv) optionally-substituted $C_{2-6}$ alkynyl group, the (v) optionally-substituted 3- to 8-membered cycloalkyl group, the (vi) optionally-substituted 4- to 8-membered cycloalkenyl group, the (vii) optionally-substituted 4- to 8-membered saturated aliphatic heterocyclyl group, the (viii) optionally-substituted 5- to 10-membered unsaturated aliphatic heterocyclyl group, the (ix) optionally-substituted 6- to 10-membered aryl group, and the (x) optionally-substituted 5- to 10-membered heteroaryl group are independently one or more substituents selected independently from the group consisting of hydroxy group, methoxy group, ethoxy group, carboxyl group, carbamoyl group which may be substituted with one or two the same or different $C_{1-3}$ alkyl, and amino group which may be substituted with one or two the same or different $C_{1-3}$ alkyl, the part of $X\text{====}Y\text{====}Z$ is $X=Y-Z$, $X-Y=Z$, or $X-Y-Z$, X is nitrogen atom, $NR^4$, or oxygen atom, provided that X is not oxygen atom in the case of formula (2'), $R^4$ is
(i) hydrogen atom,
(ii) optionally-substituted $C_{1-6}$ alkyl group,
(iii) optionally-substituted $C_{2-6}$ alkenyl group,
(iv) optionally-substituted $C_{2-6}$ alkynyl group, (v) optionally-substituted 3- to 8-membered cycloalkyl group, (vi) optionally-substituted 4- to 8-membered cycloalkenyl group, (vii) optionally-substituted 4- to 8-membered saturated aliphatic heterocyclyl group, (viii) optionally-substituted 5- to 10-membered unsaturated aliphatic heterocyclyl group, (ix) optionally-substituted 6- to 10-membered aryl group, or (x) optionally-substituted 5- to 10-membered heteroaryl group, wherein the substituent(s) of the (ii) optionally-substituted $C_{1-6}$ alkyl group, the (iii) optionally-substituted $C_{2-6}$ alkenyl group, the (iv) optionally-substituted $C_{2-6}$ alkynyl group, the (v) optionally-substituted 3- to 8-membered cycloalkyl group, the (vi) optionally-substituted 4- to 8-membered cycloalkenyl group, the (vii) optionally-substituted 4- to 8-membered saturated aliphatic heterocyclyl group, the (viii) optionally-substituted 5- to 10-membered unsaturated aliphatic heterocyclyl group, the (ix) optionally-substituted 6- to 10-membered aryl group, and the (x) optionally-substituted 5- to 10-membered heteroaryl group are independently one or more substituents selected independently from the group consisting of hydroxy group, methoxy group, ethoxy group, carboxyl group, carbamoyl group which may be substituted with one or two the same or different $C_{1-3}$ alkyl, and amino group which may be substituted with one or two the same or different $C_{1-3}$ alkyl, Y is carbon atom or CH, and Z is carbon atom, CH, or nitrogen atom, provided that the combination of X, Y, and Z should be any one of chemically-possible selections.

The compounds of formula (1) in Term 1 include those of formula (1'). The groups of formulae (2) and (3) in Term 1 include those of formulae (2') and (3').

Term 3

The compound of Term 2 or a pharmaceutically acceptable salt thereof, wherein $R^2$ is hydrogen atom.

Term 4

The compound of Term 2 or 3 or a pharmaceutically acceptable salt thereof, wherein $R^3$ is (i) hydrogen atom, (ii) $C_{1-3}$ alkyl group, or (v) 3- to 6-membered cycloalkyl group.

Term 5

The compound of any one of Terms 2-4 or a pharmaceutically acceptable salt thereof, wherein $R^3$ is hydrogen atom or methyl group.

Term 6

The compound of any one of Terms 2-5 or a pharmaceutically acceptable salt thereof, wherein $R^4$ is (i) hydrogen atom, (ii) $C_{1-3}$ alkyl group, or (v) 3- to 6-membered cycloalkyl group.

Term 7

The compound of any one of Terms 2-6 or a pharmaceutically acceptable salt thereof, wherein $R^4$ is methyl group.

Term 8

The compound of any one of Terms 2-7 or a pharmaceutically acceptable salt thereof, wherein $R^1$ is (i) hydrogen atom, or (ii) optionally-substituted $C_{1-6}$ alkyl group, wherein the substituent(s) of the (ii) optionally-substituted $C_{1-6}$ alkyl group is one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, $C_{1-3}$ alkyl group, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and optionally-substituted 5- to 10-membered heteroaryl group (wherein the substituent(s) of said optionally-substituted 5- to 10-membered heteroaryl group is one or more substituents selected independently from the group consisting of amino group which may be substituted with one or two the same or different $C_{1-3}$ alkyl, $C_{1-3}$ alkyl group, hydroxy group, and carboxyl group), or the (ii) optionally-substituted $C_{1-6}$ alkyl group may be any one of the groups of formulae (4)-(6).

Term 9

The compound of any one of Terms 2-7 or a pharmaceutically acceptable salt thereof, wherein $R^1$ is (i) hydrogen atom, (ii) optionally-substituted $C_{1-3}$ alkyl group, (iii) optionally-substituted $C_{2-4}$ alkenyl group, (iv) optionally-substituted $C_{2-4}$ alkynyl group, (v) optionally-substituted 3- to 6-membered cycloalkyl group, (vi) optionally-substituted 4- to 6-membered cycloalkenyl group, (vii) optionally-substituted 4- to 6-membered saturated aliphatic heterocyclyl group, (viii) optionally-substituted 5- to 6-membered unsaturated aliphatic heterocyclyl group, (ix) optionally-substituted 6- to 10-membered aryl group, or (x) optionally-substituted 5- to 10-membered heteroaryl group, wherein the substituent(s) of the (ii) optionally-substituted $C_{1-3}$ alkyl group is one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, $C_{1-3}$ alkyl group, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and optionally-substituted 5- to 10-membered heteroaryl group (wherein the substituent(s) of said optionally-substituted 5- to 10-membered heteroaryl group is one or more substituents selected independently from the group consisting of amino group which may be substituted with one or two the same or different $C_{1-3}$ alkyl, $C_{1-3}$ alkyl group, hydroxy group, and carboxyl group), or the (ii) optionally-substituted $C_{1-3}$ alkyl group may be any one of the groups of formulae (4)-(6), in formula (4), m is 1, $R^7$ is amino acid group (which binds to C(O) at its N terminus), in formula (5), q is 1, 2, 3, 4, or 5, $L^2$ is single bond or C(O), $R^8$ is hydroxy group or amino acid group (which binds to $L^2$ at its N terminus), in formula (6), $L^3$ is C(O), $R^9$ is hydroxy group or amino acid group (which binds to $L^3$ at its N terminus), the substituent(s) of the (iii) optionally-substituted $C_{2-4}$ alkenyl group, and the (iv) optionally-substituted $C_{2-4}$ alkynyl group are independently one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and 5- to 10-membered heteroaryl group, the substituent(s) of the (v) optionally-substituted 3- to 6-membered cycloalkyl group, the (vi) optionally-substituted 4- to 6-membered cycloalkenyl group, the (vii) optionally-substituted 4- to 6-membered saturated aliphatic heterocyclyl group, the (viii) optionally-substituted 5- to 6-membered unsaturated aliphatic heterocyclyl group, the (ix) optionally-substituted 6- to 10-membered aryl group, and the (x) optionally-substituted 5- to 10-membered heteroaryl group are independently one or more substituents selected independently from the group consisting of hydroxy group, methoxy group, ethoxy group, amino group which may be substituted with one or two the same or different $C_{1-3}$ alkyl, and carboxyl group.

Term 10

The compound of any one of Terms 2-9 or a pharmaceutically acceptable salt thereof, wherein $R^1$ is (i) hydrogen atom, or (ii) optionally-substituted $C_{1-3}$ alkyl group, wherein the substituent(s) of the (ii) optionally-substituted $C_{1-3}$ alkyl group is one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, $C_{1-3}$ alkyl group, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and optionally-substituted 5- to 10-membered heteroaryl group (wherein the substituent(s) of said optionally-substituted 5- to 10-membered heteroaryl group is one or more substituents selected independently from the group consisting of amino group which may be substituted with one or two the same or different $C_{1-3}$ alkyl, $C_{1-3}$ alkyl group, hydroxy group, and carboxyl group), or the (ii) optionally-substituted $C_{1-3}$ alkyl group may be any one of the groups of formulae (4)-(6), in formula (4), m is 1, $R^7$ is amino acid group (which binds to C(O) at its N terminus), in formula (5), q is 1, 2, 3, 4, or 5, $L^2$ is single bond or C(O), $R^8$ is hydroxy group or amino acid group (which binds to $L^2$ at its N terminus), in formula (6), $L^3$ is C(O), $R^9$ is hydroxy group or amino acid group (which binds to $L^3$ at its N terminus).

Term 11

The compound of any one of Terms 2-10 or a pharmaceutically acceptable salt thereof, wherein $R^1$ is hydrogen atom, or the group of formula (6), in formula (6), $L^3$ is C(O), $R^9$ is amino acid group (which binds to $L^3$ at its N terminus).

Term 12

The compound of any one of Terms 2-11 or a pharmaceutically acceptable salt thereof, wherein Ring A is the group of formula (2').

Term 13

The compound of Term 12 or a pharmaceutically acceptable salt thereof, wherein the part of X=Y=Z in formula (2') is N=C—CH, N=C—N, $NR^4$—C=C, $NR^4$—CH—N, or $NR^4$—CH—CH.

Term 14

The compound of Term 12 or 13 or a pharmaceutically acceptable salt thereof, wherein the part of X=Y=Z in formula (2') is N=C—N or $NR^4$—C=C.

Term 15

The compound of any one of Terms 2-11 or a pharmaceutically acceptable salt thereof, wherein Ring A is the group of formula (3').

Term 16

The compound of Term 15 or a pharmaceutically acceptable salt thereof, wherein the part of X=Y=Z in formula (3') is N=C—CH, N=C—N, $NR^4$—C=C, $NR^4$—CH—N, $NR^4$—CH—CH, O—C=C, O—CH—N, or O—CH—CH.

Term 17

The compound of Term 15 or 16 or a pharmaceutically acceptable salt thereof, wherein the part of X=Y=Z in formula (3') is $NR^4$—C=C or O—C=C.

Term 18

The compound of Term 2 or a pharmaceutically acceptable salt thereof, wherein $R^1$ is (ii) optionally-substituted $C_{1-6}$ alkyl group, (iii) optionally-substituted $C_{2-6}$ alkenyl group, (iv) optionally-substituted $C_{2-6}$ alkynyl group, (v) optionally-substituted 3- to 8-membered cycloalkyl group, (vi) optionally-substituted 4- to 8-membered cycloalkenyl group, (vii) optionally-substituted 4- to 8-membered saturated aliphatic heterocyclyl group, (viii) optionally-substituted 5- to 10-membered unsaturated aliphatic heterocyclyl group, (ix) optionally-substituted 6- to 10-membered aryl group, or (x) optionally-substituted 5- to 10-membered heteroaryl group, wherein the substituent(s) of the (ii) optionally-substituted $C_{1-6}$ alkyl group is one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, $C_{1-3}$ alkyl group, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and optionally-substituted 5- to 10-membered heteroaryl group (wherein the substituent(s) of said optionally-substituted 5- to 10-membered heteroaryl group is one or more substituents selected independently from the group consisting of amino group which may be substituted with one or two the same or different $C_{1-3}$ alkyl, $C_{1-3}$ alkyl group, hydroxy group, and carboxyl group), or the (ii) optionally-substituted $C_{1-6}$ alkyl group may be any one of the groups of formulae (4)-(6), in formula (4), m is 1, 2, 3, 4, or 5, $R^7$ is amino acid group (which binds to C(O) at its N terminus), or peptide consisting of 2-3 amino acid residues (which binds to C(O) at its N terminus), in formula (5), q is 1, 2, 3, 4, or 5, $L^2$ is single bond or C(O), $R^8$ is hydroxy group, amino group which may be substituted with one or two the same or different $C_{1-3}$ alkyl, amino acid group (which binds to $L^2$ at its N terminus), or peptide consisting of 2-3 amino acid residues (which binds to $L^2$ at its N terminus), in formula (6), $L^3$ is $CH_2$ or C(O), $R^9$ is hydroxy group, amino group which may be substituted with one or two the same or different $C_{1-3}$ alkyl, amino acid group (which binds to $L^3$ at its N terminus), or peptide consisting of 2-3 amino acid residues (which binds to $L^3$ at its N terminus), the substituent(s) of the (iii) optionally-substituted $C_{2-6}$ alkenyl group, and the (iv) optionally-substituted $C_{2-6}$ alkynyl group are independently one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and 5- to 10-membered heteroaryl group, the substituent(s) of the (v) optionally-substituted 3- to 8-membered cycloalkyl group, the (vi) optionally-substituted 4- to 8-membered cycloalkenyl group, the (vii) optionally-substituted 4- to 8-membered saturated aliphatic heterocyclyl group, the (viii) optionally-substituted 5- to 10-membered unsaturated aliphatic heterocyclyl group, the (ix) optionally-substituted 6- to 10-membered aryl group, and the (x) optionally-substituted 5- to 10-membered heteroaryl group are independently one or more substituents selected independently from the group consisting of hydroxy group, methoxy group, ethoxy group, amino group which may be substituted with one or two the same or different $C_{1-3}$ alkyl, and carboxyl group;

$R^2$ is hydrogen atom; and

Ring A is a group of formula (2') or (3'), when Ring A is a group of formula (2'), $R^3$ is (i) hydrogen atom, (ii) $C_{1-3}$ alkyl group, or (v) 3- to 6-membered cycloalkyl group, the part of x⋯y⋯z is N=C—N or $NR^4$—C=C wherein $R^4$ is (i) hydrogen atom, (ii) $C_{1-3}$ alkyl group, or (v) 3- to 6-membered cycloalkyl group, when Ring A is a group of formula (3'), $R^3$ is (i) hydrogen atom, (ii) $C_{1-3}$ alkyl group, or (v) 3- to 6-membered cycloalkyl group, the part of x⋯y⋯z is $NR^4$—C=C or O—C=C wherein $R^4$ is (i) hydrogen atom, (ii) $C_{1-3}$ alkyl group, or (v) 3- to 6-membered cycloalkyl group.

Term 19

The compound of Term 2 or 18 or a pharmaceutically acceptable salt thereof, wherein $R^1$ is (i) hydrogen atom, or (ii) optionally-substituted $C_{1-6}$ alkyl group, wherein the substituent(s) of the (ii) optionally-substituted $C_{1-6}$ alkyl group is one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, $C_{1-3}$ alkyl group, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and optionally-substituted 5- to 10-membered heteroaryl group (wherein the substituent(s) of said optionally-substituted 5- to 10-membered heteroaryl group is one or more substituents selected independently from the group consisting of amino group which may be substituted with one or two the same or different $C_{1-3}$ alkyl, $C_{1-3}$ alkyl group, hydroxy group, and carboxyl group), or the (ii) optionally-substituted $C_{1-6}$ alkyl group may be any one of the groups of formulae (4)-(6), in formula (4), m is 1, 2, 3, 4, or 5, $R^7$ is amino acid group (which binds to C(O) at its N terminus), or peptide consisting of 2-3 amino acid residues (which binds to C(O) at its N terminus), in formula (5), q is 1, 2, 3, 4, or 5, $L^2$ is single bond or C(O), $R^8$ is hydroxy group, amino group which may be substituted with one or two the same or different $C_{1-3}$ alkyl, amino acid group (which binds to $L^2$ at its N terminus), or peptide consisting of 2-3 amino acid residues (which binds to $L^2$ at its N terminus), in formula (6), $L^3$ is $CH_2$ or C(O), $R^9$ is hydroxy group, amino group which may be substituted with one or two the same or different $C_{1-3}$ alkyl, amino acid group (which binds to $L^3$ at its N terminus), or peptide consisting of 2-3 amino acid residues (which binds to $L^3$ at its N terminus);

$R^2$ is hydrogen atom; and

Ring A is a group of formula (2') or (3'), when Ring A is a group of formula (2'), $R^3$ is (i) hydrogen atom, (ii) $C_{1-3}$ alkyl group, or (v) 3- to 6-membered cycloalkyl group, the part of x===y===z is N=C—N or $NR^4$—C=C wherein $R^4$ is (i) hydrogen atom, (ii) $C_{1-3}$ alkyl group, or (v) 3- to 6-membered cycloalkyl group, when Ring A is a group of formula (3'), $R^3$ is (i) hydrogen atom, (ii) $C_{1-3}$ alkyl group, or (v) 3- to 6-membered cycloalkyl group, the part of x===y===z Z is $NR^4$—C=C or O—C=C wherein $R^4$ is (i) hydrogen atom, (ii) $C_{1-3}$ alkyl group, or (v) 3- to 6-membered cycloalkyl group.

Term 20

The compound of Term 2 or 18 or a pharmaceutically acceptable salt thereof, wherein $R^1$ is (i) hydrogen atom, (ii) optionally-substituted $C_{1-3}$ alkyl group, (iii) optionally-substituted $C_{2-4}$ alkenyl group, (iv) optionally-substituted $C_{2-4}$ alkynyl group, (v) optionally-substituted 3- to 6-membered cycloalkyl group, (vi) optionally-substituted 4- to 6-membered cycloalkenyl group, (vii) optionally-substituted 4- to 6-membered saturated aliphatic heterocyclyl group, (viii) optionally-substituted 5- to 6-membered unsaturated aliphatic heterocyclyl group, (ix) optionally-substituted 6- to 10-membered aryl group, or (x) optionally-substituted 5- to 10-membered heteroaryl group, wherein the substituent(s) of the (ii) optionally-substituted $C_{1-3}$ alkyl group is one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, $C_{1-3}$ alkyl group, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and optionally-substituted 5- to 10-membered heteroaryl group (wherein the substituent(s) of said optionally-substituted 5- to 10-membered heteroaryl group is one or more substituents selected independently from the group consisting of amino group which may be substituted with one or two the same or different $C_{1-3}$ alkyl, $C_{1-3}$ alkyl group, hydroxy group, and carboxyl group), or the (ii) optionally-substituted $C_{1-3}$ alkyl group may be any one of the groups of formulae (4)-(6), in formula (4), m is 1, $R^7$ is amino acid group (which binds to C(O) at its N terminus), in formula (5), q is 1, 2, 3, 4, or 5, $L^2$ is single bond or C(O), $R^8$ is hydroxy group or amino acid group (which binds to $L^2$ at its N terminus), in formula (6), $L^3$ is C(O), $R^9$ is hydroxy group or amino acid group (which binds to $L^3$ at its N terminus), the substituent(s) of the (iii) optionally-substituted $C_{2-4}$ alkenyl group, and the (iv) optionally-substituted $C_{2-4}$ alkynyl group are independently one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and 5- to 10-membered heteroaryl group, the substituent(s) of the (v) optionally-substituted 3- to 6-membered cycloalkyl group, the (vi) optionally-substituted 4- to 6-membered cycloalkenyl group, the (vii) optionally-substituted 4- to 6-membered saturated aliphatic heterocyclyl group, the (viii) optionally-substituted 5- to 6-membered unsaturated aliphatic heterocyclyl group, the (ix) optionally-substituted 6- to 10-membered aryl group, and the (x) optionally-substituted 5- to 10-membered heteroaryl group are independently one or more substituents selected independently from the group consisting of hydroxy group, methoxy group, ethoxy group, amino group which may be substituted with one or two the same or different $C_{1-3}$ alkyl, and carboxyl group;

$R^2$ is hydrogen atom; and

Ring A is a group of formula (2') or (3'), when Ring A is a group of formula (2'), $R^3$ is (i) hydrogen atom, (ii) $C_{1-3}$ alkyl group, or (v) 3- to 6-membered cycloalkyl group, the part of x═══y═══z is N═C—N or $NR^4$—C═C wherein $R^4$ is (i) hydrogen atom, (ii) $C_{1-3}$ alkyl group, or (v) 3- to 6-membered cycloalkyl group, when Ring A is a group of formula (3'), $R^3$ is (i) hydrogen atom, (ii) $C_{1-3}$ alkyl group, or (v) 3- to 6-membered cycloalkyl group, the part of x═══y═══z is $NR^4$—C═C or O—C═C wherein $R^4$ is (i) hydrogen atom, (ii) $C_3$ alkyl group, or (v) 3- to 6-membered cycloalkyl group.

Term 21

The compound of any one of Terms 2 and 18-20 or a pharmaceutically acceptable salt thereof, wherein $R^1$ is (i) hydrogen atom, or (ii) optionally-substituted $C_{1-3}$ alkyl group, wherein the substituent(s) of the (ii) optionally-substituted $C_{1-3}$ alkyl group is one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, $C_{1-3}$ alkyl group, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and optionally-substituted 5- to 10-membered heteroaryl group (wherein the substituent(s) of said optionally-substituted 5- to 10-membered heteroaryl group is one or more substituents selected independently from the group consisting of amino group which may be substituted with one or two the same or different $C_{1-3}$ alkyl, $C_{1-3}$ alkyl group, hydroxy group, and carboxyl group), or the (ii) optionally-substituted $C_{1-3}$ alkyl group may be any one of the groups of formulae (4)-(6), in formula (4), m is 1, $R^7$ is amino acid group (which binds to C(O) at its N terminus), in formula (5), q is 1, 2, 3, 4, or 5, $L^2$ is single bond or C(O), $R^8$ is hydroxy group or amino acid group (which binds to $L^2$ at its N terminus), in formula (6), $L^3$ is C(O), $R^9$ is hydroxy group or amino acid group (which binds to $L^3$ at its N terminus);

$R^2$ is hydrogen atom; and

Ring A is a group of formula (2') or (3'), when Ring A is a group of formula (2'), $R^3$ is (i) hydrogen atom, (ii) $C_{1-3}$ alkyl group, or (v) 3- to 6-membered cycloalkyl group, the part of x═══y═══z is N═C—N or $NR^4$—C═C wherein $R^4$ is (i) hydrogen atom, (ii) $C_{1-3}$ alkyl group, or (v) 3- to 6-membered cycloalkyl group, when Ring A is a group of formula (3'), $R^3$ is (i) hydrogen atom, (ii) $C_{1-3}$ alkyl group, or (v) 3- to 6-membered cycloalkyl group, the part of x═══y═══z is $NR^4$—C═C or O—C═C wherein $R^4$ is (i) hydrogen atom, (ii) $C_{1-3}$ alkyl group, or (v) 3- to 6-membered cycloalkyl group.

Term 22

The compound of Term 2 or 18 or a pharmaceutically acceptable salt thereof, wherein $R^1$ is (ii) optionally-substituted $C_{1-6}$ alkyl group, (iii) optionally-substituted $C_{2-6}$ alkenyl group, (iv) optionally-substituted $C_{2-6}$ alkynyl group, (v) optionally-substituted 3- to 8-membered cycloalkyl group, (vi) optionally-substituted 4- to 8-membered cycloalkenyl group, (vii) optionally-substituted 4- to 8-membered saturated aliphatic heterocyclyl group, (viii) optionally-substituted 5- to 10-membered unsaturated aliphatic heterocyclyl group, (ix) optionally-substituted 6- to 10-membered aryl group, or (x) optionally-substituted 5- to 10-membered heteroaryl group, wherein the substituent(s) of the (ii) optionally-substituted $C_{1-6}$ alkyl group is one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, $C_{1-3}$ alkyl group, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and optionally-substituted 5- to 10-membered heteroaryl group (wherein the substituent(s) of said optionally-substituted 5- to 10-membered heteroaryl group is one or more substituents selected independently from the group consisting of amino group which may be substituted with one or two the same or different $C_{1-3}$ alkyl, $C_{1-3}$ alkyl group, hydroxy group, and carboxyl group), or the (ii) optionally-substituted $C_{1-6}$ alkyl group may be any one of the groups of formulae (4)-(6), in formula (4), m is 1, 2, 3, 4, or 5, $R^7$ is amino acid group (which binds to C(O) at its N terminus), or peptide consisting of 2-3 amino acid residues (which binds to C(O) at its N terminus), in formula (5), q is 1, 2, 3, 4, or 5, $L^2$ is single bond or C(O), $R^8$ is hydroxy group, amino group which may be substituted with one or two the same or different $C_{1-3}$ alkyl, amino acid group (which binds to $L^2$ at its N terminus), or peptide consisting of 2-3 amino acid residues (which binds to $L^2$ at its N terminus), in formula (6), $L^3$ is $CH_2$ or C(O), $R^9$ is hydroxy group, amino group which may be substituted with one or two the same or different $C_{1-3}$ alkyl, amino acid group (which binds to $L^3$ at its N terminus), or peptide consisting of 2-3 amino acid residues (which binds to $L^3$ at its N terminus), the substituent(s) of the (iii) optionally-substituted $C_{2-6}$ alkenyl group, and the (iv) optionally-substituted $C_{2-6}$ alkynyl group are independently one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and 5- to 10-membered heteroaryl group, the substituent(s) of the (v) optionally-substituted 3- to 8-membered cycloalkyl group, the (vi) optionally-substituted 4- to 8-membered cycloalkenyl group, the (vii) optionally-substituted 4- to 8-membered saturated aliphatic heterocyclyl group, the (viii) optionally-substituted 5- to 10-membered unsaturated aliphatic heterocyclyl group, the (ix) optionally-substituted 6- to 10-membered aryl group, and the (x) optionally-substituted 5- to 10-membered heteroaryl group are independently one or more substituents selected independently from the group consisting of hydroxy group, methoxy group, ethoxy group, amino group which may be substituted with one or two the same or different $C_{1-3}$ alkyl, and carboxyl group;

$R^2$ is hydrogen atom; and

Ring A is a group of formula (2') or (3'), when Ring A is a group of formula (2'), $R^3$ is hydrogen atom or methyl group, the part of x═══y═══z is N═C—N or $NCH_3$—C═C, when Ring A is a group of formula (3'), $R^3$ is hydrogen atom or methyl group, the part of x═══y═══z is $NCH_3$—C═C or O—C═C.

Term 23

The compound of any one of Terms 2, 18, 19, and 22 or a pharmaceutically acceptable salt thereof, wherein $R^1$ is (i) hydrogen atom, or (ii) optionally-substituted $C_{1-6}$ alkyl group, wherein the substituent(s) of the (ii) optionally-substituted $C_{1-6}$ alkyl group is one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, $C_{1-3}$ alkyl group, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and optionally-substituted 5- to 10-membered heteroaryl group (wherein the substituent(s) of said optionally-substituted 5- to 10-membered heteroaryl group is one or more substituents selected independently from the group consisting of amino group which may be substituted with one or two the same or different $C_{1-3}$ alkyl, $C_{1-3}$ alkyl group, hydroxy group, and carboxyl group), or the (ii) optionally-substituted $C_{1-6}$ alkyl group may be any one of the groups of formulae (4)-(6), in formula (4), m is 1, 2, 3, 4, or 5, $R^7$ is amino acid group (which binds to C(O) at its N terminus), or peptide consisting of 2-3 amino acid residues (which binds to C(O) at its N terminus), in formula (5), q is 1, 2, 3, 4, or 5, $L^2$ is single bond or C(O), $R^8$ is hydroxy group, amino group which may be substituted with one or two the same or different $C_{1-3}$ alkyl, amino acid group (which binds to $L^2$ at its N terminus), or peptide consisting of 2-3 amino acid residues (which binds to $L^2$ at its N terminus), in formula (6), $L^3$ is $CH_2$ or C(O), $R^9$ is hydroxy group, amino group which may be substituted with one or two the same or different $C_{1-3}$ alkyl, amino acid group (which binds to $L^3$ at its N terminus), or peptide consisting of 2-3 amino acid residues (which binds to $L^3$ at its N terminus);

$R^2$ is hydrogen atom; and

Ring A is a group of formula (2') or (3'), when Ring A is a group of formula (2'), $R^3$ is hydrogen atom or methyl group, the part of x═══y═══z is N═C—N or $NCH_3$—C═C, when Ring A is a group of formula (3'), $R^3$ is hydrogen atom or methyl group, the part of x═══y═══z is $NCH_3$—C═C or O—C═C.

Term 24

The compound of any one of Terms 2, 18, 20, and 22 or a pharmaceutically acceptable salt thereof, wherein $R^1$ is (i) hydrogen atom, (ii) optionally-substituted $C_{1-3}$ alkyl group, (iii) optionally-substituted $C_{2-4}$ alkenyl group, (iv) optionally-substituted $C_{2-4}$ alkynyl group, (v) optionally-substituted 3- to 6-membered cycloalkyl group, (vi) optionally-substituted 4- to 6-membered cycloalkenyl group, (vii) optionally-substituted 4- to 6-membered saturated aliphatic heterocyclyl group, (viii) optionally-substituted 5- to 6-membered unsaturated aliphatic heterocyclyl group, (ix) optionally-substituted 6- to 10-membered aryl group, or (x) optionally-substituted 5- to 10-membered heteroaryl group, wherein the substituent(s) of the (ii) optionally-substituted $C_{1-3}$ alkyl group is one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, $C_{1-3}$ alkyl group, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and optionally-substituted 5- to 10-membered heteroaryl group (wherein the substituent(s) of said optionally-substituted 5- to 10-membered heteroaryl group is one or more substituents selected independently from the group consisting of amino group which may be substituted with one or two the same or different $C_{1-3}$ alkyl, $C_{1-3}$ alkyl group, hydroxy group, and carboxyl group), or the (ii) optionally-substituted $C_{1-3}$ alkyl group may be any one of the groups of formulae (4)-(6), in formula (4), m is 1, $R^7$ is amino acid group (which binds to C(O) at its N terminus), in formula (5), q is 1, 2, 3, 4, or 5, $L^2$ is single bond or C(O), $R^8$ is hydroxy group or amino acid group (which binds to $L^2$ at its N terminus), in formula (6), $L^3$ is C(O), $R^9$ is hydroxy group or amino acid group (which binds to $L^3$ at its N terminus), the substituent(s) of the (iii) optionally-substituted $C_{2-4}$ alkenyl group, and the (iv) optionally-substituted $C_{2-4}$ alkynyl group are independently one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and 5- to 10-membered heteroaryl group, the substituent(s) of the (v) optionally-substituted 3- to 6-membered cycloalkyl group, the (vi) optionally-substituted 4- to 6-membered cycloalkenyl group, the (vii) optionally-substituted 4- to 6-membered saturated aliphatic heterocyclyl group, the (viii) optionally-substituted 5- to 6-membered unsaturated aliphatic heterocyclyl group, the (ix) optionally-substituted 6- to 10-membered aryl group, and the (x) optionally-substituted 5- to 10-membered heteroaryl group are independently one or more substituents selected independently from the group consisting of hydroxy group, methoxy group, ethoxy group, amino group which may be substituted with one or two the same or different $C_{1-3}$ alkyl, and carboxyl group;

$R^2$ is hydrogen atom; and

Ring A is a group of formula (2') or (3'), when Ring A is a group of formula (2'), $R^3$ is hydrogen atom or methyl group, the part of x═══y═══z is N═C—N or NCH$_3$—C═C, when Ring A is a group of formula (3'), $R^3$ is hydrogen atom or methyl group, the part of x═══y═══z is NCH$_3$—C═C or O—C═C.

Term 25

The compound of any one of Terms 2 and 18-24 or a pharmaceutically acceptable salt thereof, wherein $R^1$ is (i) hydrogen atom, or (ii) optionally-substituted $C_{1-3}$ alkyl group, wherein the substituent(s) of the (ii) optionally-substituted $C_{1-3}$ alkyl group is one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, $C_{1-3}$ alkyl group, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and optionally-substituted 5- to 10-membered heteroaryl group (wherein the substituent(s) of said optionally-substituted 5- to 10-membered heteroaryl group is one or more substituents selected independently from the group consisting of amino group which may be substituted with one or two the same or different $C_{1-3}$ alkyl, $C_{1-3}$ alkyl group, hydroxy group, and carboxyl group), or the (ii) optionally-substituted $C_{1-3}$ alkyl group may be any one of the groups of formulae (4)-(6), in formula (4), m is 1, $R^7$ is amino acid group (which binds to C(O) at its N terminus), in formula (5), q is 1, 2, 3, 4, or 5, $L^2$ is single bond or C(O), $R^8$ is hydroxy group or amino acid group (which binds to $L^2$ at its N terminus), in formula (6), $L^3$ is C(O), $R^9$ is hydroxy group or amino acid group (which binds to $L^3$ at its N terminus);

$R^2$ is hydrogen atom; and

Ring A is a group of formula (2') or (3'), when Ring A is a group of formula (2'), $R^3$ is hydrogen atom or methyl group, the part of x═══y═══z is N═C—N or NCH$_3$—C═C, x═══y═══z when Ring A is a group of formula (3'), $R^3$ is hydrogen atom or methyl group, the part of x═══y═══z is NCH$_3$—C═C or O—C═C.

Term 26

The compound of any one of Terms 2, 18-25 or a pharmaceutically acceptable salt thereof, wherein $R^1$ is, hydrogen atom, or the group of formula (6), in formula (6), $L^3$ is C(O), $R^9$ is amino acid group (which binds to $L^3$ at its N terminus);

$R^2$ is hydrogen atom; and

Ring A is a group of formula (2') or (3'), when Ring A is a group of formula (2'), $R^3$ is hydrogen atom or methyl group, the part of x===y===z is N=C—N or $NCH_3$—C=C, when Ring A is a group of formula (3'), $R^3$ is hydrogen atom or methyl group, the part of x===y===z is $NCH_3$—C=C or O—C=C.

Term 27

The compound of Term 1 or 2 or a pharmaceutically acceptable salt thereof which is represented by formula (7):

(7)

(8)

(9)

(10)

wherein

Ring B is a group of formula (8), (9), or (10);

$R^1$ is (i) hydrogen atom, (ii) $C_{1-3}$ alkyl group which may be substituted with one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), 3- to 6-membered cycloalkyl group (which may be substituted with one or more substituents selected independently from the group consisting of amino group which may be substituted with one or two the same or different $C_{1-3}$ alkyl, $C_{1-3}$ alkyl group, hydroxy group, and carboxyl group), 4- to 6-membered saturated aliphatic heterocyclyl group (which may be substituted with one or more substituents selected independently from the group consisting of amino group which may be substituted with one or two the same or different $C_{1-3}$ alkyl, $C_{1-3}$ alkyl group, hydroxy group, and carboxyl group), and 5- to 10-membered heteroaryl group (which may be substituted with one or more substituents selected independently from the group consisting of amino group which may be substituted with one or two the same or different $C_{1-3}$ alkyl, $C_{1-3}$ alkyl group, hydroxy group, and carboxyl group), (iii) the group of formula (4):

$$R^7-C(=O)-(CH_2)_m\rightarrow \quad (4)$$

wherein m is 1, 2, 3, 4, or 5, $R^7$ is $C_{1-3}$ alkoxy group, amino acid group (which binds to C(O) at its N terminus), and peptide consisting of 2-3 amino acid residues (which binds to C(O) at its N terminus), (iv) the group of formula (5):

$$R^8\text{-}L^2\text{-}((CH_2CH_2CH_2O)CH_2CH_2\rightarrow \quad (5)$$

wherein q is 1, 2, 3, 4, or 5, $L^2$ is single bond or C(O), $R^8$ is hydroxy group, $C_{1-3}$ alkoxy group, amino group which may be substituted with one or two the same or different $C_{1-3}$ alkyl, amino acid group (which binds to $L^2$ at its N terminus), or peptide consisting of 2-3 amino acid residues (which binds to $L^2$ at its N terminus), or (v) the group of formula (6):

(6)

wherein $L^3$ is $CH_2$ or C(O), and $R^9$ is hydroxy group, $C_{1-3}$ alkoxy group, amino group which may be substituted with one or two the same or different $C_{1-3}$ alkyl, amino acid group (which binds to $L^3$ at its N terminus), or peptide consisting of 2-3 amino acid residues (which binds to $L^3$ at its N terminus);

$X^1$ is O or $NR^{14}$; and $R^{13}$ and $R^{14}$ are independently hydrogen atom, $C_{1-3}$ alkyl group, or 3- to 6-membered cycloalkyl group.

Term 28

The compound of Term 27 or a pharmaceutically acceptable salt thereof, wherein Ring B is the group of formula (8).

Term 29

The compound of Term 27 or 28 or a pharmaceutically acceptable salt thereof, wherein $R^1$ is the group of formula (4), (5), or (6).

Term 30

The compound of any one of Terms 27-29 or a pharmaceutically acceptable salt thereof, wherein $L^2$ and $L^3$ are C(O).

Term 31

The compound of any one of Terms 27-29 or a pharmaceutically acceptable salt thereof, wherein $R^1$ is the group of formula (4).

Term 32
The compound of any one of Terms 27-30 or a pharmaceutically acceptable salt thereof, wherein $R^1$ is the group of formula (6).

Term 33
The compound of any one of Terms 27-32 or a pharmaceutically acceptable salt thereof, wherein $R^7$, $R^8$, or $R^9$ is amino acid group (which binds to C(O), $L^2$, or $L^3$ at its N terminus).

Term 34
The compound of any one of Terms 27-33 or a pharmaceutically acceptable salt thereof, wherein $R^7$, $R^8$, or $R^9$ is L-glutamic acid (which binds to C(O), $L^2$, or $L^3$ at its N terminus).

Term 35
The compound of any one of Terms 27-34 or a pharmaceutically acceptable salt thereof, wherein $R^{13}$ is hydrogen atom.

Term 36
The compound of any one of Terms 27-35 or a pharmaceutically acceptable salt thereof, wherein $X^1$ is $NR^{14}$ Term 37
The compound of any one of Terms 27-36 or a pharmaceutically acceptable salt thereof wherein $R^{14}$ is methyl group.

Term 38
The compound of Term 1 or 2 or a pharmaceutically acceptable salt thereof, which is selected from the following compounds:
3-(6,7-dihydroxy-1-methyl-4-oxo-1,4-dihydroquinolin-3-yl)-6,7-dihydroxy-4-oxo-4H-chromene-5-carboxylic acid (Example 1),
prop-2-yn-1-yl 3-(6,7-dihydroxy-1-methyl-4-oxo-1,4-dihydroquinolin-3-yl)-6,7-dihydroxy-4-oxo-4H-chromene-5-carboxylate (Example 2),
N-({4-[({[3-(6,7-dihydroxy-1-methyl-4-oxo-1,4-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid (Example 3),
$N^2$-({4-[({[3-(6,7-dihydroxy-1-methyl-4-oxo-1,4-dihydroquinolin-3-yl)-6,7-dihydroxy-4-oxo-4H-chromen-5-yl]carbonyl}oxy)methyl]-1H-1,2,3-triazol-1-yl}acetyl)-L-arginine (Example 4),
N-{[3-(6,7-dihydroxy-1-methyl-4-oxo-1,4-dihydroquinolin-3-yl)-6,7-dihydroxy-4-oxo-4H-chromen-5-yl]carbonyl}-L-glutamic acid (Example 5),
3-(6,7-dihydroxy-1-methyl-4-oxo-1,4-dihydroquinolin-3-yl)-6,7-dihydroxy-4-oxo-N-(prop-2-yn-1-yl)-4H-chromene-5-carboxamide (Example 6),
3-(6,7-dihydroxy-1,2-dimethyl-4-oxo-1,4-dihydroquinolin-3-yl)-6,7-dihydroxy-4-oxo-4H-chromene-5-carboxylic acid (Example 7),
N-({4-[({[3-(6,7-dihydroxy-1,2-dimethyl-4-oxo-1,4-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid (Example 8),
6,6',7,7'-tetrahydroxy-2,4'-dioxo-2H,4'H-3,3'-bichromene-5'-carboxylic acid (Example 9),
prop-2-yn-1-yl 6,6',7,7'-tetrahydroxy-2,4'-dioxo-2H,4'H-3,3'-bichromene-5'-carboxylate (Example 10),
N-{[4-({[(6,6',7,7'-tetrahydroxy-2,4'-dioxo-2H,4'H-3,3'-bichromen-5'-yl)carbonyl]oxy}methyl)-1H-1,2,3-triazol-1-yl]acetyl}-L-glutamic acid (Example 11),
$N^2$-{[4-({[(6,6',7,7'-tetrahydroxy-2,4'-dioxo-2H,4'H-3,3'-bichromen-5'-yl)carbonyl]oxy}methyl)-1H-1,2,3-triazol-1-yl]acetyl}-L-arginine (Example 12),
3-(6,7-dihydroxy-1-methyl-2-oxo-1,2-dihydroquinolin-3-yl)-6,7-dihydroxy-4-oxo-4H-chromene-5-carboxylic acid (Example 13),
N-({4-[({[3-(6,7-dihydroxy-1-methyl-2-oxo-1,2-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid (Example 14),
N-({4-[({[3-(6,7-dihydroxy-1,4-dimethyl-2-oxo-1,2-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid (Example 15),
3-(7,8-dihydroxy-2-methyl-4-oxo-4H-pyrido[1,2-a]pyrimidin-3-yl)-6,7-dihydroxy-4-oxo-4H-chromene-5-carboxylic acid (Example 16),
N-({4-[({[3-(7,8-dihydroxy-2-methyl-4-oxo-4H-pyrido[1,2-a]pyrimidin-3-yl)-6,7-dihydroxy-4-oxo-4H-chromen-5-yl]carbonyl}oxy)methyl]-1H-1,2,3-triazol-1-yl}acetyl)-L-glutamic acid (Example 17),
N-[({[3-(7,8-dihydroxy-2-methyl-4-oxo-4H-pyrido[1,2-a]pyrimidin-3-yl)-6,7-dihydroxy-4-oxo-4H-chromen-5-yl]carbonyl}oxy)acetyl]-L-glutamic acid (Example 18),
N-[({[3-(6,7-dihydroxy-1-methyl-4-oxo-1,4-dihydroquinolin-3-yl)-6,7-dihydroxy-4-oxo-4H-chromen-5-yl]carbonyl}oxy)acetyl]-L-glutamic acid (Example 19),
3-[2-({[3-(6,7-dihydroxy-1-methyl-4-oxo-1,4-dihydroquinolin-3-yl)-6,7-dihydroxy-4-oxo-4H-chromen-5-yl]carbonyl}oxy)ethoxy]propanoic acid (Example 20),
N-{3-[2-({[3-(6,7-dihydroxy-1-methyl-4-oxo-1,4-dihydroquinolin-3-yl)-6,7-dihydroxy-4-oxo-4H-chromen-5-yl]carbonyl}oxy)ethoxy]propanoyl}-L-glutamic acid (Example 21),
2,2'-{[2-({[3-(6,7-dihydroxy-1-methyl-4-oxo-1,4-dihydroquinolin-3-yl)-6,7-dihydroxy-4-oxo-4H-chromen-5-yl]carbonyl}oxy)ethyl]imino}-diacetic acid (Example 22),
2,3-dihydroxypropyl 3-(6,7-dihydroxy-1-methyl-4-oxo-1,4-dihydroquinolin-3-yl)-6,7-dihydroxy-4-oxo-4H-chromene-5-carboxylate (Example 23),
(trans-4-aminocyclohexyl)methyl 3-(6,7-dihydroxy-1-methyl-4-oxo-1,4-dihydroquinolin-3-yl)-6,7-dihydroxy-4-oxo-4H-chromene-5-carboxylate (Example 24),
(1,4-dimethylpiperazin-2-yl)methyl 3-(6,7-dihydroxy-1-methyl-4-oxo-1,4-dihydroquinolin-3-yl)-6,7-dihydroxy-4-oxo-4H-chromene-5-carboxylate (Example 25),
(1-methyl-1H-imidazol-2-yl)methyl 3-(6,7-dihydroxy-1-methyl-4-oxo-1,4-dihydroquinolin-3-yl)-6,7-dihydroxy-4-oxo-4H-chromene-5-carboxylate (Example 26),
O-{[3-(6,7-dihydroxy-1-methyl-4-oxo-1,4-dihydroquinolin-3-yl)-6,7-dihydroxy-4-oxo-4H-chromen-5-yl]carbonyl}-L-homoserine (Example 27),
2-(3-hydroxypyrrolidin-1-yl)ethyl 3-(6,7-dihydroxy-1-methyl-4-oxo-1,4-dihydroquinolin-3-yl)-6,7-dihydroxy-4-oxo-4H-chromene-5-carboxylate (Example 28),
14-hydroxy-3,6,9,12-tetraoxatetradec-1-yl 3-(6,7-dihydroxy-1-methyl-4-oxo-1,4-dihydroquinolin-3-yl)-6,7-dihydroxy-4-oxo-4H-chromene-5-carboxylate (Example 29), and
2-amino-2-oxoethyl 3-(6,7-dihydroxy-1-methyl-4-oxo-1,4-dihydroquinolin-3-yl)-6,7-dihydroxy-4-oxo-4H-chromene-5-carboxylate (Example 30).

Term 39
The compound of Term 1 or 2 or a pharmaceutically acceptable salt thereof, which is selected from the following compounds:
3-(6,7-dihydroxy-1-methyl-4-oxo-1,4-dihydroquinolin-3-yl)-6,7-dihydroxy-4-oxo-4H-chromene-5-carboxylic acid (Example 1), prop-2-yn-1-yl 3-(6,7-dihydroxy-1-methyl-4-oxo-1,4-dihydroquinolin-3-yl)-6,7-dihydroxy-4-oxo-4H-chromene-5-carboxylate (Example 2), N-({4-[({[3-(6,7-dihydroxy-1-methyl-4-oxo-1,4-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid (Example 3), N²-({4-[({[3-(6,7-dihydroxy-1-methyl-4-oxo-1,4-dihydroquinolin-3-yl)-6,7-dihydroxy-4-oxo-4H-chromen-5-yl]carbonyl}oxy)methyl]-1H-1,2,3-triazol-1-yl}acetyl)-L-arginine (Example 4), N-{[3-(6,7-dihydroxy-1-methyl-4-oxo-1,4-dihydroquinolin-3-yl)-6,7-dihydroxy-4-oxo-4H-chromen-5-yl]carbonyl}-L-glutamic acid (Example 5), 3-(6,7-dihydroxy-1-methyl-4-oxo-1,4-dihydroquinolin-3-yl)-6,7-dihydroxy-4-oxo-N-(prop-2-yn-1-yl)-4H-chromene-5-carboxamide (Example 6), 3-(6,7-dihydroxy-1,2-dimethyl-4-oxo-1,4-dihydroquinolin-3-yl)-6,7-dihydroxy-4-oxo-4H-chromene-5-carboxylic acid (Example 7), N-({4-[({[3-(6,7-dihydroxy-1,2-dimethyl-4-oxo-1,4-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid (Example 8), 6,6',7,7'-tetrahydroxy-2,4'-dioxo-2H,4'H-3,3'-bichromene-5'-carboxylic acid (Example 9), prop-2-yn-1-yl 6,6',7,7'-tetrahydroxy-2,4'-dioxo-2H,4'H-3,3'-bichromene-5'-carboxylate (Example 10), N-{[4-({[(6,6',7,7'-tetrahydroxy-2,4'-dioxo-2H,4'H-3,3'-bichromen-5'-yl)carbonyl]oxy}methyl)-1H-1,2,3-triazol-1-yl]acetyl}-L-glutamic acid (Example 11), N²-{[4-({[(6,6',7,7'-tetrahydroxy-2,4'-dioxo-2H,4'H-3,3'-bichromen-5'-yl)carbonyl]oxy}methyl)-1H-1,2,3-triazol-1-yl]acetyl}-L-arginine (Example 12), 3-(6,7-dihydroxy-1-methyl-2-oxo-1,2-dihydroquinolin-3-yl)-6,7-dihydroxy-4-oxo-4H-chromene-5-carboxylic acid (Example 13), N-({4-[({[3-(6,7-dihydroxy-1-methyl-2-oxo-1,2-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid (Example 14), N-({4-[({[3-(6,7-dihydroxy-1,4-dimethyl-2-oxo-1,2-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid (Example 15), 3-(7,8-dihydroxy-2-methyl-4-oxo-4H-pyrido[1,2-a]pyrimidin-3-yl)-6,7-dihydroxy-4-oxo-4H-chromene-5-carboxylic acid (Example 16), N-({4-[({[3-(7,8-dihydroxy-2-methyl-4-oxo-4H-pyrido[1,2-a]pyrimidin-3-yl)-6,7-dihydroxy-4-oxo-4H-chromen-5-yl]carbonyl}oxy)methyl]-1H-1,2,3-triazol-1-yl}acetyl)-L-glutamic acid (Example 17), N-[({[3-(7,8-dihydroxy-2-methyl-4-oxo-4H-pyrido[1,2-a]pyrimidin-3-yl)-6,7-dihydroxy-4-oxo-4H-chromen-5-yl]carbonyl}oxy)acetyl]-L-glutamic acid (Example 18), and N-[({[3-(6,7-dihydroxy-1-methyl-4-oxo-1,4-dihydroquinolin-3-yl)-6,7-dihydroxy-4-oxo-4H-chromen-5-yl]carbonyl}oxy)acetyl]-L-glutamic acid (Example 19).

Term 41

The compound of Term 1 or 2 or a pharmaceutically acceptable salt thereof, which is selected from the following compounds:

3-(6,7-dihydroxy-1-methyl-4-oxo-1,4-dihydroquinolin-3-yl)-6,7-dihydroxy-4-oxo-4H-chromene-5-carboxylic acid (Example 1), prop-2-yn-1-yl 3-(6,7-dihydroxy-1-methyl-4-oxo-1,4-dihydroquinolin-3-yl)-6,7-dihydroxy-4-oxo-4H-chromene-5-carboxylate (Example 2), N-({4-[({[3-(6,7-dihydroxy-1-methyl-4-oxo-1,4-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid (Example 3), N²-({4-[({[3-(6,7-dihydroxy-1-methyl-4-oxo-1,4-dihydroquinolin-3-yl)-6,7-dihydroxy-4-oxo-4H-chromen-5-yl]carbonyl}oxy)methyl]-1H-1,2,3-triazol-1-yl}acetyl)-L-arginine (Example 4), N-{[3-(6,7-dihydroxy-1-methyl-4-oxo-1,4-dihydroquinolin-3-yl)-6,7-dihydroxy-4-oxo-4H-chromen-5-yl]carbonyl}-L-glutamic acid (Example 5), 3-(6,7-dihydroxy-1-methyl-4-oxo-1,4-dihydroquinolin-3-yl)-6,7-dihydroxy-4-oxo-N-(prop-2-yn-1-yl)-4H-chromene-5-carboxamide (Example 6), 3-(6,7-dihydroxy-1,2-dimethyl-4-oxo-1,4-dihydroquinolin-3-yl)-6,7-dihydroxy-4-oxo-4H-chromene-5-carboxylic acid (Example 7), N-({4-[({[3-(6,7-dihydroxy-1,2-dimethyl-4-oxo-1,4-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid (Example 8), 3-(7,8-dihydroxy-2-methyl-4-oxo-4H-pyrido[1,2-a]pyrimidin-3-yl)-6,7-dihydroxy-4-oxo-4H-chromene-5-carboxylic acid (Example 16), N-({4-[({[3-(7,8-dihydroxy-2-methyl-4-oxo-4H-pyrido[1,2-a]pyrimidin-3-yl)-6,7-dihydroxy-4-oxo-4H-chromen-5-yl]carbonyl}oxy)methyl]-1H-1,2,3-triazol-1-yl}acetyl)-L-glutamic acid (Example 17), N-[({[3-(7,8-dihydroxy-2-methyl-4-oxo-4H-pyrido[1,2-a]pyrimidin-3-yl)-6,7-dihydroxy-4-oxo-4H-chromen-5-yl]carbonyl}oxy)acetyl]-L-glutamic acid (Example 18), N-[({[3-(6,7-dihydroxy-1-methyl-4-oxo-1,4-dihydroquinolin-3-yl)-6,7-dihydroxy-4-oxo-4H-chromen-5-yl]carbonyl}oxy)acetyl]-L-glutamic acid (Example 19), 3-[2-({[3-(6,7-dihydroxy-1-methyl-4-oxo-1,4-dihydroquinolin-3-yl)-6,7-dihydroxy-4-oxo-4H-chromen-5-yl]carbonyl}oxy)ethoxy]propanoic acid (Example 20), N-{3-[2-({[3-(6,7-dihydroxy-1-methyl-4-oxo-1,4-dihydroquinolin-3-yl)-6,7-dihydroxy-4-oxo-4H-chromen-5-yl]carbonyl}oxy)ethoxy]propanoyl}-L-glutamic acid (Example 21), 2,2'-{[2-({[3-(6,7-dihydroxy-1-methyl-4-oxo-1,4-dihydroquinolin-3-yl)-6,7-dihydroxy-4-oxo-4H-chromen-5-yl]carbonyl}oxy)ethyl]imino}-diacetic acid (Example 22), 2,3-dihydroxypropyl 3-(6,7-dihydroxy-1-methyl-4-oxo-1,4-dihydroquinolin-3-yl)-6,7-dihydroxy-4-oxo-4H-chromene-5-carboxylate (Example 23), (trans-4-aminocyclohexyl)methyl 3-(6,7-dihydroxy-1-methyl-4-oxo-1,4-dihydroquinolin-3-yl)-6,7-dihydroxy-4-oxo-4H-chromene-5-carboxylate (Example 24), (1,4-dimethylpiperazin-2-yl)methyl 3-(6,7-dihydroxy-1-methyl-4-oxo-1,4-dihydroquinolin-3-yl)-6,7-dihydroxy-4-oxo-4H-chromene-5-carboxylate (Example 25), (1-methyl-1H-imidazol-2-yl)methyl 3-(6,7-dihydroxy-1-methyl-4-oxo-1,4-dihydroquinolin-3-yl)-6,7-dihydroxy-4-oxo-4H-chromene-5-carboxylate (Example 26), O-{[3-(6,7-dihydroxy-1-methyl-4-oxo-1,4-dihydroquinolin-3-yl)-6,7-dihydroxy-4-oxo-4H-chromen-5-yl]carbonyl}-L-homoserine (Example 27), 2-(3-hydroxypyrrolidin-1-yl)ethyl 3-(6,7-dihydroxy-1-methyl-4-oxo-1,4-dihydroquinolin-3-yl)-6,7-dihydroxy-4-oxo-4H-chromene-5-carboxylate (Example 28), 14-hydroxy-3,6,9,12-tetraoxatetradec-1-yl 3-(6,7-dihydroxy-1-methyl-4-oxo-1,4-dihydroquinolin-3-yl)-6,7-dihydroxy-4-oxo-4H-chromene-5-carboxylate (Example 29), and 2-amino-2-oxoethyl 3-(6,7-dihydroxy-1-methyl-4-oxo-1,4-dihydroquinolin-3-yl)-6,7-dihydroxy-4-oxo-4H-chromene-5-carboxylate (Example 30).

Term 42

The compound of Term 1 or 2 or a pharmaceutically acceptable salt thereof, which is selected from the following compounds:

3-(6,7-dihydroxy-1-methyl-4-oxo-1,4-dihydroquinolin-3-yl)-6,7-dihydroxy-4-oxo-4H-chromene-5-carboxylic acid (Example 1), prop-2-yn-1-yl 3-(6,7-dihydroxy-1-methyl-4-oxo-1,4-dihydroquinolin-3-yl)-6,7-dihydroxy-4-oxo-4H-chromene-5-carboxylate (Example 2), N-({4-[({[3-(6,7-dihydroxy-1-methyl-4-oxo-1,4-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid (Example 3), N²-({4-[({[3-(6,7-dihydroxy-1-methyl-4-oxo-1,4-dihydroquinolin-3-yl)-6,7-dihydroxy-4-oxo-4H-chromen-5-yl]carbonyl}oxy)methyl]-1H-1,2,3-triazol-1-yl}acetyl)-L-arginine (Example 4), N-{[3-(6,7-dihydroxy-1-methyl-4-oxo-1,4-dihydroquinolin-3-yl)-6,7-dihydroxy-4-oxo-4H-chromen-5-yl]carbonyl}-L-glutamic acid (Example 5), 3-(6,7-dihydroxy-1-methyl-4-oxo-1,4-dihydroquinolin-3-yl)-6,7-dihydroxy-4-oxo-N-(prop-2-yn-1-yl)-4H-chromene-5-carboxamide (Example 6), 3-(6,7-dihydroxy-1,2-dimethyl-4-oxo-1,4-dihydroquinolin-3-yl)-6,7-dihydroxy-4-oxo-4H-chromene-5-carboxylic acid (Example 7), N-({4-[({[3-(6,7-dihydroxy-1,2-dimethyl-4-oxo-1,4-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid (Example 8), 3-(7,8-dihydroxy-2-methyl-4-oxo-4H-pyrido[1,2-a]pyrimidin-3-yl)-6,7-dihydroxy-4-oxo-4H-chromene-5-carboxylic acid (Example 16), N-({4-[({[3-(7,8-dihydroxy-2-methyl-4-oxo-4H-pyrido[1,2-a]pyrimidin-3-yl)-6,7-dihydroxy-4-oxo-4H-chromen-5-yl]carbonyl}oxy)methyl]-1H-1,2,3-triazol-1-yl}acetyl)-L-glutamic acid (Example 17), N-[({[3-(7,8-dihydroxy-2-methyl-4-oxo-4H-pyrido[1,2-a]pyrimidin-3-yl)-6,7-dihydroxy-4-oxo-4H-chromen-5-yl]carbonyl}oxy)acetyl]-L-glutamic acid (Example 18), and N-[({[3-(6,7-dihydroxy-1-methyl-4-oxo-1,4-dihydroquinolin-3-yl)-6,7-dihydroxy-4-oxo-4H-chromen-5-yl]carbonyl}oxy)acetyl]-L-glutamic acid (Example 19).

Term 43

The compound of Term 1 or 2 or a pharmaceutically acceptable salt thereof, which is selected from the following compounds:

3-(6,7-dihydroxy-1-methyl-4-oxo-1,4-dihydroquinolin-3-yl)-6,7-dihydroxy-4-oxo-4H-chromene-5-carboxylic acid (Example 1), N-({4-[({[3-(6,7-dihydroxy-1-methyl-4-oxo-1,4-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid (Example 3), N²-({4-[({[3-(6,7-dihydroxy-1-methyl-4-oxo-1,4-dihydroquinolin-3-yl)-6,7-dihydroxy-4-oxo-4H-chromen-5-yl]carbonyl}oxy)methyl]-1H-1,2,3-triazol-1-yl}acetyl)-L-arginine (Example 4), N-{[3-(6,7-dihydroxy-1-methyl-4-oxo-1,4-dihydroquinolin-3-yl)-6,7-dihydroxy-4-oxo-4H-chromen-5-yl]carbonyl}-L-glutamic acid (Example 5), 3-(6,7-dihydroxy-1,2-dimethyl-4-oxo-1,4-dihydroquinolin-3-yl)-6,7-dihydroxy-4-oxo-4H-chromene-5-carboxylic acid (Example 7), N-({4-[({[3-(6,7-dihydroxy-1,2-dimethyl-4-oxo-1,4-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid (Example 8),
3-(7,8-dihydroxy-2-methyl-4-oxo-4H-pyrido[1,2-a]pyrimidin-3-yl)-6,7-dihydroxy-4-oxo-4H-chromene-5-carboxylic acid (Example 16),
N-({4-[({[3-(7,8-dihydroxy-2-methyl-4-oxo-4H-pyrido[1,2-a]pyrimidin-3-yl)-6,7-dihydroxy-4-oxo-4H-chromen-5-yl]carbonyl}oxy)methyl]-1H-1,2,3-triazol-1-yl}acetyl)-L-glutamic acid (Example 17),
N-[({[3-(7,8-dihydroxy-2-methyl-4-oxo-4H-pyrido[1,2-a]pyrimidin-3-yl)-6,7-dihydroxy-4-oxo-4H-chromen-5-yl]carbonyl}oxy)acetyl]-L-glutamic acid (Example 18), and
N-[({[3-(6,7-dihydroxy-1-methyl-4-oxo-1,4-dihydroquinolin-3-yl)-6,7-dihydroxy-4-oxo-4H-chromen-5-yl]carbonyl}oxy)acetyl]-L-glutamic acid (Example 19).

Term 44
The compound of Term 1 or 2 or a pharmaceutically acceptable salt thereof, which is selected from the following compounds:
6,6',7,7'-tetrahydroxy-2,4'-dioxo-2H,4'H-3,3'-bichromene-5'-carboxylic acid (Example 9),
prop-2-yn-1-yl 6,6',7,7'-tetrahydroxy-2,4'-dioxo-2H,4'H-3,3'-bichromene-5'-carboxylate (Example 10),
N-{[4-({[(6,6',7,7'-tetrahydroxy-2,4'-dioxo-2H,4'H-3,3'-bichromen-5'-yl)carbonyl]oxy}methyl)-1H-1,2,3-triazol-1-yl]acetyl}-L-glutamic acid (Example 11),
$N^2$-{[4-({[(6,6',7,7'-tetrahydroxy-2,4'-dioxo-2H,4'H-3,3'-bichromen-5'-yl)carbonyl]oxy}methyl)-1H-1,2,3-triazol-1-yl]acetyl}-L-arginine (Example 12),
3-(6,7-dihydroxy-1-methyl-2-oxo-1,2-dihydroquinolin-3-yl)-6,7-dihydroxy-4-oxo-4H-chromene-5-carboxylic acid (Example 13),
N-({4-[({[3-(6,7-dihydroxy-1-methyl-2-oxo-1,2-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid (Example 14), and
N-({4-[({[3-(6,7-dihydroxy-1,4-dimethyl-2-oxo-1,2-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid (Example 15).

Term 45
The compound of Term 1 or 2 or a pharmaceutically acceptable salt thereof, which is selected from the following compounds:
6,6',7,7'-tetrahydroxy-2,4'-dioxo-2H,4'H-3,3'-bichromene-5'-carboxylic acid (Example 9),
N-{[4-({[(6,6',7,7'-tetrahydroxy-2,4'-dioxo-2H,4'H-3,3'-bichromen-5'-yl)carbonyl]oxy}methyl)-1H-1,2,3-triazol-1-yl]acetyl}-L-glutamic acid (Example 11),
$N^2$-{[4-({[(6,6',7,7'-tetrahydroxy-2,4'-dioxo-2H,4'H-3,3'-bichromen-5'-yl)carbonyl]oxy}methyl)-1H-1,2,3-triazol-1-yl]acetyl}-L-arginine (Example 12),
3-(6,7-dihydroxy-1-methyl-2-oxo-1,2-dihydroquinolin-3-yl)-6,7-dihydroxy-4-oxo-4H-chromene-5-carboxylic acid (Example 13),
N-({4-[({[3-(6,7-dihydroxy-1-methyl-2-oxo-1,2-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid (Example 14), and
N-({4-[({[3-(6,7-dihydroxy-1,4-dimethyl-2-oxo-1,2-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid (Example 15).

Term 46
A pharmaceutical composition comprising the compound of any one of Terms 1-45 or a pharmaceutically acceptable salt thereof.

Term 47
A semaphorin inhibitor comprising the compound of any one of Terms 1-45 or a pharmaceutically acceptable salt thereof as an active ingredient.

Term 48
The semaphorin inhibitor of Term 47, wherein the semaphorin is class 3 semaphorins.

Term 49
The semaphorin inhibitor of Term 48, wherein the class 3 semaphorins is semaphorin 3A.

Term 50
An inhibitor for a nerve outgrowth repelling factor comprising the compound of any one of Terms 1-45 or a pharmaceutically acceptable salt thereof as an active ingredient.

Term 51
A medicament having suppressing action on the growth cone collapse activity and/or suppressing action on the nerve outgrowth inhibitory activity in a collagen gel, comprising the compound of any one of Terms 1-45 or a pharmaceutically acceptable salt thereof as an active ingredient.

Term 52
A nerve regeneration promoter comprising the compound of any one of Terms 1-45 or a pharmaceutically acceptable salt thereof as an active ingredient.

Term 53
A medicament for treating and/or preventing a disease associated with neurodegeneration or neurological disorder, comprising the compound of any one of Terms 1-45 or a pharmaceutically acceptable salt thereof as an active ingredient.

Term 54
A medicament for treating and/or preventing a neurological disease associated with ischemic damage, comprising the compound of any one of Terms 1-45 or a pharmaceutically acceptable salt thereof as an active ingredient.

Term 55
The medicament of Term 54, wherein the neurological disease associated with ischemic damage is retinal neurological disorder caused by ischemia or ischemic cerebrovascular disease.

Term 56
The medicament of Term 55, wherein the retinal neurological disorder is glaucoma, central retinal artery occlusion, central branch retinal artery occlusion, central retinal vein occlusion, central branch retinal vein occlusion, ischemic optic neuropathy, diabetic retinopathy, macular degeneration, or retinopathy of prematurity.

Term 57
The medicament of Term 55, wherein the ischemic cerebrovascular disease is cerebral emboli, transient cerebral ischemia, subclavian steal syndrome, Wallenberg's syndrome (lateral medullary syndrome), cerebral thrombosis, lacunar infarct, reversible ischemic neurological deficit, cerebral infarct, moyamoya disease (spontaneous occlusion of the circle of Willis), cerebral hypoxia, sinus thrombosis, or postoperative spinal cord ischemia.

Term 58
A medicament for treating and/or preventing corneal disease, comprising the compound of any one of Terms 1-45 or a pharmaceutically acceptable salt thereof as an active ingredient.

Term 59
The medicament of Term 58, wherein the corneal disease is dry eye, keratitis, leukoma, corneal infection, corneal degeneration, corneal dystrophy, corneal stromal dystrophy, bullous keratopathy, keratoconus, corneal endothelial decompensation, corneal ulcer, nerve-paralytic keratopathy, diabetic keratopathy, chemical ocular injury or corneal burn.
Term 60
The medicament of Term 59, wherein the corneal disease is dry eye, keratitis, bullous keratopathy, corneal ulcer, nerve-paralytic keratopathy, or diabetic keratopathy.
Term 61
The medicament of Term 59, wherein the corneal disease is dry eye.
Term 62
The medicament of any one of Terms 58-61, wherein the corneal disease is a disease associated with neurodegeneration or neurological disorder.
Term 63
A medicament for treating and/or preventing a disease associated with degeneration and damage in central nerve and peripheral nerve, comprising the compound of any one of Terms 1-45 or a pharmaceutically acceptable salt thereof as an active ingredient.
Term 64
A medicament for treating and/or preventing dysosmia, traumatic neurological disorder, cerebral-infarct neurological disorder, facial palsy, diabetic neurosis, glaucoma, retinitis pigmentosa, dry eye, Alzheimer's disease, Parkinson's disease, neurodegenerative disease, muscular dysgenic lateral sclerosis, amyotrophic lateral sclerosis, Huntington's disease, cerebral infarct, or traumatic neurodegenerative disease, comprising the compound of any one of Terms 1-45 or a pharmaceutically acceptable salt thereof as an active ingredient.
Term 65
A medicament for treating and/or preventing dry eye, comprising the compound of any one of Terms 1-45 or a pharmaceutically acceptable salt thereof as an active ingredient.
Term 66
A method for treating and/or preventing a disease associated with neurodegeneration or neurological disorder, comprising administering a therapeutically effective amount of the compound of any one of Terms 1-45 or a pharmaceutically acceptable salt thereof to a patient in need thereof.
Term 67
A method for treating and/or preventing a neurological disease associated with ischemic damage, comprising administering a therapeutically effective amount of the compound of any one of Terms 1-45 or a pharmaceutically acceptable salt thereof to a patient in need thereof.
Term 68
The method of Term 67, wherein the neurological disease associated with ischemic damage is retinal neurological disorder caused by ischemia or ischemic cerebrovascular disease.
Term 69
The method of Term 68, wherein the retinal neurological disorder is glaucoma, central retinal artery occlusion, central branch retinal artery occlusion, central retinal vein occlusion, central branch retinal vein occlusion, ischemic optic neuropathy, diabetic retinopathy, macular degeneration, or retinopathy of prematurity.
Term 70
The method of Term 68, wherein the ischemic cerebrovascular disease is cerebral emboli, transient cerebral ischemia, subclavian steal syndrome, Wallenberg's syndrome (lateral medullary syndrome), cerebral thrombosis, lacunar infarct, reversible ischemic neurological deficit, cerebral infarct, moyamoya disease (spontaneous occlusion of the circle of Willis), cerebral hypoxia, sinus thrombosis, or postoperative spinal cord ischemia.
Term 71
A method for treating and/or preventing corneal disease, comprising administering a therapeutically effective amount of the compound of any one of Terms 1-45 or a pharmaceutically acceptable salt thereof to a patient in need thereof.
Term 72
The method of Term 71, wherein the corneal disease is dry eye, keratitis, leukoma, corneal infection, corneal degeneration, corneal dystrophy, corneal stromal dystrophy, bullous keratopathy, keratoconus, corneal endothelial decompensation, corneal ulcer, nerve-paralytic keratopathy, diabetic keratopathy, chemical ocular injury, or corneal burn.
Term 73
The method of Term 72, wherein the corneal disease is dry eye, keratitis, bullous keratopathy, corneal ulcer, nerve-paralytic keratopathy, or diabetic keratopathy.
Term 74
The method of Term 72, wherein the corneal disease is dry eye.
Term 75
The method of any one of Terms 71-74, wherein the corneal disease is a disease associated with neurodegeneration or neurological disorder.
Term 76
A method for treating and/or preventing a disease associated with degeneration and damage in central nerve and peripheral nerve, comprising administering a therapeutically effective amount of the compound of any one of Terms 1-45 or a pharmaceutically acceptable salt thereof to a patient in need thereof.
Term 77
A method for treating and/or preventing dysosmia, traumatic neurological disorder, cerebral-infarct neurological disorder, facial palsy, diabetic neurosis, glaucoma, retinitis pigmentosa, dry eye, Alzheimer's disease, Parkinson's disease, neurodegenerative disease, muscular dysgenic lateral sclerosis, amyotrophic lateral sclerosis, Huntington's disease, cerebral infarct, or traumatic neurodegenerative disease, comprising administering a therapeutically effective amount of the compound of any one of Terms 1-45 or a pharmaceutically acceptable salt thereof to a patient in need thereof.
Term 78
A method for treating and/or preventing dry eye, comprising administering a therapeutically effective amount of the compound of any one of Terms 1-45 or a pharmaceutically acceptable salt thereof to a patient in need thereof.
Term 79 Use of the compound of any one of Terms 1-45 or a pharmaceutically acceptable salt thereof, in the preparation of a medicament for treating and/or preventing a disease associated with neurodegeneration or neurological disorder.
Term 80
Use of the compound of any one of Terms 1-45 or a pharmaceutically acceptable salt thereof, in the preparation of a medicament for treating and/or preventing a neurological disease associated with ischemic damage.
Term 81
The use of Term 80, wherein the neurological disease associated with ischemic damage is retinal neurological disorder caused by ischemia, or ischemic cerebrovascular disease.

Term 82
The use of Term 81, wherein the retinal neurological disorder is glaucoma, central retinal artery occlusion, central branch retinal artery occlusion, central retinal vein occlusion, central branch retinal vein occlusion, ischemic optic neuropathy, diabetic retinopathy, macular degeneration, or retinopathy of prematurity.
Term 83
The use of Term 81, wherein the ischemic cerebrovascular disease is cerebral emboli, transient cerebral ischemia, subclavian steal syndrome, Wallenberg's syndrome (lateral medullary syndrome), cerebral thrombosis, lacunar infarct, reversible ischemic neurological deficit, cerebral infarct, moyamoya disease (spontaneous occlusion of the circle of Willis), cerebral hypoxia, sinus thrombosis, or postoperative spinal cord ischemia.
Term 84
Use of the compound of any one of Terms 1-45 or a pharmaceutically acceptable salt thereof, in the preparation of a medicament for treating and/or preventing corneal disease.
Term 85
The use of Term 84, wherein the corneal disease is dry eye, keratitis, leukoma, corneal infection, corneal degeneration, corneal dystrophy, corneal stromal dystrophy, bullous keratopathy, keratoconus, corneal endothelial decompensation, corneal ulcer, nerve-paralytic keratopathy, diabetic keratopathy, chemical ocular injury, or corneal burn.
Term 86
The use of Term 85, wherein the corneal disease is dry eye, keratitis, bullous keratopathy, corneal ulcer, nerve-paralytic keratopathy, or diabetic keratopathy.
Term 87
The use of Term 85, wherein the corneal disease is dry eye.
Term 88
The use of any one of Terms 84-87, wherein the corneal disease is a disease associated with neurodegeneration or neurological disorder.
Term 89
Use of the compound of any one of Terms 1-45 or a pharmaceutically acceptable salt thereof, in the preparation of a medicament for treating and/or preventing a disease associated with degeneration and damage in central nerve and peripheral nerve.
Term 90
Use of the compound of any one of Terms 1-45 or a pharmaceutically acceptable salt thereof, in the preparation of a medicament for treating or preventing dysosmia, traumatic neurological disorder, cerebral-infarct neurological disorder, facial palsy, diabetic neurosis, glaucoma, retinitis pigmentosa, dry eye, Alzheimer's disease, Parkinson's disease, neurodegenerative disease, muscular dysgenic lateral sclerosis, amyotrophic lateral sclerosis, Huntington's disease, cerebral infarct, or traumatic neurodegenerative disease.
Term 91
Use of the compound of any one of Terms 1-45 or a pharmaceutically acceptable salt thereof, in the preparation of a medicament for treating and/or preventing dry eye.
Term 92
The compound of any one of Terms 1-45 or a pharmaceutically acceptable salt thereof, in use for treating and/or preventing a disease associated with neurodegeneration or neurological disorder.
Term 93
The compound of any one of Terms 1-45 or a pharmaceutically acceptable salt thereof, in use for treating and/or preventing a neurological disease associated with ischemic damage.
Term 94
The medicament of Term 93, wherein the neurological disease associated with ischemic damage is retinal neurological disorder caused by ischemia or ischemic cerebrovascular disease.
Term 95
The compound of Term 94 or a pharmaceutically acceptable salt thereof, wherein the retinal neurological disorder is glaucoma, central retinal artery occlusion, central branch retinal artery occlusion, central retinal vein occlusion, central branch retinal vein occlusion, ischemic optic neuropathy, diabetic retinopathy, macular degeneration, or retinopathy of prematurity.
Term 96
The compound of Term 94 or a pharmaceutically acceptable salt thereof, wherein the ischemic cerebrovascular disease is cerebral emboli, transient cerebral ischemia, subclavian steal syndrome, Wallenberg's syndrome (lateral medullary syndrome), cerebral thrombosis, lacunar infarct, reversible ischemic neurological deficit, cerebral infarct, moyamoya disease (spontaneous occlusion of the circle of Willis), cerebral hypoxia, sinus thrombosis, or postoperative spinal cord ischemia.
Term 97
The compound of any one of Terms 1-45 or a pharmaceutically acceptable salt thereof, in use for treating and/or preventing corneal disease.
Term 98
The compound of Term 97 or a pharmaceutically acceptable salt thereof, wherein the corneal disease is dry eye, keratitis, leukoma, corneal infection, corneal degeneration, corneal dystrophy, corneal stromal dystrophy, bullous keratopathy, keratoconus, corneal endothelial decompensation, corneal ulcer, nerve-paralytic keratopathy, diabetic keratopathy, chemical ocular injury, or corneal burn.
Term 99
The compound of Term 98 or a pharmaceutically acceptable salt thereof, wherein the corneal disease is dry eye, keratitis, bullous keratopathy, corneal ulcer, nerve-paralytic keratopathy, or diabetic keratopathy.
Term 100
The compound of Term 98 or a pharmaceutically acceptable salt thereof, wherein the corneal disease is dry eye.
Term 101
The compound of any one of Terms 97-100 or a pharmaceutically acceptable salt thereof, wherein the corneal disease is a disease associated with neurodegeneration or neurological disorder.
Term 102
The compound of any one of Terms 1-45 or a pharmaceutically acceptable salt thereof, in use for treating and/or preventing a disease associated with degeneration and damage in central nerve and peripheral nerve.
Term 103
The compound of any one of Terms 1-45 or a pharmaceutically acceptable salt thereof, in use for treating and/or preventing dysosmia, traumatic neurological disorder, cerebral-infarct neurological disorder, facial palsy, diabetic neurosis, glaucoma, retinitis pigmentosa, dry eye, Alzheimer's disease, Parkinson's disease, neurodegenerative disease, muscular dysgenic lateral sclerosis, amyotrophic lateral sclerosis, Huntington's disease, cerebral infarct, or traumatic neurodegenerative disease.

Term 104

The compound of any one of Terms 1-45 or a pharmaceutically acceptable salt thereof, in use for treating and/or preventing dry eye.

Effect of Invention

The present invention provides the compound of formula (1) or a pharmaceutically acceptable salt thereof. The compound or a pharmaceutically acceptable salt thereof has a semaphorin inhibitory activity and it is useful as a medicament for treating or preventing neuropathic disease, neurodegenerative disease, neurological disease associated with ischemic deficit, and corneal disease.

DESCRIPTION OF EMBODIMENTS

Figure 1:
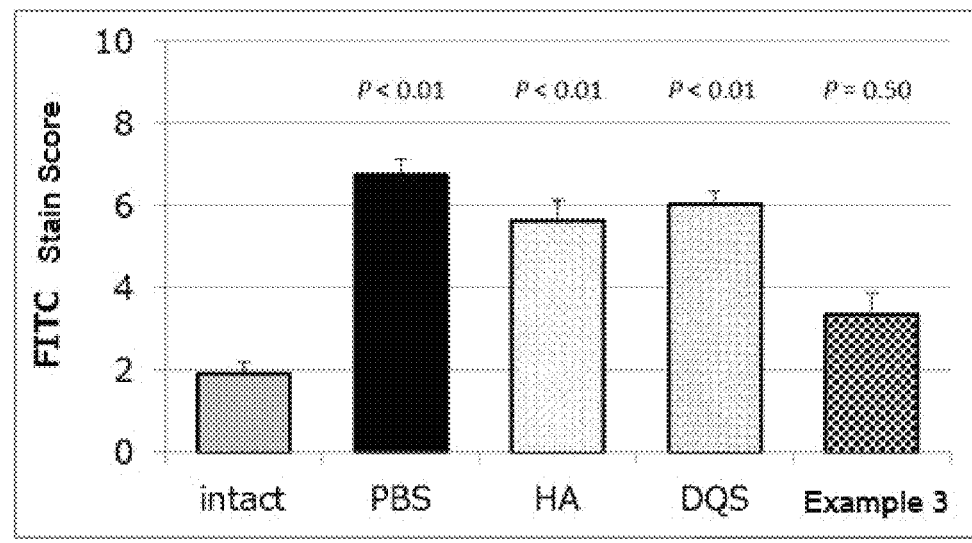
FIG. 1 shows results of the evaluation on the pharmacological action for corneal disorder, in which hyaluronic acid, diquafosol sodium, and the compound of Example 3 were administered to the dry eye-model rat in Test 3.
Figure 2:
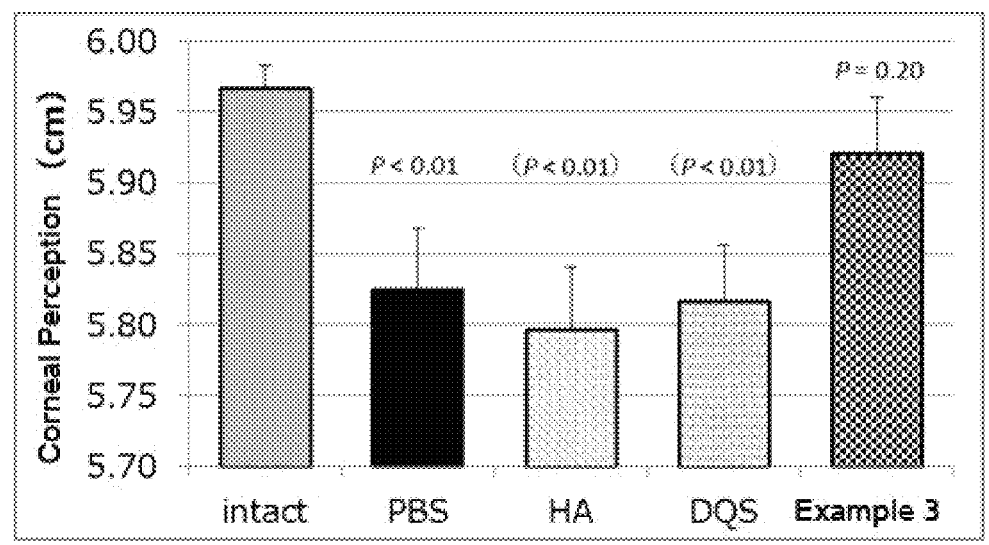
FIG. 2 shows results of the evaluation on the pharmacological action for dysfunction of corneal nerves, in which hyaluronic acid, diquafosol sodium, and the compound of Example 3 were administered to the dry eye-model rat in Test 4.
Figure 3:
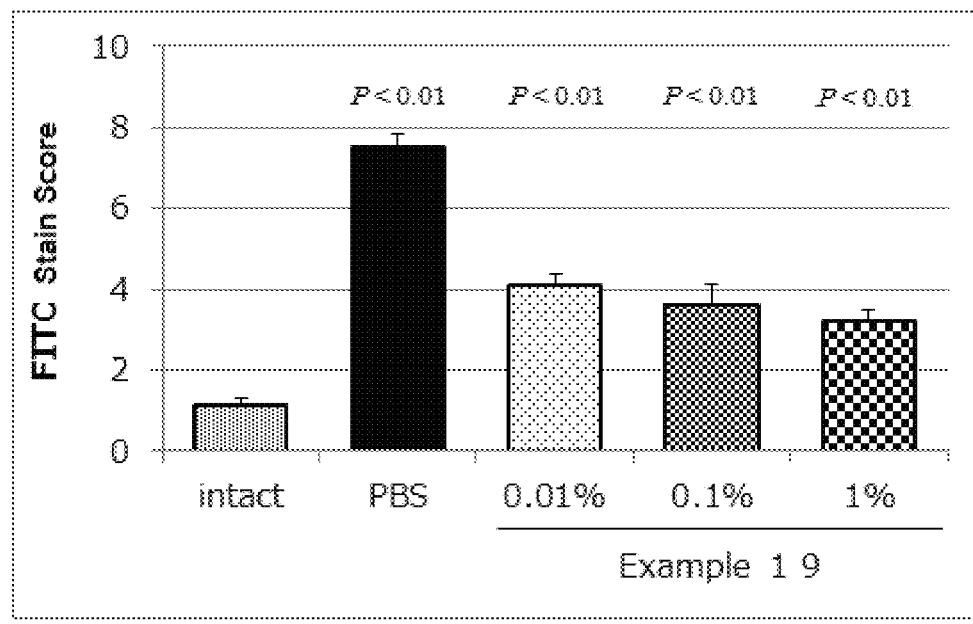
FIG. 3 shows results of the evaluation on the pharmacological action for corneal disorder, in which 0.01%, 0.1%, and 1% the ophthalmic solutions of the compound of Example 19 were administered to the dry eye-model rat in Test 5.

Each preferable embodiment in the present invention mentioned below may be combined with another preferable embodiment, or its correspondent example defined in the above Terms 1 to 93.

The "one or more" in one or more substituents, one or more alkyl groups, and the like which are used in defining the substituents in the present invention includes, for example, 1-7, 1-6, 1-5, 1-4, 1-3, and 1-2, which means that substituents may be used within the chemically-possible number. The "1—plural" also has the same meaning. When substituted with plural substituents, the substituents may be the same or a combination of any different substituents. In case of three or more substituents, the substituents may be all the same, partially the same, or all different.

The compound of the present invention may be in a form of hydrate and/or solvate, thus the compound of formula (1) or a pharmaceutically acceptable salt thereof encompasses such hydrate and/or solvate.

In addition, the compound of formula (1) in which any one or more $^1H$ atoms are replaced by $^2H(D)$ atoms (deuterium form) is within the scope of the present invention of formula (1).

There may exist a polymorphism in a crystal of the compound of formula (1) or a pharmaceutically acceptable salt thereof, and hence such crystal polymorphism is also within the scope of the present invention.

The "halogen atom" used herein means the atoms belonging to group 17 in the periodic table, including, for example, fluorine, chlorine, bromine and iodine. In addition, the "halo" in "haloalkyl group", "haloalkoxy (haloalkyloxy) group", and the like means fluoro, chloro, bromo, and iodo, and the above exemplified groups mean alkyl or alkoxy group which is substituted with one or more the same or different halogen atoms.

The "alkyl group" used herein means straight or branched chain saturated hydrocarbon group having 1 to 10 carbon atoms. The alkyl group preferably includes $C_{1-6}$ alkyl group, for example, methyl group, ethyl group, propyl group (1-propyl group) and isopropyl group (2-propyl group), butyl group (1-butyl group), sec-butyl group (2-butyl group), isobutyl group (2-methyl-1-propyl group), t-butyl group (2-methyl-2-propyl group), pentyl group (1-pentyl group), and hexyl group (1-hexyl group). The alkyl group more preferably includes $C_{1-3}$ alkyl group, for example, methyl group, ethyl group, propyl group (1-propyl group), and isopropyl group (2-propyl group). Even more preferably, the alkyl group is methyl group or ethyl group. The alkyl moiety in "haloalkyl group", "alkoxy (alkyloxy) group", "haloalkoxy (haloalkyloxy) group", "alkoxycarbonyl group", "alkylcarbonyl group", "alkylcarbonyloxy group", "alkylthio group", "alkylsulfonyl group", and the like used herein is as defined in the above "alkyl group".

The "alkenyl group" used herein means straight or branched chain unsaturated hydrocarbon group having 2 to 10 carbon atoms and at least one double bond. The alkenyl group preferably includes $C_{2-6}$ alkenyl group, for example, vinyl group, 1-propenyl group, 2-propenyl group, 1-methylvinyl group, 1-butenyl group, 1-ethylvinyl group, 1-methyl-2-propenyl group, 2-butenyl group, 3-butenyl group, 2-methyl-1-propenyl group, 2-methyl-2-propenyl group, 1-pentenyl group, and 1-hexenyl group. The alkenyl group more preferably includes $C_{2-4}$ alkenyl group, for example, vinyl group, 1-propenyl group, 2-propenyl group, and 1-methylvinyl group. Even more preferably, the alkenyl group is vinyl group, 1-propenyl group, 2-propenyl group, or 1-methylvinyl group. The number of the double bonds in the alkenyl group may be one or two.

The "alkynyl group" used herein means straight or branched chain unsaturated hydrocarbon group having 2 to 10 carbon atoms and at least one triple bond. The alkynyl group preferably includes $C_{2-6}$ alkynyl group, for example, ethynyl group, 1-propynyl group, 2-propynyl group, 1-butynyl group, 1-methyl-2-propynyl group, 3-butynyl group, 1-pentynyl group, and 1-hexynyl group. The alkynyl group more preferably includes "$C_{2-4}$ alkynyl group", for example, ethynyl group, 1-propynyl group, and 2-propynyl group. Even more preferably, the alkynyl group is ethynyl group, 1-propynyl group, or 2-propynyl group.

The "cycloalkyl group" used herein means mono-, bi-, or tri-cyclic saturated hydrocarbon having 3 to 14 carbon atoms. The cycloalkyl group preferably includes 3- to 8-membered cycloalkyl group which may be mono- or bi-cyclic group, for example, cyclopropyl group, cyclobutyl group, cyclopentyl group, cyclohexyl group, cycloheptyl group, and cyclooctyl group. The cycloalkyl group more preferably includes mono-cyclic 3- to 6-membered cycloalkyl group, for example, cyclopropyl group, cyclobutyl group, cyclopentyl group, and cyclohexyl group. Even more preferably, the cycloalkyl group is cyclopropyl group or cyclobutyl group.

The "cycloalkenyl group" used herein means mono-, bi-, or tri-cyclic unsaturated hydrocarbon group having 4 to 14 carbon atoms and at least one double bond. The position of the double bond in the ring is not limited. The cycloalkenyl group preferably includes 4- to 8-membered cycloalkenyl group which may be mono- or bi-cyclic group, for example, cyclobutenyl group, cyclopentenyl group, cyclohexenyl group, cycloheptenyl group, and cyclooctenyl group. The cycloalkenyl group more preferably includes 4- to 6-membered cycloalkenyl group, for example, cyclobutenyl group, and cyclopentenyl group.

The "saturated aliphatic heterocyclyl group" used herein means mono-, bi-, or tri-cyclic saturated aliphatic heterocyclyl group having 1 to 3 heteroatoms selected independently from the group consisting of nitrogen atom, oxygen atom, and sulfur atom and 2-12 carbon atoms. Each maximum number of oxygen atom and sulfur atom in the saturated aliphatic heterocyclyl group is two, and the position of the heteroatoms in the ring is not limited as long as it is chemically stable. The saturated aliphatic heterocyclyl group preferably includes 4- to 8-membered saturated aliphatic heterocyclyl group which may be mono- or bi-cyclic group. The saturated aliphatic heterocyclyl group more preferably includes mono-cyclic 4- to 6-membered saturated aliphatic heterocyclyl group, for example, azetidinyl group, pyrrolidinyl group, piperidyl group, piperidino group, piperazinyl group, tetrahydrofuryl group, tetrahydrothienyl group, tetrahydropyranyl group, morpholinyl group, morpholino group, thiomorpholinyl group, and 1,4-dioxanyl group.

The "unsaturated aliphatic heterocyclyl group" used herein means mono-, bi-, or tri-cyclic unsaturated aliphatic heterocyclyl group having 1 to 3 heteroatoms selected independently from the group consisting of nitrogen atom, oxygen atom, and sulfur atom, 1-3 double bonds, and 3-12 carbon atoms, which does not include aromatic heterocyclyl groups, but includes a fused ring group of aliphatic heterocycle and aromatic ring. Each maximum number of oxygen atom and sulfur atom in the unsaturated aliphatic heterocyclyl group is two, and the position of the heteroatoms and the double bonds in the ring is not limited as long as it is chemically stable. The unsaturated aliphatic heterocyclyl group preferably includes 5- to 10-membered unsaturated aliphatic heterocyclyl group which may be mono- or bi-cyclic group, for example, 2-pyrrolinyl group, 2-imidazolinyl group, and tetrahydroisoquinolyl group. The unsaturated aliphatic heterocyclyl group more preferably includes mono-cyclic 5- to 6-membered unsaturated aliphatic heterocyclyl group, for example, 2-pyrrolinyl group, and 2-imidazolinyl group.

The "aryl group" used herein means mono-, bi-, or tri-cyclic aromatic hydrocarbon group having 6-14 carbon atoms. The aryl group preferably includes 6- to 10-membered aryl group which may be mono- or bi-cyclic group, for example, phenyl group, 1-naphthyl group, and 2-naphthyl group.

The aryl moiety in "aryloxy group", "arylcarbonyl group", "arylsulfonyl group", and the like used herein is as defined in the above "aryl group".

The "heteroaryl group" used herein means mono-, bi-, or tri-cyclic aromatic heterocyclyl group having 1 to 4 heteroatoms selected independently from the group consisting of nitrogen atom, oxygen atom, and sulfur atom and 1-14 carbon atoms. Each maximum number of oxygen atom and sulfur atom in the heteroaryl group is two, and the position of the heteroatoms in the ring is not limited as long as it is chemically stable. The heteroaryl group preferably includes 5- to 10-membered heteroaryl group which includes mono-cyclic 5- to 7-membered heteroaryl group and bi-cyclic 8- to 10-membered heteroaryl group, for example, furyl group, thienyl group, pyrrolyl group, oxazolyl group, isoxazolyl group, thiazolyl group, isothiazolyl group, imidazolyl group, pyrazolyl group, furazanyl group, oxadiazolyl group, triazolyl group, pyridyl group, pyrimidinyl group, pyrazinyl group, indolyl group, quinolyl group, isoquinolyl group, quinazolinyl group, and imidazo[2,1-b][1,3]thiazolyl group.

The heteroaryl moiety in "heteroaryloxy group", "heteroarylcarbonyl group", "heteroarylsulfonyl group", and the like used herein is as defined in the above "heteroaryl group"

The substituent of "optionally-substituted alkyl group", "optionally-substituted alkenyl group", and "optionally-substituted alkynyl group" in the present invention includes one or more selected independently from the following substituents of (ai)-(avi):

(ai) halogen atom, hydroxy group, carboxyl group, cyano group, (aii) optionally-substituted amino group, optionally-substituted carbamoyl group, optionally-substituted sulfamoyl group, (aiii) optionally-substituted alkoxy group, wherein the substituent(s) of the optionally-substituted alkoxy group is one or more substituents selected independently from the group consisting of halogen atom, hydroxy group, carboxyl group, amino group which may be substituted with one or two the same or different alkyl, carbamoyl group which may be substituted with one or two the same or different alkyl, haloalkoxy group, alkoxycarbonyl group, optionally-substituted alkoxy group, optionally-substituted aryl group, and optionally-substituted heteroaryl group, wherein the substituent(s) of the optionally-substituted alkoxy group may be HO—$(CH_2CH_2O)_n$— (wherein n is 1-5), HOOC—$(CH_2CH_2O)_n$— (wherein n is 1-5), $R^aR^bN$—$(CH_2CH_2O)_n$— (wherein n is 1-5), $R^aR^bNOC$—$(CH_2CH_2O)_n$— (wherein n is 1-5), $R^c$—$(CH_2CH_2O)_n$— (wherein n is 1-5), or $R^cCO$—$(CH_2CH_2O)_n$— (wherein n is 1-5), wherein $R^a$ and $R^b$ are independently hydrogen atom or $C_{1-3}$ alkyl group, and $R^c$ is amino acid group (which binds to C(O) at its N terminus) or peptide (which binds to C(O) at its N terminus), wherein the substituent of the optionally-substituted aryl group and the optionally-substituted heteroaryl group is independently one or more substituents selected independently from the group consisting of halogen atom, hydroxy group, carboxyl group, alkyl group, haloalkyl group, alkoxy group, haloalkoxy group, alkoxycarbonyl group, nitro group, cyano group, and carbamoyl group, (aiv) optionally-substituted alkylcarbonyl group, optionally-substituted alkylcarbonyloxy group, optionally-substituted alkoxycarbonyl group, optionally-substituted alkylthio group, optionally-substituted alkylsulfonyl group, wherein the substituent(s) of each optionally-substituted group is independently one or more substituents selected independently from the group consisting of halogen atom, hydroxy group, carboxyl group, amino group which may be substituted with one or two the same or different alkyl, carbamoyl group which may be substituted with one or two the same or different alkyl, alkoxy group, haloalkoxy group, alkoxycarbonyl group, optionally-substituted aryl group, and optionally-substituted heteroaryl group, and wherein the substituent(s) of the optionally-substituted aryl group and the optionally-substituted heteroaryl group is independently one or more substituents selected independently from the group consisting of halogen atom, hydroxy group, carboxyl group, alkyl group, haloalkyl group, alkoxy group, haloalkoxy group, alkoxycarbonyl group, nitro group, cyano group, and carbamoyl group, (av) optionally-substituted cycloalkyl group, optionally-substituted cycloalkenyl group, optionally-substituted saturated aliphatic heterocyclyl group, optionally-substituted unsaturated aliphatic heterocyclyl group, wherein the substituent(s) of each optionally-substituted group is independently one or more substituents selected independently from the group consisting of halogen atom, hydroxy group, carboxyl group, oxo group, thioxo group, amino group which may be substituted with one or two the same or different alkyl, carbamoyl group which may be substituted with one or two the same or different alkyl, alkoxy group, haloalkoxy group, optionally-substituted alkoxycarbonyl group, optionally-substituted alkylcarbonyl group, optionally-substituted alkylsulfonyl group, optionally-substituted alkyl group, optionally-substituted aryl group, and optionally-substituted heteroaryl group, wherein the substituent(s) of the optionally-substituted alkoxycarbonyl group, the optionally-substituted alkylcarbonyl group, the optionally-substituted alkylsulfonyl group, and the optionally-substituted alkyl group is independently one or more substituents selected independently from the group consisting of halogen atom, hydroxy group, carboxyl group, alkoxy group, haloalkoxy group, and carbamoyl group, and wherein the substituent(s) of the optionally-substituted aryl group and the optionally-substituted heteroaryl group is independently one or more substituents selected independently from the group consisting of halogen atom, hydroxy group, carboxyl group, alkyl group, haloalkyl group, alkoxy group, haloalkoxy group, alkoxycarbonyl group, nitro group, cyano group, and carbamoyl group, and (avi) optionally-substituted aryl group, optionally-substituted heteroaryl group, optionally-substituted aryloxy group, optionally-substituted heteroaryloxy group, optionally-substituted arylcarbonyl group, optionally-substituted heteroarylcarbonyl group, optionally-substituted arylsulfonyl group, optionally-substituted heteroarylsulfonyl group, wherein the substituent(s) of each optionally-substituted group is independently one or more substituents selected independently from the group consisting of halogen atom, hydroxy group, carboxyl group, optionally-substituted amino group, optionally-substituted carbamoyl group, optionally-substituted sulfamoyl group, alkoxy group, haloalkoxy group, alkoxycarbonyl group, optionally-substituted alkyl group, optionally-substituted aryl group, and optionally-substituted heteroaryl group, wherein the substituent(s) of the optionally-substituted alkyl group is one or more substituents selected independently from the group consisting of halogen atom, hydroxy group, carboxyl group, alkoxy group, haloalkoxy group, amino group which may be substituted with one or two the same or different alkyl, carbamoyl group which may be substituted with one or two the same or different alkyl, amino acid group (which binds to the alkyl group at its N terminus), peptide (which binds to the alkyl group at its N terminus), and $R^dC(O)-$ wherein $R^d$ is amino acid group or peptide (which binds to the carbonyl group at its N terminus), and wherein the substituent(s) of the optionally-substituted aryl group and the optionally-substituted heteroaryl group is independently one or more substituents selected independently from the group consisting of halogen atom, hydroxy group, carboxyl group, alkyl group, haloalkyl group, alkoxy group, haloalkoxy group, alkoxycarbonyl group, nitro group, cyano group, and carbamoyl group.

The substituent of "optionally-substituted cycloalkyl group", "optionally-substituted cycloalkenyl group", "optionally-substituted saturated aliphatic heterocyclyl group", and "optionally-substituted unsaturated aliphatic heterocyclyl group" in the present invention includes one or more selected independently from the following substituents of (bi)-(bv):

(bi) halogen atom, hydroxy group, carboxyl group, cyano group, oxo group, thioxo group, amidino group optionally-substituted with one or two the same or different alkoxycarbonyl group, (bii) optionally-substituted amino group, optionally-substituted carbamoyl group, optionally-substituted sulfamoyl group, (biii) optionally-substituted alkyl group, optionally-substituted alkoxy group, optionally-substituted alkylcarbonyl group, optionally-substituted alkylcarbonyloxy group, optionally-substituted alkoxycarbonyl group, optionally-substituted alkylthio group, optionally-substituted alkylsulfonyl group, wherein the substituent(s) of each optionally-substituted group is independently one or more substituents selected independently from the group consisting of halogen atom, hydroxy group, carboxyl group, carbamoyl group which may be substituted with one or two the same or different alkyl, alkoxy group which may be substituted with alkoxy group and/or carbamoyl group, haloalkoxy group, alkylthio group, alkoxycarbonyl group, optionally-substituted aryloxy group, optionally-substituted heteroaryloxy group, optionally-substituted aryl group, optionally-substituted heteroaryl group, and optionally-substituted amino group, wherein the substituent(s) of the optionally-substituted aryloxy group, the optionally-substituted heteroaryloxy group, the optionally-substituted aryl group, and the optionally-substituted heteroaryl group is independently one or more substituents selected independently from the group consisting of halogen atom, hydroxy group, carboxyl group, alkyl group, haloalkyl group, alkoxy group, haloalkoxy group, alkoxycarbonyl group, nitro group, cyano group, and carbamoyl group, and wherein the substituent(s) of the optionally-substituted amino group is one or two substituents selected independently from the group consisting of optionally-substituted alkyl group, optionally-substituted alkylcarbonyl group, optionally-substituted alkylsulfonyl group, and carbamoyl group which may be substituted with one or two the same or different optionally-substituted alkyl group, wherein the substituent(s) of the optionally-substituted alkyl group, the optionally-substituted alkylcarbonyl group, the optionally-substituted alkylsulfonyl group, and the optionally-substituted alkyl group in the carbamoyl group is independently one or more substituents selected independently from the group consisting of halogen atom, hydroxy group, carboxyl group, alkoxy group, haloalkoxy group, and carbamoyl group, and (biv) optionally-substituted cycloalkyl group, optionally-substituted cycloalkenyl group, optionally-substituted saturated aliphatic heterocyclyl group, optionally-substituted unsaturated aliphatic heterocyclyl group, wherein the substituent(s) of each optionally-substituted group is independently one or more substituents selected independently from the group consisting of halogen atom, hydroxy group, carboxyl group, oxo group, thioxo group, amino group which may be substituted with one or two the same or different alkyl, alkoxy group, haloalkoxy group, alkoxycarbonyl group, optionally-substituted alkyl group, optionally-substituted aryl group, and optionally-substituted heteroaryl group, wherein the substituent(s) of the optionally-substituted alkyl group is one or more substituents selected independently from the group consisting of halogen atom, hydroxy group, carboxyl group, alkoxy group, and haloalkoxy group, and wherein the substituent(s) of the optionally-substituted aryl group and the optionally-substituted heteroaryl group is independently one or more substituents selected independently from the group consisting of halogen atom, hydroxy group, carboxyl group, alkyl group, haloalkyl group, alkoxy group, haloalkoxy group, alkoxycarbonyl group, nitro group, cyano group, and carbamoyl group, (bv) optionally-substituted aryl group, optionally-substituted heteroaryl group, optionally-substituted aryloxy group, optionally-substituted heteroaryloxy group, optionally-substituted arylcarbonyl group, optionally-substituted heteroarylcarbonyl group, optionally-substituted arylsulfonyl group, optionally-substituted heteroarylsulfonyl group, wherein the substituent(s) of each optionally-substituted group is independently one or more substituents selected independently from the group consisting of halogen atom, hydroxy group, carboxyl group, cyano group, optionally-substituted amino group, optionally-substituted carbamoyl group, optionally-substituted sulfamoyl group, alkoxy group, haloalkoxy group, alkoxycarbonyl group, optionally-substituted alkyl group, optionally-substituted aryl group, and optionally-substituted heteroaryl group, wherein the substituent(s) of the optionally-substituted alkyl group is one or more substituents selected independently from the group consisting of halogen atom, hydroxy group, carboxyl group, alkoxy group, and haloalkoxy group, and wherein the substituent(s) of the optionally-substituted aryl group and the optionally-substituted heteroaryl group is independently one or more substituents selected independently from the group consisting of halogen atom, hydroxy group, carboxyl group, alkyl group, haloalkyl group, alkoxy group, haloalkoxy group, alkoxycarbonyl group, nitro group, cyano group, and carbamoyl group.

The substituent of "optionally-substituted aryl group" and "optionally-substituted heteroaryl group" in the present invention includes one or more selected independently from the following substituents of (ci)-(cv):

(ci) halogen atom, hydroxy group, carboxyl group, cyano group, nitro group, methylenedioxy group, ethylenedioxy group, (cii) optionally-substituted amino group, optionally-substituted carbamoyl group, optionally-substituted sulfamoyl group, (ciii) optionally-substituted alkyl group, optionally-substituted alkenyl group, optionally-substituted alkynyl group, optionally-substituted alkoxy group, optionally-substituted alkylcarbonyl group, optionally-substituted alkylcarbonyloxy group, optionally-substituted alkoxycarbonyl group, optionally-substituted alkylthio group, optionally-substituted alkylsulfonyl group, wherein the substituent(s) of each optionally-substituted group is independently one or more substituents selected independently from the group consisting of halogen atom, hydroxy group, carboxyl group, amino group which may be substituted with one or two the same or different alkyl, optionally-substituted alkoxy group, haloalkoxy group, alkoxycarbonyl group, optionally-substituted aryl group, and optionally-substituted heteroaryl group, wherein the substituent(s) of the optionally-substituted alkoxy group, the optionally-substituted aryl group, and the optionally-substituted heteroaryl group is independently one or more substituents selected independently from the group consisting of halogen atom, hydroxy group, carboxyl group, alkyl group, haloalkyl group, alkoxy group, haloalkoxy group, alkoxycarbonyl group, nitro group, cyano group, and carbamoyl group, (civ) optionally-substituted cycloalkyl group, optionally-substituted cycloalkenyl group, optionally-substituted saturated aliphatic heterocyclyl group, optionally-substituted unsaturated aliphatic heterocyclyl group, wherein the substituent(s) of each optionally-substituted group is independently one or more substituents selected independently from the group consisting of halogen atom, hydroxy group, carboxyl group, oxo group, thioxo group, amino group which may be substituted with one or two the same or different alkyl, alkoxy group, haloalkoxy group, alkoxycarbonyl group, optionally-substituted alkyl group, optionally-substituted aryl group, and optionally-substituted heteroaryl group, wherein the substituent(s) of the optionally-substituted alkyl group is one or more substituents selected independently from the group consisting of halogen atom, hydroxy group, carboxyl group, alkoxy group, and haloalkoxy group, and wherein the substituent(s) of the optionally-substituted aryl group and the optionally-substituted heteroaryl group is independently one or more substituents selected independently from the group consisting of halogen atom, hydroxy group, carboxyl group, alkyl group, haloalkyl group, alkoxy group, haloalkoxy group, alkoxycarbonyl group, nitro group, cyano group, and carbamoyl group, and (cv) optionally-substituted aryl group, optionally-substituted heteroaryl group, optionally-substituted aryloxy group, optionally-substituted heteroaryloxy group, optionally-substituted arylcarbonyl group, optionally-substituted heteroarylcarbonyl group, optionally-substituted arylsulfonyl group, optionally-substituted heteroarylsulfonyl group, wherein the substituent(s) of each optionally-substituted group is independently one or more substituents selected independently from the group consisting of halogen atom, hydroxy group, carboxyl group, optionally-substituted amino group, optionally-substituted carbamoyl group, optionally-substituted sulfamoyl group, alkoxy group, haloalkoxy group, alkoxycarbonyl group, optionally-substituted alkyl group, optionally-substituted aryl group, and optionally-substituted heteroaryl group, wherein the substituent(s) of the optionally-substituted alkyl group is one or more substituents selected independently from the group consisting of halogen atom, hydroxy group, carboxyl group, alkoxy group, and haloalkoxy group, and wherein the substituent(s) of the optionally-substituted aryl group and the optionally-substituted heteroaryl group is independently one or more substituents selected independently from the group consisting of halogen atom, hydroxy group, carboxyl group, alkyl group, haloalkyl group, alkoxy group, haloalkoxy group, alkoxycarbonyl group, nitro group, cyano group, and carbamoyl group.

The substituent of "optionally-substituted amino group" in the present invention includes one or two selected independently from the following substituents of (di)-(diii):

(di) optionally-substituted alkyl group, optionally-substituted alkenyl group, optionally-substituted alkynyl group, optionally-substituted alkylcarbonyl group, optionally-substituted alkylsulfonyl group, optionally-substituted alkoxycarbonyl group, wherein the substituent(s) of each optionally-substituted group is independently one or more substituents selected independently from the group consisting of halogen atom, hydroxy group, carboxyl group, amino group which may be substituted with one or two the same or different alkyl, carbamoyl group, alkoxy group, haloalkoxy group, alkoxycarbonyl group, saturated aliphatic heterocyclyl group, unsaturated aliphatic heterocyclyl group, optionally-substituted aryl group, and optionally-substituted heteroaryl group, wherein the substituent(s) of the optionally-substituted aryl group and the optionally-substituted heteroaryl group is independently one or more substituents selected independently from the group consisting of halogen atom, hydroxy group, carboxyl group, alkyl group, haloalkyl group, alkoxy group, haloalkoxy group, alkoxycarbonyl group, nitro group, cyano group, and carbamoyl group, (dii) optionally-substituted cycloalkyl group, optionally-substituted cycloalkenyl group, optionally-substituted saturated aliphatic heterocyclyl group, optionally-substituted unsaturated aliphatic heterocyclyl group, wherein the substituent(s) of each optionally-substituted group is independently one or more substituents selected independently from the group consisting of halogen atom, hydroxy group, carboxyl group, oxo group, thioxo group, amino group which may be substituted with one or two the same or different alkyl, alkoxy group, haloalkoxy group, alkoxycarbonyl group, optionally-substituted alkyl group, optionally-substituted aryl group, and optionally-substituted heteroaryl group, wherein the substituent(s) of the optionally-substituted alkyl group is one or more substituents selected independently from the group consisting of halogen atom, hydroxy group, carboxyl group, alkoxy group, and haloalkoxy group, and wherein the substituent(s) of the optionally-substituted aryl group and the optionally-substituted heteroaryl group is independently one or more substituents selected independently from the group consisting of halogen atom, hydroxy group, carboxyl group, alkyl group, haloalkyl group, alkoxy group, haloalkoxy group, alkoxycarbonyl group, nitro group, cyano group, and carbamoyl group, and (diii) optionally-substituted aryl group, optionally-substituted heteroaryl group, optionally-substituted arylcarbonyl group, optionally-substituted heteroarylcarbonyl group, optionally-substituted arylsulfonyl group, optionally-substituted heteroarylsulfonyl group, wherein the substituent(s) of each optionally-substituted group is independently one or more substituents selected independently from the group consisting of halogen atom, hydroxy group, carboxyl group, amino group which may be substituted with one or two the same or different alkyl, carbamoyl group which may be substituted with one or two the same or different alkyl, sulfamoyl group which may be substituted with one or two the same or different alkyl, alkoxy group, haloalkoxy group, alkoxycarbonyl group, optionally-substituted alkyl group, optionally-substituted aryl group, and optionally-substituted heteroaryl group, wherein the substituent(s) of the optionally-substituted alkyl group is one or more substituents selected independently from the group consisting of halogen atom, hydroxy group, carboxyl group, alkoxy group, and haloalkoxy group, and wherein the substituent(s) of the optionally-substituted aryl group and the optionally-substituted heteroaryl group is independently one or more substituents selected independently from the group consisting of halogen atom, hydroxy group, carboxyl group, alkyl group, haloalkyl group, alkoxy group, haloalkoxy group, alkoxycarbonyl group, nitro group, cyano group, and carbamoyl group.

The substituent of "optionally-substituted carbamoyl group" in the present invention includes one or two selected independently from the following substituents of (ei)-(eiv):

(ei) optionally-substituted alkyl group, optionally-substituted haloalkyl group, optionally-substituted alkenyl group, optionally-substituted alkynyl group, optionally-substituted alkylcarbonyl group, optionally-substituted alkylsulfonyl group, optionally-substituted alkoxycarbonyl group, wherein the substituent(s) of each optionally-substituted group is independently one or more substituents selected independently from the group consisting of halogen atom, hydroxy group, amino group which may be substituted with one or two the same or different alkyl, carbamoyl group, alkoxy group, haloalkoxy group, alkoxycarbonyl group, saturated aliphatic heterocyclyl group, unsaturated aliphatic heterocyclyl group, optionally-substituted aryl group, and optionally-substituted heteroaryl group, wherein the substituent(s) of the optionally-substituted aryl group and the optionally-substituted heteroaryl group is independently one or more substituents selected independently from the group consisting of halogen atom, hydroxy group, carboxyl group, alkyl group, haloalkyl group, alkoxy group, haloalkoxy group, alkoxycarbonyl group, nitro group, cyano group, and carbamoyl group, (eii) optionally-substituted cycloalkyl group, optionally-substituted cycloalkenyl group, optionally-substituted saturated aliphatic heterocyclyl group, optionally-substituted unsaturated aliphatic heterocyclyl group, wherein the substituent(s) of each optionally-substituted group is independently one or more substituents selected independently from the group consisting of halogen atom, hydroxy group, carboxyl group, oxo group, thioxo group, amino group which may be substituted with one or two the same or different alkyl, alkoxy group, haloalkoxy group, alkoxycarbonyl group, optionally-substituted alkyl group, optionally-substituted aryl group, and optionally-substituted heteroaryl group, wherein the substituent(s) of the optionally-substituted alkyl group is one or more substituents selected independently from the group consisting of halogen atom, hydroxy group, carboxyl group, alkoxy group, and haloalkoxy group, and wherein the substituent(s) of the optionally-substituted aryl group and the optionally-substituted heteroaryl group is independently one or more substituents selected independently from the group consisting of halogen atom, hydroxy group, carboxyl group, alkyl group, haloalkyl group, alkoxy group, haloalkoxy group, alkoxycarbonyl group, nitro group, cyano group, and carbamoyl group, (eiii) optionally-substituted aryl group, optionally-substituted heteroaryl group, optionally-substituted arylcarbonyl group, optionally-substituted heteroarylcarbonyl group, optionally-substituted arylsulfonyl group, optionally-substituted heteroarylsulfonyl group, wherein the substituent(s) of each optionally-substituted group is independently one or more substituents selected independently from the group consisting of halogen atom, hydroxy group, carboxyl group, amino group which may be substituted with one or two the same or different alkyl, carbamoyl group which may be substituted with one or two the same or different alkyl, sulfamoyl group which may be substituted with one or two the same or different alkyl, alkoxy group, haloalkoxy group, alkoxycarbonyl group, optionally-substituted alkyl group, optionally-substituted aryl group, and optionally-substituted heteroaryl group, wherein the substituent(s) of the optionally-substituted alkyl group is one or more substituents selected independently from the group consisting of halogen atom, hydroxy group, carboxyl group, alkoxy group, and haloalkoxy group, and wherein the substituent(s) of the optionally-substituted aryl group and the optionally-substituted heteroaryl group is independently one or more substituents selected independently from the group consisting of halogen atom, hydroxy group, carboxyl group, alkyl group, haloalkyl group, alkoxy group, haloalkoxy group, alkoxycarbonyl group, nitro group, cyano group, and carbamoyl group, and (eiv) C(O)Re wherein Re is amino acid group or peptide (which binds to C(O) at its N terminus), including carbamoyl group.

The substituent of "optionally-substituted sulfamoyl group" in the present invention includes one or more selected independently from the following substituents of (fi)-(fiii):

(fi) optionally-substituted alkyl group, optionally-substituted haloalkyl group, optionally-substituted alkenyl group, optionally-substituted alkynyl group, optionally-substituted alkylcarbonyl group, optionally-substituted alkylsulfonyl group, optionally-substituted alkoxycarbonyl group, wherein the substituent(s) of each optionally-substituted group is independently one or more substituents selected independently from the group consisting of halogen atom, hydroxy group, amino group which may be substituted with one or two the same or different alkyl, carbamoyl group, alkoxy group, haloalkoxy group, alkoxycarbonyl group, saturated aliphatic heterocyclyl group, unsaturated aliphatic heterocyclyl group, optionally-substituted aryl group, and optionally-substituted heteroaryl group, wherein the substituent(s) of the optionally-substituted aryl group and the optionally-substituted heteroaryl group is independently one or more substituents selected independently from the group consisting of halogen atom, hydroxy group, carboxyl group, alkyl group, haloalkyl group, alkoxy group, haloalkoxy group, alkoxycarbonyl group, nitro group, cyano group, and carbamoyl group, (fii) optionally-substituted cycloalkyl group, optionally-substituted cycloalkenyl group, optionally-substituted saturated aliphatic heterocyclyl group, optionally-substituted unsaturated aliphatic heterocyclyl group, wherein the substituent(s) of each optionally-substituted group is independently one or more substituents selected independently from the group consisting of halogen atom, hydroxy group, carboxyl group, oxo group, thioxo group, amino group which may be substituted with one or two the same or different alkyl, alkoxy group, haloalkoxy group, alkoxycarbonyl group, optionally-substituted alkyl group, optionally-substituted aryl group, and optionally-substituted heteroaryl group, wherein the substituent(s) of the optionally-substituted alkyl group is one or more substituents selected independently from the group consisting of halogen atom, hydroxy group, carboxyl group, alkoxy group, and haloalkoxy group, and wherein the substituent(s) of the optionally-substituted aryl group and the optionally-substituted heteroaryl group is independently one or more substituents selected independently from the group consisting of halogen atom, hydroxy group, carboxyl group, alkyl group, haloalkyl group, alkoxy group, haloalkoxy group, alkoxycarbonyl group, nitro group, cyano group, and carbamoyl group, and (fiii) optionally-substituted aryl group, optionally-substituted heteroaryl group, optionally-substituted arylcarbonyl group, optionally-substituted heteroarylcarbonyl group, optionally-substituted arylsulfonyl group, optionally-substituted heteroarylsulfonyl group, wherein the substituent(s) of each optionally-substituted group is independently one or more substituents selected independently from the group consisting of halogen atom, hydroxy group, carboxyl group, amino group which may be substituted with one or two the same or different alkyl, carbamoyl group which may be substituted with one or two the same or different alkyl, sulfamoyl group which may be substituted with one or two the same or different alkyl, alkoxy group, haloalkoxy group, alkoxycarbonyl group, optionally-substituted alkyl group, optionally-substituted aryl group, and optionally-substituted heteroaryl group, wherein the substituent(s) of the optionally-substituted alkyl group is one or more substituents selected independently from the group consisting of halogen atom, hydroxy group, carboxyl group, alkoxy group, and haloalkoxy group, and wherein the substituent(s) of the optionally-substituted aryl group and the optionally-substituted heteroaryl group is independently one or more substituents selected independently from the group consisting of halogen atom, hydroxy group, carboxyl group, alkyl group, haloalkyl group, alkoxy group, haloalkoxy group, alkoxycarbonyl group, nitro group, cyano group, and carbamoyl group.

In addition, two substituents in "optionally-substituted amino group", "optionally-substituted carbamoyl group", or "optionally-substituted sulfamoyl group" may be combined together with the nitrogen atom to which they are attached to form a 5- to 10-membered saturated or unsaturated nitrogen-containing aliphatic heterocycle. Said nitrogen-containing aliphatic heterocycle includes pyrrolidine, piperidine, azepane, azocane, piperazine, morpholine, thiomorpholine, and tetrahydroisoquinoline. And, said nitrogen-containing aliphatic heterocycle may be substituted with one or more substituents selected independently from the group consisting of halogen, hydroxy group, carboxyl group, optionally-substituted alkyl group, haloalkyl group, alkoxy group, and haloalkoxy group, wherein the substituent(s) of the optionally-substituted alkyl group include halogen atom, hydroxy group, carboxyl group, alkoxy group, haloalkoxy group, and carbamoyl group.

The "amino acid group" used herein means an amino acid in which the hydrogen atom in its N terminus is desorbed and the nitrogen in its dehydrogened N terminus is attached to a carbon atom of another molecule.

The "amino acid" used herein should be broadly construed, and may be natural or unnatural ones. The natural amino acid used herein includes, for example, the amino acids mentioned below, and the unnatural amino acid used herein includes, for example, besides the amino acids mentioned below, an amino acid whose main chain structure is different from those of natural amino acids such as α,α-disubstituted amino acid (α-methylalanine and the like), N-alkyl-α-amino acid, D-amino acid, β-amino acid, and α-hydroxylic acid; an amino acid whose side chain structure is different from those of natural amino acids such as norleucine and homohistidine; and an amino acid which has an extra methylene at the side chain such as "homo" amino acid, homophenylalanine, and homohistidine.

The "peptide" used herein is a polymer composed of plural amino acids. The number of amino acids is not limited, but includes, for example, 2-50, 2-30, 2-10, 2-5, and 2-3 amino acids. The formation of the polymer may be linear or branch chain form, or cyclic form. Each "amino acid" which composes the peptide may be natural or unnatural one, which should be broadly construed.

The specific amino acid residues of natural or unnatural amino acids of the present invention are shown below, but the unnatural amino acids are not limited thereto.

Ala or A: alanine residue
Arg or R: arginine residue
Asn or N: asparagine residue
Asp or D: aspartate residue
Cys or C: cysteine residue
Gln or Q: glutamine residue
Glu or E: glutamate residue
Gly or G: glycine residue
His or H: histidine residue
Ile or I: isoleucine residue
Leu or L: leucine residue
Lys or K: lysine residue
Met or M: methionine residue Phe or F: phenylalanine residue
Pro or P: proline residue
Ser or S: serine residue
Thr or T: threonine residue
Trp or W: tryptophan residue
Tyr or Y: tyrosine residue
Val or V: valine residue
Abu: 2-aminobutyrate residue (also referred to as α-aminobutyrate residue)
Orn: ornithine residue
Cit: citrulline residue In the present compounds of formula (1), preferred substituents are shown as follows.

Formula (1):

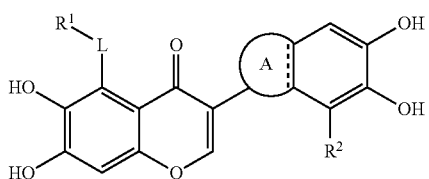

wherein $R^1$-L- is $R^1$—OC(O)— or $R^1$—NHC(O)—, which shows that the carbonyl group of $R^1$—OC(O)— or $R^1$—NHC(O)— is attached to the benzene ring, and its oxygen atom or nitrogen atom is attached to $R^1$.

Wherein $R^1$ is
(i) hydrogen atom,
(ii) optionally-substituted $C_{1-6}$ alkyl group,
(iii) optionally-substituted $C_{2-6}$ alkenyl group,
(iv) optionally-substituted $C_{2-6}$ alkynyl group,
(v) optionally-substituted 3- to 8-membered cycloalkyl group,
(vi) optionally-substituted 4- to 8-membered cycloalkenyl group,
(vii) optionally-substituted 4- to 8-membered saturated aliphatic heterocyclyl group,
(viii) optionally-substituted 5- to 10-membered unsaturated aliphatic heterocyclyl group,
(ix) optionally-substituted 6- to 10-membered aryl group, or
(x) optionally-substituted 5- to 10-membered heteroaryl group.

Preferably, $R^1$ is
(i) hydrogen atom,
(ii) optionally-substituted $C_{1-6}$ alkyl group,
(iii) optionally-substituted $C_{2-6}$ alkenyl group,
(iv) optionally-substituted $C_{2-6}$ alkynyl group,
(v) optionally-substituted 3- to 8-membered cycloalkyl group,
(vi) optionally-substituted 4- to 8-membered cycloalkenyl group,
(vii) optionally-substituted 4- to 8-membered saturated aliphatic heterocyclyl group,
(viii) optionally-substituted 5- to 10-membered unsaturated aliphatic heterocyclyl group,
(ix) optionally-substituted 6- to 10-membered aryl group, or
(x) optionally-substituted 5- to 10-membered heteroaryl group, wherein the substituent(s) of the (ii) optionally-substituted $C_{1-6}$ alkyl group is one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, $C_{1-3}$ alkyl group, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and optionally-substituted 5- to 10-membered heteroaryl group (wherein the substituent(s) of said optionally-substituted 5- to 10-membered heteroaryl group is one or more substituents selected independently from the group consisting of amino group which may be substituted with one or two the same or different $C_{1-3}$ alkyl, $C_{1-3}$ alkyl group, hydroxy group, and carboxyl group), or the (ii) optionally-substituted $C_{1-6}$ alkyl group may be any one of the following groups of formulae (4)-(6):

formula (4):

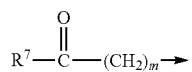

wherein m is 1, 2, 3, 4, or 5, $R^7$ is $C_{1-3}$ alkoxy group, amino acid group (which binds to C(O) at its N terminus), and peptide consisting of 2-3 amino acid residues (which binds to C(O) at its N terminus), formula (5):

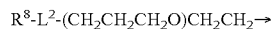

wherein q is 1, 2, 3, 4, or 5, $L^2$ is single bond or C(O), $R^8$ is hydroxy group, $C_{1-3}$ alkoxy group, amino group which may be substituted with one or two the same or different $C_{1-3}$ alkyl, amino acid group (which binds to $L^2$ at its N terminus), or peptide consisting of 2-3 amino acid residues (which binds to $L^2$ at its N terminus), formula (6):

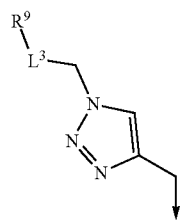

wherein $L^3$ is —$CH_2$— or C(O), and $R^9$ is hydroxy group, $C_{1-3}$ alkoxy group, amino group which may be substituted with one or two the same or different $C_{1-3}$ alkyl, amino acid group (which binds to $L^3$ at its N terminus), or peptide consisting of 2-3 amino acid residues (which binds to $L^3$ at its N terminus), the substituent(s) of the (iii) optionally-substituted $C_{2-6}$ alkenyl group, and the (iv) optionally-substituted $C_{2-6}$ alkynyl group are independently one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and 5- to 10-membered heteroaryl group, the substituent(s) of the (v) optionally-substituted 3- to 8-membered cycloalkyl group, the (vi) optionally-substituted 4- to 8-membered cycloalkenyl group, the (vii) optionally-substituted 4- to 8-membered saturated aliphatic heterocyclyl group, the (viii) optionally-substituted 5- to 10-membered unsaturated aliphatic heterocyclyl group, the (ix) optionally-substituted 6- to 10-membered aryl group, and the (x) optionally-substituted 5- to 10-membered heteroaryl group are independently one or more substituents selected independently from the group consisting of hydroxy group, methoxy group, ethoxy group, amino group which may be substituted with one or two the same or different $C_{1-3}$ alkyl, and carboxyl group.

In an embodiment, $R^1$ is hydrogen atom, optionally-substituted $C_{1-6}$ alkyl group, or any one of substituents of formula (4)-(6).

In another embodiment, $R^1$ is
(i) hydrogen atom,
(ii) optionally-substituted $C_{1-3}$ alkyl group,
(iii) optionally-substituted $C_{2-4}$ alkenyl group,
(iv) optionally-substituted $C_{2-4}$ alkynyl group,
(v) optionally-substituted 3- to 6-membered cycloalkyl group,
(vi) optionally-substituted 4- to 6-membered cycloalkenyl group,
(vii) optionally-substituted 4- to 6-membered saturated aliphatic heterocyclyl group,
(viii) optionally-substituted 5- to 6-membered unsaturated aliphatic heterocyclyl group,
(ix) optionally-substituted 6- to 10-membered aryl group, or
(x) optionally-substituted 5- to 10-membered heteroaryl group.

In the above-mentioned preferred $R^1$, the optionally-substituted alkyl group includes, preferably, one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, $C_{1-3}$ alkyl group, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and optionally-substituted 5- to 10-membered heteroaryl group (wherein the substituent(s) of said optionally-substituted 5- to 10-membered heteroaryl group is one or more substituents selected independently from the group consisting of amino group which may be substituted with one or two the same or different $C_{1-3}$ alkyl, $C_{1-3}$ alkyl group, hydroxy group, and carboxyl group).

The preferred optionally-substituted alkyl group includes, for example, hydrogen atom, methyl group, ethyl group, propyl group, isopropyl group, cyclopropyl group, cyclobutyl group, carboxymethyl group, carbamoylmethyl group, N,N-di(carboxymethyl)aminoethyl group, N,N-di(hydroxyethyl)aminoethyl group, 4-carboxycyclohexylmethyl group, 4-hydroxycyclohexylmethyl group, 4-aminocyclohexylmethyl group, 1,4-dimethylpiperazin-2-ylmethyl group, (1-methyl-1H-imidazol-2-yl)methyl group, 2-hydroxyethyl group, 2-aminoethyl group, 2-carboxyethyl group, 2-methoxyethyl group, 2-ethoxyethyl group, 2,2-dimethyl-2-hydroxyethyl group, 3-hydroxypropyl group, 3-aminopropyl group, 3-carboxyethyl group, 3-methoxypropyl group, 3-ethoxypropyl group, 2,3-dihydroxypropyl group, 3-amino-3-carboxylpropyl group, tetrahydropyranyl group, tetrahydrofuryl group, piperidinyl group, pyrrolidinyl group, and 3-hydroxypyrrolidin-1-ylethyl group, more preferably, hydrogen atom, methyl group, ethyl group, propyl group, isopropyl group, cyclopropyl group, cyclobutyl group, carboxymethyl group, carbamoylmethyl group, N,N-di(carboxymethyl)aminoethyl group, 4-aminocyclohexylmethyl group, 1,4-dimethylpiperazin-2-ylmethyl group, (1-methyl-1H-imidazol-2-yl)methyl group, 2,3-dihydroxypropyl group, 3-amino-3-carboxylpropyl group, 3-hydroxypyrrolidin-1-ylethyl group, and 1,3-dicarboxylpropan-2-yl group.

In the above-mentioned preferred $R^1$, a preferred embodiment of the optionally-substituted alkyl group is any one group of formula (4)-(6), in formula (4), m is 1, $R^7$ is amino acid group (which binds to C(O) at its N terminus),
in formula (5), q is 1, 2, 3, 4, or 5, $L^2$ is single bond or C(O), $R^8$ is hydroxy group or amino acid group (which binds to $L^2$ at its N terminus),
in formula (6), $L^3$ is C(O), $R^9$ is hydroxy group or amino acid group (which binds to $L^3$ at its N terminus).

Even more preferably, it is any one group of formula (4)-(6),
in formula (4), m is 1, $R^7$ is amino acid group such as glutamic acid and arginine,
in formula (5), q is 1, $L^2$ is C(O), $R^8$ is hydroxy group, or amino acid group such as glutamic acid and arginine,
in formula (6), $L^3$ is C(O), $R^9$ is amino acid group such as glutamic acid and arginine.

In another embodiment, $R^1$ is hydrogen atom.

$R^2$ is hydrogen atom, hydroxy group, or carboxyl group, preferably hydrogen atom.

Ring A is a group of formula (2) or formula (3):

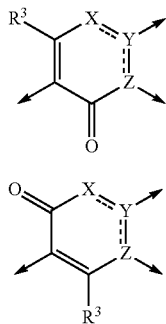

R³ in Ring A is
(i) hydrogen atom,
(ii) optionally-substituted $C_{1-6}$ alkyl group,
(iii) optionally-substituted $C_{2-6}$ alkenyl group,
(iv) optionally-substituted $C_{2-6}$ alkynyl group,
(v) optionally-substituted 3- to 8-membered cycloalkyl group,
(vi) optionally-substituted 4- to 8-membered cycloalkenyl group,
(vii) optionally-substituted 4- to 8-membered saturated aliphatic heterocyclyl group,
(viii) optionally-substituted 5- to 10-membered unsaturated aliphatic heterocyclyl group,
(ix) optionally-substituted 6- to 10-membered aryl group, or
(x) 5- to 10-membered heteroaryl group,
wherein the substituent(s) of the (ii) optionally-substituted $C_{1-6}$ alkyl group, the (iii) optionally-substituted $C_{2-6}$ alkenyl group, the (iv) optionally-substituted $C_{2-6}$ alkynyl group, the (v) optionally-substituted 3- to 8-membered cycloalkyl group, the (vi) optionally-substituted 4- to 8-membered cycloalkenyl group, the (vii) optionally-substituted 4- to 8-membered saturated aliphatic heterocyclyl group, the (viii) optionally-substituted 5- to 10-membered unsaturated aliphatic heterocyclyl group, the (ix) optionally-substituted 6- to 10-membered aryl group, and the (x) optionally-substituted 5- to 10-membered heteroaryl group are independently one or more substituents selected independently from the group consisting of hydroxy group, methoxy group, ethoxy group, carboxyl group, carbamoyl group which may be substituted with one or two the same or different $C_{1-3}$ alkyl, and amino group which may be substituted with one or two the same or different $C_{1-3}$ alkyl.

More preferably, R³ is hydrogen atom, $C_{1-3}$ alkyl group, or 3- to 6-membered cycloalkyl group, even more preferably hydrogen atom or methyl group.

R³ includes, for example, hydrogen atom, methyl group, ethyl group, propyl group (1-propyl group), isopropyl group (2-propyl group), cyclopropyl group, cyclobutyl group, cyclopentyl group, and cyclohexyl group, preferably hydrogen atom or methyl group.

X in Ring A is nitrogen atom, NR⁴, or oxygen atom, provided that X is not oxygen atom in the case of formula (2),
R⁴ in NR⁴ is
(i) hydrogen atom,
(ii) optionally-substituted $C_{1-6}$ alkyl group,
(iii) optionally-substituted $C_{2-6}$ alkenyl group,
(iv) optionally-substituted $C_{2-6}$ alkynyl group,
(v) optionally-substituted 3- to 8-membered cycloalkyl group,
(vi) optionally-substituted 4- to 8-membered cycloalkenyl group,
(vii) optionally-substituted 4- to 8-membered saturated aliphatic heterocyclyl group,
(viii) optionally-substituted 5- to 10-membered unsaturated aliphatic heterocyclyl group,
(ix) optionally-substituted 6- to 10-membered aryl group, or
(x) optionally-substituted 5- to 10-membered heteroaryl group,
wherein the substituent(s) of the (ii) optionally-substituted $C_{1-6}$ alkyl group, the (iii) optionally-substituted $C_{2-6}$ alkenyl group, the (iv) optionally-substituted $C_{2-6}$ alkynyl group, the (v) optionally-substituted 3- to 8-membered cycloalkyl group, the (vi) optionally-substituted 4- to 8-membered cycloalkenyl group, the (vii) optionally-substituted 4- to 8-membered saturated aliphatic heterocyclyl group, the (viii) optionally-substituted 5- to 10-membered unsaturated aliphatic heterocyclyl group, the (ix) optionally-substituted 6- to 10-membered aryl group, and the (x) optionally-substituted 5- to 10-membered heteroaryl group are independently one or more substituents selected independently from the group consisting of hydroxy group, methoxy group, ethoxy group, carboxyl group, carbamoyl group which may be substituted with one or two the same or different $C_{1-3}$ alkyl, and amino group which may be substituted with one or two the same or different $C_{1-3}$ alkyl.

Preferably, R⁴ in NR⁴ is hydrogen atom, $C_{1-3}$ alkyl group, or 3- to 6-membered cycloalkyl group, and more preferably R⁴ is methyl group.

X includes, for example, nitrogen atom, NR⁴, and oxygen atom, provided that X is not oxygen atom in the case of formula (2), and R⁴ includes hydrogen atom, methyl group, ethyl group, propyl group, isopropyl group, cyclopropyl group, cyclobutyl group, cyclopentyl group, cyclohexyl group, tetrahydropyranyl group, tetrahydrofuryl group, piperidinyl group, and pyrrolidinyl group. Preferably, X is nitrogen atom, NR⁴, or oxygen atom, provided that X is not oxygen atom in the case that Ring A is the group of formula (2), and R⁴ is hydrogen atom, methyl group, ethyl group, propyl group, isopropyl group, or cyclopropyl group. More preferably, X is nitrogen atom, NCH₃ or oxygen atom, provided that X is not oxygen atom in the case that Ring A is the group of formula (2).

Y in Ring A is carbon atom or CH.

Z in Ring A is carbon atom, CH, or nitrogen atom.

The combination of X, Y, and Z should be any one of chemically-possible selections, which is X=Y—Z, X—Y=Z, or X—Y—Z.

When Ring A is the group of formula (2), the part of X⋯Y⋯Z is N=C—CH, N=C—N, NR⁴—C=C, NR⁴—CH—N, or NR⁴—CH—CH, preferably N=C—N or NR⁴—C=C. Specifically, it is N=C—CH, N=C—N, NCH₃—C=C, NCH₃—CH—N, or NCH₃—CH—CH, preferably N=C—N or NCH₃—C=C.

When Ring A is the group of formula formula (3), the part of X⋯Y⋯Z is N=C—CH, N=C—N, NR⁴—C=C, NR⁴—CH—N, NR⁴—CH—CH, O—C=C, O—CH—N, or O—CH—CH, preferably NR⁴—C=C or O—C=C. Specifically, it is N=C—CH, N=C—N, NCH₃—C=C, NCH₃—CH—N, NCH₃—CH—CH, O—C=C, O—CH—N, or O—CH—CH, preferably NCH₃—C=C or O—C=C.

In the present compounds of formula (1), the most preferred combination of substituents are shown as follows.

In formula (1),

R$^1$ is hydrogen atom, or the group of formula (6), in formula (6), L$^3$ is C(O), R$^9$ is amino acid group (which binds to L$^3$ at its N terminus), R$^2$ is hydrogen atom, Ring A is the group of formula (2) or formula (3), when Ring A is the group of formula (2), R$^3$ is hydrogen atom or methyl group, the part of x====y====z is N=C—N or NCH$_3$—C=C, when Ring A is the group of formula (3), R$^3$ is hydrogen atom or methyl group, the part of x====y====z is NCH$_3$—C=C or O—C=C.

The present compound of formula (1) includes, preferably the following compound of formula (7).

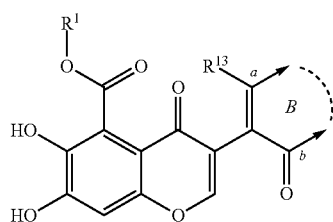

(7)

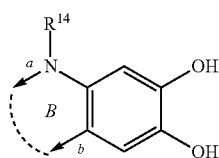

(8)

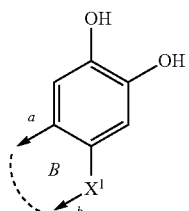

(9)

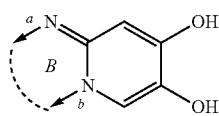

(10)

Wherein Ring B is a group of formula (8), (9), or (10), R$^1$ is (i) hydrogen atom, (ii) C$_{1-3}$ alkyl group which may be substituted with one or more substituents selected independently from the group consisting of hydroxy group, methoxy group, ethoxy group, carboxyl group, carbamoyl group (which may be substituted with one or two the same or different C$_{1-3}$ alkyl), NR$^5$R$^6$ (wherein R$^5$ and R$^6$ are independently hydrogen atom, C$_{1-3}$ alkyl group, carboxylmethyl group, 2-hydroxyethyl group, or 2-aminoethyl group), 3- to 6-membered cycloalkyl group (which may be substituted with one or more substituents selected independently from the group consisting of amino group which may be substituted with one or two the same or different C$_{1-3}$ alkyl, C$_{1-3}$ alkyl group, hydroxy group, and carboxyl group), 4- to 6-membered saturated aliphatic heterocyclyl group (which may be substituted with one or more substituents selected independently from the group consisting of amino group which may be substituted with one or two the same or different C$_{1-3}$ alkyl, C$_{1-3}$ alkyl group, hydroxy group, and carboxyl group), and 5- to 10-membered heteroaryl group (which may be substituted with one or more substituents selected independently from the group consisting of amino group which may be substituted with one or two the same or different C$_{1-3}$ alkyl, C$_{1-3}$ alkyl group, hydroxy group, and carboxyl group), (iii) the group of formula (4):

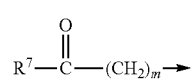

(4)

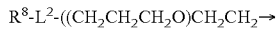

wherein m is 1, 2, 3, 4, or 5, R$^7$ is C$_{1-3}$ alkoxy group, amino acid group (which binds to C(O) at its N terminus), and peptide consisting of 2-3 amino acid residues (which binds to C(O) at its N terminus), (iv) the group of formula (5):

R$^8$-L$^2$-((CH$_2$CH$_2$CH$_2$O)CH$_2$CH$_2$→ (5)

wherein q is 1, 2, 3, 4, or 5, L$^2$ is single bond or C(O), R$^8$ is hydroxy group, C$_{1-3}$ alkoxy group, amino group which may be substituted with one or two the same or different C$_{1-3}$ alkyl, amino acid group (which binds to L$^2$ at its N terminus), or peptide consisting of 2-3 amino acid residues (which binds to L$^2$ at its N terminus), or (v) the group of formula (6):

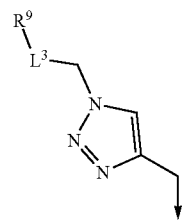

(6)

wherein L$^3$ is CH$_2$ or C(O), and R$^9$ is hydroxy group, C$_{1-3}$ alkoxy group, amino group which may be substituted with one or two the same or different C$_{1-3}$ alkyl, amino acid group (which binds to L$^3$ at its N terminus), or peptide consisting of 2-3 amino acid residues (which binds to L$^3$ at its N terminus);

X$^1$ is O or NR$^{14}$; and

R$^{13}$ and R$^{14}$ are independently hydrogen atom, C$_{1-3}$ alkyl group, or 3- to 6-membered cycloalkyl group.

Preferably, R$^1$ is any one group of formula (4)-(6), in formula (4), m is 1, R$^7$ is amino acid group (which binds to C(O) at its N terminus), in formula (5), q is 1 or 2, L$^2$ is single bond or C(O), R$^8$ is hydroxy group, C$_{1-3}$ alkoxy group, or amino acid group (which binds to L$^2$ at its N terminus), in formula (6), L$^3$ is C(O), R$^9$ is hydroxy group or amino acid group (which binds to L$^3$ at its N terminus).

More preferably, R$^1$ is a group of formula (6), L$^3$ is C(O), R$^9$ is L-glutamic acid.

In another embodiment, more preferably R$^1$ is a group of formula (4), m is 1, R$^7$ is L-glutamic acid.

In another embodiment, R$^1$ is hydrogen atom.

Preferably, Ring B is the group of formula (8).

More preferably, $R^{13}$ is hydrogen atom.

More preferably, $R^{14}$ is methyl group.

The "pharmaceutically acceptable salt of the compound of formula (1)" in the present invention includes a salt of the present compound having an acidic functional group (such as carboxyl group and phenolic hydroxy group) and a base, and a salt of the present compound having a basic functional group (such as amino group and guanidyl) and an acid. The salt of the present compound having an acidic functional group and a base includes, for example, inorganic salts such as sodium salt, potassium salt, calcium salt, magnesium salt, aluminium salt, and ammonium salt; organic salts such as triethylammonium salt, triethanolammonium salt, pyridinium salt, and diisopropylammonium salt; and basic amino acid salt such as arginine salt and lysine salt. The salt of the present compound having a basic functional group and an acid includes, for example, hydrochloride, hydrobromide, sulfate, nitrate, acetate, trifluoroacetate, methanesulfonate, toluenesulfonate, and citrate. These salts can be prepared by reacting the compound of formula (1) with a base or an acid in an appropriate solvent such as water, methanol, ethanol, acetone, ethyl acetate, chloroform, and ether. The product after mixing with a base or an acid may be purified in a conventional method such as recrystallization.

In order to obtain the present compound as a salt, when the product is obtained in a salt form, it can be just purified without any process, or when the product is a free form, it can be obtained by a conventional salt-formation method, i.e., dissolving/suspending the product in an appropriate solvent and then adding an acid or a base thereto.

The compound of formula (1) and a pharmaceutically acceptable salt thereof can be in a solvate with water or various solvents, which is encompassed in the present invention.

The present invention encompasses the compound of formula (1) or a pharmaceutically acceptable salt thereof. In addition, the present invention encompasses a hydrate thereof and a solvate thereof such as ethanolate thereof. Furthermore, the present invention encompasses all tautomers, stereoisomers, and crystal forms thereof.

The compound of the present invention also includes an optical isomer which is based on chiral center, an atropisomer which is based on axiality caused by intramolecular rotational hindrance or planar-chirality, other stereoisomers, tautomer, and geometric isomer, all possible isomers of which and a mixture thereof are encompassed in the present invention.

In particular, optical isomers and atropisomers can be obtained as racemate, or as optically active substance when using optically active starting material or intermediate. If necessary, racemates of the corresponding material or intermediate, or the final product can be physically or optically divided to optically active enantiomers at an appropriate step in the process mentioned below in a known separating method such as optically active column chromatography and fractional crystallization. For example, by diastereomer method, racemates can be transformed to two diastereomers by using an optically-active resolving agent, and then the two diastereomers can be separated by a known method such as fractional crystallization because such different diastereomers generally have different physical characters.

As one of the compound-groups of formula (1), the present compound of formula (1A) can be prepared from compounds of formula (1a) and formula (1b), for example, according to Scheme 1 shown below.

Scheme 1:

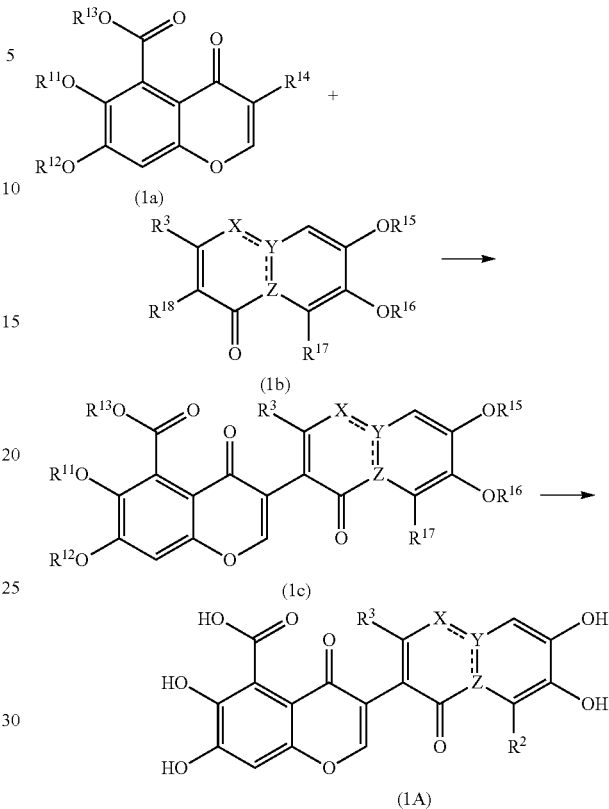

Wherein $R^{11}$, $R^{12}$, $R^{15}$, and $R^{16}$ are independently a protecting group of hydroxy group; $R^{13}$ is a protecting group of carboxyl group; $R^{14}$ is a functional group such as tributyltin group, pinacolboryl group, and hydroxyboryl group; $R^{17}$ is hydrogen atom, a protected hydroxy group, or a protected carboxyl group; $R^{18}$ is a halogen atom such as iodine and bromine; $R^2$, $R^3$, X═Y═Z, X, Y, and Z are as defined in Term 1.

That is, the compound of formula (1a) and the compound of formula (1b) can be coupled at 20° C.-200° C. in a solvent (such as propionitrile, acetonitrile, tetrahydrofuran, 1,4-dioxane, and water, or a combined solvent thereof), in the presence of a base (such as potassium carbonate, triethylamine, and diisopropylethylamine), a phosphine ligand (such as 2-dicyclohexylphosphino-2',6'-dimethoxybiphenyl, and 2-dicyclohexylphosphino-2',4',6'-triisopropylbiphenyl), a copper catalyst (such as copper(I) iodide), and a palladium catalyst (such as tetrakis(triphenylphosphine)palladium and tris(dibenzylideneacetone)dipalladium) to prepare a compound of formula (1c). The compound of formula (1A) which is one of the compound-groups of formula (1) can be prepared by suitably deprotecting the protecting groups from the compound of formula (1c) in manner well-known by a skilled person.

In the compounds of formulae (1a) and (1b), each protection groups of $R^{11}$, $R^{12}$, $R^{13}$, $R^{15}$, and $R^{16}$, and a protecting group in $R^{17}$ are not limited as long as they are protecting groups for hydroxy group or carboxyl group, which are not cleaved during the above coupling reaction. It is possible to suitably use protecting groups well-known by a skilled person, which are described in Protective Group in Organic Synthesis, 3rd edition (edited by Theodora W.

Green, Peter G. M. Wuts, issued by John Wiley & Sons Inc, in 1999). For example, the protecting group for carboxyl group includes ester-type groups such as methyl group, ethyl group, trimethylsilylethyl group and tert-butyl group, and the protecting group for hydroxy group includes methyl group, pivaloyl group, and methoxymethyl group.

As one of the compound-groups of formula (1), the present compound of formula (1B) can be prepared from a compound of formula (1A), for example, according to Scheme 2 shown below.

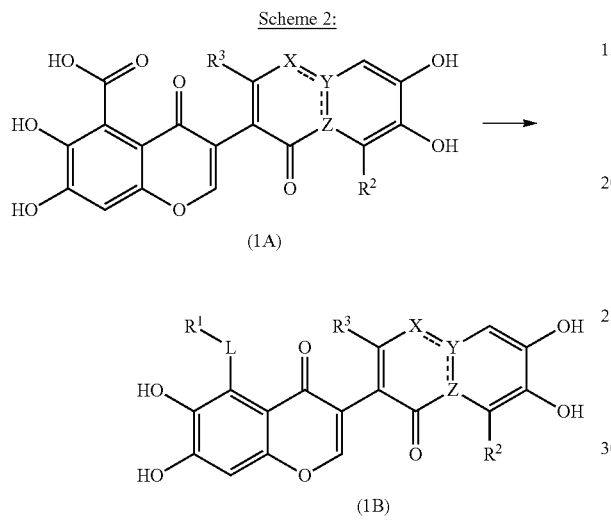

Wherein $R^1$, $R^2$, $R^3$, x═══y═══z, X, Y, Z, and L are as defined in Term 1.

That is, the compound of formula (1A) which is one of the compound-groups of formula (1) can be reacted at 20° C.-120° C. in an inert solvent (such as toluene, dichloromethane, and chloroform), in the presence of a halogenating agent (such as 1-chloro-N,N,2-trimethylpropenylamine, phosphorus oxychloride, phosphorus trichloride, thionyl chloride, and phosphorus pentachloride), and then reacted with an alcohol compound or an amine compound which corresponds to a desired $R^1$ (such as propargyl alcohol and propargylamine) at 0° C.-50° C. in an inert solvent (such as dichloromethane and chloroform) to give a compound of formula (1B) which is one of the compound-groups of formula (1).

As one of the compound-groups of formula (1B), the present compound of formula (1Ba) can be prepared from compound (1c), for example, according to Scheme 3 shown below.

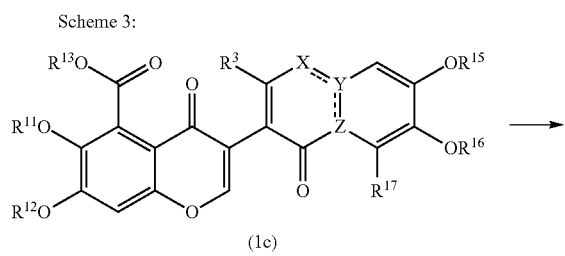

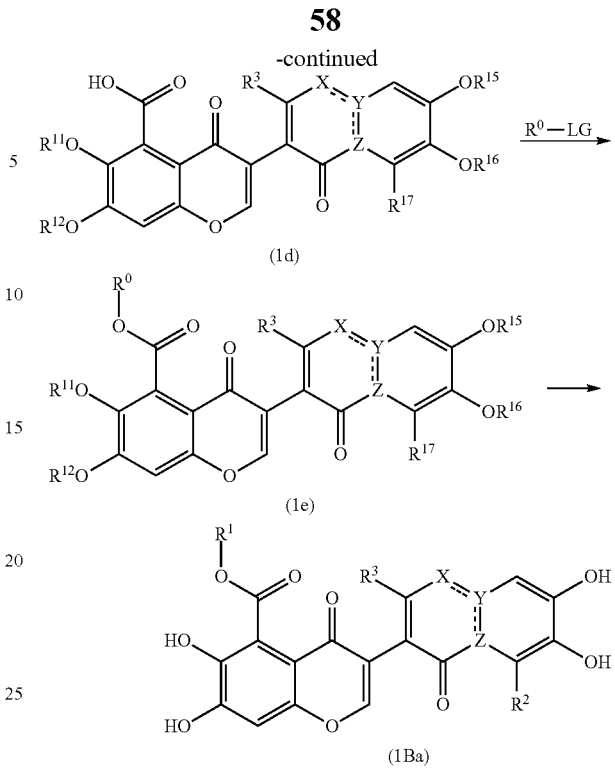

Wherein $R^0$ is $R^1$ or a protected $R^1$; LG is a leaving group such as halogen atom, alkylsulfonyloxy group, and arylsulfonyloxy group; $R^{11}$, $R^{12}$, $R^{13}$, $R^{15}$, $R^{16}$ and $R^{17}$ are as defined in Scheme 1; $R^1$, $R^2$, $R^3$, x═══y═══z, X, Y, and Z are as defined in Term 1.

That is, among the protecting groups in the compound of formula (1c), R can be suitably de-protected in manner well-known by a skilled person to give a compound of formula (1d). Compound (1d) can be reacted with $R^0$-LG at 0° C.-50° C. in an inert solvent in the presence of a base as necessary to give compound (1e). The base used herein is not limited as long as it is used in a normal reaction, which includes, for example, an organic base such as N-methylmorpholine, triethylamine, diisopropylethylamine, tributylamine, and pyridine; and an inorganic base such as sodium hydrogencarbonate, potassium hydrogen carbonate, sodium carbonate, and potassium carbonate. The inert solvent used herein includes, for example, ether type solvents such as tetrahydrofuran, 1,4-dioxane, and 1,2-dimethoxyethane; halogenated hydrocarbon solvents such as dichloromethane, chloroform, and dichloroethane; ketone solvents such as acetone; and aprotic solvents such as acetonitrile, N,N-dimethylformamide, dimethylsulfoxide, and hexamethylphosphoramide, and a mixture thereof. The compound of formula (1Ba) which is one of the compound-groups of formula (1B) can be prepared by suitably deprotecting the protecting groups from the compound of formula (1e) in manner well-known by a skilled person.

In the compound of formula (1c), each protecting groups of $R^{11}$, $R^{12}$, $R^{15}$, and $R^{16}$, and a protecting group in $R^7$ are not limited as long as they are not cleaved under the above deprotection condition of $R^{13}$. It is possible to suitably use protecting groups well-known by a skilled person, which are described in Protective Group in Organic Synthesis, 3rd edition (edited by Theodora W. Green, Peter G. M. Wuts, issued by John Wiley & Sons Inc, in 1999).

The compound of formula (1h) which is in the scope of the above-mentioned compound of $R^0$-LG can be prepared from compound of formula (1f), for example, according to Scheme 4 shown below.

Scheme 4:

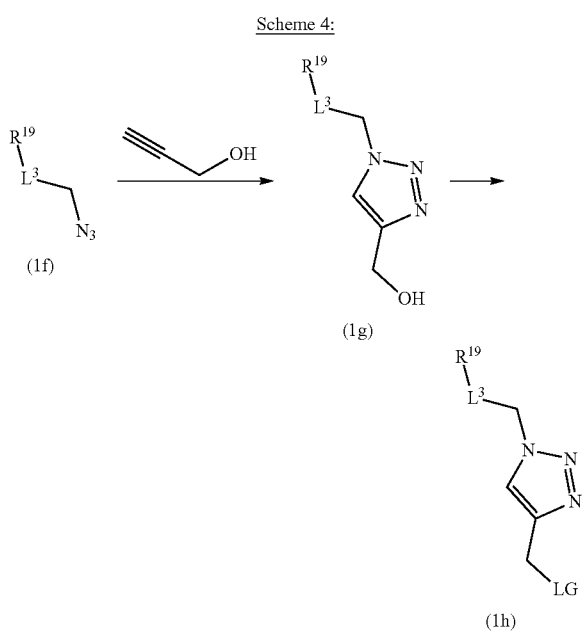

Wherein $R^{19}$ is a protected $R^9$, LG is as defined in Scheme 3, $R^9$ and $L^3$ are as defined in Term 2.

That is, the compound of formula (1f) can be reacted with propargyl alcohol at 0° C.-50° C. in a solvent (such as dimethylsulfoxide, N,N-dimethylformamide, 1,4-dioxane, tert-butyl alcohol, and water, or a combined solvent thereof), in the presence of a reducing agent (such as sodium ascorbate), a ligand (such as tris[(1-benzyl-1H-1,2,3-triazol-4-yl)methyl]amine), and a copper catalyst (such as copper sulfate and copper iodide) to give the compound of formula (1g). For example, compound (1h) can be prepared by reacting the compound of formula (1g) with methanesulfonyl chloride, p-toluenesulfonyl chloride, or the like at 0° C.-50° C. in the presence of a base such as triethylamine, diisopropylethylamine, pyridine, dimethylaminopyridine, sodium carbonate, and potassium carbonate.

The compounds of formulae (1fa) and (1j) which are in the scope of the above-mentioned compound (1f) can be prepared from bromoacetic acid, for example, according to Scheme 5 shown below.

Scheme 5:

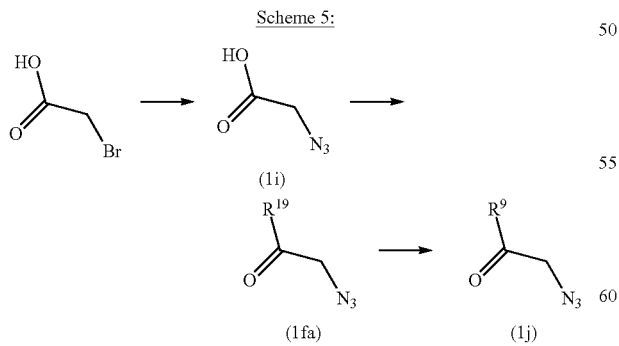

Wherein $R^9$ is as defined in Term 2, $R^{19}$ is as defined in Scheme 4.

That is, to bromoacetic acid in a solvent (such as dimethylsulfoxide and N,N-dimethylformamide) is added sodium azide, and then the mixture can be reacted at 0° C.-50° C. to give the compound of formula (1i). To the compound of formula (1i) in a solvent (such as dimethylsulfoxide and N,N-dimethylformamide) are added a condensing agent (such as N,N'-diisopropylcarbodiimide and N,N'-dicyclohexylcarbodiimide), and an amino acid or peptide (whose N terminus is unprotected and the other functional groups are unprotected or protected), and then the reaction mixture can be reacted at 0° C.-50° C. to give the compound of formula (1fa). The compound of formula (1j) can be prepared by suitably deprotecting the protecting group from the compound of formula (1fa) in manner well-known by a skilled person.

In the compound of formula (1fa), each protecting group is not limited as long as it is not cleaved under the above reaction condition. It is possible to suitably use protecting groups well-known by a skilled person, which are described in Protective Group in Organic Synthesis, 3rd edition (edited by Theodora W. Green, Peter G. M. Wuts, issued by John Wiley & Sons Inc, in 1999). For example, the protecting group for carboxyl group includes ester-type groups such as methyl group, ethyl group, and tert-butyl group, and the protecting group for guanidyl group includes 4-methoxy-2,3,6-trimethylbenzenesulfonyl group, 2,2,5,7,8-pentamethylchromane-6-sulfonyl group, and 2,2,4,6,7-pentamethyldihydrobenzofuran-5-sulfonyl group.

As one of the compound-groups of formula (1B), the present compound of formula (1Bb) can be prepared from compound (1d), for example, according to Scheme 6 shown below.

Scheme 6:

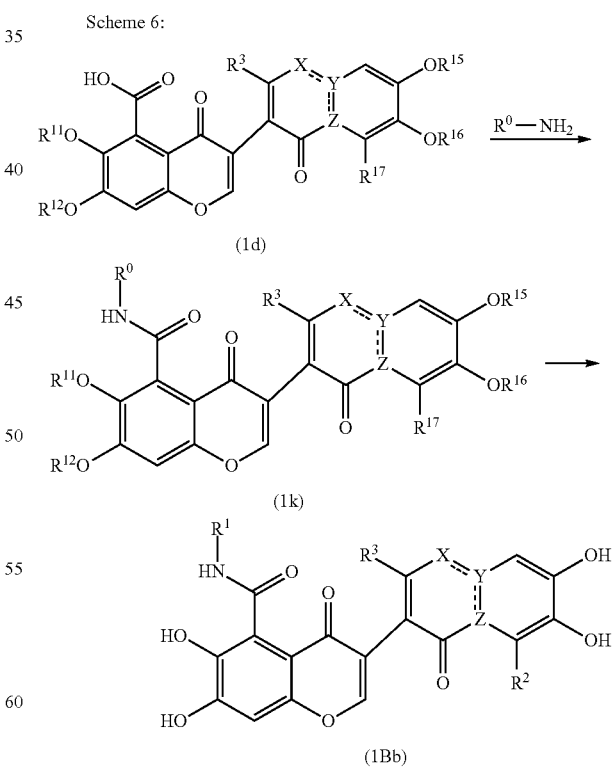

Wherein $R^0$ is as defined in Scheme 3; $R^{11}$, $R^{12}$, $R^{15}$, $R^{16}$, and $R^1$ are as defined in Scheme 1; $R^1$, $R^2$, $R^3$, x═══y═══z, X, Y, and Z are as defined in Term 1.

That is, the compound of formula (1d) can be reacted with R⁰NH₂ at 0° C.-50° C. in an inert solvent together with a condensing agent in the presence of a base as necessary to give compound (1k).

The base used herein is not limited as long as it is used in a normal reaction, which includes, for example, an organic base such as N-methylmorpholine, triethylamine, diisopropylethylamine, tributylamine, and pyridine; and an inorganic base such as sodium hydrogencarbonate, potassium hydrogen carbonate, sodium carbonate, and potassium carbonate.

The condensing agent used herein includes what are disclosed in the 4th Series of Experimental Chemistry, Vol. 22 (Jikken Kagaku Kouza, edited by the Chemical Society of Japan, issued by MARUZEN). It includes, for example, phosphates such as diethyl cyanophosphate and diphenylphosphoryl azide; carbodiimides such as 1-ethyl-3-(3-dimethylaminopropyl)-carbodiimide hydrochloride (WSC.HCl (also referred to as EDC)) and dicyclohexylcarbodiimide (DCC); a combination of a disulfide (such as 2,2'-dipyridyl disulfide) and a phosphine (such as triphenylphosphine); phosphine halides such as N,N'-bis(2-oxo-3-oxazolidinyl) phosphinic chloride (BOPCl); a combination of an azodicarboxylate diester (such as diethyl azodicarboxylate) and a phosphine (such as triphenylphosphine); 2-halo-1-(lower alkyl)pyridinium halides such as 2-chloro-1-methylpyridinium iodide; 1,1'-carbonyl diimidazole (CDI); diphenylphosphoryl azide (DPPA); diethyl phosphoryl cyanide (DEPC); tetrafluoroborates such as 2-(1H-benzotriazol-1-yl)-1,1,3,3-tetramethyluronium tetrafluoroborate (TBTU) and 2-chloro-1,3-dimethylimidazolidinium tetrafluoroborate (CIB); phosphates such as 2-(1H-benzotriazol-1-yl)-1,1,3,3-tetramethyluronium hexafluorophosphate (HBTU), benzotriazol-1-yloxytris(dimethylamino)phosphonium hexafluorophosphate (BOP), benzotriazol-1-yloxytris(pyrrolidino) phosphonium hexafluorophosphate (PYBOP), and 2-(7-aza-1H-benzotriazol-1-yl)-1,1,3,3-tetramethyluronium hexafluorophosphate (HATU).

The inert solvent used herein includes, for example, ether type solvents such as tetrahydrofuran, 1,4-dioxane, and 1,2-dimethoxyethane; halogenated hydrocarbon solvents such as dichloromethane, chloroform, and dichloroethane; and aprotic solvents such as acetonitrile, N,N-dimethylformamide, dimethylsulfoxide, and hexamethylphosphoramide, and a mixture thereof.

In addition, the compound of formula (1d) is reacted with a halogenating agent (such as 1-chloro-N,N,2-trimethylpropenylamine, phosphorus oxychloride, phosphorus trichloride, thionyl chloride, and phosphorus pentachloride) at 20° C.-120° C. to give an acid halide thereof, and then the acid halide can be reacted with R⁰NH₂ at 0° C.-50° C. in an inert solvent in the presence of a base as necessary to prepare compound (1k).

The inert solvent used herein includes, for example, ether type solvents such as tetrahydrofuran, 1,4-dioxane, and 1,2-dimethoxyethane; halogenated hydrocarbon solvents such as dichloromethane, chloroform, and dichloroethane; and aprotic solvents such as acetonitrile, N,N-dimethylformamide, dimethylsulfoxide, and hexamethylphosphoramide. The base used herein is not limited as long as it is used in a normal reaction, which includes, for example, an organic base such as N-methylmorpholine, triethylamine, diisopropylethylamine, tributylamine, and pyridine; and an inorganic base such as sodium hydrogencarbonate, potassium hydrogen carbonate, sodium carbonate, and potassium carbonate.

The compound of formula (1Bb) which is one of the compound-groups of formula (1B) can be prepared by suitably deprotecting the protecting groups from the compound of formula (1k) in manner well-known by a skilled person.

As one of the compound-groups of formula (1B), the present compound of formula (1Bd) can be prepared from compound (1Bc), for example, according to Scheme 7 shown below.

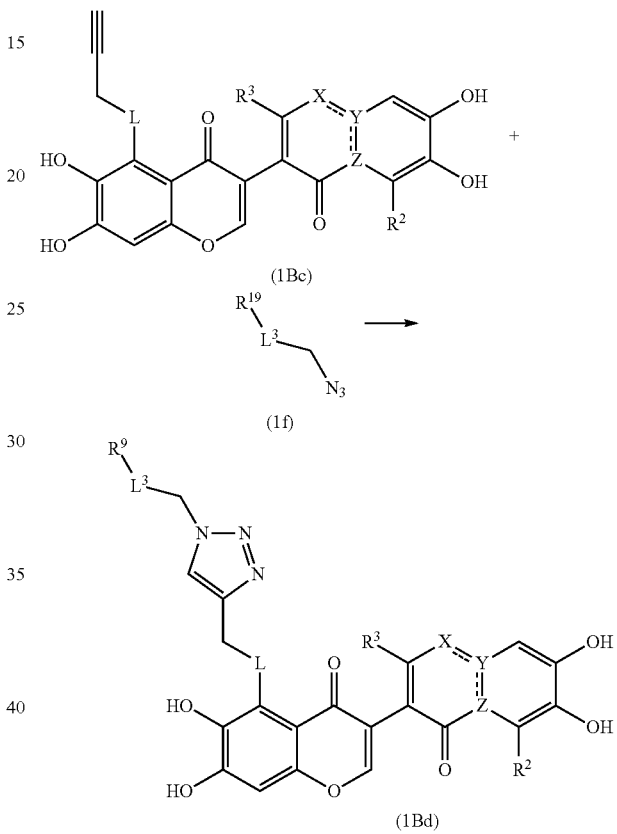

Wherein R⁹ and L³ are as defined in Term 2; R¹⁹ is as defined in Scheme 4; R², R³, x═══y═══z, X, Y, Z, and L are as defined in Term 1.

That is, the compound of formula (1Bc) which is one of the compound-groups of formula (1B) is reacted with a compound of formula (1f) at 0° C.-50° C. in a solvent (such as dimethylsulfoxide, N,N-dimethylformamide, 1,4-dioxane, tert-butanol, and water, or a combined solvent thereof), in the presence of a reducing agent (such as sodium ascorbate), a ligand (such as tris[(1-benzyl-1H-1,2,3-triazol-4-yl) methyl]amine), and a copper catalyst (such as copper sulfate and copper iodide). The compound of formula (1Bd) can be prepared by suitably deprotecting the protecting groups from the product in manner well-known by a skilled person. In addition, the compound of formula (1Bd) can be also obtained by using the compound of formula (1j) instead of the compound of formula (1f) in the above reaction.

The above-mentioned compound (1a) can be prepared from a compound of formula (1l), for example, according to Scheme 8 shown below.

Scheme 8:

[Structure (1I): chromone with $R^{13}O\text{-}C(=O)$, $R^{11}O$, $R^{12}O$ substituents and 3-iodo]

[Structure (1a): chromone with $R^{13}O\text{-}C(=O)$, $R^{11}O$, $R^{12}O$ substituents and 3-$R^{14}$]

Wherein $R^{11}$, $R^{12}$, $R^{13}$, and $R^{14}$ are as defined in Scheme 1.

That is, the compound of formula (1I) can be reacted with a tin reagent such as tributyltin chloride, and a Grignard reagent such as isopropylmagnesium chloride at −78° C. to 30° C. in a solvent (such as tetrahydrofuran and 1,4-dioxane), or with a boronating reagent (such as trimethoxyborane), and a Grignard reagent (such as isopropylmagnesium chloride-lithium chloride complex) at −78° C. to 30° C. in a solvent (such as tetrahydrofuran and 1,4-dioxane) to give the compound of formula (1a).

The compound of formula (1I) is a known compound (for example, compounds disclosed in *Angew. Chem. Int. Ed.*, 52, p 3421-3424 (2013), or *Chem Lett.*, 36, p 1382 (2007)), or can be prepared in manner well-known by a skilled person. For example, the compounds described in the present reference examples may be used.

As one of the compound-groups of compound (1b), the compound of formula (1ba) can be prepared from a compound of formula (1m), according to Scheme 9 shown below.

Scheme 9:

[Structure (1m): aminopyridine with $OR^{15}$, $OR^{16}$, $R^{17}$ substituents]

[Structure (1n): pyrido-pyrimidinone-type with $R^3$, $OR^{15}$, $OR^{16}$, $R^{17}$]

[Structure (1ba): with additional $R^{18}$ substituent]

Wherein $R^3$ is as defined in Term 1, $R^{15}$, $R^{16}$, $R^{17}$, and $R^{18}$ are as defined in Scheme 1.

That is, the compound of formula (1m) can be reacted with a reagent corresponding to $R^3$ (such as ethyl 3-oxopropanoate, ethyl acetoacetate, and ethyl 3-oxovalerate) at 0° C.-150° C. in a solvent such as polyphosphoric acid to give a compound of formula (1n). The compound of formula (1n) can be reacted with (Ai) a halogenating agent such as N-iodosuccinimide at 0° C.-100° C. in a solvent such as acetonitrile, tetrahydrofuran and 1,4-dioxane, (Aii) sodium acetate or the like, and a halogenating agent such as bromine at 0° C.-100° C. in a solvent such as acetic acid, or (Aiii) potassium iodide or the like, and a halogenating agent such as iodine at 0° C.-100° C. in an aqueous sodium hydroxide solution, to give the compound of formula (1ba).

The compound of formula (1m) can be prepared, for example, in the manner disclosed in *J. Med. Chem.*, 2015, 58(5), p 2195-2205, or is commercially available.

As one of the above-mentioned compound (1b), the compound of formula (1bb) can be prepared from a compound of formula (1o), for example, according to Scheme 10 shown below.

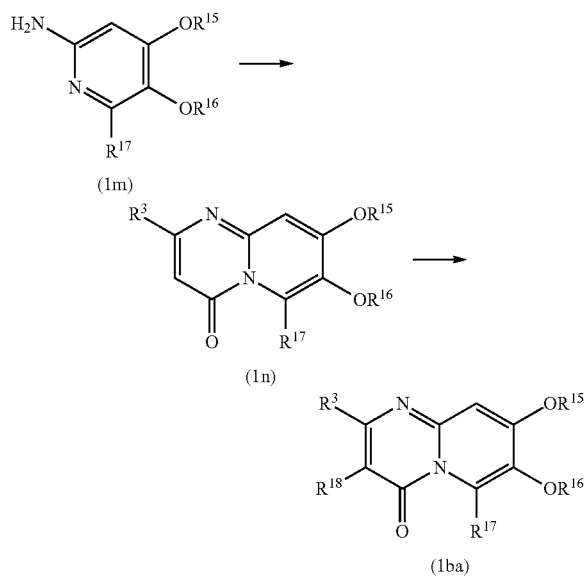

Scheme 10:

[Structures (1o), (1p), (1q), (1bb)]

Wherein $R^3$ and $R^4$ are as defined in Term 1, $R^{15}$, $R^6$, $R^{17}$, and $R^{18}$ are as defined in Scheme 1.

That is, the compound of formula (1o) is reacted with a base (such as sodium methoxide) and a reagent corresponding to $R^3$ (such as ethyl formate and ethyl acetate) at 0° C.-50° C. in a solvent (such as dimethoxyethane, 1,4- dioxane and cyclopentylmethyl ether), and then the reaction mixture can be reacted at 0° C.-120° C. in 4 mol/L hydrochloric acid/a solvent (such as dioxane) to give the compound of formula (1p). The compound of formula (1p) can be reacted with (Bi) a halogenating agent such as N-iodosuccinimide at 0° C.-100° C. in a solvent (such as acetonitrile, tetrahydrofuran and 1, 4-dioxane), (Bii) sodium acetate or the like, and a halogenating agent such as bromine at 0° C.-100° C. in a solvent (such as acetic acid), or (Biii) potassium iodide or the like, and a halogenating agent such as iodine at 0° C.-100° C. in an aqueous sodium hydroxide solution, to give a compound of formula (1q). The compound of formula (1q) can be reacted with a base (such as potassium carbonate and cesium carbonate), and an alkylating agent corresponding to $R^4$ (such as methyl iodide, ethyl iodide, and propyl iodide) at 0° C.-100° C. in a solvent (such as N,N-dimethylformamide and dimethylsulfoxide) to give the compound of formula (1bb). It is unnecessary to transfer from formula (1q) to formula (1bb) when $R^4$ is hydrogen atom.

The aniline compound of formula (1o) can be prepared, for example, in the manner disclosed in *Tetrahedron*, Volume 63, Issue 2, p 474-491 (2007), or is commercially available.

Besides the above-mentioned process, the quinolin-4 (1H)-one compound of formula (1p) can be prepared, for example, in the manner disclosed in *Bioorg. Med. Chem.* 13, p 1661-1671 (2005), or *Tetrahedron Lett.* 50, p 6494-6497 (2009), or is commercially available.

As one of the compound-groups of formula (1), the present compound of formula (1C) can be prepared from compounds of formula (1a) and formula (1r), for example, according to Scheme 11 shown below.

Scheme 11:

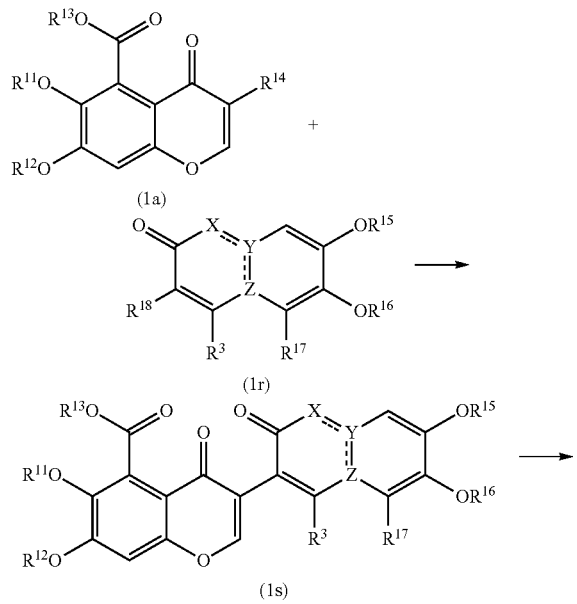

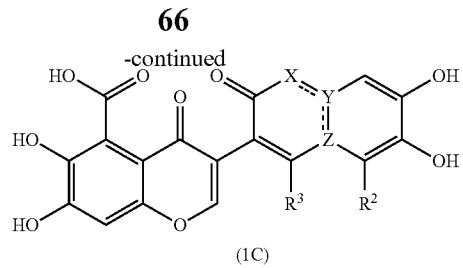

Wherein $R^{11}$, $R^{12}$, $R^{13}$, $R^{14}$, $R^{15}$, $R^{16}$, $R^{17}$, and R are as defined in Scheme 1, $R^2$, $R^3$, x═══y═══z, X, Y, and Z are as defined in Term 1.

That is, the compound of formula (1a) and the compound of formula (1r) can be coupled at 20° C.-200° C. in a solvent (such as propionitrile, acetonitrile, tetrahydrofuran, 1,4-dioxane, and water, or a combined solvent thereof), in the presence of a base (such as potassium carbonate, triethylamine and diisopropylethylamine), a phosphine ligand (such as 2-dicyclohexylphosphino-2',6'-dimethoxybiphenyl and 2-dicyclohexylphosphino-2',4',6'-triisopropylbiphenyl), a copper catalyst (such as copper(I) iodide), and a palladium catalyst (such as tetrakis(triphenylphosphine)palladium and tris(dibenzylideneacetone)dipalladium) to prepare a compound of formula (1s). The compound of formula (1C) which is one of the compound-groups of formula (1) can be prepared by suitably deprotecting the protecting groups from the compound of formula (1s) in manner well-known by a skilled person.

In the compounds of formula (1a) and formula (1r), each protection groups of $R^{11}$, $R^{12}$, $R^{13}$, $R^{15}$, and $R^{16}$, and a protecting group in $R^{17}$ are not limited as long as they are protecting groups for hydroxy group or carboxyl group, which are not cleaved during the above coupling reaction. It is possible to suitably use protecting groups well-known by a skilled person, which are described in Protective Group in Organic Synthesis, 3rd edition (edited by Theodora W. Green, Peter G. M. Wuts, issued by John Wiley & Sons Inc, in 1999). For example, the protecting group for carboxyl group includes ester-type groups such as methyl group, ethyl group, and tert-butyl group, and the protecting group for hydroxy group includes methyl group, pivaloyl group, and methoxymethyl group.

As one of the compound-groups of formula (1), the present compound of formula (1D) can be prepared from compounds of formula (1C), for example, according to Scheme 12 shown below.

Scheme 12:

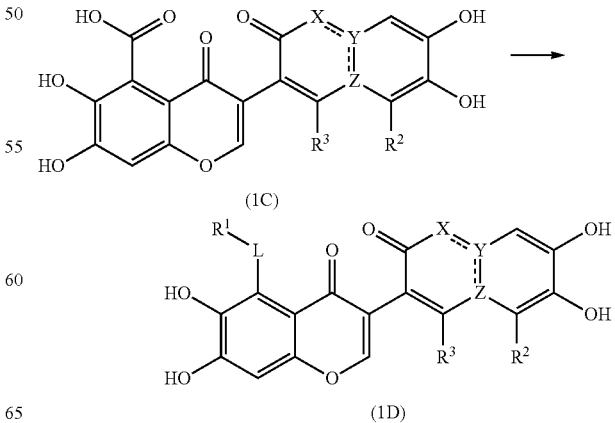

Wherein $R^1$, $R^2$, $R^3$, x═══y═══z, X, Y, Z, and L are as defined in Term 1i.

That is, the compound of formula (1C) which is one of the compound-groups of formula (1) can be reacted at 20° C.-120° C. in an inert solvent (such as toluene, dichloromethane, and chloroform), in the presence of a halogenating agent (such as 1-chloro-N,N,2-trimethylpropenylamine, phosphorus oxychloride, phosphorus trichloride, thionyl chloride, and phosphorus pentachloride), and then reacted with an alcohol compound or an amine compound which corresponds to a desired $R^1$ (such as propargyl alcohol and propargylamine) at 0° C.-50° C. in an inert solvent (such as dichloromethane and chloroform) to give the compound of formula (1D) which is one of the compound-groups of formula (1).

As one of the compound-groups of formula (1D), the compound of formula (1Da) can be prepared from compound (1s), for example, according to Scheme 13 shown below.

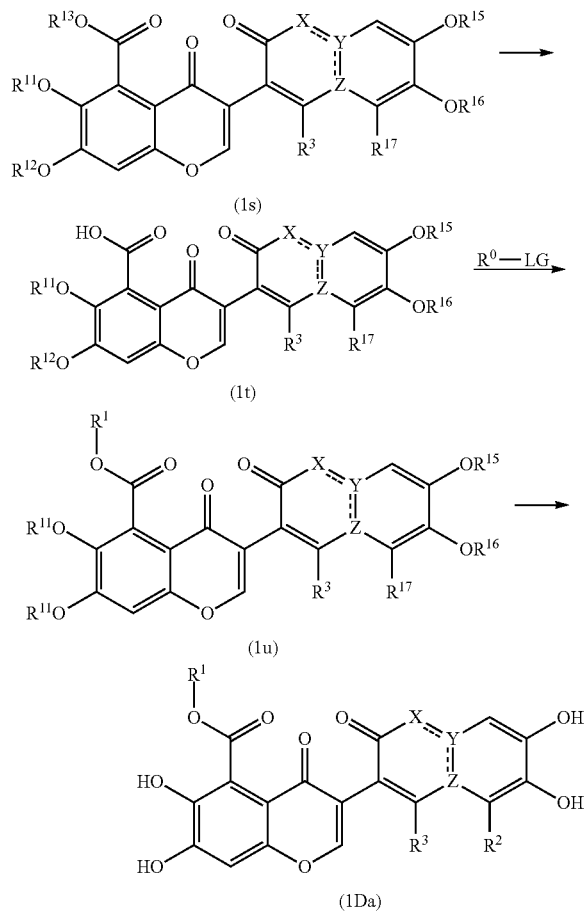

Wherein $R^{11}$, $R^{12}$, $R^{13}$, $R^{15}$, $R^{16}$, and $R^{17}$ are as defined in Scheme 1, $R^0$ and LG are as defined in Scheme 3, $R^1$, $R^2$, $R^3$, x═══y═══z, X, Y, and Z is as defined in Term 1.

That is, among the protecting groups in the compound of formula (1s), R can be suitably de-protected in manner well-known by a skilled person to give a compound of formula (1t). Compound (1t) can be reacted with $R^0$-LG at 0° C.-50° C. in an inert solvent in the presence of a base as necessary to give compound (1u). The base used herein is not limited as long as it is used in a normal reaction, which includes, for example, an organic base such as N-methylmorpholine, triethylamine, diisopropylethylamine, tributylamine, and pyridine; and an inorganic base such as sodium hydrogencarbonate, potassium hydrogen carbonate, sodium carbonate, and potassium carbonate. The inert solvent used herein includes, for example, ether type solvents such as tetrahydrofuran, 1,4-dioxane, and 1,2-dimethoxyethane; halogenated hydrocarbon solvents such as dichloromethane, chloroform, and dichloroethane; and aprotic solvents such as acetonitrile, N,N-dimethylformamide, dimethylsulfoxide, and hexamethylphosphoramide, and a mixture thereof. The compound of formula (1Da) which is one of the compound-groups of formula (1D) can be prepared by suitably deprotecting the protecting groups from the compound of formula (1u) in manner well-known by a skilled person.

In the compound of formula (1s), each protection groups of $R^{11}$, $R^{12}$, $R^{15}$, and $R^{16}$, and a protecting group in $R^{17}$ are not limited as long as they are not cleaved under the above deprotection condition of $R^{13}$. It is possible to suitably use protecting groups well-known by a skilled person, which are described in Protective Group in Organic Synthesis, 3rd edition (edited by Theodora W. Green, Peter G. M. Wuts, issued by John Wiley & Sons Inc, in 1999).

As one of the compound-groups of formula (1D), the compound of formula (1Db) can be prepared from compound (1t), for example, according to Scheme 14 shown below.

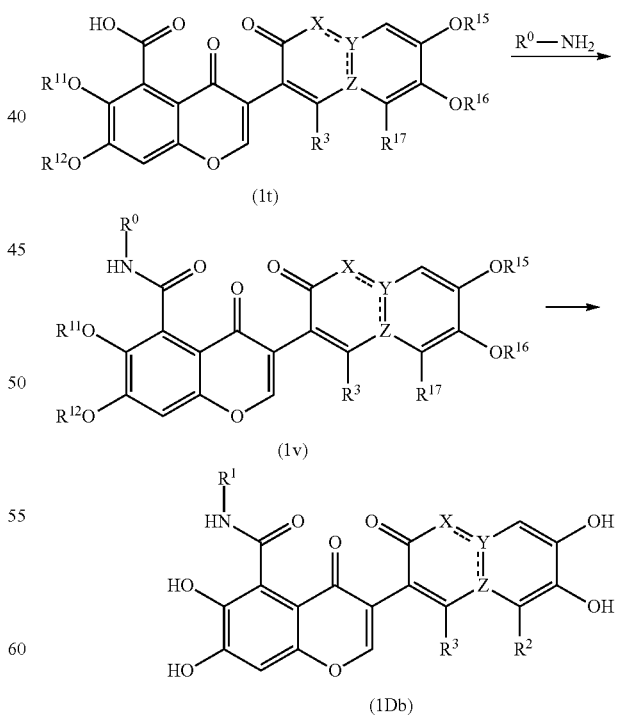

Wherein $R^{11}$, $R^{12}$, $R^{15}$, $R^{16}$, and $R^{17}$ are as defined in Scheme 1, $R^0$ is as defined in Scheme 3, $R^1$, $R^2$, $R^3$, x═══y═══z, X, Y, and Z are as defined in Term 1.

That is, the compound of formula (1t) can be reacted with R⁰NH₂ at 0° C.-50° C. in an inert solvent together with a condensing agent in the presence of a base as necessary to give compound (1v).

The base used herein is not limited as long as it is used in a normal reaction, which includes, for example, an organic base such as N-methylmorpholine, triethylamine, diisopropylethylamine, tributylamine, and pyridine; and an inorganic base such as sodium hydrogencarbonate, potassium hydrogen carbonate, sodium carbonate, and potassium carbonate.

The condensing agent used herein includes what are disclosed in the 4th Series of Experimental Chemistry, Vol. 22 (Jikken Kagaku Kouza, edited by the Chemical Society of Japan, issued by MARUZEN). It includes, for example, phosphates such as diethyl cyanophosphate and diphenylphosphoryl azide; carbodiimides such as 1-ethyl-3-(3-dimethylaminopropyl)-carbodiimide hydrochloride (WSC.HCl (also referred to as EDC)) and dicyclohexylcarbodiimide (DCC); a combination of a disulfide (such as 2,2'-dipyridyl disulfide) and a phosphine (such as triphenylphosphine); phosphine halides such as N,N'-bis(2-oxo-3-oxazolidinyl) phosphinic chloride (BOPCl); a combination of an azodicarboxylate diester (such as diethyl azodicarboxylate) and a phosphine (such as triphenylphosphine); 2-halo-1-(lower alkyl)pyridinium halides such as 2-chloro-1-methylpyridinium iodide; 1,1'-carbonyl diimidazole (CDI); diphenylphosphoryl azide (DPPA); diethyl phosphoryl cyanide (DEPC); tetrafluoroborates such as 2-(1H-benzotriazol-1-yl)-1,1,3,3-tetramethyluronium tetrafluoroborate (TBTU) and 2-chloro-1,3-dimethylimidazolidinium tetrafluoroborate (CIB); phosphates such as 2-(1H-benzotriazol-1-yl)-1,1,3,3-tetramethyluronium hexafluorophosphate (HBTU), benzotriazol-1-yloxytris(dimethylamino)phosphonium hexafluorophosphate (BOP), benzotriazol-1-yloxytris(pyrrolidino) phosphonium hexafluorophosphate (PYBOP), and 2-(7-aza-1H-benzotriazol-1-yl)-1,1,3,3-tetramethyluronium hexafluorophosphate (HATU).

The inert solvent used herein includes, for example, ether type solvents such as tetrahydrofuran, 1,4-dioxane, and 1,2-dimethoxyethane; halogenated hydrocarbon solvents such as dichloromethane, chloroform, and dichloroethane; and aprotic solvents such as acetonitrile, N,N-dimethylformamide, dimethylsulfoxide, and hexamethylphosphoramide, and a mixture thereof.

In addition, the compound of formula (1t) is reacted with a halogenating agent (such as 1-chloro-N,N,2-trimethylpropenylamine, phosphorus oxychloride, phosphorus trichloride, thionyl chloride, and phosphorus pentachloride) at 20° C.-120° C. to give an acid halide thereof, and then the acid halide can be reacted with R⁰NH₂ at 0° C.-50° C. in an inert solvent in the presence of a base as necessary to prepare compound (1v).

The inert solvent used herein includes, for example, ether type solvents such as tetrahydrofuran, 1,4-dioxane, and 1,2-dimethoxyethane; halogenated hydrocarbon solvents such as dichloromethane, chloroform, and dichloroethane; and aprotic solvents such as acetonitrile, N,N-dimethylformamide, dimethylsulfoxide, and hexamethylphosphoramide, and a mixture thereof. The base used herein is not limited as long as it is used in a normal reaction, which includes, for example, an organic base such as N-methylmorpholine, triethylamine, diisopropylethylamine, tributylamine, and pyridine; and an inorganic base such as sodium hydrogencarbonate, potassium hydrogen carbonate, sodium carbonate, and potassium carbonate.

The compound of formula (1Db) which is one of the compound-groups of formula (1D) can be prepared by suitably deprotecting the protecting groups from the compound of formula (1v) in manner well-known by a skilled person.

As one of the compound-groups of formula (1D), the present compound of formula (1Dd) can be prepared from compound of formula (1Dc), for example, according to Scheme 15 shown below.

Scheme 15:

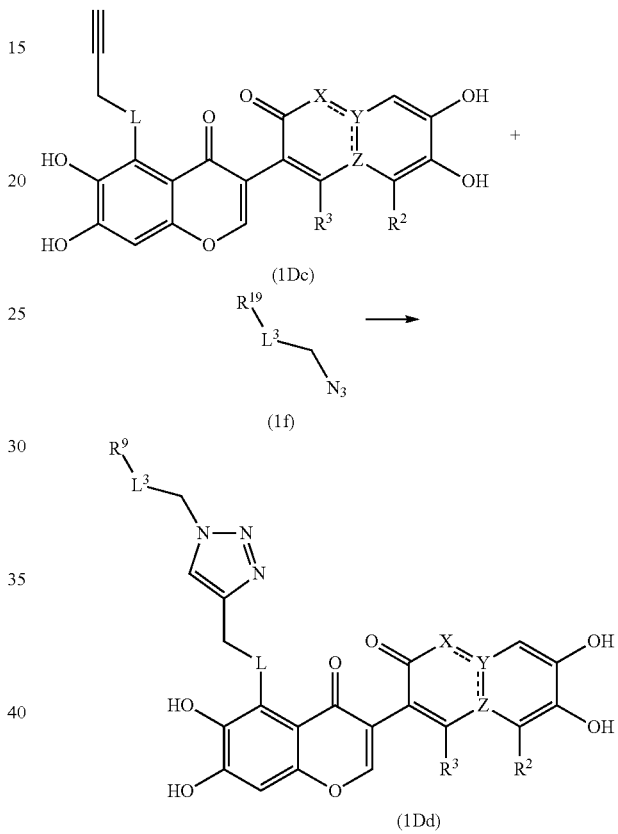

Wherein $R^9$ and $L^3$ are as defined in Term 2, $R^{19}$ is as defined in Scheme 4, $R^2$, $R^3$, x═══y═══z, X, Y, Z, and L are as defined in Term 1.

That is, the compound of formula (1Dc) which is one of the compound-groups of formula (1D) is reacted with a compound of formula (1f) at 0° C.-50° C. in a solvent (such as dimethylsulfoxide, N,N-dimethylformamide, 1,4-dioxane, tert-butanol, and water, or a combined solvent thereof), in the presence of a reducing agent (such as sodium ascorbate), a ligand (such as tris[(1-benzyl-1H-1,2,3-triazol-4-yl) methyl]amine), and a copper catalyst (such as copper sulfate and copper iodide). The compound of formula (1Dd) can be prepared by suitably deprotecting the protecting groups from the product in manner well-known by a skilled person. In addition, the compound of formula (1Dd) can be also obtained by using the compound of formula (1j) instead of the compound of formula (1f) in the above reaction.

The compound of formula (1ra) which is in the scope of the above-mentioned compound (1r) can be prepared from compound of formula (1w), for example, according to Scheme 16 shown below.

Scheme 16:

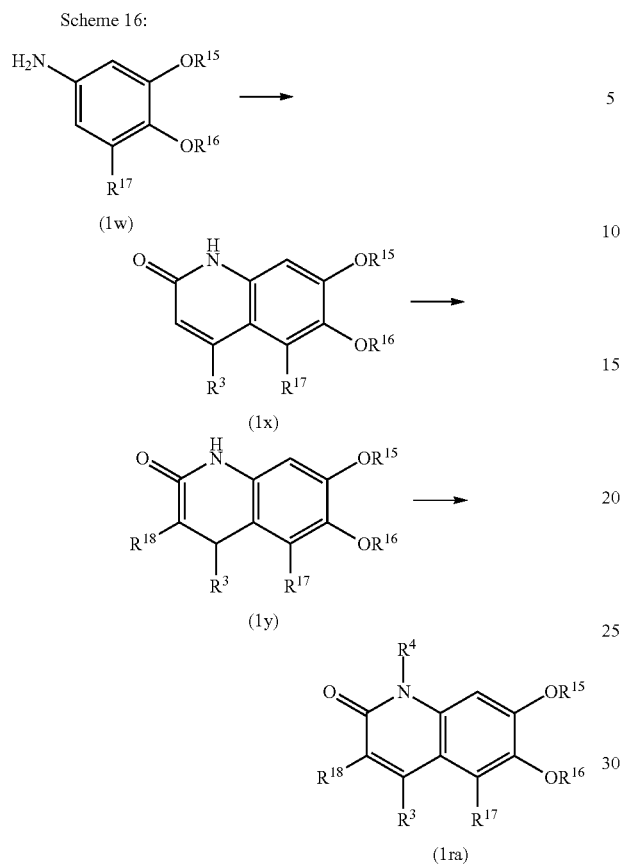

Scheme 17:

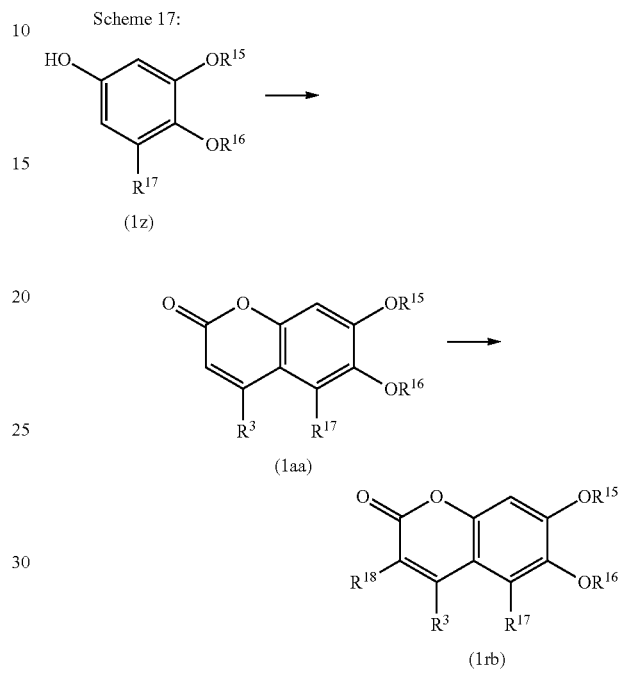

Wherein $R^3$ and $R^4$ is as defined in Term 1, $R^{15}$, $R^{16}$, $R^{17}$, and $R^{18}$ are as defined in Scheme 1.

That is, the compound of formula (1w) is reacted with a reagent corresponding to $R^3$ (such as ethyl 3-oxopropanoate, ethyl acetoacetate, and ethyl 3-oxovalerate) at 100° C.-200° C. without a solvent or in a solvent (such as toluene and xylene), and then the reaction mixture can be reacted at 0° C.-100° C. under acidic condition (such as under concentrated sulfuric acid) to give a compound of formula (1x). The compound of formula (1x) can be reacted with a halogenating agent such as N-iodosuccinimide and N-bromosuccinimide at 0° C.-100° C. in a solvent such as acetonitrile, tetrahydrofuran, N,N-dimethylformamide, and 1, 4-dioxane, sodium acetate or the like, and a halogenating agent such as bromine at 0° C.-100° C. in a solvent such as acetic acid, or potassium iodide or the like, and a halogenating agent such as iodine at 0° C.-100° C. in an aqueous sodium hydroxide solution, to give the compound of formula (1y).

The compound of formula (1y) can be reacted with a base (such as potassium carbonate and cesium carbonate), and an alkylating agent corresponding to $R^4$ (such as methyl iodide, ethyl iodide, and propyl iodide) at 0° C.-100° C. in a solvent (such as N,N-dimethylformamide and dimethylsulfoxide) to give the compound of formula (1ra).

The aniline compound of formula (1w) can be prepared, for example, in the manner disclosed in WO 2003/099762, or is commercially available.

The quinolin-2(1H)-one compound of formula (1x) can be prepared, for example, in the manner disclosed in *Heterocycles*, 65, p 2095-2105 (2005), or *Org. Lett.*, 16, p 3568-3571 (2014), or is commercially available.

The compound of formula (1rb) which is in the scope of the above-mentioned compound (1r) can be prepared from compound of formula (1z), for example, according to Scheme 17 shown below.

Wherein $R^3$ is as defined in Term 1, $R^{15}$, $R^{16}$, $R^{17}$, and $R^{18}$ are as defined in Scheme 1.

That is, the compound of formula (1z) can be reacted with a reagent corresponding to $R^3$ (such as ethyl 3-oxopropanoate, ethyl acetoacetate, and ethyl 3-oxovalerate) at 0° C.-100° C. under acidic condition (such as concentrated sulfuric acid, methanesulfonic acid, and p-toluenesulfonic acid) to give a compound of formula (1aa). In addition, the 2H-chromen-2-one compound of formula (1aa) is commercially available. The compound of formula (1aa) can be reacted with (i) a halogenating agent such as N-iodosuccinimide at 0° C.-100° C. in a solvent (such as acetonitrile, tetrahydrofuran and 1,4-dioxane), (ii) sodium acetate or the like, and a halogenating agent such as bromine at 0° C.-100° C. in a solvent (such as acetic acid), or (iii) potassium iodide or the like, and a halogenating agent such as iodine at 0° C.-100° C. in an aqueous sodium hydroxide solution, to give a compound of formula (1rb).

The compound of formula (1z) can be prepared, for example, in the manner disclosed in WO 2005/000838, or is commercially available.

The compound of formula (1ac) which is in the scope of the above-mentioned compound of $R^0$-LG can be prepared from compound of formula (1ab), for example, according to Scheme 18 shown below.

Scheme 18:

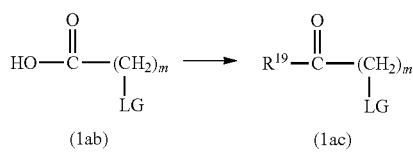

Wherein $R^{19}$ is as defined in Scheme 4, LG is as defined in Scheme 3, m is as defined in Term 2.

That is, compound (1ac) can be prepared by reacting a compound of formula (1ab) with an amino acid or peptide which is protected by using a condensing agent at 0° C.-50° C., in the presence of a base as necessary. The solvent used herein includes, for example, ether type solvents such as tetrahydrofuran, 1,4-dioxane, and 1,2-dimethoxyethane; halogenated hydrocarbon solvents such as dichloromethane, chloroform, and dichloroethane; and aprotic solvents such as acetonitrile, N,N-dimethylformamide, and dimethylsulfoxide. The base used herein includes, for example, triethylamine, diisopropylethylamine, pyridine, sodium hydrogencarbonate, potassium hydrogen carbonate, sodium carbonate, and potassium carbonate, which is not limited as long as it is used in a normal reaction. The condensing agent used herein includes what are disclosed in the 4th Series of Experimental Chemistry, Vol. 22 (Jikken Kagaku Kouza, edited by the Chemical Society of Japan, issued by MARUZEN).

In addition, the compound of formula (1ab) is reacted with a halogenating agent (such as 1-chloro-N,N,2-trimethylpropenylamine, phosphorus oxychloride, phosphorus trichloride, thionyl chloride, and phosphorus pentachloride) at 20° C.-120° C. to give an acid halide thereof, and then the acid halide can be reacted with a protected amino acid or a protected peptide at 0° C.-50° C. in the presence of a base as necessary to prepare compound (1ac). As the acid halide compound of formula (1ab), a commercially available one may be used. The solvent used herein includes, for example, ether type solvents such as tetrahydrofuran, 1,4-dioxane, and 1,2-dimethoxyethane; halogenated hydrocarbon solvents such as dichloromethane, chloroform, and dichloroethane; and aprotic solvents such as acetonitrile, N,N-dimethylformamide, and dimethylsulfoxide. The base used herein includes, for example, triethylamine, diisopropylethylamine, pyridine, sodium hydrogencarbonate, potassium hydrogen carbonate, sodium carbonate, and potassium carbonate, which is not limited as long as it is used in a normal reaction.

The carboxylic acid compound of formula (1ab) is commercially available.

The compound of formula (1ag) which is in the scope of the above-mentioned $R^0$-LG can be prepared from compound of formula (1ad), for example, according to Scheme 19 shown below.

Scheme 19:

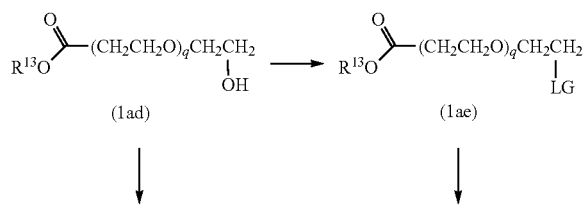

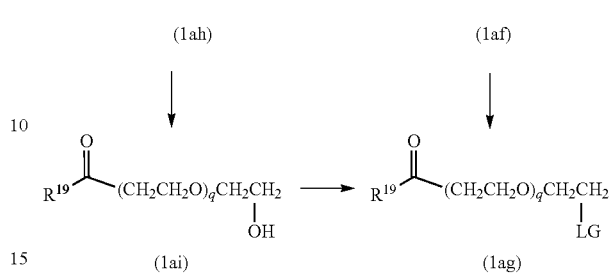

Wherein $R^{13}$ is as defined in Scheme 1, $R^{19}$ is as defined in Scheme 4, LG is as defined in Scheme 3, q is as defined in Term 2.

That is, compound (1ae) can be prepared by reacting compound (1ad) with methanesulfonyl chloride, p-toluenesulfonyl chloride, or the like at 0° C.-50° C. in the presence of a base such as triethylamine, diisopropylethylamine, pyridine, dimethylaminopyridine, sodium carbonate, and potassium carbonate. The compound of compound (1af) can be prepared by suitably deprotecting the protecting group $R^{13}$ from the compound of compound (1ae) in manner well-known by a skilled person. The compound (1af) can be reacted with a protected amino acid or a protected peptide together with a condensing agent in a solvent (such as tetrahydrofuran, dichloromethane, chloroform, acetonitrile, N,N-dimethylformamide, and dimethylsulfoxide), in the presence of a base as necessary to prepare compound (1ag). The base used herein includes, for example, triethylamine, diisopropylethylamine, pyridine, sodium hydrogencarbonate, potassium hydrogen carbonate, sodium carbonate, and potassium carbonate, which is not limited as long as it is used in a normal reaction. The condensing agent used herein includes what are disclosed in the 4th Series of Experimental Chemistry, Vol. 22 (Jikken Kagaku Kouza, edited by the Chemical Society of Japan, issued by MARUZEN). In addition, the compound (1af) is reacted with a halogenating agent (such as 1-chloro-N,N,2-trimethylpropenylamine, phosphorus oxychloride, phosphorus trichloride, thionyl chloride, and phosphorus pentachloride) at 20° C.-120° C. to give an acid halide thereof, and then the acid halide can be reacted with a protected amino acid or a protected peptide at 0° C.-50° C. in a solvent (such as tetrahydrofuran, dichloromethane, chloroform, acetonitrile, N,N-dimethylformamide, and dimethylsulfoxide), in the presence of a base as necessary to prepare compound (1ag). The base used herein includes, for example, triethylamine, diisopropylethylamine, pyridine, sodium hydrogencarbonate, potassium hydrogen carbonate, sodium carbonate, and potassium carbonate, which is not limited as long as it is used in a normal reaction. In the above-mentioned process from compound (1ad) to compound (1ag), it is possible to change the routes, i.e., first preparing compound (1ah), then transferring it to compound (1ai), and finally obtaining compound (1ag), as each method is the same as above.

The above-mentioned compound (1ad) is commercially available or can be prepared from a compound of formula (1aj), for example, according to Scheme 20 shown below.

Scheme 20:

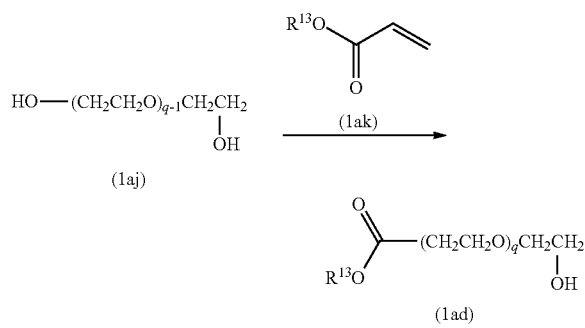

Wherein $R^{13}$ is as defined in Scheme 1, q is as defined in Term 2.

That is, compound (1ad) can be prepared by reacting compound (1aj) with compound (1ak) at 0° C.-80° C. under a basic condition. The base used herein includes, for example, metallic hydride such as sodium hydride, and metallic alkoxide such as potassium t-butoxide. The solvent used herein includes, for example, ether type solvents such as tetrahydrofuran, 1,4-dioxane, and 1,2-dimethoxyethane; halogenated hydrocarbon solvents such as dichloromethane, chloroform, and dichloroethane; and aprotic solvents such as acetonitrile, N,N-dimethylformamide, and dimethylsulfoxide.

The diol compound of formula (1aj) is commercially available.

In any processes of the present invention, if it is necessary to protect a specific functional group (such as hydroxy group and carboxyl group) in reactant reagents with a suitable protecting group, the functional group may be protected/deprotected with one or more protecting groups in manner well-known by a skilled person in a suitable step.

The compound of formula (1) or a pharmaceutically acceptable salt thereof exhibits the inhibitory activity of neuronal outgrowth-inhibitory factor, i.e., semaphorin inhibitory activity, specifically, semaphorin 3A inhibitory activity, and hence it is useful as a nerve regeneration promoter.

In addition, the compound of formula (1) or a pharmaceutically acceptable salt thereof is useful as a medicament for treating or preventing neurodegenerative disease or neuropathy disorder which includes a disease associated with neurodegeneration or neuropathy (neurological disorder) such as spinal cord injury. The typical disorder/disease includes, for example, dysosmia, traumatic neurological disorder, cerebral-infarct neurological disorder, facial palsy, diabetic neurosis, glaucoma, retinitis pigmentosa, dry eye, Alzheimer's disease, Parkinson's disease, neurodegenerative disease, muscular dysgenic lateral sclerosis, amyotrophic lateral sclerosis, Huntington's disease, cerebral infarct, and traumatic neurodegenerative disease.

The above-mentioned neuropathy disorder or neurodegenerative disease which includes a disease associated with neurodegeneration or neurological disorder such as spinal cord injury includes, for example, neuropathy disorder including a disease associated with central nerve injury, neuropathy disorder including a disease associated with peripheral nerve injury, and central neurodegenerative disease.

The neuropathy disorder including a disease associated with central nerve injury includes, for example, neurological disorder caused by injury such as spinal cord injury, neurological disorder caused by cerebral infarct or the like, and facial palsy.

The neuropathy disorder including a disease associated with peripheral nerve injury includes, for example, dysosmia caused by aging or the like, facial palsy, diabetic neurosis, glaucoma, and dry eye. The central neurodegenerative disease includes, for example, Alzheimer's disease, Parkinson's disease, amyotrophic lateral sclerosis, Huntington's disease, traumatic neurodegenerative disease, and muscular dysgenic lateral sclerosis.

Furthermore, the compound of formula (1) or a pharmaceutically acceptable salt thereof is useful as a medicament for treating or preventing a disease associated with angiogenesis that VEGF165 takes a role in, which have a common receptor, neuropilin.

The compound of formula (1) or a pharmaceutically acceptable salt thereof can promote the regeneration of olfactory nerve or sensory nerve which is a peripheral nerve; and the regeneration of central nerve which is located medial to cerebrospinal barrier, such as olfactory bulb, cerebral cortex, hippocampus, striatum, thalamus, diencephalon, midbrain, cerebellum, pons, medulla oblongata, spinal cord, and retina in brain or spinal cord.

The compound of formula (1) or a pharmaceutically acceptable salt thereof is useful as a medicament for treating or preventing a neurological disease associated with ischemic damage. The neurological disease associated with ischemic damage (ischemic neuronal disease) used herein includes retinal neurological disorder caused by ischemia, and ischemic cerebrovascular disease. The retinal neurological disorder used herein includes, for example, glaucoma, central retinal artery occlusion, central branch retinal artery occlusion, central retinal vein occlusion, central branch retinal vein occlusion, ischemic optic neuropathy, diabetic retinopathy, macular degeneration, and retinopathy of prematurity, preferably diabetic retinopathy. And, the ischemic cerebrovascular disease used herein includes, for example, cerebral emboli, transient cerebral ischemia, subclavian steal syndrome, Wallenberg's syndrome (lateral medullary syndrome), cerebral thrombosis, lacunar infarct, reversible ischemic neurological deficit, cerebral infarct, moyamoya disease (spontaneous occlusion of the circle of Willis), cerebral hypoxia, sinus thrombosis, and postoperative spinal cord ischemia. The compound of the present invention has a protective effect for retinal neuron, and it is useful for treating or preventing retinal neurological disorder caused by ischemia, especially.

In addition, the compound of formula (1) or a pharmaceutically acceptable salt thereof is useful as a medicament for treating or preventing corneal disease. The corneal disease used herein includes, for example, dry eye, keratitis, leukoma, corneal infection, corneal degeneration, corneal dystrophy, corneal stromal dystrophy, bullous keratopathy, keratoconus, corneal endothelial decompensation, corneal ulcer, nerve-paralytic keratopathy, diabetic keratopathy, chemical ocular injury, and corneal burn. Preferably, it includes dry eye, keratitis, bullous keratopathy, corneal ulcer, nerve-paralytic keratopathy, and diabetic keratopathy, more preferably dry eye.

The promoting activity of nerve regeneration in a nerve regeneration promoter denotes a promoting effect of nerve regeneration in central nerve and/or peripheral nerve, i.e., which means promoting activity for nerve regeneration in central tissue composed of brain, spinal cord, and the like, and peripheral tissue that is various tissues of body surface and body inside located in marginal/peripheral sites which are other than central tissue. The nerve regeneration for nerve regeneration in central nerve includes, not only nerve regeneration that the perikaryon located in central region such as retinal neuron and cerebral cortical neuron puts out axon to project to another nerve cell located in the same central region, but also nerve regeneration that nerve out of perikaryon located in peripheral region (for example, central fiber such as olfactory nerve, dorsal root ganglion neuron) regenerates in circumstance of neuroaxis regeneration in central tissue. The nerve regeneration for nerve regeneration in peripheral nerve includes, not only nerve regeneration that the perikaryon located in peripheral region puts out axon which extends in peripheral tissue, but also nerve regeneration that nerve out of perikaryon located in central region such as brain and spinal cord regenerates in circumstance of peripheral tissue. The latter includes, for example, promoting activity of nerve regeneration in spinal cord motor nerve, and preganglionic neuron in autonomic nervous system of sympathetic nerve/parasympathetic nerve. In addition, it also includes promoting activity of nerve regeneration involved in the above both nerves such as sciatic nerve.

The growth cone collapse activity of semaphorin means the activity to abolish the growth cone observed in the culture prepared in the following process: cultivating nerve cell (in general, a tissue fragment of ganglion) in vitro for a given period, getting the extended neurite and the growth cone in the tip of the neurite to be in an observable state, then adding semaphorin having a give concentration (for example, about 3 units/mL; in which 1 unit/mL means the concentration of semaphorin to retract the growth cone in 50%) thereto, and continuing the cultivation additionally for a given period (for example, one hour). In order to get the extended neurite and the growth cone in the tip of the neurite to be in an observable state, the in vitro cultivation of nerve cell is done generally for 10 hours to 20 hours, but it may be suitably changed depending on the kind of the nerve and the condition of cultivation. In this experiment, for example, if semaphorin is added to the medium 1-60 minutes after a compound having a certain concentration is added thereto, and the growth cone collapse caused by semaphorin is suppressed, it can be assessed that the compound is a semaphorin inhibitor, in particular, a compound having the suppressing action on the growth cone collapse activity caused by semaphorin.

And, the nerve outgrowth inhibitory activity in a collagen gel of semaphorin means, for example, a nerve outgrowth inhibitory activity observed in a collagen gel containing both of semaphorin-producing cell and nerve cell (generally, ganglion). The suppressing action on the neuronal outgrowth inhibitory activity is assessed by cultivating semaphorin-producing cell close to nerve cell in a collagen gel, keeping the culture generally for more than one overnight, and then observing the neurite outgrowth therein.

The semaphorin in the present invention means a collective term of proteins having a similar semaphorin domain structure composed of about 500 amino acid residues, more than about 20 proteins of which have been reported until now, but the present invention should not be limited to these known semaphorins. The semaphorin in the present invention includes semaphorins of mammal such as human being, preferably class 3, 4, 5 or 6 semaphorins which are defined in literatures, more preferably class 3 or 6 semaphorins. The class 3 semaphorins include semaphorin 3A, and the class 6 semaphorins include semaphorin 6C. The gene sequence information encoding these semaphorins is published in GenBank database or known literatures.

The pharmaceutical composition comprising the compound of formula (1) or a pharmaceutically acceptable salt thereof as an active ingredient may be transformed with suitable additives to a drug formulation and be administered orally or parenterally. The method for parenteral administration includes, for example, transdermal, transnasal, injectable, ophthalmic, and internal. The formulation for oral administration includes, for example, tablet, pill, powder, granule, capsule, syrup, emulsion, liquid, and suspension. And the formulation for parenteral administration includes, for example, intramuscular injection, subcutaneous injection, intradermal injection, eye drop, eye ointment, endermic liniment (such as ointment, lotion, and cream), nasal drop (spray for nasal administration), patch, and suppository. The liquid formulation can be suitably selected to solution, emulsion, suspension, or the like. The formulation of the present invention can be prepared with pharmaceutically acceptable additives in a known manner.

The above-mentioned additives include a pharmaceutically acceptable conventional carrier, and according to the intended use, an excipient, a disintegrant, a diluent, a pH adjuster, an isotonic agent, a binder, a fluidizer, a lubricant, a coating agent, a solubilizer, a solubilizing agent, a thickener, a dispersant, a stabilizing agent, a sweetening agent, a surfactant, an emulsifying agent, a flavor, etc. can be used. The additive used herein includes, for example, lactose, mannitol, microcrystalline cellulose, low-substituted hydroxypropylcellulose, cornstarch, partially-pregelatinized starch, carmellose calcium, croscarmellose sodium, hydroxypropylcellulose, hydroxypropyl methylcellulose, polyvinyl alcohol, magnesium stearate, sodium stearyl fumarate, polyethylene glycol, propylene glycol, titanium oxide, talc, and the like.

The dose and the administration frequency can depend on the administration route and patient's age, body weight, condition, etc., but it is preferable to administer the drug formulation topically to lesion site. It is preferable to administer the drug once a day, or two or more a day. When the drug is administered two or more times, it is preferable to do repeatedly in days or in suitable intervals. It takes generally more than several days to several months to regenerate nerve, thus it is preferable to administer the drug continually in the therapy duration to inhibit the semaphorin action.

In case of sustained-release formulation, it is not necessary to administer the drug repeatedly as long as the drug is sustainably released after the administration.

The dose for an adult can be 50 µg-2 g, preferably 5 mg-100 mg per day, as the amount of the active ingredient, and can be administered once or in portions a day. In order to reduce the administration frequency, it is possible to use a sustained-release formulation, or administer the drug gradually for a long time by using an osmotic pump. When the drug is parenterally administered, the dose for an adult can be 0.01 mg-100 mg a day, more preferably 0.1 mg-50 mg a day, and can be administered once or in portions a day. In particular, as for eye drop, the daily dose of the active ingredient includes 0.01-10 mg a day, preferably 0.1 mg-1 mg a day. In case of sustained-release formulation, the dose to be administered can be adjusted so that the daily releasing amount can be in the above-mentioned range, thereby it is possible to reduce the administration frequency.

In case of eye drop, the formulation can be administered in 0.01 w/v %-10 w/v %, preferably 0.05 w/v %-5 w/v % to an adult patient, and preferably 1-several drops for one administration, 1-6 times a day, depending on the patient's condition. And in case of eye ointment, the formulation can be administered in 0.01 w/w %-10 w/w %, preferably 0.1 w/w %-5 w/w %, and preferably 1-6 times a day, depending on the patient's condition.

For any administration methods, it is preferable to choose the administration route and the administration details to make the drug concentration enough to inhibit semaphorin action in the therapy site.

In addition, the utility of the present medicament for treatment or prevention should not be limited to drugs for treatment or prevention of neuropathy disorder and/or neurodegenerative disease, that is, it can be used as a veterinary drug, and additionally as an experimental reagent which is industrially important as an inhibitor of semaphorin signal.

EXAMPLES

The present invention is explained in more detail in the following by referring to Reference examples, Examples, and Tests; however, the technical scope of the present invention is not limited to such Examples and the like. Each compound was identified with high-performance liquid chromatograph-mass spectrometer, LCMS, NMR spectrum, high-performance liquid chromatography (HPLC), and other instruments.

In the following Reference examples, Examples, and Tables in Examples, the abbreviations shown below may be sometimes used to simplify the description of the present specification. The abbreviations in the substituents mean as follows: Me: methyl, Bu: butyl, tBu: tert-butyl, Ac: acetyl, Piv: pivaloyl, MOM: methoxymethyl, TMS: trimethylsilyl. The abbreviations in the solvents mean as follows: DMF: N,N-dimethylformamide, NMP: N-methyl-2-pyrrolidone, THF: tetrahydrofuran. The abbreviations in the NMR data mean as follows: s: singlet, d: doublet, dd: double doublet, t: triplet, td: triple doublet, q: quartet, m: multiplet, br: broad, brs: broad singlet, brm: broad multiplet, and J: coupling constant. The abbreviation in the LC/MS means, Rt: retention time.

High-performance liquid chromatography-mass spectrometer: the measuring condition of LCMS is shown below, and the detected value of mass spectrography [MS (m/z)] is shown as M+H.

Condition (1)
MS detector: ACQUITY SQD
HPLC: ACQUITY UPLC
Column: ACQUITY UPLC BEH C18 1.7 μm, 2.1×50 mm
Flow rate: 0.75 mL/min
Wave length: 254 nm
Mobile phase: A: 0.05% aqueous formic acid
  B: acetonitrile
Time Program:

| Step | Time (min) |
|---|---|
| 1 | 0.0-1.3 A:B = 90:10 => 1:99 |
| 2 | 1.3-1.5 A:B = 1:99 |
| 3 | 1.5-2.0 A:B = 90:10 |

Condition (2)
MS detector: SHIMADZU SPD-M20A
HPLC: SHIMADZU LCMS-2020
Column: Kinetix 1.7 u C-18 100 A
Flow rate: 0.50 mL/min
Wave length: 220, 254 nm
Mobile phase: A: 0.05% aqueous formic acid
  B: acetonitrile
Time program:

| Step | Time (min) |
|---|---|
| 1 | 0.0-1.7 A:B = 90:10 => 1:99 |
| 2 | 1.7-1.9 A:B = 1:99 |
| 3 | 1.9-3.0 A:B = 90:10 |

Condition (3)
MS detector: ACQUITY SQD
HPLC: Waters ACQUITY UltraPerformance LC
Column: ACQITY UPLC BEH C18 1.7 μm 2.1×30 mm
Flow rate: 0.80 mL/min
Wave length: 254 nm
Mobile phase: A: 0.05% aqueous formic acid
  B: acetonitrile
Time program:

| Step | Time (min) |
|---|---|
| 1 | 0.0-1.3 A:B = 90:10 => 1:99 |
| 2 | 1.3-1.5 A:B = 1:99 |
| 3 | 1.5-2.0 A:B = 90:10 |

Reference Example 1

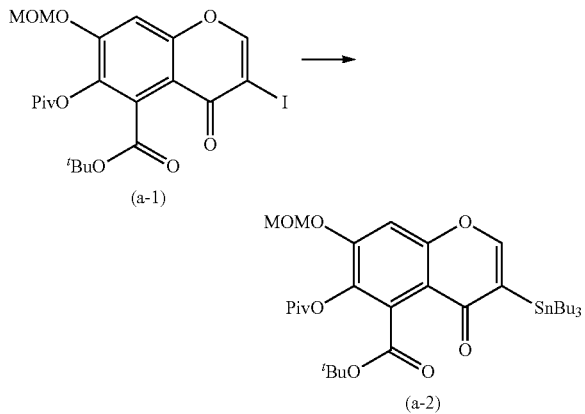

According to a literature (*Angew. Chem. Int. Ed.*, 52, p 3421-3424 (2013)), Compound (a-1) was synthesized. The prepared Compound (a-1) (5.3 g, 10 mmol) was dissolved in tetrahydrofuran (30 mL), and the mixture was cooled to −78° C. To the cooled mixture was added 2 mol/L isopropylmagnesium chloride solution (5.5 mL, 11 mmol) The mixture was stirred at −78° C. for 30 minutes, and then tributyltin chloride (3.3 mL, 12 mmol) was added thereto. The reaction mixture was stirred at −78° C. for one hour. Water was added thereto, and the mixture was extracted with ethyl acetate. The organic layer was washed with brine, dried over magnesium sulfate, and concentrated in vacuo. The obtained residue was purified by silica gel column chromatography (hexane:ethyl acetate=90:10-5:95) to give Compound (a-2) (3.7 g, 53% yield).

$^1$H-NMR (CDCl$_3$, 300 MHz) δ: 7.40 (s, 1H), 7.08 (s, 1H), 5.18 (s, 2H), 3.42 (s, 3H), 1.57 (s, 9H), 1.45-1.56 (m, 6H), 1.35 (s, 9H), 1.22-1.33 (m, 6H), 1.06-1.00 (m, 6H), 0.86 (t, J=7.5 Hz, 9H).

Reference Example 2

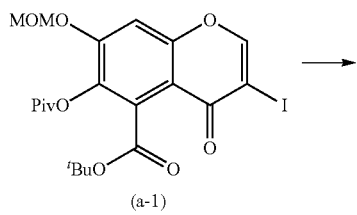

(a-1)

→

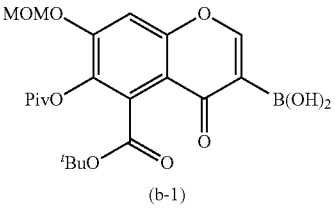

(b-1)

Compound (a-1) (21.28 g, 40.0 mmol) was dissolved in tetrahydrofuran (100 mL), and the solution was cooled in acetone-dry ice bath. To the solution was added 1.3 mol/L isopropylmagnesium chloride-lithium chloride/tetrahydrofuran solution (43.1 mL, 56.0 mmol) dropwise over 15 minutes, and the mixture was stirred for 15 minutes. To the mixture was added trimethyl borate (10.4 g, 100 mmol) dropwise, and the mixture was warmed to room temperature. 5% Aqueous ammonium chloride (280 mL) was added thereto, and the mixture was extracted with a mixture of toluene (240 mL) and ethyl acetate (50 mL). The organic layer was washed with water, and concentrated in vacuo to dryness. The obtained crude product was stirred in toluene (30 g) to obtain a suspension, and the suspension was filtrated. The product on the filter was dried to give Compound (b-1) (15.8 g, 88% yield).

$^1$H-NMR (CDCl$_3$, 400 MHz) δ: 8.24 (s, 1H), 7.19 (s, 1H), 6.85-6.70 (brs, 2H), 5.22 (s, 2H), 3.43 (s, 3H), 1.60 (s, 9H), 1.36 (s, 9H)

Reference Example 3

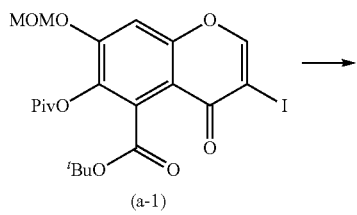

(a-1)

→

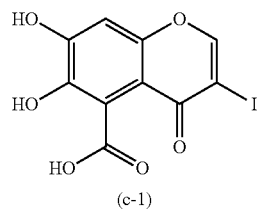

(c-1)

Compound (a-1) (63.88 g, 120 mmol) was suspended in toluene (255 g), and trifluoroacetic acid (410 g, 3.60 mol) was added to the suspension. The suspension was stirred at room temperature for one hour, warmed to 50° C., and then stood at the same temperature for 2.5 hours to deposit a crystal. The suspension was cooled in ice bath and the precipitated crystal was collected on a filter. The crystal was washed with toluene (250 mL) and acetonitrile (250 mL), and dried in vacuo to give Compound (c-1) (29.97 g, 71.8% yield).

$^1$H-NMR (DMSO-d$_6$, 400 MHz); 13.5-12.0 (brs, 1H), 11.37 (s, 1H), 9.41 (brs, 1H), 8.63 (s, 1H), 6.92 (s, 1H).

Reference Example 4

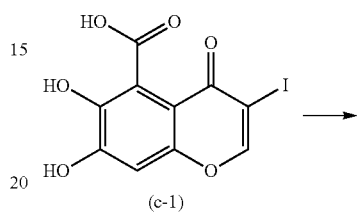

(c-1)

→

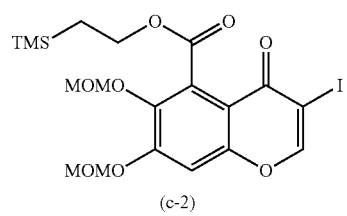

(c-2)

Compound (c-1) (13.92 g, 40.0 mmol) was suspended in dichloromethane (200 mL), and dry N,N-dimethylformamide (7.7 mL, 100 mmol) was added to the suspension. To the ice-cooled suspension were added oxalyl chloride (7.11 g, 56.0 mol) dropwise over 20 minutes, and then additional oxalyl chloride (2.03 g, 16.0 mmol) dropwise. After stirring the mixture for 30 minutes, (2-trimethylsilyl)ethanol (25.0 g, 280 mmol) was added dropwise thereto. After stirring the mixture for 20 minutes, the reaction mixture was concentrated in vacuo to remove about 50 mL of the solvent. To the concentrated residue was added toluene (50 mL), and the mixture was cooled in ice bath. The mixture was filtrated and washed with a small amount of dichloromethane. The filtrate was cooled in ice bath, and N,N-diisopropylethylamine (65.16 g, 504 mmol) and chloromethyl methyl ether (24.2 g, 300 mmol) were added dropwise to the filtrate. Water (100 mL) was added thereto, and the mixture was concentrated in vacuo to remove most of the dichloromethane. To the concentrated mixture were added toluene (150 mL) and water (50 mL), and the mixture was separated with a separating funnel. The aqueous layer was extracted with toluene (100 mL). The combined organic layer was washed with water, and concentrated in vacuo. To the residual liquid was added n-heptane (100 mL), and the precipitated crystal was collected on a filter. To the obtained crude crystal (18.95 g) was added 2-propanol (55.7 g), and the mixture was heated at about 60° C. to be dissolved. Then, water (27.8 g) was added dropwise thereto. The obtained homogeneous solution was cooled to deposit a crystal. The suspension was cooled and the precipitated crystal was collected on a filter. The crystal was washed with 67% aqueous 2-propanol, and dried in vacuo to give Compound (c-2) (14.25 g, 67% yield).

$^1$H-NMR (CDCl$_3$, 400 MHz) δ: 8.19 (s, 1H), 7.21 (s, 1H), 5.31 (s, 2H), 5.18 (s, 2H), 4.65-4.50 (m, 2H), 3.58 (s, 3H), 3.51 (s, 3H), 1.20-1.10 (m, 2H), 0.07 (s, 9H).

Reference Example 5

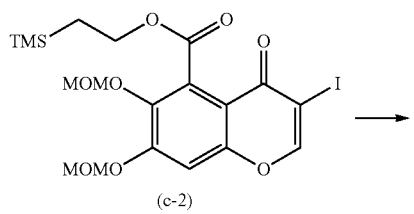

A solution of Compound (c-2) (9.84 g, 18.4 mmol) in dry tetrahydrofuran (100 mL) was cooled in acetone-dry ice bath. To the solution was added 1.3 mol/L isopropylmagnesium chloride-lithium chloride/tetrahydrofuran solution (20.0 mL, 26.0 mmol) dropwise, and the mixture was stirred for 40 minutes. To the mixture was added trimethyl borate (5.72 g, 55.1 mmol) dropwise, and the mixture was warmed to room temperature. 2% Aqueous ammonium chloride (120 mL) was added thereto, and most of the tetrahydrofuran was removed out by the concentration in vacuo. The mixture was extracted with ethyl acetate (150 mL), and the organic layer was washed with water (100 mL), dried over anhydrous sodium sulfate, and concentrated in vacuo to dryness. The obtained crude product was re-crystallized from ethyl acetate-heptane to give Compound (c-3) (5.89 g, 71% yield).

$^1$H-NMR (DMSO-$d_6$, 400 MHz) δ: 8.46 (s, 1H), 8.41 (s, 1H), 7.41 (s, 1H), 5.44 (s, 2H), 5.12 (s, 2H), 4.45-4.30 (m, 2H), 3.46 (s, 3H), 3.44 (s, 3H), 1.10-1.00 (m, 2H), 0.03 (s, 9H).

Reference Example 6

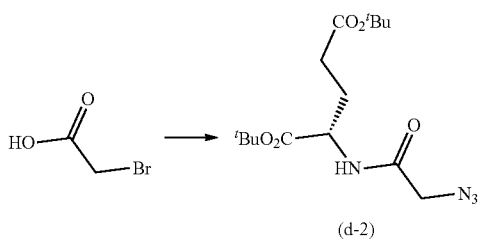 [SMILES: O=C(O)CBr ; CC(C)(C)OC(=O)CC[C@H](NC(=O)CN=[N+]=[N-])C(=O)OC(C)(C)C]

To a solution of 2-bromoacetic acid (1.7 g, 12 mmol) in N,N-dimethylformamide (12 mL) was added sodium azide (0.78 g, 12 mmol). The mixture was stirred at room temperature for 16 hours, and then N,N'-diisopropylcarbodiimide (0.76 g, 6.0 mmol) was added thereto. After stirring the reaction mixture at room temperature for one hour, di-tert-butyl L-glutamate hydrochloride (0.89 g, 3.0 mmol) and diisopropylethylamine (0.51 mL, 3.0 mmol) were added thereto. After stirring the reaction mixture at room temperature for 8 hours, water was added to the reaction mixture, and the mixture was extracted with ethyl acetate. The organic layer was washed with brine, dried over magnesium sulfate, and then concentrated in vacuo. The obtained residue was purified by silica gel column chromatography (hexane:ethyl acetate=90:10-50:50) to give Compound (d-2) (0.87 g, 85% yield).

$^1$H-NMR (CDCl$_3$, 300 MHz) δ: 6.98-6.94 (br, 1H), 4.44-4.51 (m, 1H), 3.98 (s, 2H), 1.88-2.32 (m, 4H), 1.46 (s, 9H), 1.43 (s, 9H).

Reference Example 7

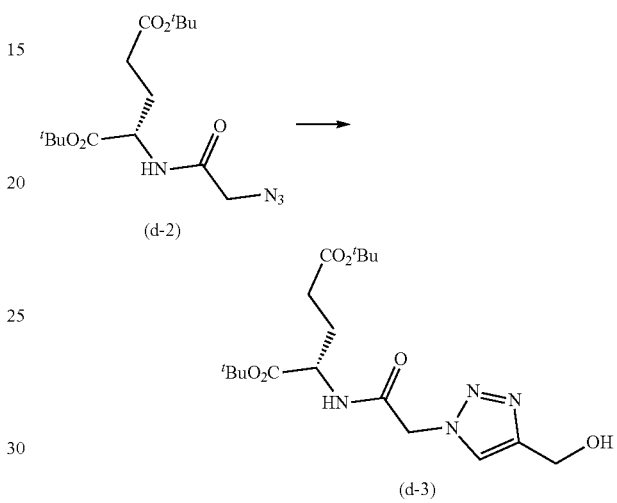

To a solution of Compound (d-2) (1.71 g, 5.00 mmol) in NMP (5 mL) was added propargyl alcohol (390 mg, 6.00 mmol). To the mixture were added a solution of copper sulfate pentahydrate (62 mg, 0.250 mmol) in water (1 mL), and then sodium ascorbate (99 mg, 0.500 mmol). The reaction mixture was stirred at room temperature. After one hour, water was added thereto, and the mixture was extracted with chloroform 3 times. The combined organic layer was washed with water, and concentrated in vacuo to dryness. The obtained crude product was purified by silica gel column chromatography (chloroform—methanol) to give Compound (d-3) (1.84 g, 92% yield).

$^1$H-NMR (CDCl$_3$, 400 MHz) δ: 7.72 (s, 1H), 6.80 (d, J=7.6 Hz, 1H), 5.10 (d, J=16.4 Hz, 1H), 5.05 (d, J=16.4 Hz, 1H), 4.82 (s, 2H), 4.46 (ddd, J=8.0, 8.0, 4.8 Hz, 1H), 2.32-2.20 (m, 2H), 2.15-2.05 (m, 1H), 1.95-1.85 (m, 1H), 1.45 (s, 9H), 1.44 (s, 9H).

Reference Example 8

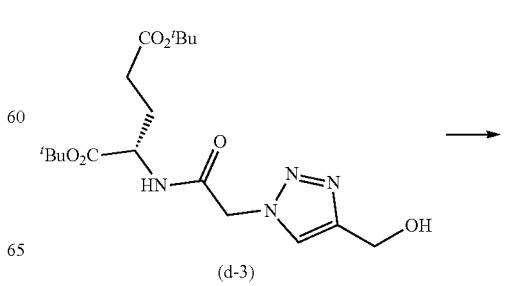

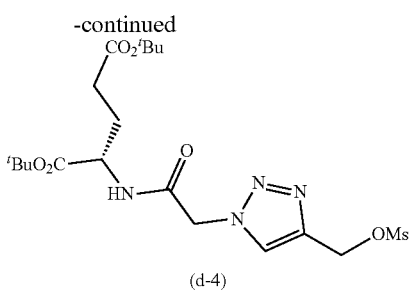

(d-4)

To a solution of Compound (d-3) (1.25 g, 3.14 mmol) in dichloromethane (15 mL) was added triethylamine (0.65 g, 5.02 mmol) at ice temperature, then methanesulfonyl chloride (0.47 g, 4.08 mmol) dropwise. After 30 minutes, water (10 mL) was added thereto, and the organic layer was separated out. The aqueous layer was extracted with dichloromethane (10 mL), and the combined organic layer was concentrated in vacuo to dryness. The obtained crude product was purified by silica gel column chromatography (chloroform—ethyl acetate) to give Compound (d-4) (1.13 g, 75.6% yield).

$^1$H-NMR (CDCl$_3$, 400 MHz) δ: 7.92 (s, 1H), 6.83 (d, J=7.2 Hz, 1H), 5.40 (s, 2H), 5.12 (d, J=16.4 Hz, 1H), 5.08 (d, J=16.4 Hz, 1H), 4.45 (ddd, J=4.8, 4.8, 2.0 Hz, 1H), 3.03 (s, 3H), 2.40-1.90 (m, 4H), 1.46 (s, 9H), 1.44 (s, 9H).

Reference Example 9

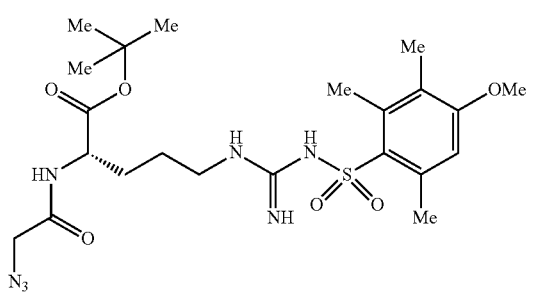

(e-1)

According to the method described in Reference example 6, provided that tert-butyl N-w-(4-methoxy-2,3,6-trimethylbenzenesulfonyl)-L-arginine (1.3 g, 3.0 mmol) was used instead of di-tert-butyl glutamate hydrochloride (0.89 g, 3.0 mmol), Compound (e-1) was prepared (1.0 g, 63% yield).

$^1$H-NMR (CDCl$_3$, 300 MHz) δ: 7.00-7.03 (br, 1H), 6.51 (s, 1H), 6.11-6.02 (br, 3H), 4.37-4.44 (m, 1H), 3.98 (s, 2H), 3.80 (s, 3H), 3.19-3.31 (m, 2H), 2.67 (s, 3H), 2.59 (s, 3H), 2.15 (s, 3H), 1.52-1.88 (m, 4H), 1.45 (s, 9H).

Reference Example 10

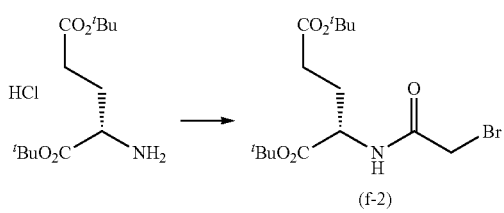 [SMILES: Cl ; CC(C)(C)OC(=O)CC[C@H](N)C(=O)OC(C)(C)C ; CC(C)(C)OC(=O)CC[C@H](NC(=O)CBr)C(=O)OC(C)(C)C]

(f-2)

di-tert-Butyl glutamate hydrochloride (0.70 g, 2.3 mmol) was dissolved in chloroform (11 mL), and then bromoacetyl bromide (0.43 g, 2.2 mmol) was added thereto. After stirring the reaction mixture at room temperature for 3 hours, saturated aqueous ammonium chloride was added to the reaction mixture, and the mixture was extracted with chloroform. The organic layer was washed with brine, dried over sodium sulfate, and then concentrated in vacuo. The obtained residue was purified by silica gel column chromatography (chloroform:methanol=100:0-98:2) to give Compound (f-2) (0.82 g, 100% yield).

$^1$H-NMR (CDCl$_3$, 400 MHz) δ: 7.09 (d, J=7.8 Hz, 1H), 4.47 (td, J=7.8, 4.6 Hz, 1H), 3.88 (s, 2H), 2.38-2.13 (m, 3H), 2.00-1.91 (m, 1H), 1.48 (s, 9H), 1.45 (s, 9H).

Reference Example 11

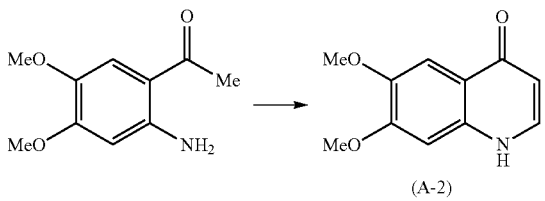

(A-2)

To a solution of 2'-amino-4',5'-dimethoxyacetophenone (4.9 g, 25 mmol) in dimethoxyethane (150 mL) was added sodium methoxide (7.5 g, 0.14 mol), and the reaction mixture was stirred at room temperature for 30 minutes. Ethyl formate (12 mL, 0.15 mol) was added thereto. After stirring the reaction mixture at room temperature for 2 hours, 2 mol/L hydrochloric acid (25 mL) was added to the reaction mixture, and the mixture was extracted with ethyl acetate. The organic layer was washed with brine, dried over magnesium sulfate, and then concentrated in vacuo. To the residue was added 4 mol/L hydrogen chloride in dioxane (30 mL). After stirring the reaction mixture at 50° C. for one hour, the reaction mixture was cooled to room temperature, and the generated solid was collected on a filter and dried to give Compound (A-2) (3.5 g, 68% yield). LC/MS (Condition (1)): [M+H]$^+$/Rt=206/0.42 min Reference Example 12

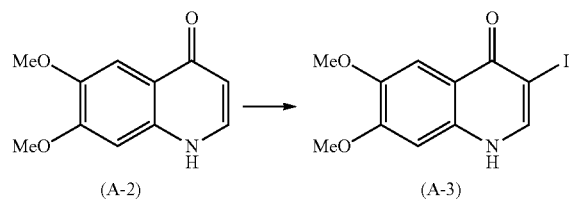

(A-2)    (A-3)

Compound (A-2) (2.0 g, 9.8 mmol) was dissolved in 2 mol/L aqueous sodium hydroxide (20 mL), and then iodine (3.0 g, 12 mmol) in 20% aqueous potassium iodide (20 mL) was added thereto. After stirring the reaction mixture at room temperature for one hour, the reaction mixture was neutralized with acetic acid, and the generated solid was collected on a filter. The obtained solid was washed with ethanol and dried to give Compound (A-3) (2.2 g, 68% yield).

LC/MS (Condition (1)): [M+H]$^+$/Rt=331/0.55 min

Reference Example 13

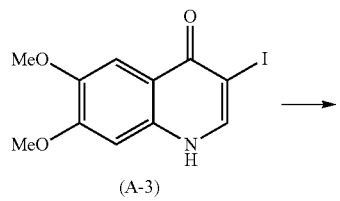

(A-3)

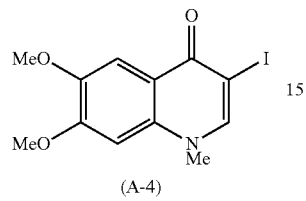

(A-4)

To a solution of Compound (A-3) (1.50 g, 4.5 mmol) in N,N-dimethylformamide (20 mL) were added cesium carbonate (2.2 g, 6.8 mmol) and methyl iodide (1.4 mL, 23 mmol), and the reaction mixture was stirred at room temperature for one hour. Water was added to the reaction solution, and the generated solid was collected on a filter. The obtained crude product was washed with ethanol to give Compound (A-4) (1.2 g, 78% yield).

LC/MS (Condition (1)): [M+H]$^+$/Rt=345/0.63 min

Reference Example 14

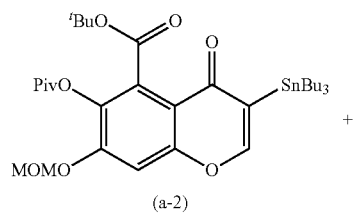

(a-2)

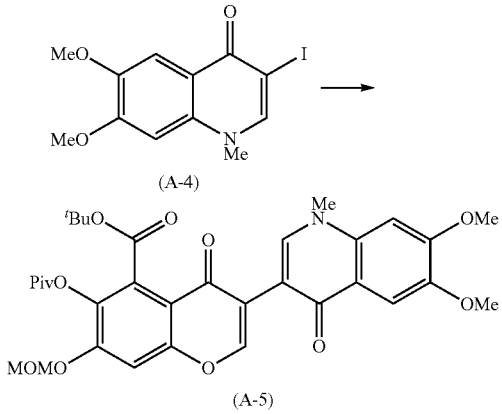

(A-5)

To a solution of Compound (A-4) (17 mg, 50 nmol) in N,N-dimethylformamide (0.5 mL) were added toluene (0.5 mL), Compound (a-2) (35 mg, 50 nmol), potassium carbonate (35 mg, 0.25 mmol), copper iodide (1.0 mg, 5.0 nmol), and tetrakis(triphenylphosphine)palladium (2.9 mg, 2.5 nmol). After stirring the reaction mixture at 100° C. under nitrogen atmosphere for 2 hours, the reaction mixture was cooled to room temperature, water was added to the reaction mixture, and the mixture was extracted with ethyl acetate. The organic layer was washed with brine, dried over magnesium sulfate, and then concentrated in vacuo. The obtained residue was purified by silica gel column chromatography (chloroform:methanol=99:1-80:20) to give Compound (A-5) (10 mg, 32% yield).

LC/MS (Condition (1)): [M+H]$^+$/Rt=624/1.13 min

Example 1

3-(6,7-Dihydroxy-1-methyl-4-oxo-1,4-dihydroquinolin-3-yl)-6,7-dihydroxy-4-oxo-4H-chromene-5-carboxylic acid

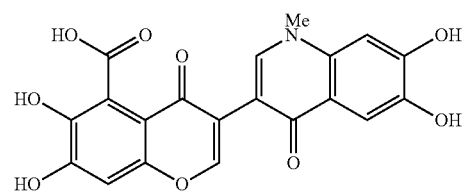 [SMILES: Cn1cc(-c2coc3cc(O)c(O)c(C(=O)O)c3c2=O)c(=O)c2cc(O)c(O)cc21]

To a solution of Compound (A-5) (10 mg, 16 nmol) in chloroform (1 mL) was added boron tribromide (1 mol/L dichloromethane solution) (1 mL, 1 mmol). After stirring the reaction mixture at room temperature for one hour, methanol and toluene were added to the reaction mixture, and water in the mixture was removed by azeotropy to obtain a dried residue. The obtained crude product was washed with methanol to give the title compound (3 mg, 45% yield)

LC/MS (Condition (1)): [M+H]$^+$/Rt=412/0.49 min $^1$H-NMR (DMSO-d$_6$, 400 MHz) δ: 11.28 (brs, 1H), 10.21 (brs, 1H), 9.81 (brs, 1H), 9.42 (brs, 1H), 8.63 (s, 1H), 8.33 (s, 1H), 7.57 (s, 1H), 6.99 (s, 1H), 6.94 (s, 1H), 3.82 (s, 3H).

Example 2

Prop-2-yn-1-yl 3-(6,7-dihydroxy-1-methyl-4-oxo-1,4-dihydroquinolin-3-yl)-6,7-dihydroxy-4-oxo-4H-chromene-5-carboxylate

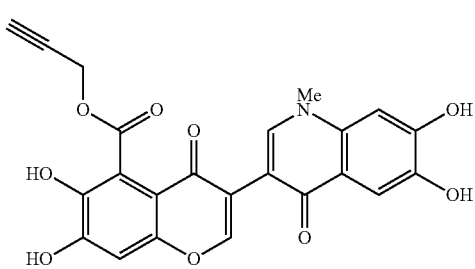 [SMILES: C#CCOC(=O)c1c(O)c(O)cc2occ(-c3cn(C)c4cc(O)c(O)cc4c3=O)c(=O)c12]

To a solution of the compound of Example 1 (10 mg, 24 nmol) in toluene (1 mL) was added thionyl chloride (1 mL), and the reaction mixture was stirred at 80° C. for one hour. The reaction mixture was cooled to room temperature and concentrated in vacuo, and then a solution of propargyl alcohol (0.1 mL, 1.73 mmol) in dichloromethane (0.5 mL) was added to the residue. After stirring the reaction mixture at room temperature for one hour, toluene was added to the reaction mixture, and the mixture was concentrated in vacuo to give the title compound (11 mg, 93% yield).

LC/MS (Condition (1)): [M+H]⁺/Rt=450/0.54 min
¹H-NMR (DMSO-d₆, 400 MHz) δ: 8.58 (s, 1H), 8.22 (s, 1H), 7.56 (s, 1H), 6.99 (s, 1H), 6.96 (s, 1H), 3.79 (s, 3H), 3.54-3.55 (m, 1H), 2.48-2.50 (m, 2H).

Example 3

N-({4-[({[3-(6,7-Dihydroxy-1-methyl-4-oxo-1,4-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid

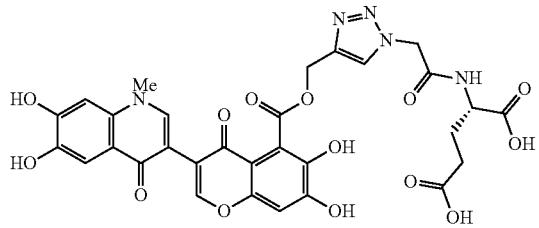 [SMILES: Cn1cc(-c2coc3cc(O)c(O)c(C(=O)OCc4cn(CC(=O)N[C@@H](CCC(=O)O)C(=O)O)nn4)c3c2=O)c(=O)c2cc(O)c(O)cc21]

Compound (d-2) (51 mg, 0.15 mmol) was dissolved in trifluoroacetic acid/water/triisopropylsilane (95/2.5/2.5) (1 mL), and the reaction mixture was stirred at room temperature for one hour and then concentrated in vacuo. The obtained residue was washed with diethyl ether, and dried. The obtained crude product was dissolved in dimethylsulfoxide (0.2 mL), and then tert-butyl alcohol/water (95/5) (1 mL), the compound of Example 2 (11 mg, 24 nmol), tris[(1-benzyl-1H-1,2,3-triazol-4-yl)methyl]amine (0.005 mol/L dimethylsulfoxide solution) (120 µL), 0.4 mol/L aqueous sodium ascorbate (60 µL), and 0.3 mol/L aqueous copper sulfate (30 µL) were added to the solution. After stirring the reaction mixture at room temperature for 4 hours, the reaction mixture was concentrated in vacuo. The obtained residue was purified by reverse phase chromatography with an ODS column (0.05% aqueous trifluoroacetic acid:acetonitrile) to give the title compound (2.7 mg, 17% yield).

LC/MS (Condition (1)): [M+H]⁺/Rt=680/0.44 min
¹H-NMR (CD₃OD) δ: 8.50 (s, 1H), 8.21 (s, 1H), 8.14 (s, 1H), 7.70 (s, 1H), 7.05 (s, 1H), 6.97 (s, 1H), 5.48 (s, 2H), 5.21 (s, 2H), 4.38-4.44 (m, 1H), 3.92 (s, 3H), 2.36-2.41 (m, 2H), 1.92-2.20 (m, 2H).

Example 4

N²-({4-[({[3-(6,7-Dihydroxy-1-methyl-4-oxo-1,4-dihydroquinolin-3-yl)-6,7-dihydroxy-4-oxo-4H-chromen-5-yl]carbonyl}oxy)methyl]-1H-1,2,3-triazol-1-yl}acetyl)-L-arginine Trifluoroacetate

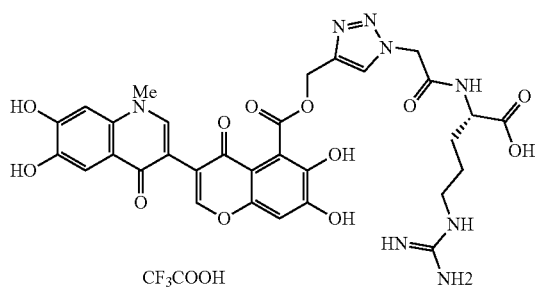 [SMILES: Cn1cc(-c2coc3cc(O)c(O)c(C(=O)OCc4cn(CC(=O)N[C@@H](CCCNC(=N)N)C(=O)O)nn4)c3c2=O)c(=O)c2cc(O)c(O)cc21 ; "CF3COOH"]

According to the method described in Example 3, the title compound (13 mg) was prepared from the compound of Example 2 and Compound (e-1).

LC/MS (Condition (1)): [M+H]⁺/Rt=707/0.41 min
¹H-NMR (CD₃OD) δ: 8.42 (s, 1H), 8.20 (s, 1H), 8.16 (s, 1H), 7.67 (s, 1H), 7.09 (s, 1H), 6.95 (s, 1H), 5.49 (s, 2H), 5.22 (brs, 2H), 4.33-4.36 (m, 1H), 3.96 (s, 3H), 3.02-3.14 (m, 2H), 1.49-1.92 (m, 4H).

Reference Example 15

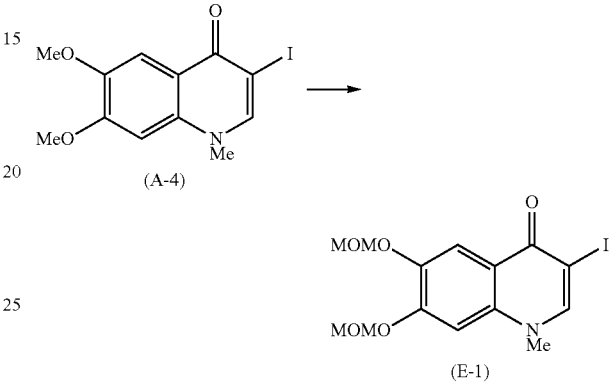

To a slurry of Compound (A-4) (34.93 g, 101.0 mmol) in dichloromethane (1250 mL) was added boron tribromide (76.07 g, 303.0 mmol) dropwise at ice temperature. After the heat generation from the reaction mixture stopped, the reaction mixture was heated to reflux for 8 hours and then allowed to cool. The reaction mixture was cooled in ice bath, and methanol (450 mL) was added dropwise thereto while the inside temperature thereof was kept around 10° C. to terminate the reaction. The obtained homogeneous solution was concentrated in vacuo to dryness with an evaporator. The residue was dissolved in methanol (750 mL) to give a homogeneous solution, and the homogeneous solution was heated to reflux for 15 minutes. The solution was concentrated in vacuo to dryness, methanol (300 mL) and toluene (400 mL) were added to the residue, and the solution was concentrated in vacuo again. To the residue was added 2-propanol (50 mL), and the mixture was stirred to give a slurry. The solid in the slurry was collected on a filter, and washed with toluene (100 mL) and ethyl acetate (100 mL). The obtained wet cake was transferred to another flask, and was suspended with dry dichloromethane (400 mL). The suspension was cooled in ice bath, and N,N-diisopropylethylamine (65 g, 506 mmol) and methoxymethyl chloride (25.0 g, 304 mmol) were added dropwise to the suspension. After completing the drop, the mixture was warmed to room temperature. After confirming the termination of the reaction with a HPLC, water (300 mL) containing potassium hydrogensulfate (41 g) was added to the reaction mixture. The mixture was separated with a separating funnel. The aqueous layer was re-extracted with dichloromethane (100 mL). The combined organic layer was washed with 0.1% aqueous sodium hydrogencarbonate (300 mL), dried over anhydrous sodium sulfate, and concentrated in vacuo to dryness. To the residue was added 125 mL of 2-propanol, and the solution was concentrated in vacuo to dryness. The procedure was repeated twice. To the residue was added 2-propanol (103 g), and the mixture was heated to reflux, in which the crystal was not dissolved. The mixture was gradually cooled over about 2 hours, and kept in ice bath for about 2 hours. The crystal was collected on a filter, washed with 2-propanol (60 mL), and dried in vacuo to give Compound (E-1) (33.93 g, 83.74 mmol).

$^1$H-NMR (DMSO-d$_6$, 400 MHz) δ: 8.53 (s, 1H), 7.79 (s, 1H), 7.22 (s, 1H), 5.43 (s, 2H), 5.29 (s, 2H), 3.81 (s, 3H), 3.45 (s, 3H), 3.42 (s, 3H).

Reference Example 16

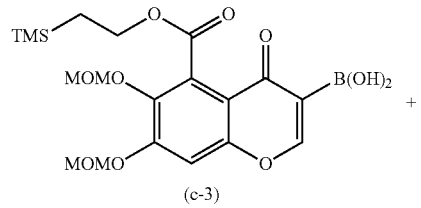

(c-3)

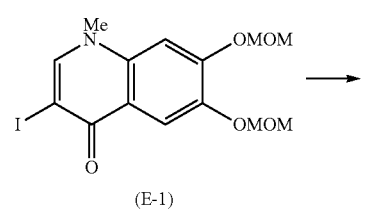

(E-1)

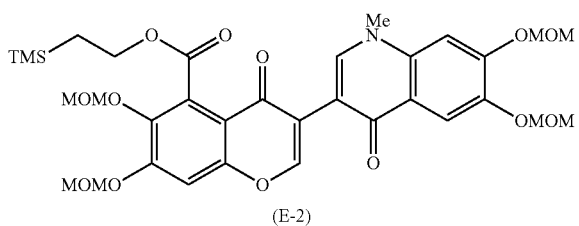

(E-2)

To a mixture of Compound (c-3) (1.99 g, 4.38 mmol), Compound (E-1) (1.42 g, 3.51 mmol), sodium carbonate (1.11 g, 10.52 mmol), bis(di-t-butyl(4-dimethylaminophenyl)phosphine)dichloropalladium(II) (127 mg, 0.175 mmol) were added tetrahydrofuran (28 mL) and ion exchanged water (7 mL) under nitrogen atmosphere, and the reaction mixture was stirred in hot water bath (65° C.) for 1.5 hours. After confirming the termination of the reaction with a HPLC, the reaction mixture was allowed to cool, and toluene (50 mL), ethyl acetate (25 mL), and water (50 mL) were added thereto. The mixture was separated with a separating funnel. The organic layer was washed with water (50 mL), and concentrated in vacuo to dryness. The residue was purified by silica gel column chromatography to give Compound (E-2) (2.37 g, 3.45 mmol).

$^1$H-NMR (CDCl$_3$, 400 MHz) δ: 9.34 (s, 1H), 8.80 (s, 1H), 8.17 (s, 1H), 7.27 (s, 1H), 7.18 (s, 1H), 5.39 (s, 2H), 5.35 (s, 2H), 5.32 (s, 2H), 5.19 (s, 2H), 4.60 (brs, 1H), 4.49 (brs, 1H), 3.85 (s, 3H), 3.60 (s, 3H), 3.56 (s, 3H), 3.54 (s, 3H), 3.52 (s, 3H), 1.20-1.10 (m, 2H), 0.06 (s, 9H).

Reference Example 17

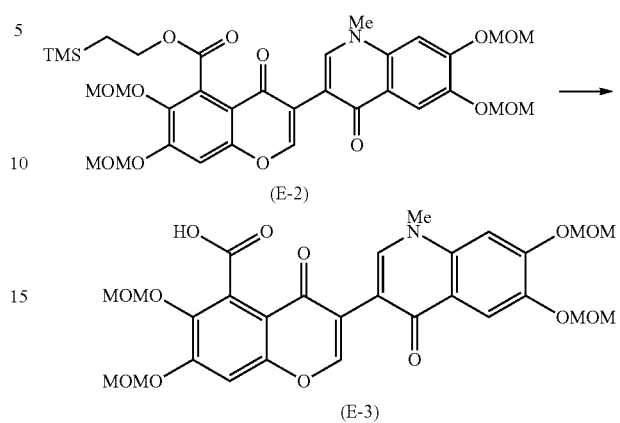

To a solution of Compound (E-2) (2.4 g, 3.5 mmol) in tetrahydrofuran (12 mL) was added 1 mol/L tetrabutylammonium fluoride in tetrahydrofuran (9.1 mL, 9.1 mmol) dropwise, and the reaction mixture was stirred at room temperature for one hour. Subsequently, 1 mol/L tetrabutylammonium fluoride in tetrahydrofuran (1.4 mL) was added thereto, and the reaction mixture was stirred at room temperature for one hour. And furthermore, 1 mol/L tetrabutylammonium fluoride in tetrahydrofuran (1.75 mL) was added thereto, and the reaction mixture was stirred at room temperature for one hour. To the reaction solution was added toluene dropwise, then the mixture was cooled in ice bath. The precipitated solid was removed by filtration. From the filtrate for crystallization, most of THF was removed by concentration in vacuo. 10% Aqueous sodium carbonate was added to the residue, and the aqueous layer was extracted with a mixture of ethyl acetate-toluene (1:1). To the aqueous layer were added ethyl acetate (10 mL), and concentrated hydrochloric acid to adjust the pH to about 3-4, and then a crystal was precipitated. The mixture was concentrated in vacuo to remove ethyl acetate, and water was added thereto. The mixture was stirred to give a suspension. The crystal was collected on a filter, washed with water and acetonitrile, and dried in vacuo to give Compound (E-3) (0.14 g, 6.6% yield).

$^1$H-NMR (DMSO-d$_6$, 400 MHz) δ: 13.04 (s, 1H), 8.83 (s, 1H), 8.40 (s, 1H), 7.88 (s, 1H), 7.38 (s, 1H), 7.27 (s, 1H), 5.443 (s, 2H), 5.440 (s, 2H), 5.29 (s, 2H), 5.13 (s, 2H), 3.86 (s, 3H), 3.50 (s, 3H), 3.47 (s, 3H), 3.46 (s, 3H), 3.43 (s, 3H), 3.33 (s, 3H).

The carboxylic acid can be also prepared by dissolving tetrabutylammonium salt thereof in water and adding hydrochloric acid to the solution to precipitate the desired product.

Reference Example 18

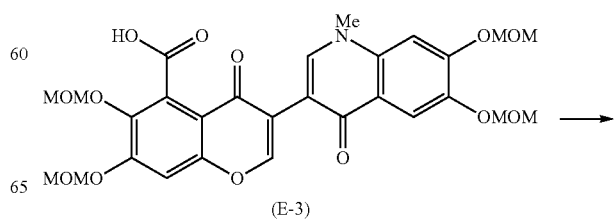

(E-3)

-continued

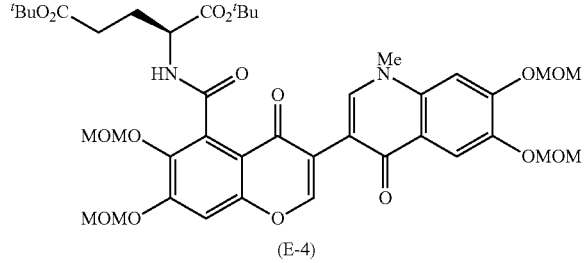

(E-4)

To a solution of Compound (E-3) (147 mg, 0.250 mmol) in dichloromethane (5 mL) were added EDC (120 mg, 0.630 mmol), N-hydroxybenzotriazole monohydrate (1.7 mg, 0.013 mmol), and di-tert-butyl glutamate hydrochloride (148 mg, 0.500 mmol), and then N,N-diisopropylethylamine (64.7 mg, 0.500 mmol) was added thereto. Two hours later, 1% aqueous hydrochloric acid (10 mL) was added to the reaction mixture, and the mixture was separated with a separating funnel. The organic layer was washed with 1% aqueous sodium hydrogencarbonate, and concentrated in vacuo to dryness. The obtained crude product was purified by silica gel column chromatography (chloroform—methanol) to give Compound (E-4) (126 mg, 61% yield).

$^1$H-NMR (DMSO-$d_6$, 400 MHz) (5:3 rotamer mixture at amide site) δ: 8.13 (s, 0.62H), 8.08 (s, 0.38H), 7.78 (s, 0.62H), 7.75 (s, 0.38H), 7.26 (s, 0.38H), 7.24 (s, 0.62H), 7.12 (s, 0.38H), 7.11 (s, 0.62H), 6.13 (s, 0.62H), 6.03 (s, 0.38H), 5.45-5.20 (m, 8H), 4.49 (dd, J=10.0, 4.8 Hz, 1H), 3.88 (s, 1.12H), 3.79 (s, 1.88H), 3.60-3.50 (m, 12H), 2.50-1.90 (m, 4H), 1.48 (s, 5.62H), 1.33 (s, 3.38H), 1.31 (s, 3.38H), 1.27 (s, 5.62H)

Example 5

N-{[3-(6,7-Dihydroxy-1-methyl-4-oxo-1,4-dihydroquinolin-3-yl)-6,7-dihydroxy-4-oxo-4H-chromen-5-yl]carbonyl}-L-glutamic acid

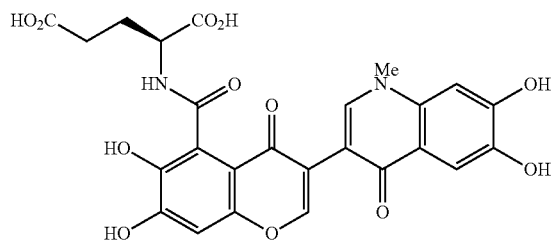 [SMILES: Cn1cc(-c2coc3cc(O)c(O)c(C(=O)N[C@@H](CCC(=O)O)C(=O)O)c3c2=O)c(=O)c2cc(O)c(O)cc21]

Compound (E-4) (37 mg, 0.045 mmol) was dissolved in trifluoroacetic acid (1 mL), and the reaction mixture was stirred at room temperature for 3 hours. The reaction solution was concentrated in vacuo by azeotropy with toluene. The obtained residue was washed with acetonitrile to give the product (18 mg, 73% yield).

LC/MS (Condition (2)): [M+H]$^+$/Rt=541/0.89 min $^1$H-NMR (CD$_3$OD, 400 MHz) δ: 7.98 (s, 3/5H), 7.91 (brs, 2/5H), 7.69 (s, 2/5H), 7.66 (s, 3/5H), 7.12 (s, 3/5H), 7.09 (s, 2/5H), 6.69 (s, 3/5H), 6.69 (s, 2/5H), 5.84 (s, 2/5H), 5.67 (s, 3/5H), 3.97 (s, 9/5H), 3.92 (s, 6/5H), 3.35-3.34 (m, 1H), 2.19-2.09 (m, 4H).

Reference Example 19

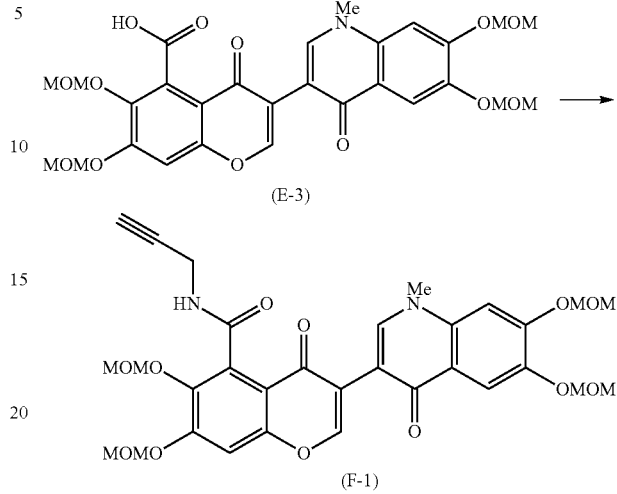

To a solution of Compound (E-3) (294 mg, 0.500 mmol) in dichloromethane (10 mL) were added EDC (288 mg, 1.25 mmol), N-hydroxybenzotriazole monohydrate (3.4 mg, 0.025 mmol), and then propargylamine (103 mg, 1.88 mmol). Six hours later, another EDC (48 mg, 0.25 mmol) was added thereto, and mixture was reacted for more 4 hours. Water (30 mL) and 3% hydrochloric acid (5 mL) were added to the reaction mixture, and the mixture was separated with a separating funnel. The organic layer was washed with 3% aqueous sodium hydrogencarbonate, and water, and concentrated in vacuo to dryness. The obtained crude product was purified by silica gel column chromatography (chloroform-methanol) to give Compound (F-1) (46 mg, 15% yield).

$^1$H-NMR (DMSO-$d_6$, 400 MHz) δ: 9.21 (s, 1H), 8.73 (s, 1H), 8.14 (s, 1H), 7.24 (s, 1H), 7.17 (s, 1H), 6.09 (m, 1H), 5.38 (s, 2H), 5.35 (s, 2H), 5.30 (s, 2H), 5.18 (s, 2H), 4.37 (brs, 2H), 3.86 (brs, 3H), 3.61 (s, 3H), 3.56 (s, 3H), 3.54 (s, 3H), 3.51 (s, 3H), 2.25 (t, J=2.4 Hz, 1H).

Example 6

3-(6,7-Dihydroxy-1-methyl-4-oxo-1,4-dihydroquinolin-3-yl)-6,7-dihydroxy-4-oxo-N-(prop-2-yn-1-yl)-4H-chromene-5-carboxamide

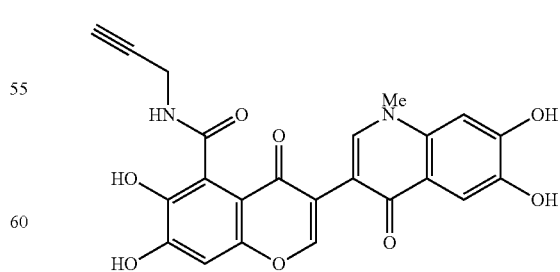

According to the method described in Example 5, the title compound (6.7 mg, 56%) was prepared from Compound (F-1) (17 mg, 0.027 mmol).

LC/MS (Condition (2)): [M+H]$^+$/Rt=449/1.16 min $^1$H-NMR (DMSO-d$_6$, 400 MHz) δ: 8.57 (s, 1H), 8.21 (t, J=5.4 Hz, 1H), 8.17 (s, 1H), 7.56 (s, 1H), 6.92 (s, 1H), 6.92-6.90 (m, 1H), 3.98 (dd, J=5.4, 2.6 Hz, 2H), 3.76 (s, 3H), 3.06 (t, J=2.6 Hz, 1H).

Reference Example 20

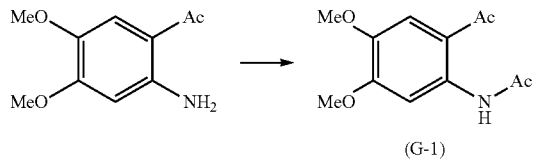 [SMILES: COc1cc(N)c(C(C)=O)cc1OC ; COc1cc(NC(C)=O)c(C(C)=O)cc1OC]

To a solution of 1-(2-amino-4,5-dimethoxyphenyl)ethanone (10 g, 51.2 mmol) in THF (200 mL) was added triethylamine (10.37 g, 102 mmol), and the reaction mixture was stirred. And, acetyl chloride (6.03 g, 77 mmol) was added thereto. After stirring the reaction mixture at room temperature for 2 hours, 10% aqueous potassium hydroxide was added to the reaction mixture, and the mixture was extracted with chloroform. The organic layer was washed with brine, dried over sodium sulfate, and then concentrated in vacuo to give Compound (G-1) (12.15 g, 100%).

LC/MS (Condition (3)): [M+H]$^+$/Rt=238/0.65 min

Reference Example 21

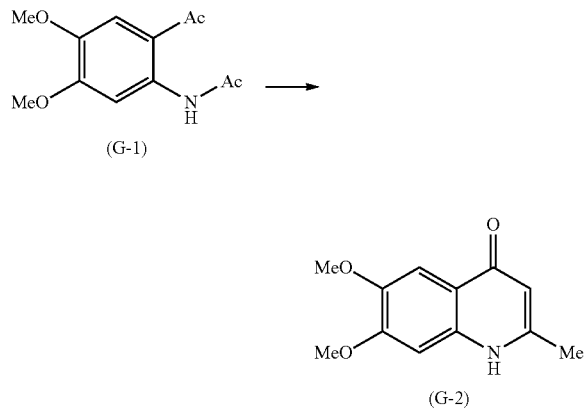

Compound (G-1) (6.1 g, 25.7 mmol) was suspended in t-butanol (50 mL), and potassium t-butoxide (15.0 g, 134.0 mmol) was added thereto. The reaction mixture was stirred at 90° C. for 8 hours. After the reaction was completed, water was added to the reaction mixture, and the mixture was extracted with ethyl acetate. The organic layer was washed with brine, dried over sodium sulfate, and then concentrated in vacuo. The obtained residue was purified by silica gel column chromatography (chloroform:methanol=100:0-90:10) to give Compound (G-2) (4.17 g, 74% yield)

$^1$H-NMR (DMSO-d$_6$, 400 MHz) δ: 11.37 (s, 1H), 7.09 (s, 1H), 6.86 (s, 1H), 6.22 (s, 1H), 3.82 (s, 3H), 3.80 (s, 3H), 2.39 (s, 3H).

Reference Example 22

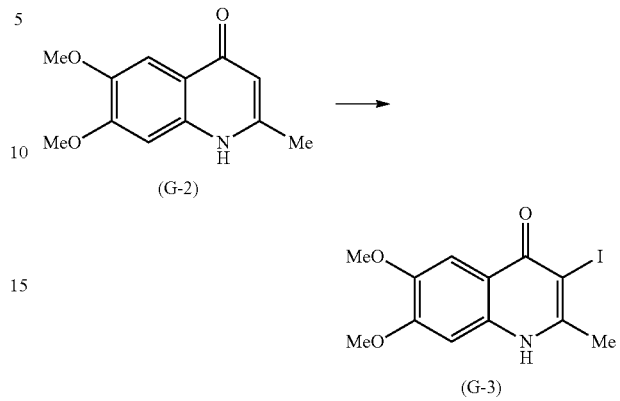

To a solution of Compound (G-2) (6.9 g, 31.5 mmol) in acetonitrile (300 mL) was added N-iodosuccinimide (14.16 g, 62.9 mmol). After stirring the reaction mixture at 80° C. for 5 hours, the reaction mixture was concentrated. To the residue was added an aqueous solution of sodium thiosulfate, and the mixture was stirred again for 30 minutes. The precipitated solid was collected on a filter, washed with water, and dried in vacuo to give Compound (G-3) (9.72 g, 89%).

$^1$H-NMR (DMSO-d$_6$, 400 MHz) δ: 11.86 (s, 1H), 7.21 (s, 1H), 6.88 (s, 1H), 3.84 (s, 3H), 3.82 (s, 3H), 2.71 (s, 3H).

Reference Example 23

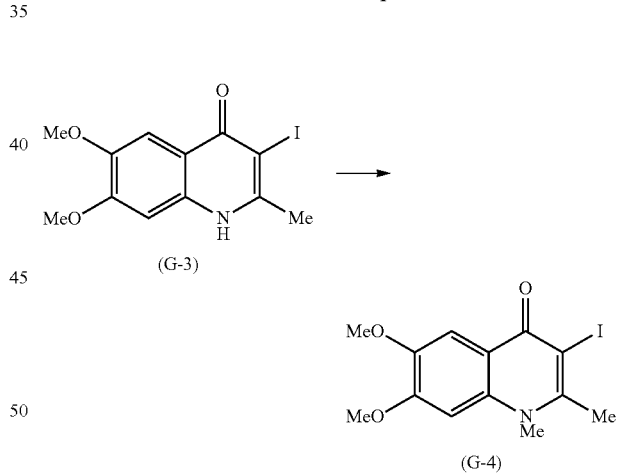

Compound (G-3) (0.9 g, 2.61 mmol) and cesium carbonate (1.27 g, 3.91 mmol) were suspended in NMP (40 mL), and then iodomethane (0.81 mL, 13.04 mmol) was added thereto. The reaction mixture was stirred at room temperature for 2 hours. After the reaction was completed, water was added to the reaction mixture, and the mixture was extracted with ethyl acetate. The organic layer was washed with brine, dried over sodium sulfate, and then concentrated in vacuo. The obtained residue was purified by silica gel column chromatography (hexane:ethyl acetate=5:95-20:80) to give Compound (G-4) (0.46 g, 49% yield).

$^1$H-NMR (DMSO-d$_6$, 400 MHz) δ: 7.29 (s, 1H), 7.00 (s, 1H), 3.94 (s, 3H), 3.86 (s, 3H), 3.74 (s, 1H), 2.74 (s, 3H).

Reference Example 24

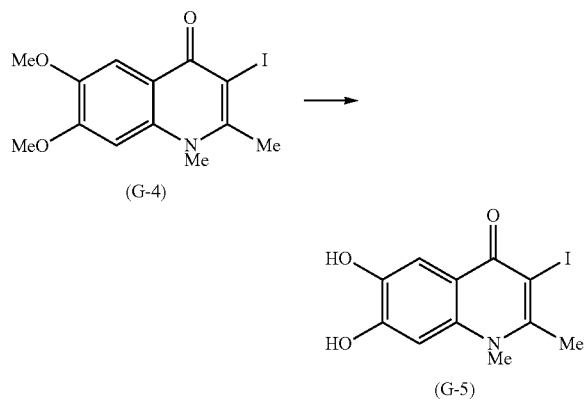

Compound (G-4) (0.46 g, 1.28 mmol) was suspended in dichloromethane (9 mL), and boron tribromide (4.47 mL, 1.28 mmol) was slowly added thereto. The reaction mixture was stirred at room temperature for 2 hours. After the reaction was completed, methanol was slowly added to the reaction mixture at 0° C., and the reaction mixture was stirred again for 30 minutes and concentrated in vacuo. To the residue was added methanol, and the mixture was stirred for 30 minutes and then concentrated in vacuo. To the residue was added methanol again, and the mixture was stirred for 30 minutes and concentrated in vacuo to give Compound (G-5) (0.42 g, 100% yield).

LC/MS (Condition (3)): $[M+H]^+$/Rt=332/0.59 min

Reference Example 25

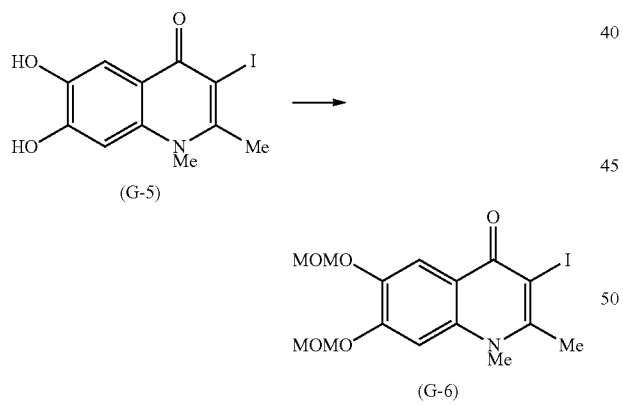

To a solution of Compound (G-5) (0.33 g, 1.0 mmol) and N,N-diisopropylethylamine (1.75 mL, 10.0 mmol) in chloroform (4 mL) was added chloromethyl methyl ether (0.46 mL, 6.0 mmol) slowly, and then the reaction mixture was stirred at room temperature for 2 hours. After the reaction was completed, water was added to the reaction mixture, and the mixture was extracted with ethyl acetate. The organic layer was washed with brine, dried over sodium sulfate, and then concentrated in vacuo. The obtained residue was purified by silica gel column chromatography (chloroform:ethyl acetate=100:0-80:20) to give Compound (G-6) (0.38 g, 90% yield).

LC/MS (Condition (3)): $[M+H]^+$/Rt=420/0.85 min

Reference Example 26

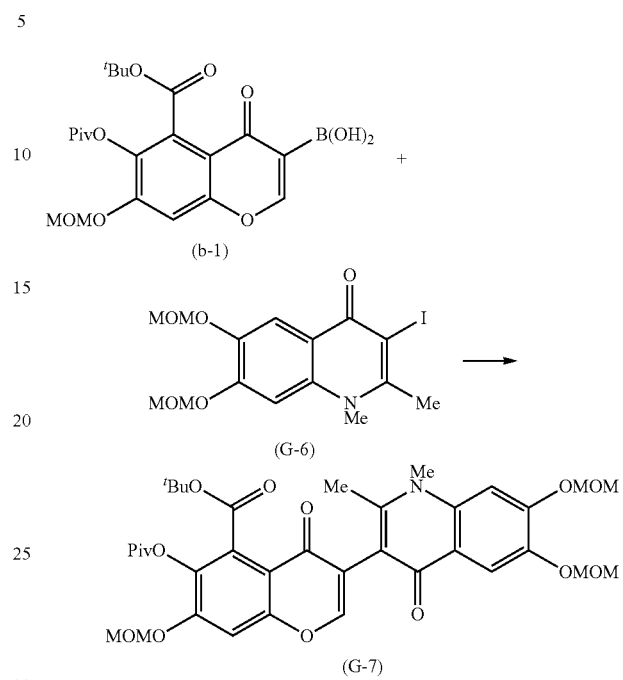

To a solution of Compound (G-6) (73 mg, 0.17 mmol), Compound (b-1) (110 mg, 0.24 mmol), bis(di-tert-butyl(4-dimethylaminophenyl)phosphine)dichloropalladium (12 mg, 0.017 mmol) in THF (1.5 mL) was added sodium carbonate (92 mg, 0.87 mmol), and then the reaction mixture was stirred at 65° C. under nitrogen atmosphere for 2 hours. Water was added to the reaction mixture, and the mixture was extracted with ethyl acetate. The organic layer was washed with brine, dried over sodium sulfate, and then concentrated in vacuo. The obtained residue was purified by silica gel column chromatography (hexane:ethyl acetate=95:5-10:90) to give Compound (G-7) (111 mg, 91% yield).

LC/MS (Condition (3)): $[M+H]^+$/Rt=698/1.15 min

Example 7

3-(6,7-Dihydroxy-1,2-dimethyl-4-oxo-1,4-dihydro-quinolin-3-yl)-6,7-dihydroxy-4-oxo-4H-chromene-5-carboxylic acid

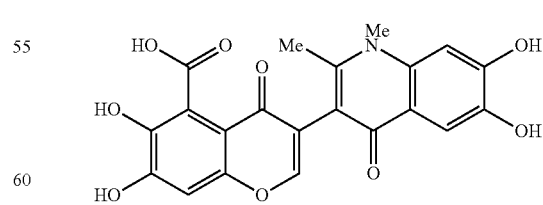

Compound (G-7) (111 mg, 0.16 mmol) was dissolved in a mixture of toluene (1 mL) and water (5.8 μl), and then trifluoroacetic acid (0.98 mL) was added thereto. The reaction mixture was stirred at 55° C. for 2 hours. The reaction solution was concentrated by azeotropy with toluene. The obtained residue was washed with acetonitrile to give the title compound (28 mg, 41% yield).

LC/MS (Condition (3)): [M+H]⁺/Rt=426/0.513 min

¹H-NMR (DMSO-d₆, 400 MHz) δ: 12.84 (bs, 1H), 11.25 (s, 1H), 9.96 (s, 1H), 9.53 (s, 1H), 9.24 (s, 1H), 8.08 (s, 1H), 7.16 (s, 1H), 6.97 (s, 1H), 6.88 (s, 1H), 3.53 (s, 3H), 2.16 (s, 3H).

Reference Example 27

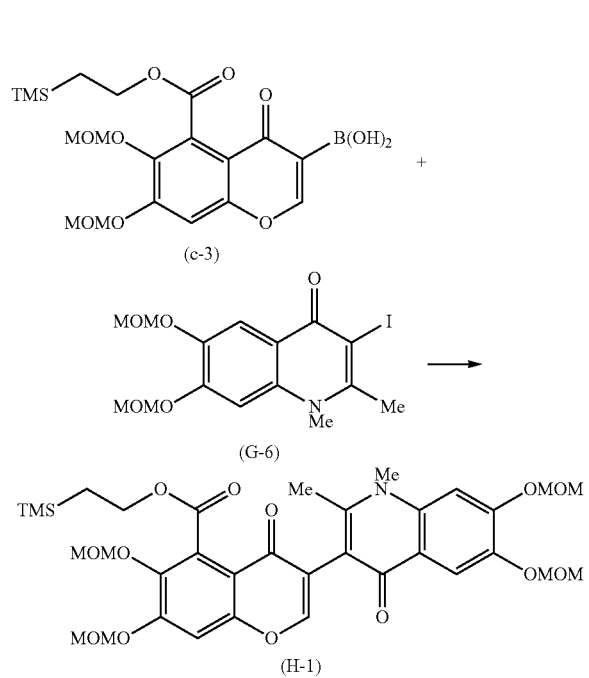

According to the method described in Reference example 26, Compound (H-1) (240 mg, 77%) was prepared from Compound (G-6) (186 mg, 0.44 mmol) and Compound (c-3) (214 mg, 0.47 mmol).

LC/MS (Condition (3)): [M+H]⁺/Rt=702/1.14 min

Reference Example 28

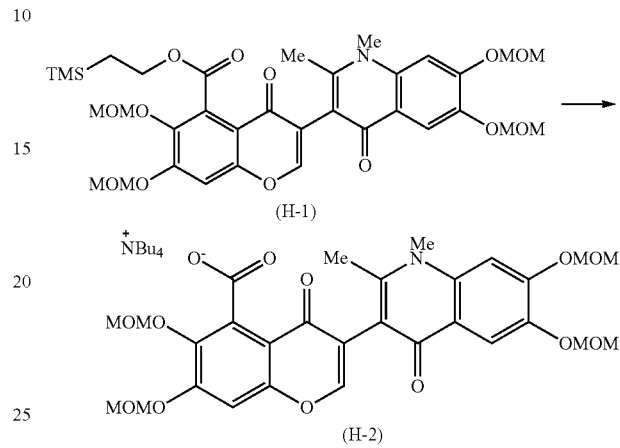

To a solution of Compound (H-1) (240 mg, 0.34 mmol) in THF (2 mL) was added tetrabutylammonium fluoride in THF (1 mol/L, 0.6 mmol, 0.60 mmol), and then the reaction mixture was stirred at room temperature for one hour. After the reaction was completed, the reaction mixture was concentrated in vacuo to give Compound (H-2) (0.71 g).

LC/MS (Condition (2)): [M+H]⁺/Rt=601/0.75 min

Reference Example 29

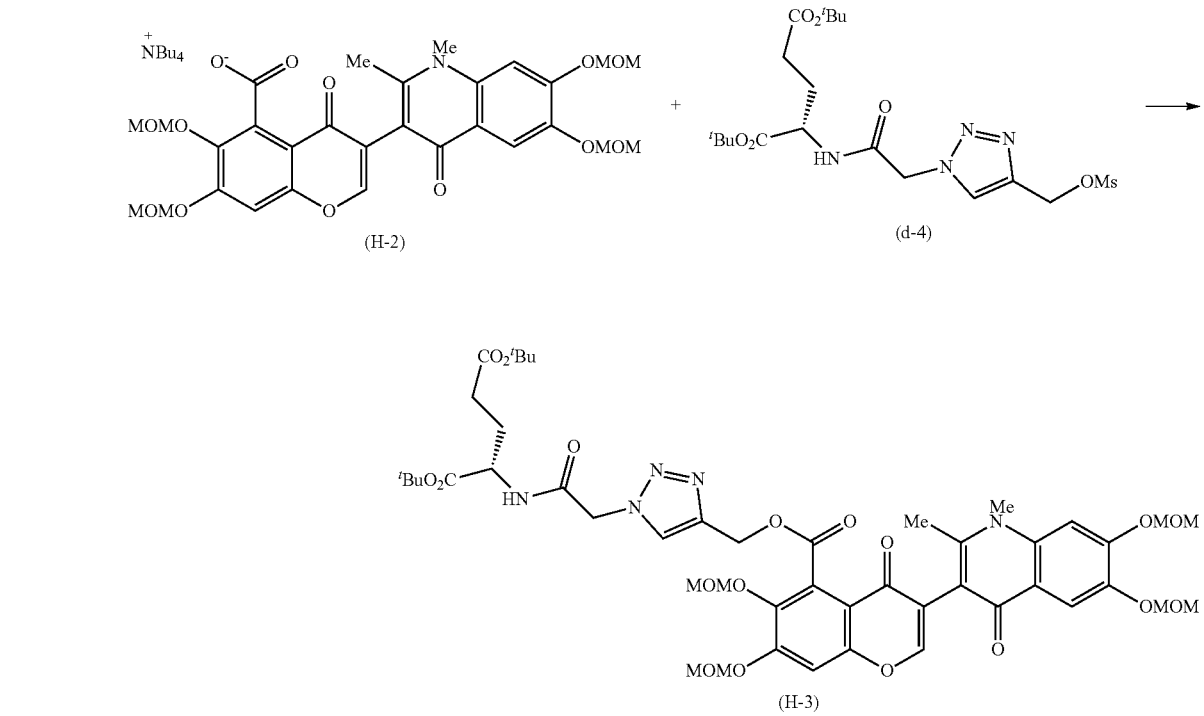

To a solution of Compound (H-2) (205 mg, 0.34 mmol) in acetonitrile (2 mL) was added Compound (d-4) (212 mg, 0.45 mmol), and then the reaction mixture was stirred at room temperature for 18 hours. Saturated aqueous ammonium chloride was added to the reaction mixture, and the mixture was extracted with chloroform. The organic layer was washed with brine, dried over sodium sulfate, and then concentrated in vacuo. The obtained residue was purified by silica gel column chromatography (chloroform:ethyl acetate=95:5-15:85, followed by chloroform:methanol=9:1) to give Compound (H-3) (225 mg, 67% yield).

LC/MS (Condition (3)): [M+H]$^+$/Rt=982/1.11 min

Example 8

N-({4-[({[3-(6,7-Dihydroxy-1,2-dimethyl-4-oxo-1,4-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid

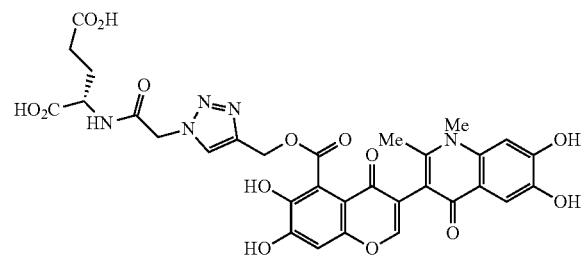 [SMILES: Cc1c(-c2coc3cc(O)c(O)c(C(=O)OCc4cn(CC(=O)N[C@@H](CCC(=O)O)C(=O)O)nn4)c3c2=O)c(=O)c2cc(O)c(O)cc2n1C]

To a solution of Compound (H-3) (225 mg, 0.23 mmol) in acetic acid (4 mL) was added hydrochloric acid (0.17 mL, 5.5 mmol) in acetic acid (4 mL), and then the reaction mixture was stirred at room temperature overnight. The reaction solution was concentrated by azeotropy with toluene, and the residue was dried in vacuo. To the obtained residue was added toluene, and the insoluble matter was removed by filtration. The filtrate was concentrated to give the title compound (40 mg, 25% yield).

LC/MS (Condition (3)): [M+H]$^+$/Rt=694/0.466 min $^1$H-NMR (DMSO-d$_6$, 400 MHz) δ: 8.71 (d, J=7.3 Hz, 1H), 8.09-8.06 (m, 2H), 7.17 (s, 1H), 7.01 (s, 1H), 6.89 (s, 1H), 5.41-5.03 (m, 4H), 4.26-4.20 (m, 1H), 3.52 (s, 3H), 2.33-2.27 (m, 2H), 2.16 (s, 3H), 2.07-1.92 (m, 2H).

Reference Example 30

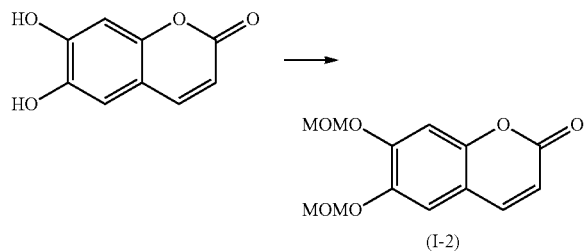

To a solution of esculetin (1.78 g, 10 mmol) in chloroform (100 mL) were added diisopropylethylamine (8.3 mL, 50 mmol) and chloromethyl methyl ether (2.3 mL, 30 mmol), and then the reaction mixture was stirred at room temperature for one hour. Water was added to the reaction mixture, and the mixture was extracted with chloroform. The organic layer was washed with brine, dried over magnesium sulfate, and then concentrated in vacuo. The obtained residue was purified by silica gel column chromatography (hexane:ethyl acetate=90:10-5:95) to give Compound (I-2) (2.6 g, 98% yield).

LC/MS (Condition (1)): [M+H]$^+$/Rt=267/0.76 min

Reference Example 31

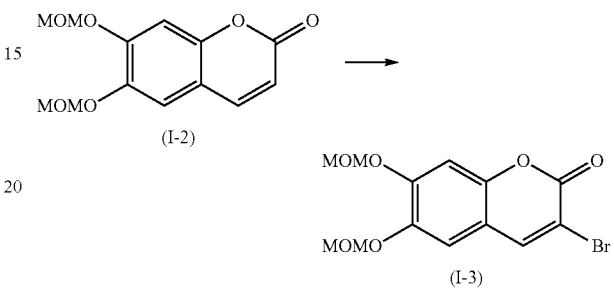

To a solution of Compound (I-2) (2.6 g, 9.8 mmol) in acetic acid (50 mL) were added sodium acetate (2.5 g, 30 mmol) and bromine (0.66 mL, 13 mmol), and then the reaction mixture was stirred at room temperature for one hour. To the reaction mixture was added water, and the precipitated solid was collected on a filter, washed with water, and dried to give Compound (I-3) (3.0 g, 87% yield).

LC/MS (Condition (1)): [M+H]$^+$/Rt=344/0.93 min

Reference Example 32

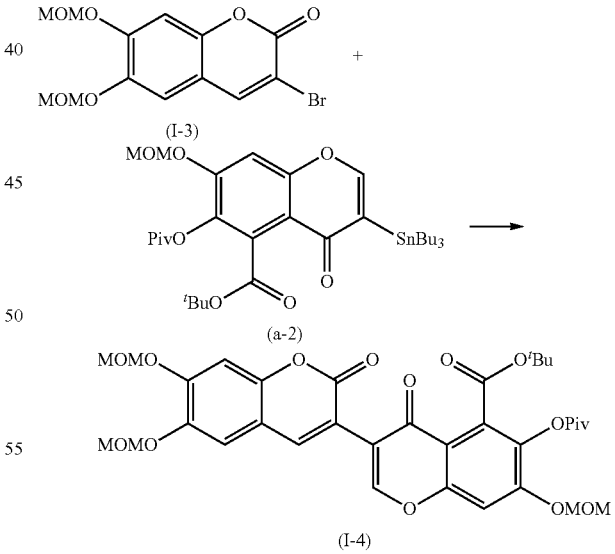

To a solution of Compound (I-3) (0.44 g, 1.27 mmol) in N,N-dimethylformamide (6.33 mL) were added Compound (a-2) (0.44 g, 0.63 mmol), copper iodide (12 mg, 0.063 mmol), and tetrakis(triphenylphosphine)palladium (37 mg, 0.032 mmol). After stirring the reaction mixture at 80° C. under nitrogen atmosphere for 2 hours, the reaction mixture was cooled to room temperature, water was added to the reaction mixture, and the mixture was extracted with ethyl acetate. The organic layer was washed with brine, dried over magnesium sulfate, and then concentrated in vacuo. The obtained residue was purified by silica gel column chromatography (hexane:ethyl acetate=90:10-5:95) to give Compound (I-4) (0.18 g, 42% yield).

LC/MS (Condition (1)): [M+H]$^+$/Rt=671/1.27 min

Example 9

6,6',7,7'-Tetrahydroxy-2,4'-dioxo-2H,4'H-3,3'-bichromene-5'-carboxylic acid

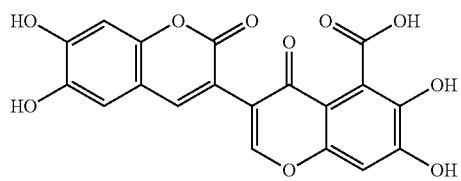 [SMILES: O=C(O)c1c(O)c(O)cc2occ(-c3cc4cc(O)c(O)cc4oc3=O)c(=O)c12]

Compound (I-4) (0.18 g, 0.27 mmol) was dissolved in trifluoroacetic acid (5 mL), and then the reaction mixture was stirred at room temperature for one hour, and concentrated in vacuo. The obtained crude product was washed with diethyl ether to give the title compound (0.10 g, 94% yield).

LC/MS (Condition (1)): [M+H]$^+$/Rt=399/0.56 min $^1$H-NMR (DMSO-d$_6$, 400 MHz) δ: 11.34 (brs, 1H), 10.29 (brs, 1H), 9.45 (brs, 1H), 9.39 (brs, 1H), 8.44 (s, 1H), 8.04 (s, 1H), 7.01 (s, 1H), 6.94 (s, 1H), 6.77 (s, 1H).

Example 10

Prop-2-yn-1-yl 6,6',7,7'-tetrahydroxy-2,4'-dioxo-2H,4'H-3,3'-bichromene-5'-carboxylate

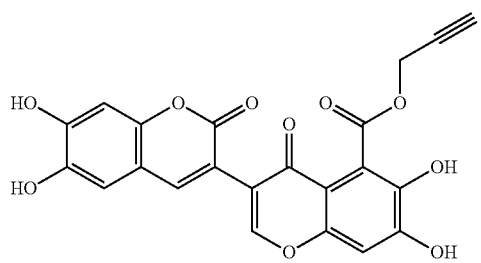 [SMILES: C#CCOC(=O)c1c(O)c(O)cc2occ(-c3cc4cc(O)c(O)cc4oc3=O)c(=O)c12]

According to the method described in Example 2, the title compound (70 mg, 64% yield) was prepared from the compound of Example 9 (0.10 g, 0.25 mmol).

LC/MS (Condition (1)): [M+H]$^+$/Rt=437/0.61 min $^1$H-NMR (DMSO-d$_6$, 400 MHz) δ: 11.52 (s, 1H), 10.30 (s, 1H), 9.64 (s, 1H), 9.45 (s, 1H), 8.45 (s, 1H), 8.01 (s, 1H), 7.01 (s, 1H), 7.00 (s, 1H), 6.77 (s, 1H), 3.55-3.56 (m, 1H), 2.52-2.55 (m, 2H).

Example 11

N-{[4-({[(6,6',7,7'-Tetrahydroxy-2,4'-dioxo-2H,4'H-3,3'-bichromen-5'-yl)carbonyl]oxy}methyl)-1H-1,2,3-triazol-1-yl]acetyl}-L-glutamic acid

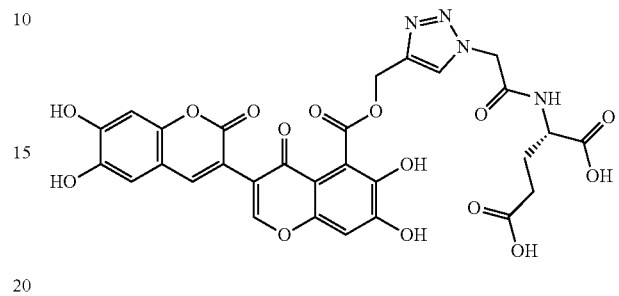

According to the method described in Example 3, the title compound (6.5 mg, 39%) was prepared from the compound of Example 10 (11 mg, 0.025 mmol).

LC/MS (Condition (1)): [M+H]$^+$/Rt=667/0.51 min $^1$H-NMR (CD$_3$OD) δ: 8.43 (s, 1H), 8.14 (s, 1H), 8.09 (s, 1H), 7.04 (s, 1H), 6.96 (s, 1H), 6.78 (s, 1H), 5.49 (s, 2H), 5.22 (s, 2H), 4.40-4.43 (m, 1H), 2.38 (t, J=7.6 Hz, 2H), 1.91-2.20 (m, 2H).

Example 12

N$^2$-{[4-({[(6,6',7,7'-Tetrahydroxy-2,4'-dioxo-2H,4'H-3,3'-bichromen-5'-yl)carbonyl]oxy}methyl)-1H-1,2,3-triazol-1-yl]acetyl}-L-arginine trifluoroacetate

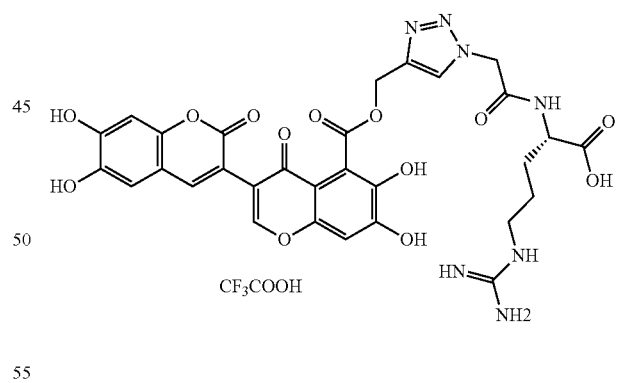

According to the method described in Example 3, the title compound (2.8 mg) was prepared from the compound of Example 2 and the compound of Example 10 (26 mg, 0.050 mmol).

LC/MS (Condition (1)): [M+H]$^+$/Rt=694/0.45 min $^1$H-NMR (CD$_3$OD) δ: 8.43 (s, 1H), 8.16 (s, 1H), 8.06 (s, 1H), 7.06 (s, 1H), 6.98 (s, 1H), 6.79 (s, 1H), 5.51 (s, 2H), 5.23 (brs, 2H), 4.33-4.38 (m, 1H), 3.02-3.14 (m, 2H), 1.49-1.92 (m, 4H).

Reference Example 33

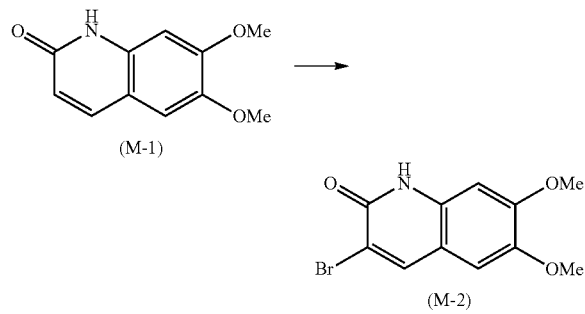

6,7-Dimethoxyquinolin-2(1H)-one (M-1) (2.8 g, 14 mmol) which was prepared according to a literature (*Heterocycles*, 65, p 2095 (2005)) was dissolved in DMF (100 mL), and N-bromosuccinimide (2.4 g, 14 mmol) was added thereto. The mixture was stirred at room temperature for one hour. Ice in water (100 mL) was added to the mixture at 0° C., and the precipitated solid was collected by suction filtration to give Compound (M-2) (3.3 g, 84% yield).

$^1$H-NMR (CDCl$_3$, 400 MHz) δ: 8.12 (s, 1H), 6.89 (s, 1H), 6.86 (s, 1H), 4.02-4.00 (m, 3H), 3.93 (s, 3H).

Reference Example 34

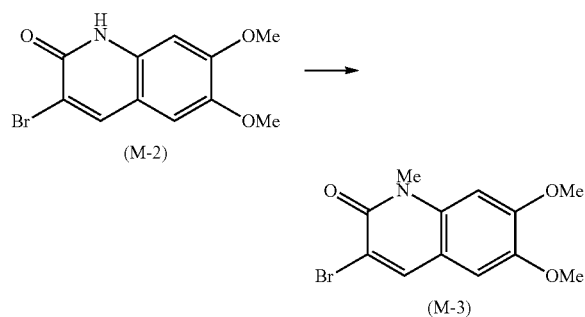

To a suspension of sodium hydride (172 mg, 4.3 mmol) in DMF (14 mL) was added Compound (M-2) (0.41 g, 1.4 mmol) at 0° C., and then the reaction mixture was stirred at the same temperature for 30 minutes. Iodomethane (0.27 mL, 4.3 mmol) was added to the reaction mixture at 0° C., and the mixture was stirred at room temperature for one hour. A saturated water solution of ammonium chloride was added to the mixture at 0° C., and the precipitated solid was collected by suction filtration, washed with water, and dried to give Compound (M-3) (0.22 g, 52% yield).

$^1$H-NMR (CDCl$_3$, 400 MHz) δ: 8.03 (s, 1H), 6.90 (s, 1H), 6.76 (s, 1H), 4.02 (s, 3H), 3.94 (s, 3H), 3.81 (s, 3H).

Reference Example 35

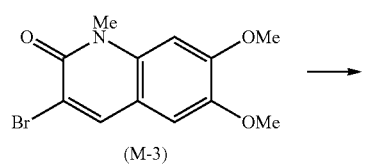

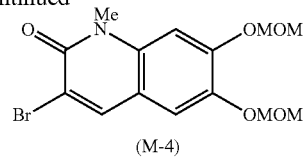

To a solution of Compound (M-3) (0.17 g, 0.58 mmol) in methylene chloride (4.5 mL) was added 1 mol/L boron tribromide in methylene chloride (3.0 mL, 3.0 mmol) at 0° C., and then the reaction mixture was stirred at room temperature for one hour. Methanol was added to the reaction mixture at 0° C., and the mixture was stirred until smoke generation stopped. The mixture was concentrated in vacuo. The obtained residue was dissolved in chloroform (7 mL), and N,N-diisopropylethylamine (0.99 mL, 5.8 mmol) and chloromethyl methyl ether (0.26 mL, 3.5 mmol) were added at 0° C. to the solution. After stirring the reaction mixture at room temperature for 4 hours, water was added to the reaction mixture, and the mixture was extracted with chloroform. The organic layer was washed with brine, dried over magnesium sulfate, and then concentrated in vacuo. The obtained residue was purified by silica gel column chromatography (chloroform:ethyl acetate=67:33-0:100) to give Compound (M-4) (0.12 g, 57% yield).

$^1$H-NMR (CDCl$_3$, 400 MHz) δ: 8.02 (s, 1H), 7.27 (s, 1H), 7.16 (s, 1H), 5.36 (s, 2H), 5.26 (s, 2H), 3.77 (s, 3H), 3.56 (s, 3H), 3.54 (s, 3H).

Reference Example 36

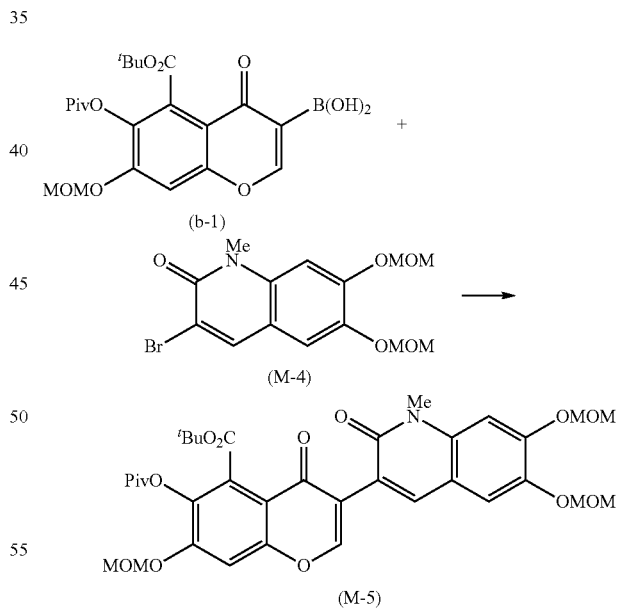

According to the method described in Reference example 26, Compound (M-5) (24 mg, 42% yield) was prepared from Compound (M-4) (30 mg, 0.083 mmol) and Compound (b-1) (52 mg, 0.12 mmol).

$^1$H-NMR (CDCl$_3$, 400 MHz) δ: 1.39 (s, 9H), 1.62 (s, 9H), 3.46 (s, 3H), 3.55 (s, 3H), 3.56 (s, 3H), 3.73 (s, 3H), 5.24 (s, 2H), 5.27 (s, 2H), 5.37 (s, 2H), 7.15 (s, 1H), 7.21 (s, 1H), 7.39 (s, 1H), 8.33 (s, 1H), 8.71 (s, 1H).

Example 13

3-(6,7-Dihydroxy-1-methyl-2-oxo-1,2-dihydroquinolin-3-yl)-6,7-dihydroxy-4-oxo-4H-chromene-5-carboxylic acid According to the method described in Example 5, the title compound (15 mg, 100% yield) was prepared from Compound (M-5) (24 mg, 0.034 mmol).

LC/MS (Condition (2)): [M+H]$^+$/Rt=412/1.32 min $^1$H-NMR (DMSO-d$_6$, 400 MHz) δ: 11.27 (s, 1H), 9.98 (s, 1H), 9.43 (s, 1H), 9.30 (s, 1H), 8.43 (s, 1H), 7.87 (s, 1H), 7.03 (s, 1H), 6.95 (s, 1H), 6.86 (s, 1H), 3.56 (s, 3H)

Reference Example 37

According to the method described in Reference example 26, Compound (N-1) (0.18 g, 80% yield) was prepared from Compound (M-4) (0.12 g, 0.33 mmol) and Compound (c-3) (0.20 g, 0.43 mmol).

$^1$H-NMR (CDCl$_3$, 400 MHz) δ: 8.78 (s, 1H), 8.38 (s, 1H), 7.41 (s, 1H), 7.26 (s, 1H), 7.15 (s, 1H), 5.37 (s, 2H), 5.32 (s, 2H), 5.27 (s, 2H), 5.19 (s, 2H), 4.60 (brs, 1H), 4.48 (brs, 1H), 3.73 (s, 3H), 3.60 (s, 3H), 3.56 (s, 3H), 3.55 (s, 3H), 3.52 (s, 3H), 1.17-1.14 (brm, 2H), 0.05 (s, 9H).

Reference Example 38

According to the method described in Reference example 28, Compound (N-2) (0.39 g) was prepared from Compound (N-1) (0.18 g, 0.27 mmol).

LC/MS (Condition (1)): [M+H]$^+$/Rt=588/1.68 min

Reference Example 39

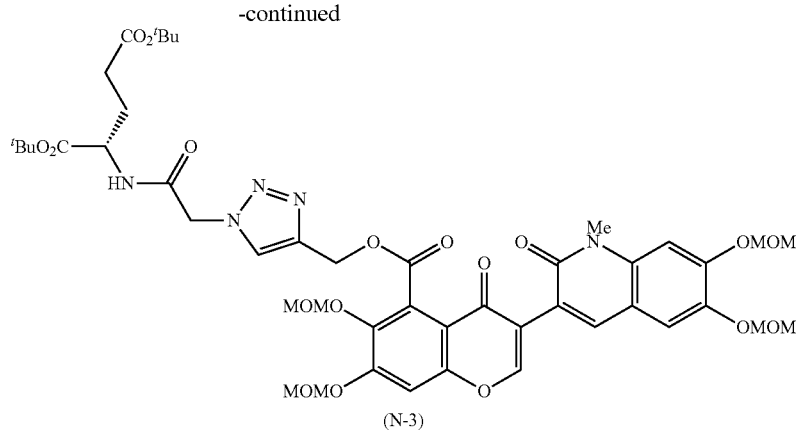

(N-3)

According to the method described in Reference example 29, Compound (N-3) (15 mg, 11% yield) was prepared from Compound (N-2) (110 mg, 0.17 mmol) and Compound (d-4) (82 mg, 0.17 mmol).

$^1$H-NMR (CDCl$_3$, 400 MHz) δ: 8.64 (s, 1H), 8.13 (s, 1H), 8.10 (s, 1H), 7.50 (s, 1H), 7.16 (s, 1H), 6.83 (d, J=7.3 Hz, 1H), 5.70 (brs, 1H), 5.53 (brs, 1H), 5.37 (s, 2H), 5.31 (s, 2H), 5.30 (brs, 2H), 5.15 (s, 2H), 5.09 (s, 2H), 4.40-4.35 (brm, 1H), 3.73 (s, 3H), 3.56 (s, 3H), 3.56 (s, 3H), 3.55 (s, 3H), 3.51 (s, 3H), 2.22-2.17 (brm, 2H), 1.79 (td, J=14.4, 8.2 Hz, 2H), 1.40 (s, 18H).

Example 14

N-({4-[({[3-(6,7-Dihydroxy-1-methyl-2-oxo-1,2-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid

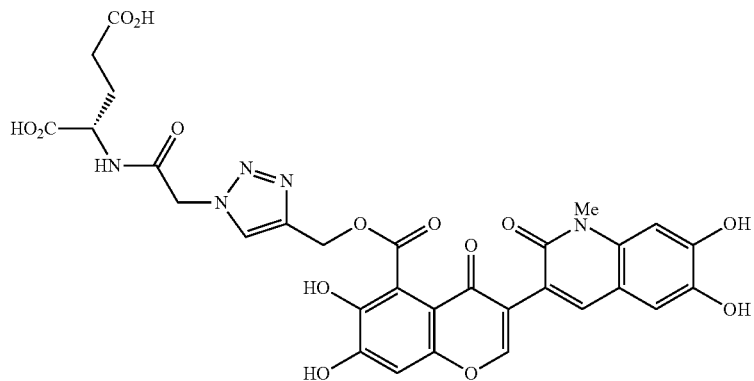 [SMILES: Cn1c(=O)c(-c2coc3cc(O)c(O)c(C(=O)OCc4cn(CC(=O)N[C@@H](CCC(=O)O)C(=O)O)nn4)c3c2=O)cc2cc(O)c(O)cc21]

To a solution of Compound (N-3) (15 mg) in acetic acid (0.3 mL) was added 36% hydrochloric acid (50 μl, 0.59 mmol) at 0° C., and then the reaction mixture was stirred at room temperature for 3 hours. The reaction mixture was concentrated in vacuo and the residue was purified by reverse phase chromatography with an ODS column (0.05% aqueous trifluoroacetic acid/0.035% trifluoroacetic acid in acetonitrile) to give the title compound (2.5 mg, 24% yield).

LC/MS (Condition (2)): [M+H]$^+$/Rt=680/1.28 min $^1$H-NMR (CD$_3$OD, 400 MHz) δ: 8.33 (d, J=1.8 Hz, 1H), 8.20 (brs, 1H), 7.91 (brs, 1H), 7.10 (d, J=2.3 Hz, 1H), 6.98 (s, 2H), 5.49 (s, 2H), 5.23 (s, 2H), 4.46-4.42 (m, 1H), 3.73 (s, 3H), 2.39 (t, J=7.5 Hz, 2H), 2.23-2.14 (m, 1H), 1.98-1.90 (m, 1H).

Reference Example 40

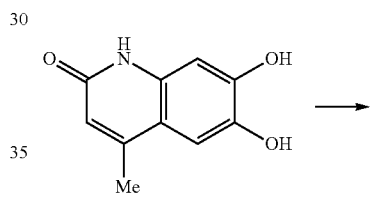

-continued

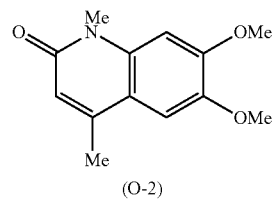

(O-2)

To a suspension of sodium hydride (0.52 g, 12 mmol) in DMF (15 mL) was added 6,7-dihydroxy-4-methyl-1,2-dihydroquinolin-2-one (0.50 g, 2.6 mmol) at 0° C., and then the reaction mixture was stirred at the same temperature for 30 minutes. Iodomethane (0.74 mL, 12 mmol) was added at 0° C. thereto, and then the mixture was stirred at room temperature for 18 hours. Saturated aqueous ammonium chloride was added to the reaction mixture at 0° C., and the mixture was extracted with ethyl acetate. The organic layer was washed with brine, dried over sodium sulfate, and then concentrated in vacuo. The obtained residue was purified by silica gel column chromatography (chloroform:methanol=100:0-90:10) to give Compound (O-2) (0.47 g, 76% yield).

$^1$H-NMR (CDCl$_3$, 400 MHz) δ: 7.07 (s, 1H), 6.81 (s, 1H), 6.55 (s, 1H), 4.02 (s, 3H), 3.96 (s, 3H), 3.73 (s, 3H), 2.45 (s, 3H).

Reference Example 41

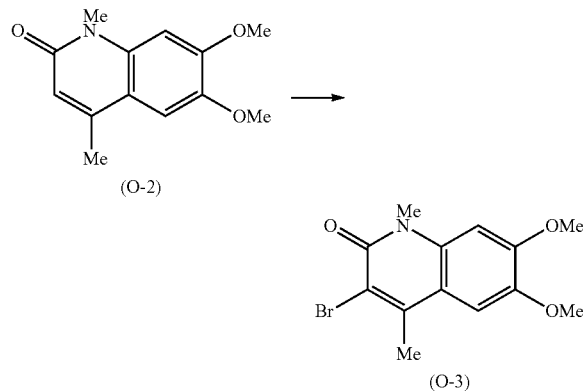

To a solution of Compound (O-2) (0.47 g, 2.0 mmol) in DMF (15 mL) was added N-bromosuccinimide (0.36 g, 2.0 mmol), and then the reaction mixture was stirred at room temperature for 20 hours. Saturated aqueous sodium thiosulfate (10 mL) was added to the reaction mixture, and the mixture was extracted with chloroform. The organic layer was washed with brine, dried over sodium sulfate, and then concentrated in vacuo. The residue was dissolved in DMF (3 mL), water (20 mL) was added thereto, and the precipitated solid was collected by suction filtration to give Compound (O-3) (0.53 g, 85% yield).

$^1$H-NMR (CDCl$_3$, 400 MHz) δ: 7.14 (s, 1H), 6.79 (s, 1H), 4.02 (s, 3H), 3.97 (s, 3H), 3.81 (s, 3H), 2.68 (s, 3H).

Reference Example 42

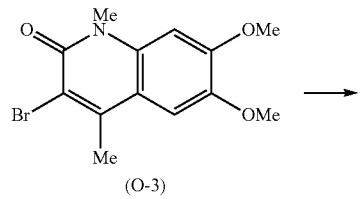

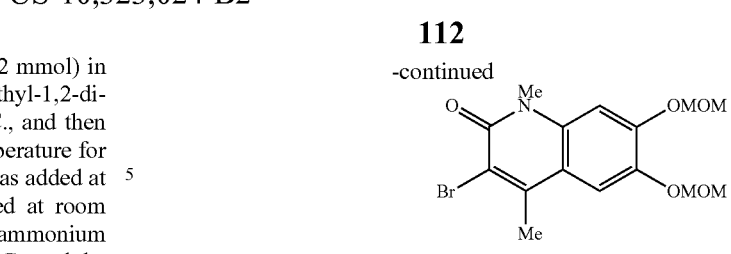

According to the method described in Reference example 35, Compound (O-4) (0.58 g, 92% yield) was prepared from Compound (O-3) (0.53 g, 1.7 mmol).

$^1$H-NMR (CDCl$_3$, 400 MHz) δ: 7.53 (s, 1H), 7.18 (s, 1H), 5.36 (s, 2H), 5.28 (s, 2H), 3.77 (s, 3H), 3.56 (s, 3H), 3.56 (s, 3H), 2.65 (s, 3H).

Reference Example 43

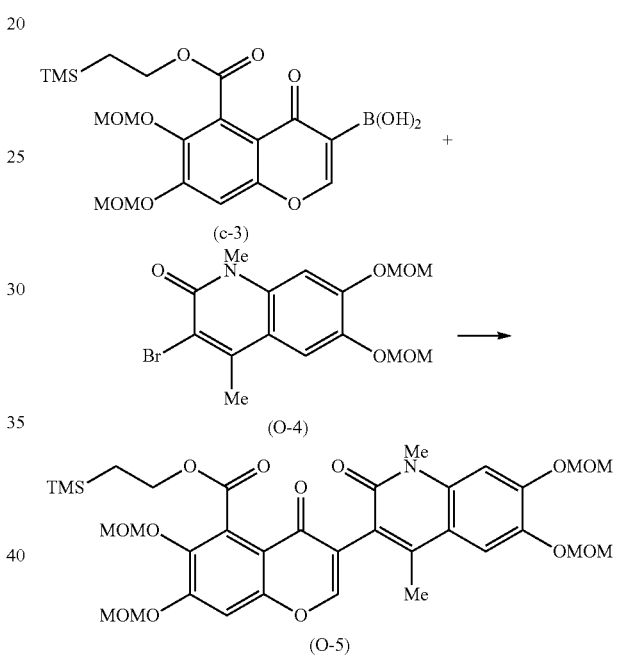

According to the method described in Reference example 26, Compound (O-5) (0.24 g, 52% yield) was prepared from Compound (O-4) (0.25 g, 0.67 mmol) and Compound (c-3) (0.43 g, 0.94 mmol).

$^1$H-NMR (CDCl$_3$, 400 MHz) δ: 7.89 (brs, 1H), 7.53 (s, 1H), 7.26 (s, 1H), 7.16 (s, 1H), 5.39-5.30 (m, 4H), 5.26 (s, 2H), 5.19 (dd, J=7.9, 5.5 Hz, 2H), 4.56-4.34 (brm, 2H), 3.69 (s, 3H), 3.59 (s, 3H), 3.56 (s, 3H), 3.54 (s, 3H), 3.52 (s, 3H), 2.31 (s, 3H), 1.10 (brs, 2H), 0.02 (s, 9H).

Reference Example 44

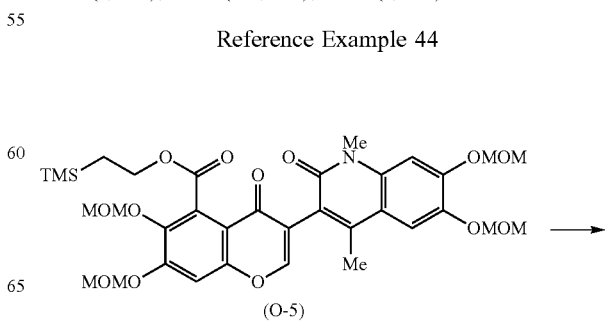

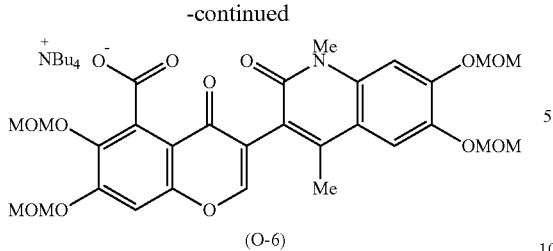
(O-6)
According to the method described in Reference example 28, Compound (O-6) (0.45 g) was prepared from Compound (O-5) (0.15 g, 0.21 mmol).
LC/MS (Condition (2)): [M+H]$^+$/Rt=602/1.67 min
Reference Example 45
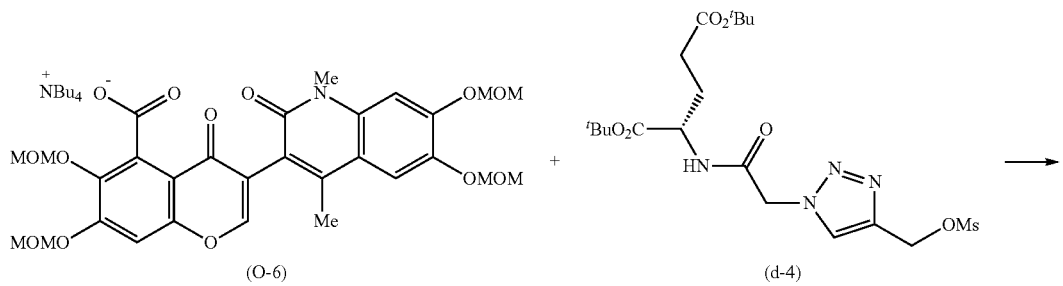
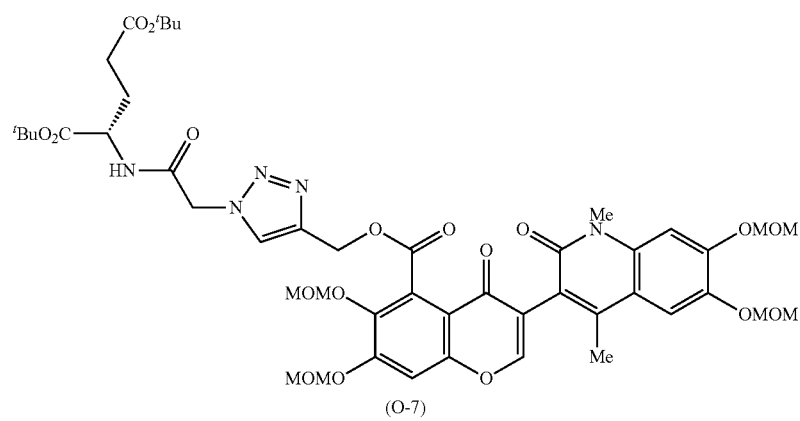
(O-7)
According to the method described in Reference example 29, Compound (O-7) (0.13 g, 61% yield) was prepared from Compound (O-6) (0.18 g) and Compound (d-4) (0.14 g, 0.30 mmol).
LC/MS (Condition (3)): [M+H]$^+$/Rt=983/1.07 min

Example 15

N-({4-[({[3-(6,7-Dihydroxy-1,4-dimethyl-2-oxo-1,2-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid

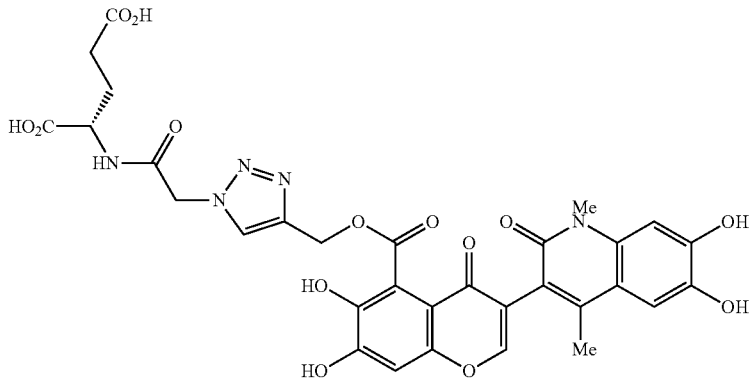 [SMILES: Cc1c(-c2coc3cc(O)c(O)c(C(=O)OCc4cn(CC(=O)N[C@@H](CCC(=O)O)C(=O)O)nn4)c3c2=O)c(=O)n(C)c2cc(O)c(O)cc12]

Compound (O-7) (0.13 g, 0.13 mmol) was dissolved in trifluoroacetic acid (2 mL), and then the reaction solution was stirred at room temperature for 2 hours. The reaction solution was concentrated by azeotropy with toluene. The obtained residue was purified by reverse phase chromatography with an ODS column (0.05% aqueous trifluoroacetic acid/0.035% trifluoroacetic acid in acetonitrile) to give the title compound (46 mg, 51% yield).

LC/MS (Condition (2)): [M+H]$^+$/Rt=694/1.27 min $^1$H-NMR (CD$_3$OD, 400 MHz) δ: 8.60 (dd, J=7.8, 3.2 Hz, 1H), 8.07 (s, 1H), 7.99 (s, 1H), 7.26 (s, 1H), 6.99 (s, 1H), 6.97 (s, 1H), 5.43 (s, 2H), 5.18 (s, 2H), 4.48-4.43 (m, 1H), 3.68 (s, 3H), 2.39 (t, J=7.5 Hz, 2H), 2.29 (s, 3H), 2.23-2.14 (m, 1H), 2.00-1.91 (m, 1H).

Reference Example 46

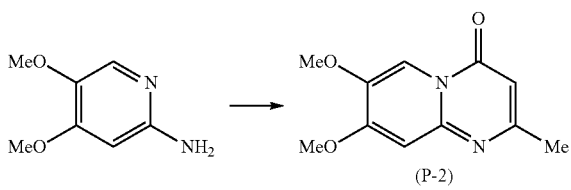

To 4,5-dimethoxy-pyridin-2-ylamine (0.15 g, 1.0 mmol) were added polyphosphoric acid (1.0 g) and ethyl acetoacetate (0.19 mL, 1.5 mmol). After stirring the reaction mixture at 100° C. for one hour, the reaction mixture was cooled to room temperature. The reaction mixture was neutralized with aqueous sodium hydroxide, and extracted with ethyl acetate. The organic layer was washed with brine, dried over magnesium sulfate, and then concentrated in vacuo. The obtained crude product was washed with ethyl acetate to give Compound (P-2) (0.10 g, 45% yield).

LC/MS (Condition (1)): [M+H]$^+$/Rt=221/0.37 min

Reference Example 47

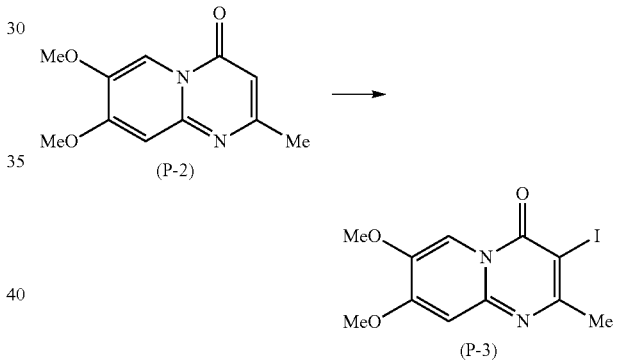

To a solution of Compound (P-2) (0.10 g, 0.45 mmol) in acetonitrile (2.5 mL) was added N-iodosuccinimide (0.17 g, 0.75 mmol). After stirring the reaction mixture at 80° C. for 2 hours, the reaction mixture was cooled to room temperature. Water was added to the reaction mixture, and the mixture was extracted with ethyl acetate. The organic layer was washed with brine, dried over magnesium sulfate, and then concentrated in vacuo. The obtained crude product was washed with hexane to give Compound (P-3) (80 mg, 51% yield).

LC/MS (Condition (1)): [M+H]$^+$/Rt=346/0.73 min

Reference Example 48

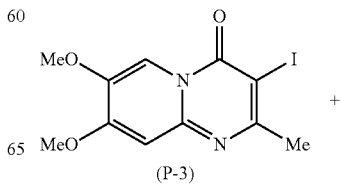

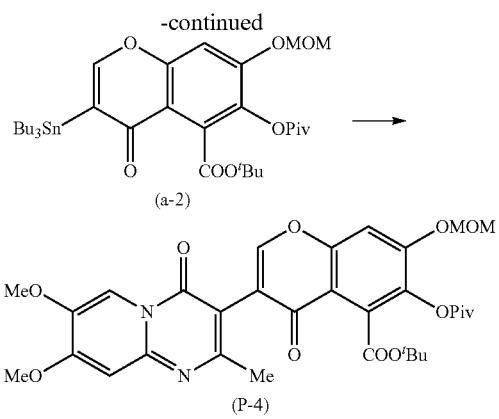

To a solution of Compound (P-3) (10 mg, 29 nmol) in N,N-dimethylformamide (1 mL) were added tripotassium phosphate (10 mg, 47 nmol), 2-dicyclohexylphosphino-2',6'-dimethoxybiphenyl (6.2 mg, 15 nmol), and tris(dibenzylideneacetone)dipalladium (6.9 mg, 7.5 nmol). The mixture was heated to 70° C., and a solution of Compound (α-2) (31 mg, 45 nmol) in N,N-dimethylformamide (1 mL) was added thereto. After stirring the reaction mixture at 70° C. for one hour, a solution of tripotassium phosphate (10 mg, 47 nmol), 2-dicyclohexylphosphino-2',6'-dimethoxybiphenyl (6.2 mg, 15 nmol), tris(dibenzylideneacetone)dipalladium (6.9 mg, 7.5 nmol), tetrakis(triphenylphosphine)palladium (37 mg, 0.032 mmol), and Compound (a-2) (31 mg, 45 nmol) in N,N-dimethylformamide (1 mL) was added thereto. After stirring the reaction mixture at 70° C. for one hour, the reaction mixture was cooled to room temperature. Water was added to the reaction mixture, and the mixture was extracted with ethyl acetate. The organic layer was washed with brine, dried over magnesium sulfate, and then concentrated in vacuo. The obtained residue was purified by silica gel column chromatography (hexane:ethyl acetate=90:10-5:95) to give Compound (P-4) (4.0 mg, 20% yield).

LC/MS (Condition (1)): [M+H]$^+$/Rt=625/1.02 min

Example 16

3-(7,8-Dihydroxy-2-methyl-4-oxo-4H-pyrido[1,2-a]pyrimidin-3-yl)-6,7-dihydroxy-4-oxo-4H-chromene-5-carboxylic acid

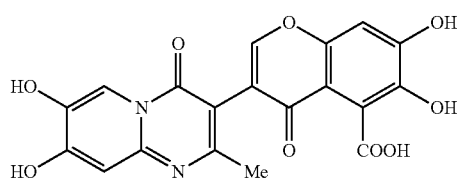 [SMILES: Cc1nc2cc(O)c(O)cn2c(=O)c1-c1coc2cc(O)c(O)c(C(=O)O)c2c1=O]

To a solution of Compound (P-4) (4.0 mg, 6.4 nmol) in chloroform (1 mL) was added boron tribromide (1 mol/L dichloromethane solution) (1 mL, 1 mmol). After stirring the reaction mixture at 50° C. for one hour, boron tribromide (1 mol/L dichloromethane solution) (1 mL, 1 mmol) was added again thereto. After stirring the reaction mixture at 50° C. for 8 hours, the reaction mixture was cooled to room temperature. Methanol and toluene were added to the reaction mixture, and water in the mixture was removed by azeotropy to obtain a dried residue. The obtained crude product was washed with methanol to give the title compound (2.0 mg, 75% yield).

LC/MS (Condition (1)): [M+H]$^+$/Rt=413/0.43 min $^1$H-NMR (DMSO-d$_6$, 400 MHz) δ: 11.37 (brs, 1H), 9.43 (brs, 1H), 8.22 (s, 1H), 8.20 (s, 1H), 6.96 (s, 1H), 6.54 (s, 1H), 2.20 (s, 3H).

Reference Example 49

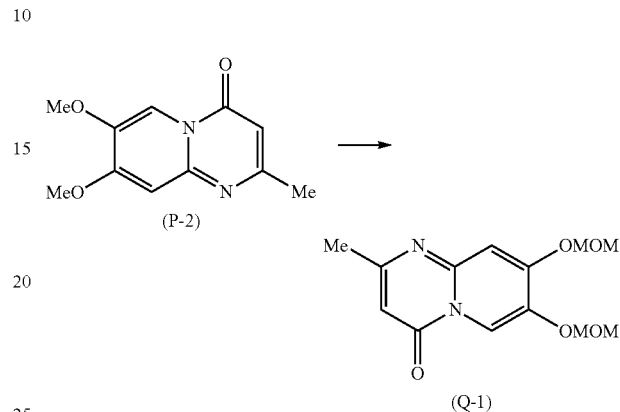

To Compound (P-2) (0.98 g, 4.5 mmol) was added boron tribromide (1 mol/L dichloromethane solution) (31 mL, 31 mmol), and then the reaction mixture was stirred under reflux for 12 hours. The reaction solution was cooled in ice bath, and methanol was added dropwise thereto. The mixture was concentrated in vacuo. The procedure was repeated three times, and the obtained residue was dried to give a crude product. To the obtained crude product was added dichloromethane (50 mL), and to the mixture in ice bath were added N,N-diisopropylethylamine (11.4 mL, 66.7 mmol) and chloromethyl methyl ether (2.3 mL, 31 mmol). The obtained solution was stirred at room temperature for one hour. To the reaction solution was added water, and the organic layer was washed. To the organic layer was added toluene, and the solution was concentrated in vacuo. The obtained residue was purified by amino-silica gel column chromatography (hexane/ethyl acetate 9:1-1:1) to give Compound (Q-1) (1.01 g, 81% yield).

$^1$H-NMR (CDCl$_3$, 400 MHz) δ: 8.81 (s, 1H), 7.22 (s, 1H), 6.18 (s, 1H), 5.40 (s, 2H), 5.31 (s, 2H), 3.55 (s, 3H), 3.54 (s, 3H), 2.41 (s, 3H).

Reference Example 50

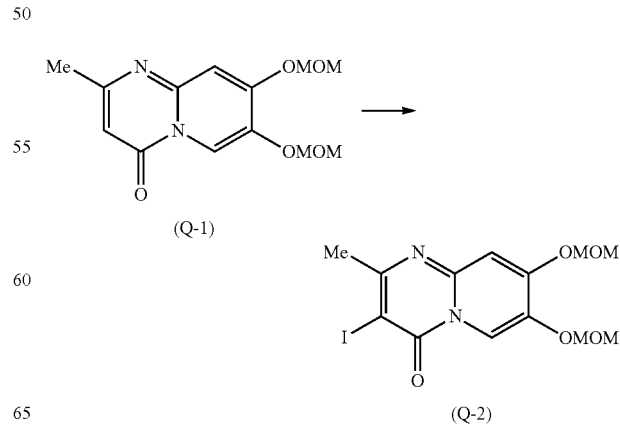

According to the method described in Reference example 47, Compound (Q-2) (0.28 g, 86% yield) was prepared from Compound (Q-1) (0.23 g, 0.82 mmol).

¹H-NMR (CDCl₃, 400 MHz) δ: 8.84 (s, 1H), 7.21 (s, 1H), 5.40 (s, 2H), 5.30 (s, 2H), 3.54 (s, 6H), 2.70 (s, 3H).

Reference Example 51

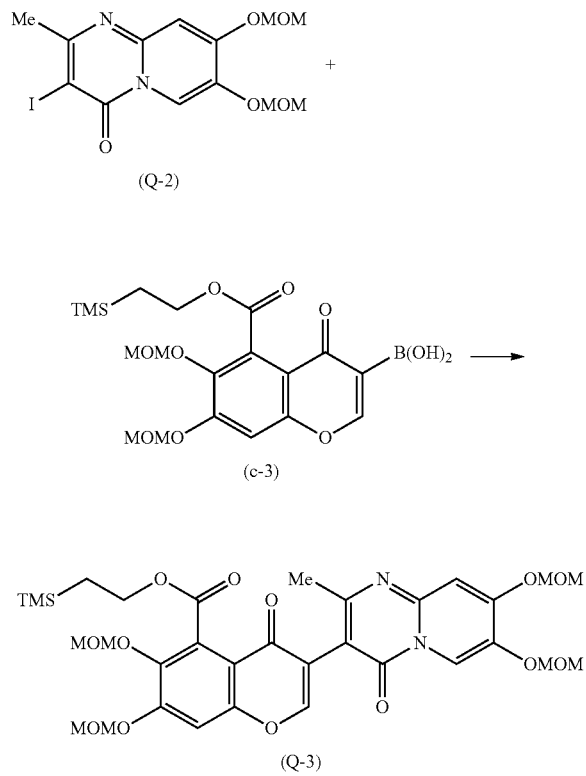

Compound (Q-2) (0.20 g, 0.50 mmol), Compound (c-3) (0.28 g, 0.62 mmol), and bis(di-tert-butyl(4-dimethylaminophenyl)phosphine)dichloropalladium (35 mg, 0.05 mmol) were dissolved in THF (4 mL) under nitrogen atmosphere, and then 2 mol/L aqueous sodium carbonate (1 mL, 2.0 mmol) was added thereto. After stirring the reaction mixture at 65° C. for 3.5 hours, saturated aqueous ammonium chloride was added to the reaction mixture, and the mixture was extracted with chloroform. The organic layer was washed with brine, dried over sodium sulfate, and then concentrated in vacuo. The obtained residue was purified by silica gel column chromatography (chloroform:ethyl acetate=25:75-0:100) to give Compound (Q-3) (0.13 g, 37% yield)

¹H NMR (CDCl₃, 400 MHz) δ: 8.79 (s, 1H), 7.95 (brs, 1H), 7.27 (s, 1H), 7.27 (s, 1H), 7.20 (s, 1H), 5.42-5.38 (m, 2H), 5.35-5.31 (m, 2H), 5.31-5.26 (m, 2H), 5.21-5.17 (m, 2H), 4.60-4.32 (brm, 2H), 3.60 (s, 3H), 3.54 (s, 3H), 3.53 (s, 3H), 3.53 (s, 3H), 2.32 (s, 3H), 1.12-1.10 (brm, 2H), 0.02 (s, 9H).

Reference Example 52

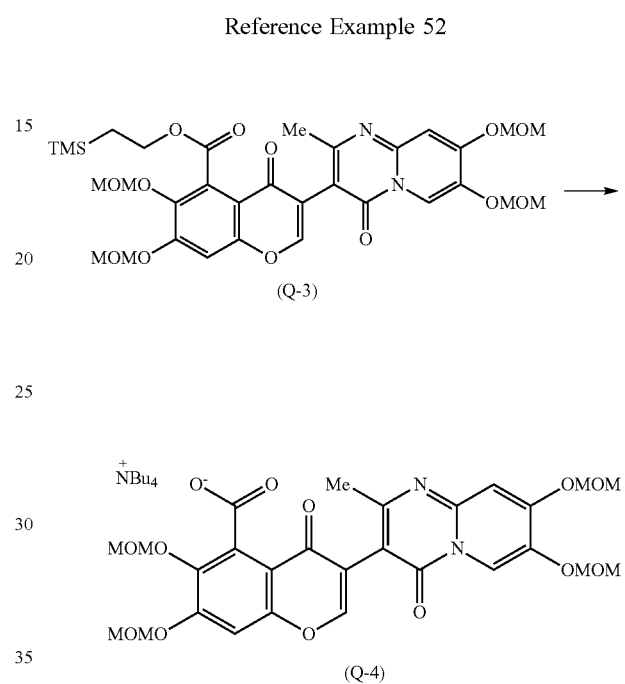

To a solution of Compound (Q-3) (0.13 g, 0.19 mmol) in THF (2 mL) was added tetrabutylammonium fluoride in THF (1 mol/L, 0.6 mL, 0.60 mmol), and then the reaction mixture was stirred at room temperature for one hour. After the reaction was terminated, the reaction solution was concentrated in vacuo to give Compound (Q-4) (0.38 g).

LC/MS (Condition (2)): [M+H]⁺/Rt=589/1.48 min

Example 17

N-({4-[({[3-(7,8-Dihydroxy-2-methyl-4-oxo-4H-pyrido[1,2-a]pyrimidin-3-yl)-6,7-dihydroxy-4-oxo-4H-chromen-5-yl]carbonyl}oxy)methyl]-1H-1,2,3-triazol-1-yl}acetyl)-L-glutamic acid

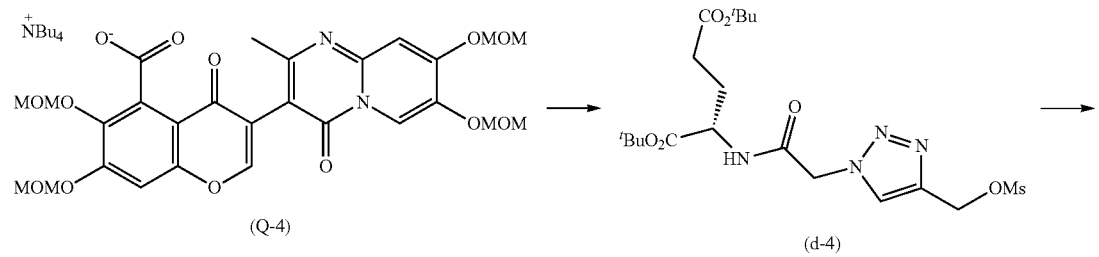

-continued

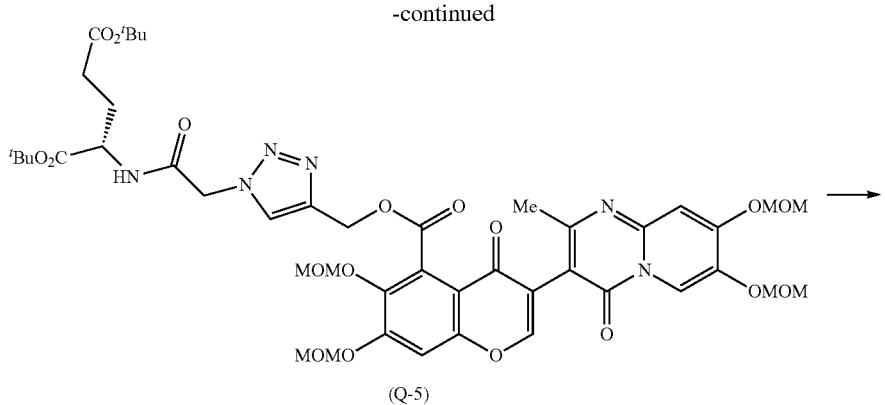

(Q-5)

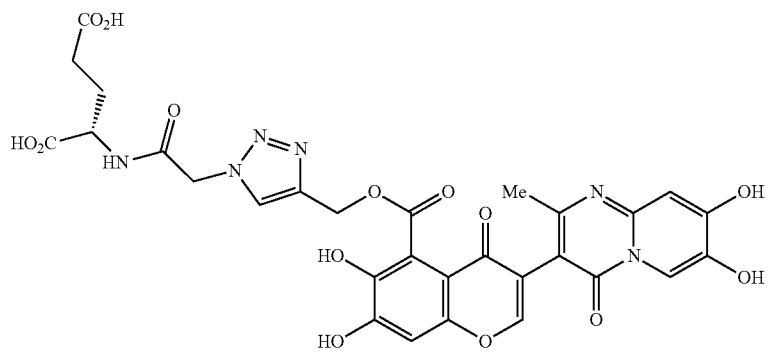

To a solution of Compound (Q-4) (0.38 g) in acetonitrile (2 mL) was added Compound (d-4) (0.20 g, 0.42 mmol), and then the reaction mixture was stirred at room temperature for 21 hours. Saturated aqueous ammonium chloride was added to the reaction mixture, and the mixture was extracted with chloroform. The organic layer was washed with brine, dried over sodium sulfate, and then concentrated in vacuo. The obtained residue was purified by silica gel column chromatography (chloroform:methanol=97:3-90:10). The obtained crude product was purified by reverse phase chromatography with an ODS column (0.05% aqueous trifluoroacetic acid/0.035% trifluoroacetic acid in acetonitrile) to give Compound (Q-5) (42.5 mg, 24% yield from Compound Q-3).

Compound (Q-5) (42.5 mg, 0.044 mmol) was dissolved in trifluoroacetic acid (1.5 mL), and the solution was stirred at room temperature for 3 hours. The reaction solution was concentrated in vacuo by azeotropy with toluene. The obtained residue was washed with acetonitrile to give the title compound (19 mg, 64% yield from Compound Q-5).

LC/MS (Condition (2)): [M+H]$^+$/Rt=681/1.20 min $^1$H-NMR (DMSO-d$_6$, 400 MHz) δ: 11.54 (s, 1H), 9.68 (s, 1H), 8.79 (d, J=7.9 Hz, 1H), 8.34 (s, 1H), 8.23-8.21 (m, 1H), 8.19 (s, 1H), 7.10 (s, 1H), 6.50-6.44 (m, 1H), 5.25 (s, 2H), 4.37-4.31 (m, 2H), 2.43-2.37 (m, 2H), 2.27 (s, 3H), 2.13-2.04 (m, 1H), 1.95-1.85 (m, 1H).

Example 18

N-[({[3-(7,8-Dihydroxy-2-methyl-4-oxo-4H-pyrido[1,2-a]pyrimidin-3-yl)-6,7-dihydroxy-4-oxo-4H-chromen-5-yl]carbonyl}oxy)acetyl]-L-glutamic acid

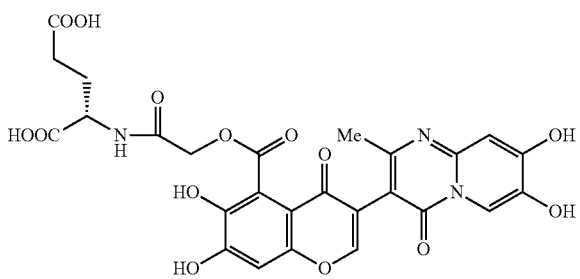 [SMILES: Cc1nc2cc(O)c(O)cn2c(=O)c1-c1coc2cc(O)c(O)c(C(=O)OCC(=O)N[C@@H](CCC(=O)O)C(=O)O)c2c1=O]

From Compound (Q-4) (0.14 g) and Compound (f-2) (94 mg, 0.25 mmol) which was prepared in a similar manner to Reference example 10, the title compound (20 mg, 20% yield from Compound Q-3) was prepared in a similar manner to Example 17.

LC/MS (Condition (2)): [M+H]$^+$/Rt=600/1.15 min $^1$H-NMR (DMSO-d$_6$, 400 MHz) δ: 11.55-11.52 (brm, 1H), 9.97 (s, 1H), 8.36-8.28 (m, 2H), 8.04 (s, 1H), 7.07 (d, J=1.2 Hz, 1H), 6.20 (brs, 1H), 4.82 (dd, J=14.8, 7.0 Hz, 1H), 4.65 (d, J=14.8 Hz, 1H), 4.30-4.22 (m, 1H), 2.20-2.10 (m, 2H), 2.15 (s, 3H), 1.93-1.84 (m, 1H), 1.78-1.68 (m, 1H).

Reference Example 53

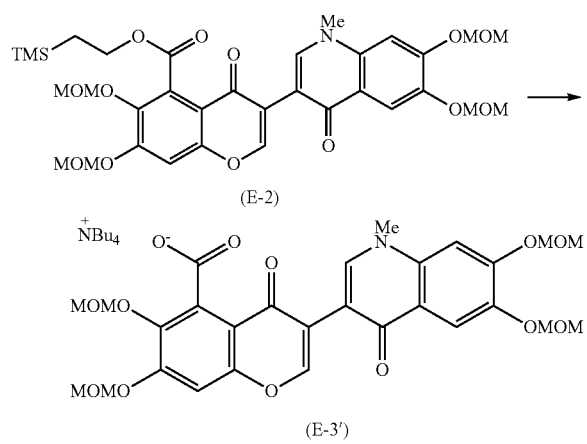

To a solution of Compound (E-2) (2.4 g, 3.5 mmol) in tetrahydrofuran (12 mL) was added 1 mol/L tetrabutylammonium fluoride in tetrahydrofuran (9.1 mL, 9.1 mmol) dropwise, and then the reaction mixture was stirred at room temperature for one hour. Subsequently, 1 mol/L tetrabutylammonium fluoride in tetrahydrofuran (1.4 mL) was added thereto, and the reaction solution was stirred at room temperature for one hour. Furthermore, 1 mol/L tetrabutylammonium fluoride in tetrahydrofuran (1.75 mL) was added thereto, and the reaction solution was stirred at room temperature for one hour. To the reaction solution was added toluene dropwise, and the mixture was cooled in ice bath. The precipitated solid was collected on a filter, and dried to give Compound (E-3') (2.45 g, 84% yield).

$^{1}$H-NMR (CDCl$_3$, 400 MHz) δ: 9.03 (s, 1H), 8.82 (s, 1H), 8.16 (s, 1H), 7.16 (s, 1H), 6.96 (s, 1H), 5.38 (s, 2H), 5.34 (s, 2H), 5.29 (s, 2H), 5.26 (s, 2H), 3.81 (s, 3H), 3.65 (s, 3H), 3.56 (s, 3H), 3.53 (s, 3H), 3.49 (s, 3H), 3.30-3.24 (m, 8H), 1.60-1.50 (m, 8H), 1.35-1.25 (m, 8H), 0.87 (t, 12H, J=7.2 Hz).

Example 19

N-[({[3-(6,7-Dihydroxy-1-methyl-4-oxo-1,4-dihydroquinolin-3-yl)-6,7-dihydroxy-4-oxo-4H-chromen-5-yl]carbonyl}oxy)acetyl]-L-glutamic acid

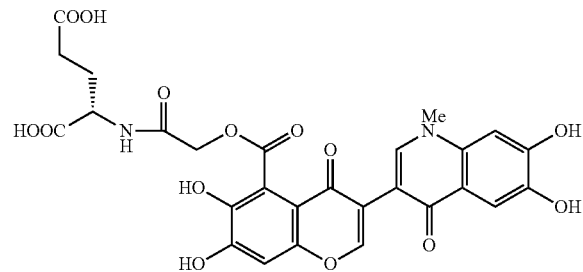 [SMILES: Cn1cc(-c2coc3cc(O)c(O)c(C(=O)OCC(=O)N[C@@H](CCC(=O)O)C(=O)O)c3c2=O)c(=O)c2cc(O)c(O)cc21]

From Compound (E-3') (0.15 g, 0.18 mmol) and Compound (f-2) (0.10 mg, 0.27 mmol) which was prepared in a similar manner to Reference example 10, the title compound (67 mg, 63% yield) was prepared in a similar manner to Example 17. LC/MS (Condition (2)): [M+H]$^+$/Rt=599/1.242 min $^{1}$H-NMR (DMSO-d$_6$, 400 MHz) δ: 11.49 (br, 1H), 9.91 (s, 1H), 8.66-8.65 (m, 1H), 8.37-8.33 (m, 1H), 8.24 (s, 1H), 7.58-7.56 (m, 1H), 7.06 (s, 1H), 7.00 (s, 1H), 4.83-4.79 (m, 1H), 4.71-4.67 (m, 1H), 4.35-4.25 (m, 1H), 3.81 (s, 3H), 2.18-2.11 (m, 2H), 2.15 (s, 3H), 1.97-1.87 (m, 1H), 1.82-1.69 (m, 1H).

Reference Example 54

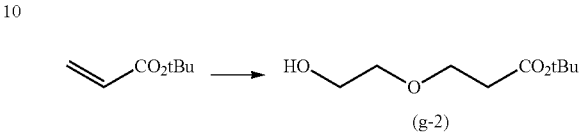

To a solution of ethylene glycol (5.0 mL) in THF (100 mL) was added sodium hydride (0.19 g, 4.7 mmol) at 0° C., and then the reaction mixture was stirred warming to room temperature for 30 minutes. To the reaction mixture at 0° C. was added a solution of tert-butyl acrylate (2 g, 16 mmol) in THF (50 mL) over 30 minutes, and the mixture was stirred at room temperature for 2 days, and concentrated in vacuo. The obtained residue was purified by silica gel column chromatography (pentane:ethyl acetate=3:1-1:1) to give Compound (g-2) (0.34 g, 6.9% yield).

$^{1}$H-NMR (CDCl$_3$, 400 MHz) δ: 4.21-4.20 (m, 2H), 3.87-3.82 (m, 1H), 3.75-3.70 (m, 2H), 3.59-3.56 (m, 2H), 2.52-2.49 (m, 2H), 1.46 (s, 9H).

Reference Example 55

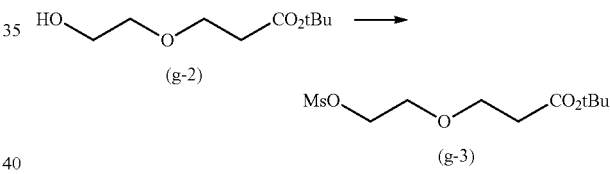

To a solution of Compound (g-2) (0.15 g, 0.79 mmol) and triethylamine (0.16 g, 1.6 mmol) in THF (10 mL) was added methanesulfonyl chloride (0.13 g, 1.2 mmol) at 0° C., and then the reaction mixture was stirred at room temperature for 16 hours. The solvent was removed under reduced pressure, and the residue was dissolved in ethyl acetate (30 mL). The solution was washed with saturated aqueous sodium hydrogencarbonate, dried with sodium sulfate, and concentrated in vacuo to give Compound (g-3) (0.21 g, 100% yield).

$^{1}$H-NMR (CDCl$_3$, 400 MHz) δ: 3.68-3.64 (m, 4H), 3.03-2.99 (m, 2H), 2.98 (s, 3H), 2.44-2.41 (m, 2H), 1.38 (s, 9H).

Reference Example 56

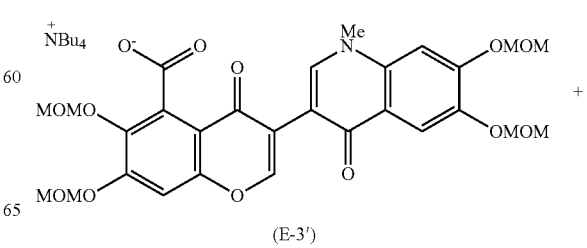

-continued

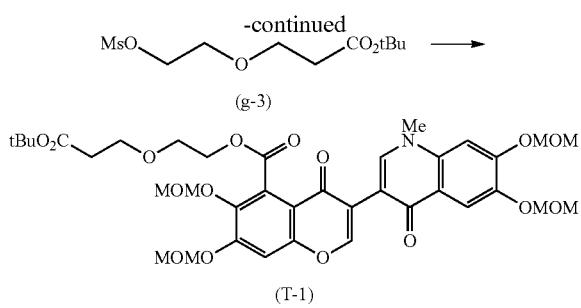

Compound (E-3') (50 mg, 0.060 mmol), Compound (g-3) (81 mg, 0.30 mmol), and triethylamine (31 mg, 0.30 mmol) were dissolved in acetonitrile (2.5 mL), and the solution was stirred at 45° C. for 24 hours. The solvent of the reaction solution was removed in vacuo, and the residue was purified by preparative TLC (methylene chloride:methanol=20:1) to give Compound (T-1) (32 mg, 70% yield).

$^1$H-NMR (CDCl$_3$, 400 MHz) δ: 9.30 (s, 1H), 8.75 (s, 1H), 8.17 (s, 1H), 7.28 (s, 1H), 7.18 (s, 1H), 5.39 (s, 2H), 5.36 (s, 2H), 5.32 (s, 2H), 5.19 (s, 2H), 4.63-4.55 (m, 2H), 3.85 (s, 3H), 3.83-3.75 (m, 2H), 3.73-3.70 (m, 2H), 3.59-3.52 (m, 12H), 2.48-2.45 (m, 2H), 1.39 (s, 9H).

Example 20

3-[2-({[3-(6,7-Dihydroxy-1-methyl-4-oxo-1,4-dihydroquinolin-3-yl)-6,7-dihydroxy-4-oxo-4H-chromen-5-yl]carbonyl}oxy)ethoxy]propanoic acid

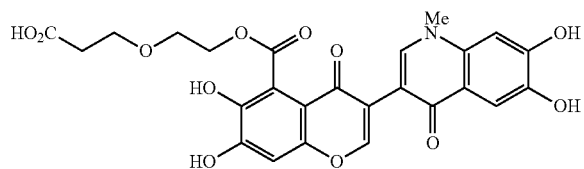 [SMILES: Cn1cc(-c2coc3cc(O)c(O)c(C(=O)OCCOCCC(=O)O)c3c2=O)c(=O)c2cc(O)c(O)cc21]

To a solution of Compound (T-1) (32 mg, 0.040 mmol) in methylene chloride (3.0 mL) was added trifluoroacetic acid (2.0 mL) at 0° C., and then the reaction mixture was stirred at room temperature for 10 hours. The solvent and trifluoroacetic acid were removed in vacuo, and then 2 mol/L hydrogen chloride in methanol (10 ml) was added to the residue and the solution was concentrated in vacuo to give the title compound (14 mg, 59% yield).

$^1$H-NMR (DMSO-d$_6$, 400 MHz) δ: 8.55 (s, 1H), 8.27 (s, 1H), 7.59 (s, 1H), 7.04-7.03 (m, 2H), 4.35-4.25 (m, 2H), 3.84 (s, 3H), 3.66-3.64 (m, 2H), 3.61 (t, J=6.3 Hz, 2H), 2.42 (t, J=6.3 Hz, 2H).

Reference Example 57

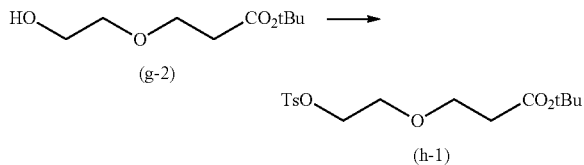

To a solution of Compound (g-2) (0.20 g, 1.1 mmol) and triethylamine (0.31 g, 3.2 mmol) in THF (15 mL) was added p-toluenesulfonyl chloride (0.30 g, 1.6 mmol) at 0° C. over 10 minutes, and then the reaction mixture was stirred at at room temperature 16 hours. The solvent was removed in vacuo, and the residue was purified by preparative TLC (pentane:ethyl acetate=4:1) to give Compound (h-1) (0.20 g, 55% yield).

$^1$H-NMR (CDCl$_3$, 400 MHz) δ: 7.71 (d, J=8.2 Hz, 2H), 7.27 (d, J=8.2 Hz, 2H), 4.07-4.05 (m, 2H), 3.55-3.54 (m, 4H), 2.39-2.33 (m, 5H), 1.36 (s, 9H).

Reference Example 58

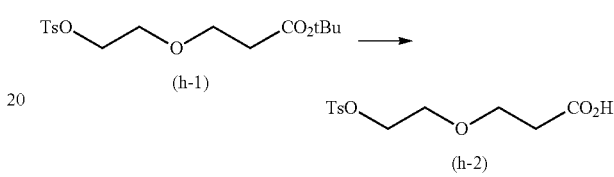

To a solution of Compound (h-1) (0.20 g, 0.57 mmol) in methylene chloride (30 mL) was added trifluoroacetic acid (0.28 g, 2.9 mmol) at 0° C., and then the reaction mixture was stirred at room temperature for 16 hours. The solvent and trifluoroacetic acid were removed in vacuo, and the residue was dried to give Compound (h-2) (0.17 g, 100% yield).

$^1$H-NMR (CDCl$_3$, 400 MHz) δ: 7.61 (d, J=8.4 Hz, 2H), 7.21 (d, J=8.4 Hz, 2H), 4.09-4.07 (m, 2H), 3.64-3.59 (m, 4H), 2.37-2.35 (m, 2H), 2.30 (s, 3H).

Reference Example 59

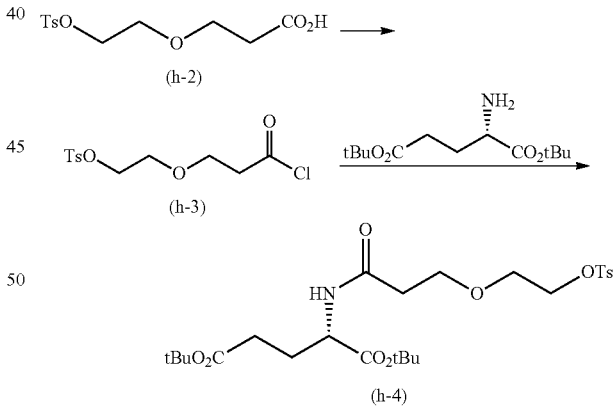

To a solution of Compound (h-2) (0.17 g, 0.57 mmol) in methylene chloride (5.0 mL) was added oxalyl chloride (0.22 g, 1.7 mmol) at 0° C., and then the reaction mixture was stirred at room temperature for 6 hours. The solvent and oxalyl chloride were removed in vacuo to give the compound of formula (h-3) (0.17 g, 100% yield from h-2). To a solution of di-tert-butyl L-glutamate hydrochloride (0.20 mg, 0.68 mmol) and triethylamine (0.17 g, 1.7 mmol) in THF (20 mL) was added the compound of formula (h-3) (0.17 g, 0.57 mmol) at 0° C., and the mixture was stirred at room temperature for 30 minutes. The mixture was concentrated and purified by preparative TLC (pentane:ethyl acetate=3:1) to give Compound (h-4) (0.24 g, h-3 yield from 62%).

$^1$H-NMR (CDCl$_3$, 400 MHz) δ: 7.79-7.76 (m, 2H), 7.27-7.27 (m, 2H), 6.51-6.49 (m, 1H), 4.43-4.37 (m, 1H), 4.12-4.10 (m, 2H), 3.63-3.57 (m, 4H), 2.38-2.29 (m, 5H), 2.29-2.12 (m, 2H), 2.09-1.97 (m, 1H), 1.86-1.73 (m, 1H), 1.39 (s, 9H), 1.36 (s, 9H).

Reference Example 60

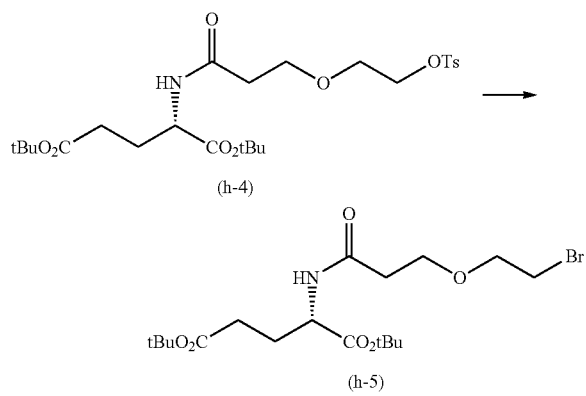

Compound (h-4) (0.30 g, 0.57 mmol), potassium bromide (0.20 g, 1.7 mmol), and tetrabutylammonium bromide (91 mg, 0.28 mmol) were dissolved in acetone (40 ml), and the reaction mixture was stirred at 80° C. for 16 hours. The reaction mixture was cooled to room temperature, and the precipitated solid was removed by filtration. The filtrate was dissolved in ethyl acetate, and the solution was washed with water and dried over sodium sulfate. The solution was concentrated in vacuo to give Compound (h-5) (0.20 g, 79% yield).

$^1$H-NMR (CDCl$_3$, 400 MHz) δ: 4.52-4.48 (m, 1H), 3.82-3.75 (m, 2H), 3.51-3.48 (m, 1H), 3.39-3.34 (m, 2H), 2.52-2.49 (m, 1H), 2.33-2.27 (m, 2H), 2.17-2.09 (m, 1H), 1.94-1.85 (m, 1H), 1.71-1.65 (m, 3H), 1.46 (s, 9H), 1.44 (s, 9H).

Reference Example 61

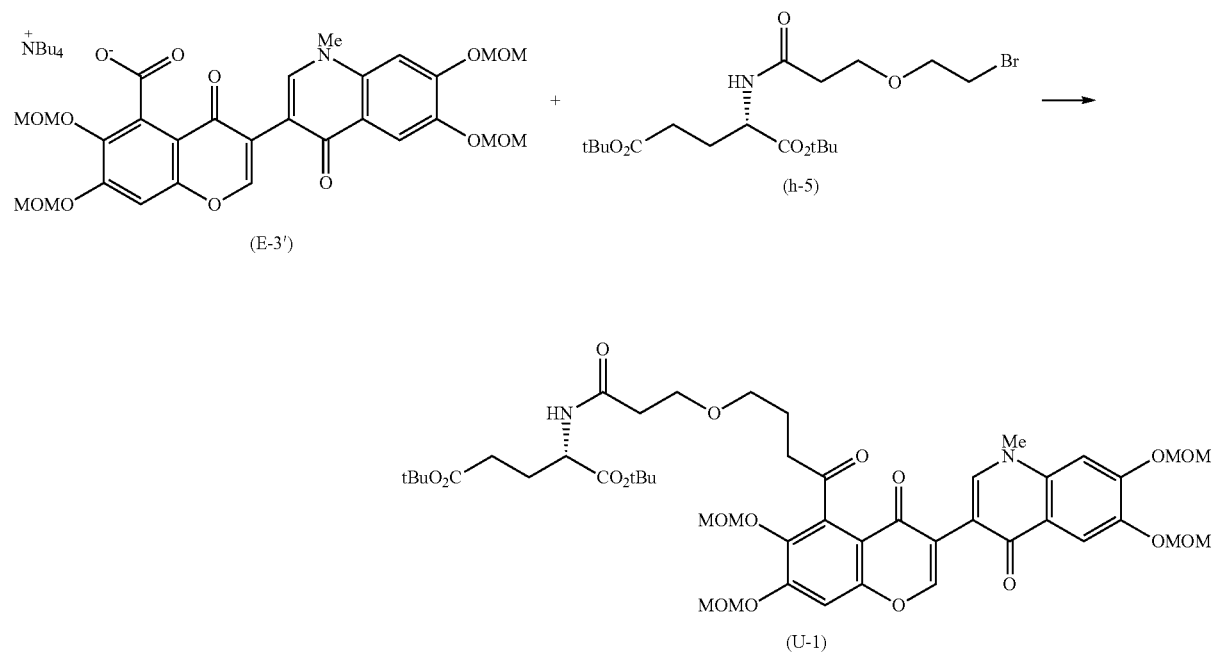

According to the method described in Reference example 56, Compound (U-1) (31 mg, 54% yield) was prepared from Compound (E-3') (50 mg, 0.060 mmol) and Compound (h-5) (0.12 g, 0.27 mmol).

$^1$H-NMR (CDCl$_3$, 400 MHz) δ: 9.28 (s, 1H), 8.73 (s, 1H), 8.17 (s, 1H), 7.28 (s, 1H), 7.18 (s, 1H), 6.71 (br, 1H), 5.39 (s, 2H), 5.35 (s, 2H), 5.32 (s, 2H), 5.18 (s, 2H), 4.65-4.60 (m, 2H), 4.49-4.43 (m, 1H), 3.85 (s, 3H), 3.88-3.83 (m, 2H), 3.80-3.74 (m, 2H), 3.60 (s, 3H), 3.56 (s, 3H), 3.54 (s, 3H), 3.52 (s, 3H), 2.35-2.18 (m, 4H), 1.90-1.75 (m, 2H), 1.46 (s, 9H), 1.41 (s, 9H).

Example 21

N-{3-[2-({[3-(6,7-Dihydroxy-1-methyl-4-oxo-1,4-dihydroquinolin-3-yl)-6,7-dihydroxy-4-oxo-4H-chromen-5-yl]carbonyl}oxy)ethoxy]propanoyl}-L-glutamic acid

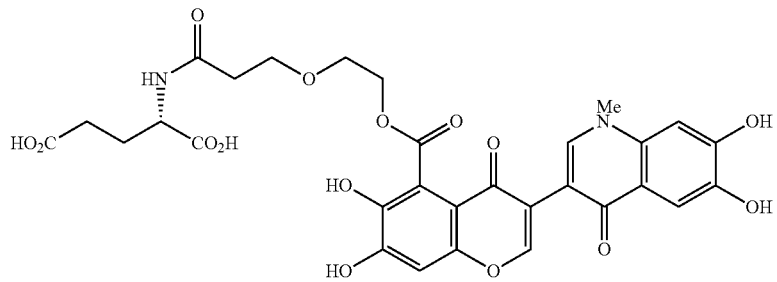 [SMILES: Cn1cc(-c2coc3cc(O)c(O)c(C(=O)OCCOCCC(=O)N[C@@H](CCC(=O)O)C(=O)O)c3c2=O)c(=O)c2cc(O)c(O)cc21]

To a solution of Compound (U-1) (31 mg, 0.033 mmol) in methylene chloride (3.0 ml) was added trifluoroacetic acid (2.0 ml) at 0° C., and the reaction mixture was stirred at room temperature for 10 hours. The reaction mixture was concentrated in vacuo, and 4 M hydrogen chloride in dioxane (1.0 ml) was added thereto. The mixture was stirred for 10 minutes. The obtained residue was dissolved in DMF (3 ml), and diethyl ether (20 ml) was added thereto. The precipitated solid was collected to give the title compound (23 mg, 100% yield).

LC/MS (Condition (2)): [M+H]$^+$/Rt=657/1.23 min

Reference Example 62

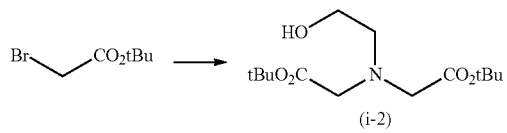 [SMILES: CC(C)(C)OC(=O)CBr ; CC(C)(C)OC(=O)CN(CCO)CC(=O)OC(C)(C)C]

To a solution of 2-aminoethanol (0.20 g, 3.3 mmol) and potassium hydrogen carbonate (1.6 g, 16 mmol) in DMF (10 ml) was added tert-butyl 2-bromoacetate (3.0 g, 16 mmol) at 0° C., and the reaction mixture was stirred at room temperature for 16 hours. The solvent of the reaction mixture was removed under reduced pressure, and then the residue was purified by preparative HPLC to give Compound (i-2) (0.63 g, 34% yield).

$^1$H-NMR (CDCl$_3$, 400 MHz) δ: 3.54-3.51 (m, 2H), 3.44 (s, 4H), 2.89-2.87 (m, 2H), 1.46 (s, 18H).

Reference Example 63

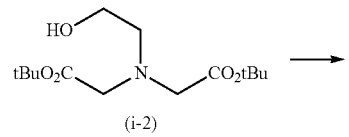

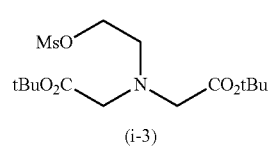 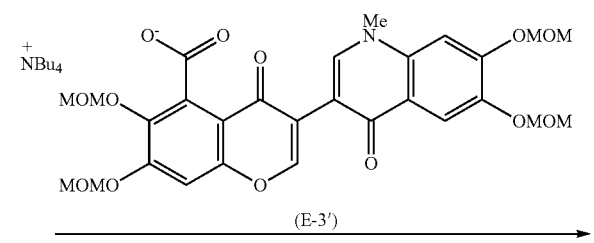

-continued

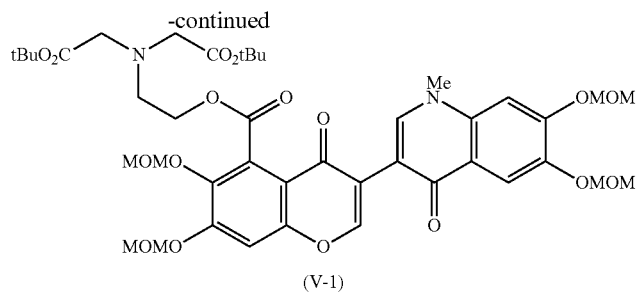

(V-1)

To a solution of Compound (i-2) (0.15 g, 0.52 mmol) and triethylamine (0.16 g, 1.6 mmol) in THF (10 mL) was added methanesulfonyl chloride (0.13 g, 1.2 mmol) at 0° C., and the reaction mixture was stirred at room temperature for 16 hours. The solvent was removed under reduced pressure, and the residue was dissolved in ethyl acetate (30 mL). The solution was washed with saturated aqueous sodium hydrogencarbonate, dried over sodium sulfate, and concentrated in vacuo to give Compound (i-3) (0.21 g, 100% yield).

According to the method described in Reference example 56, Compound (V-1) (36 mg, 70% yield from E-3') was obtained from Compound (E-3') (50 mg, 0.060 mmol) and Compound (i-3) (0.11 g, 0.30 mmol).

$^1$H-NMR (CDCl$_3$, 400 MHz) δ: 9.39 (s, 1H), 8.84 (s, 1H), 8.17 (s, 1H), 7.27 (s, 1H), 7.19 (s, 1H), 5.39 (s, 2H), 5.35 (s, 2H), 5.31 (s, 2H), 5.18 (s, 2H), 3.87 (s, 3H), 3.60-3.48 (m, 18H), 3.22-3.17 (m, 2H), 1.37 (s, 18H).

Example 22

2,2'-{[2-({[3-(6,7-Dihydroxy-1-methyl-4-oxo-1,4-dihydroquinolin-3-yl)-6,7-dihydroxy-4-oxo-4H-chromen-5-yl]carbonyl}oxy)ethyl]imino}-di-acetic acid

According to the method described in Example 21, the title compound (36 mg, 100% yield) was prepared from Compound (V-1) (36 mg, 0.042 mmol).

$^1$H-NMR (DMSO-d$_6$, 400 MHz) δ: 8.51 (s, 1H), 8.28 (s, 1H), 7.61 (s, 1H), 7.09 (s, 1H), 7.08 (s, 1H), 4.11 (s, 4H), 3.89 (s, 3H), 3.51-3.49 (m, 2H), 3.17-3.13 (m, 2H).

Reference Example 64

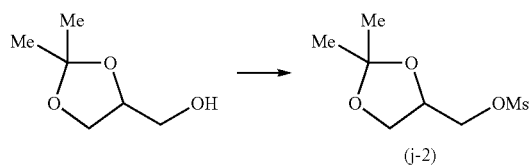 [SMILES: CC1(C)OCC(CO)O1 ; CC1(C)OCC(COS(C)(=O)=O)O1]

According to the method described in Reference example 55, Compound (j-2) (0.24 g, 100% yield) was prepared from (2,2-dimethyl-1,3-dioxolan-4-yl)methanol (0.15 g, 1.1 mmol)

$^1$H-NMR (CDCl$_3$, 400 MHz) δ: 4.41-4.35 (m, 1H), 4.23 (d, J=5.4 Hz, 2H), 4.11 (dd, J=8.7, 6.6 Hz, 1H), 3.83 (dd, J=8.7, 5.4 Hz, 1H), 3.07 (s, 3H), 1.44 (s, 3H), 1.36 (s, 3H).

Reference Example 65

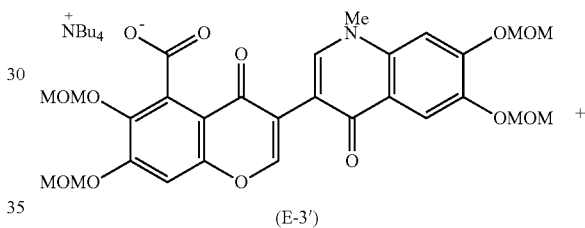

According to the method described in Reference example 56, Compound (W-1) (31 mg, 73% yield) was prepared from Compound (E-3') (50 mg, 0.060 mmol) an Compound (j-2) (63 mg, 0.30 mmol).

$^1$H-NMR (CDCl$_3$, 400 MHz) δ: 9.33 (s, 1H), 8.75 (s, 1H), 8.17 (s, 1H), 7.29 (s, 1H), 7.19 (s, 1H), 5.39 (s, 2H), 5.36 (s, 2H), 5.32 (s, 2H), 5.19 (s, 2H), 4.55-4.45 (m, 3H), 4.12-4.09 (m, 1H), 3.91-3.87 (m, 1H), 3.85 (s, 3H), 3.59-3.52 (m, 12H), 1.43 (s, 3H), 1.34 (s, 3H).

Example 23

2,3-Dihydroxypropyl 3-(6,7-dihydroxy-1-methyl-4-oxo-1,4-dihydroquinolin-3-yl)-6,7-dihydroxy-4-oxo-4H-chromene-5-carboxylate

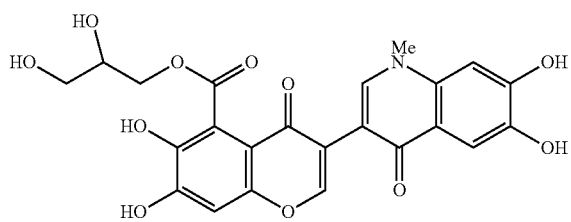 [SMILES: Cn1cc(-c2coc3cc(O)c(O)c(C(=O)OCC(O)CO)c3c2=O)c(=O)c2cc(O)c(O)cc21]

To a solution of Compound (W-1) (31 mg, 0.040 mmol) in methanol (20 mL) was added 4 mol/L hydrogen chloride in methanol (0.50 mL) at 0° C., and the reaction mixture was stirred at room temperature for 4 days. The solvent of the reaction mixture was removed under reduced pressure, and the residue was purified by preparative HPLC to give the title compound (10 mg, 39% yield).

$^1$H-NMR (DMSO-$d_6$, 400 MHz) δ: 8.53 (s, 1H), 8.14 (s, 1H), 7.57 (s, 1H), 6.95 (s, 1H), 6.82 (s, 1H), 4.27-4.24 (m, 1H), 4.12-4.07 (m, 1H), 3.76 (s, 4H), 3.38-3.36 (m, 2H).

Reference Example 66

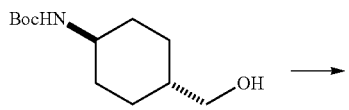

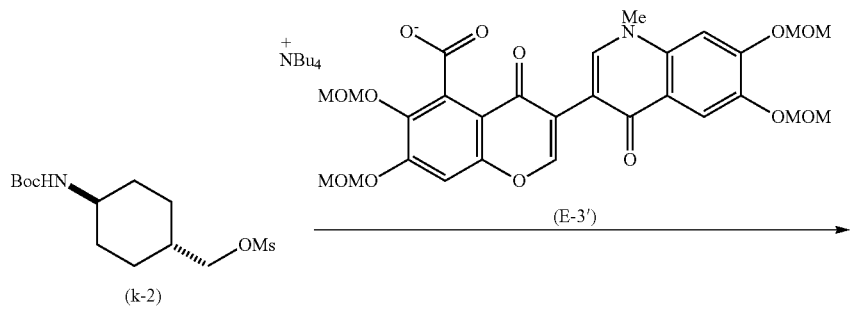

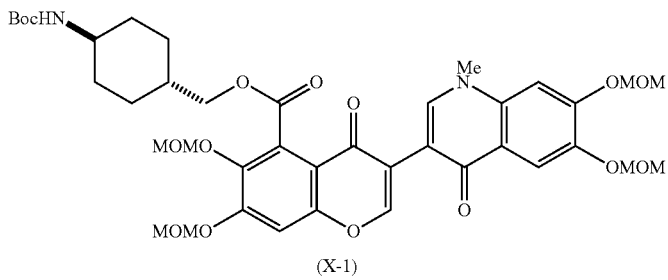

According to the method described in Reference example 55, Compound (k-2) (0.20 g, 100% yield) was prepared from tert-butyl trans-(4-hydroxymethylcyclohexyl)carbamate (0.15 g, 0.65 mmol).

According to the method described in Reference example 56, Compound (X-1) (36 mg, 75% yield from E-3') was prepared from Compound (E-3') (50 mg, 0.060 mmol) and Compound (k-2) (92 mg, 0.30 mmol).

$^1$H-NMR (CDCl$_3$, 400 MHz) δ: 9.22 (s, 1H), 8.65 (s, 1H), 8.10 (s, 1H), 7.21 (s, 1H), 7.12 (s, 1H), 5.32 (s, 2H), 5.29 (s, 2H), 5.25 (s, 2H), 5.10 (s, 2H), 4.32-4.13 (m, 4H), 3.79 (s, 3H), 3.51-3.45 (m, 12H), 1.97-1.63 (m, 9H), 1.35 (s, 9H).

Example 24

(trans-4-Aminocyclohexyl)methyl 3-(6,7-dihydroxy-1-methyl-4-oxo-1,4-dihydroquinolin-3-yl)-6,7-dihydroxy-4-oxo-4H-chromene-5-carboxylate hydrochloride

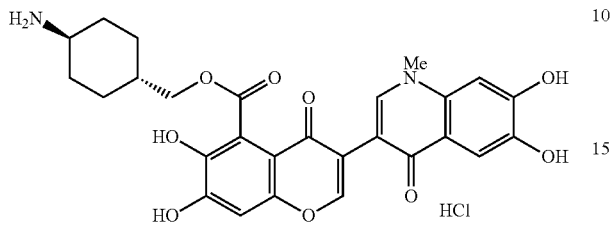

According to the method described in Example 23, the title compound (12 mg, 49% yield) was prepared from Compound (X-1) (36 mg, 0.045 mmol).

$^1$H-NMR (MeOD, 400 MHz) δ: 8.30 (s, 1H), 8.04 (s, 1H), 7.65 (s, 1H), 7.06 (s, 1H), 7.03 (s, 1H), 4.20 (s, 2H), 3.86 (s, 3H), 3.10-3.05 (m, 1H), 2.05-2.02 (m, 2H), 1.94-1.91 (m, 2H), 1.79 (s, 1H), 1.43-1.34 (m, 2H), 1.21-1.13 (m, 2H).

Reference Example 67

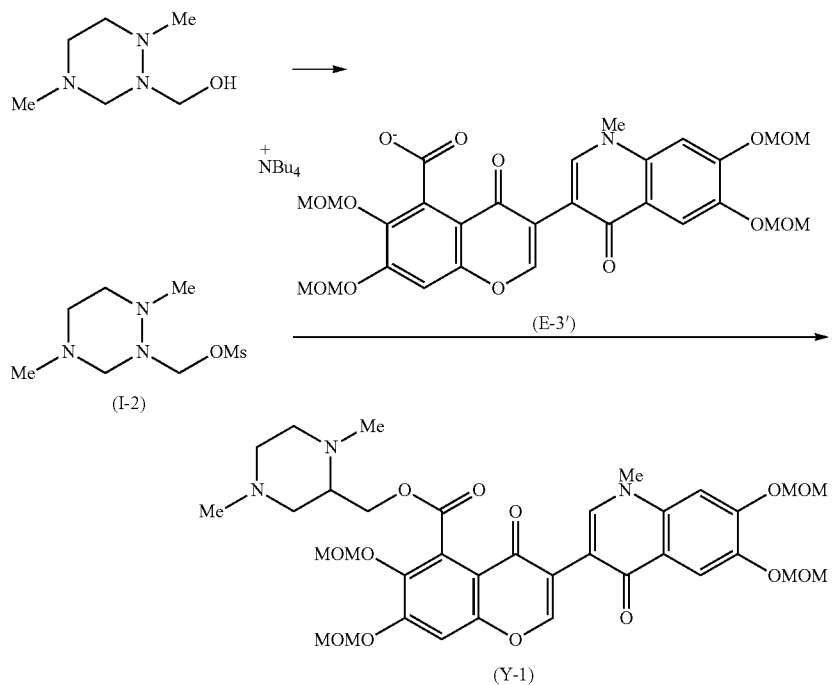

According to the method described in Reference example 55, Compound (I-2) (0.23 g, 100% yield) was prepared from (1,4-dimethylpiperazin-2-yl)methanol (0.15 g, 1.0 mmol).

According to the method described in Reference example 56, Compound (Y-1) (29 mg, 67% yield from E-3') was prepared from Compound (E-3') (50 mg, 0.060 mmol) and Compound (I-2) (67 mg, 0.30 mmol).

$^1$H-NMR (CDCl$_3$, 400 MHz) δ: 9.39-9.33 (m, 1H), 8.83-8.78 (m, 1H), 8.17 (s, 1H), 7.29 (s, 1H), 7.18 (s, 1H), 5.39 (s, 2H), 5.35 (s, H), 5.32 (s, 2H), 5.19 (s, 2H), 4.72-4.65 (m, 1H), 4.36-4.31 (m, 1H), 3.86 (s, 3H), 3.59 (s, 3H), 3.56 (s, 3H), 3.54 (s, 3H), 3.52 (s, 3H), 2.87-2.84 (m, 1H), 2.79-2.76 (m, 1H), 2.68-2.58 (m, 2H), 2.39 (s, 3H), 2.21 (s, 3H), 2.09-1.98 (m, 1H), 1.49-1.42 (m, 1H), 1.34-1.28 (m, 1H).

Example 25

(1,4-Dimethylpiperazin-2-yl)methyl 3-(6,7-dihydroxy-1-methyl-4-oxo-1,4-dihydroquinolin-3-yl)-6,7-dihydroxy-4-oxo-4H-chromene-5-carboxylate hydrochloride

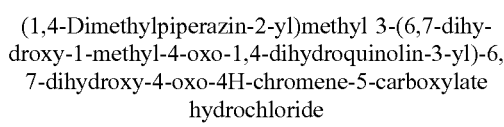
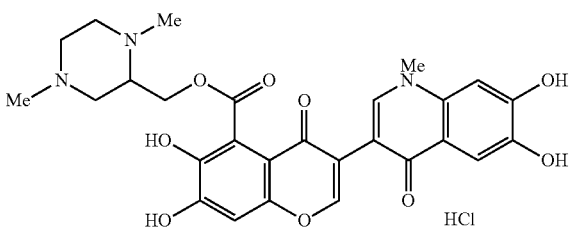 [SMILES: CN1CCN(C)C(COC(=O)c2c(O)c(O)cc3occ(-c4cn(C)c5cc(O)c(O)cc5c4=O)c(=O)c23)C1 ; Cl]

According to the method described in Example 23, the title compound (10 mg, 40% yield) was prepared from Compound (Y-1) (29 mg, 0.040 mmol).

$^1$H-NMR (MeOD, 400 MHz) δ: 8.22 (s, 1H), 8.04 (s, 1H), 7.66 (s, 1H), 7.09 (s, 1H), 6.79 (s, 1H), 3.90 (s, 3H), 3.25-3.21 (m, 2H), 3.16-3.12 (m, 2H), 3.05-3.02 (m, 2H), 2.75-2.67 (m, 3H), 2.61 (s, 3H), 2.49 (s, 3H).

Example 26

(1-Methyl-1H-imidazol-2-yl)methyl 3-(6,7-dihydroxy-1-methyl-4-oxo-1,4-dihydroquinolin-3-yl)-6,7-dihydroxy-4-oxo-4H-chromene-5-carboxylate hydrochloride

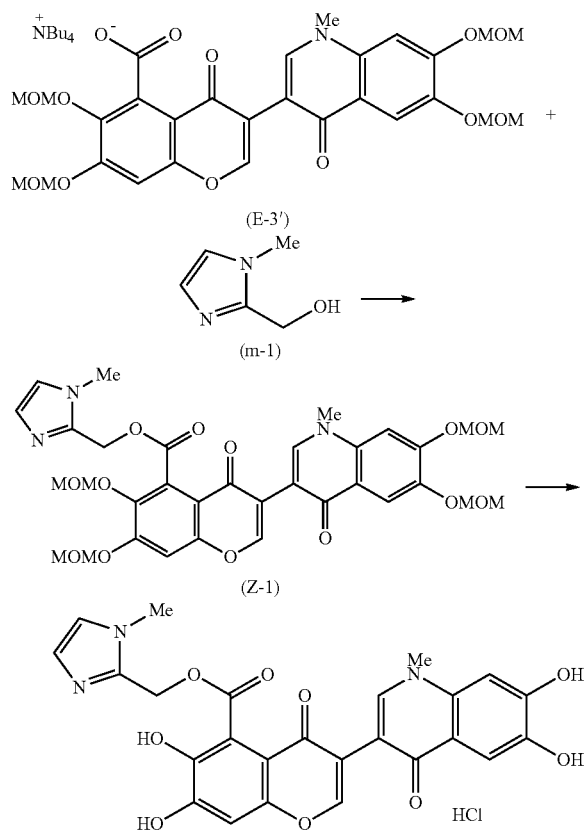

To a solution of Compound (E-3') (80 mg, 0.096 mmol), (1-methyl-1H-imidazol-2-yl)methanol (m-1) (43 mg, 0.39 mmol), and tributylphosphine (59 mg, 0.29 mmol) in THF (6.0 ml) was added diisopropyl azodicarboxylate (59 mg, 0.29 mmol) at 0° C. Under argon atmosphere, the mixture was reacted at 50° C. under microwave for 5 hours, and purified by preparative HPLC to give Compound (Z-1) (37 mg, 56% yield). According to the method described in Example 21, the title compound (14 mg, 46% yield from Z-1) was obtained from Compound (Z-1).

$^1$H-NMR (DMSO-$d_6$, 400 MHz) δ: 8.57 (s, 1H), 8.49 (s, 1H), 7.73 (s, 1H), 7.70 (s, 1H), 7.68 (s, 1H), 7.28 (s, 1H), 7.11 (s, 1H), 4.08 (s, 3H), 3.85 (s, 3H), 3.15 (s, 2H).

Reference Example 68

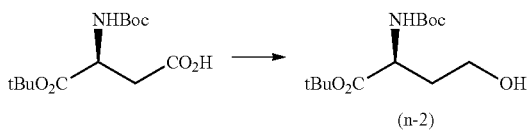 [SMILES: CC(C)(C)OC(=O)N[C@@H](CC(=O)O)C(=O)OC(C)(C)C ; CC(C)(C)OC(=O)N[C@@H](CCO)C(=O)OC(C)(C)C]

To 1-tert-butyl N-butoxycarbonyl-L-aspartate (0.20 g, 0.69 mmol) in 1,2-dimethoxyethane (10 ml) were added 4-methylmorpholine (70 mg, 0.69 mmol) and isobutyl chloroformate (94 mg, 0.69 mmol) at −15° C., and the reaction mixture was stirred for 10 minutes. The precipitation was removed by filtration and washed with cold 1,2-dimethoxyethane (20 ml). To the filtrate at −15° C. was added a solution of sodium borohydride (52 mg, 1.4 mmol) in water (5 ml). Five minutes later, water (250 ml) was added thereto. The mixture was extracted with ethyl acetate, and the organic layer was dried over sodium sulfate, and concentrated in vacuo to give Compound (n-2) (0.17 g, 92% yield).

$^1$H-NMR (CDCl$_3$, 400 MHz) δ: 5.41-5.29 (m, 1H), 4.40-4.30 (m, 1H), 3.73-3.58 (m, 2H), 3.45 (br, 1H), 3.01 (br, 1H), 2.18-2.06 (m, 1H), 1.48 (s, 9H), 1.45 (s, 9H).

Reference Example 69

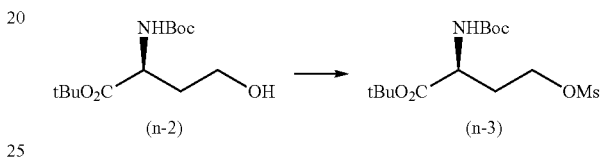

According to the method described in Reference example 55, Compound (n-3) (0.50 g, 100% yield) was prepared from Compound (n-2) (0.39 g, 1.4 mmol).

$^1$H-NMR (CDCl$_3$, 400 MHz) δ: 5.13 (br, 1H), 4.25-4.19 (m, 3H), 2.96 (s, 3H), 2.26-2.20 (m, 1H), 2.01-1.94 (m, 1H), 1.41 (s, 9H), 1.37 (s, 9H).

Reference Example 70

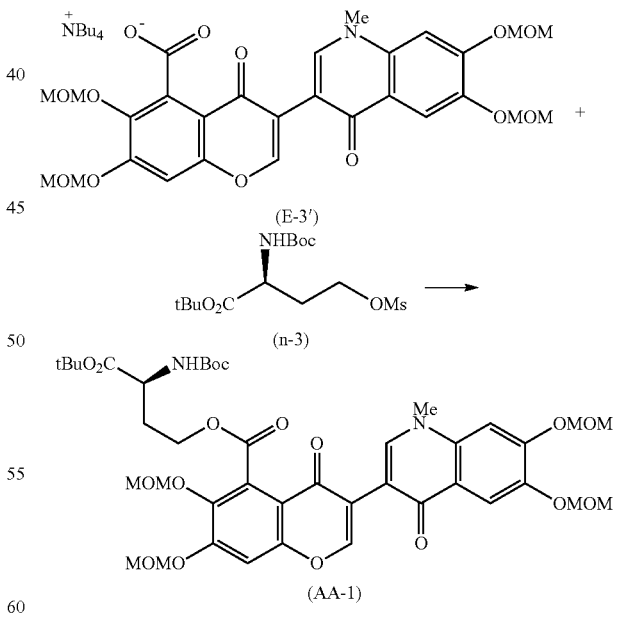

According to the method described in Reference example 56, Compound (AA-1) (34 mg, 67% yield) was prepared from Compound (E-3') (50 mg, 0.060 mmol) and Compound (n-3) (0.11 g, 0.30 mmol).

$^1$H-NMR (CDCl$_3$, 400 MHz) δ: 9.44-9.22 (m, 1H), 8.98-8.78 (m, 1H), 8.17 (s, 1H), 7.31 (s, 1H), 7.21 (s, 1H), 5.40-5.30 (m, 6H), 5.20 (br, 3H), 3.96-3.91 (m, 2H), 3.88-3.84 (m, 1H), 3.59-3.52 (m, 12H), 3.48 (s, 3H), 2.47-2.38 (m, 1H), 2.35-2.19 (m, 1H), 1.41 (s, 9H), 1.25 (s, 9H).

Example 27

O-{[3-(6,7-Dihydroxy-1-methyl-4-oxo-1,4-dihydroquinolin-3-yl)-6,7-dihydroxy-4-oxo-4H-chromen-5-yl]carbonyl}-L-homoserine hydrochloride

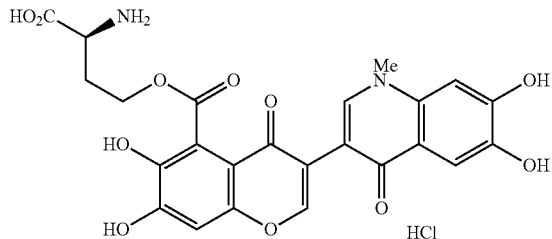 [SMILES: Cn1cc(-c2coc3cc(O)c(O)c(C(=O)OCC[C@H](N)C(=O)O)c3c2=O)c(=O)c2cc(O)c(O)cc21 ; Cl]

To a solution of Compound (AA-1) (34 mg, 0.040 mmol) in methanol (20 ml) was added 4 mol/L hydrogen chloride in dioxane (0.5 ml) at 0° C., and the reaction mixture was stirred at room temperature for 4 days. The reaction mixture was concentrated in vacuo, and the residue was purified by preparative HPLC to give the title compound (10 mg, 41% yield).

$^1$H-NMR (DMSO-$d_6$, 400 MHz) δ: 8.39 (s, 1H), 8.08 (s, 1H), 7.62 (s, 1H), 7.01 (s, 1H), 6.94 (s, 1H), 4.45-4.33 (m, 2H), 3.80 (s, 3H), 3.54-3.46 (m, 1H), 2.35-2.21 (m, 1H), 2.11-1.99 (m, 1H).

Reference Example 71

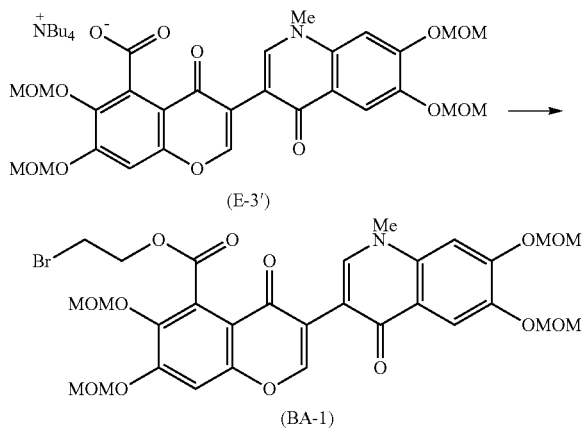

According to the method described in Reference example 56, Compound (BA-1) (47 mg, 85% yield) was prepared from Compound (E-3') (50 mg, 0.060 mmol) and 1,2-dibromoethane (72 mg, 0.39 mmol).

$^1$H-NMR (CDCl$_3$, 400 MHz) δ: 9.30 (s, 1H), 8.73 (s, 1H), 8.17 (s, 1H), 7.30 (s, 1H), 7.18 (s, 1H), 5.39 (s, 2H), 5.36 (s, 2H), 5.30 (s, 2H), 5.20 (s, 2H), 4.86-4.64 (m, 2H), 3.85 (s, 3H), 3.73-3.72 (m, 2H), 3.59 (s, 3H), 3.56 (s, 3H), 3.54 (s, 3H), 3.53 (s, 3H).

Example 28

2-(3-Hydroxypyrrolidin-1-yl)ethyl 3-(6,7-dihydroxy-1-methyl-4-oxo-1,4-dihydroquinolin-3-yl)-6,7-dihydroxy-4-oxo-4H-chromene-5-carboxylate

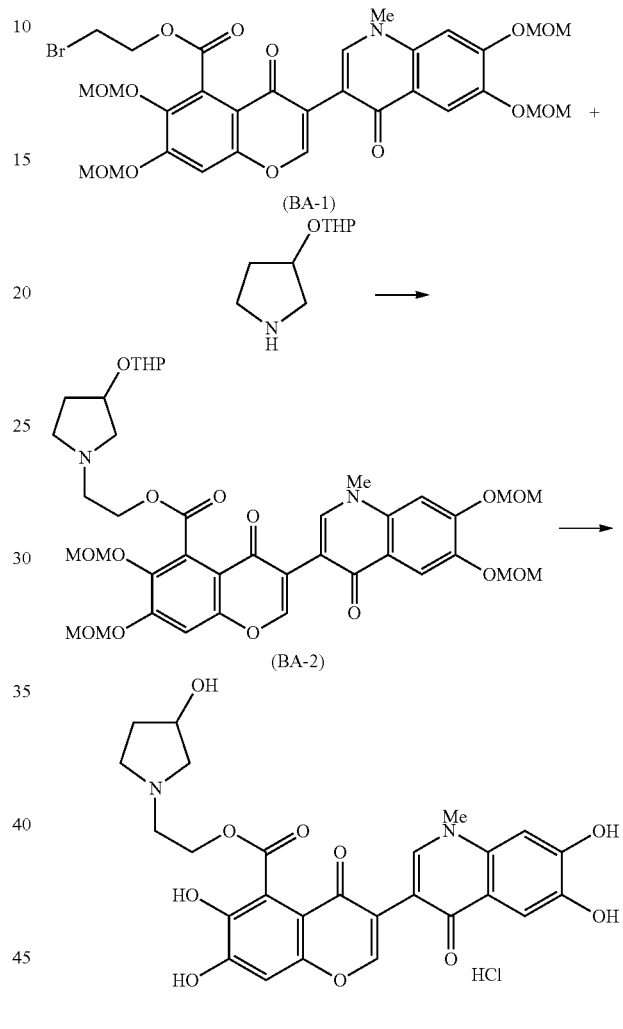

Compound (BA-1) (47 mg, 0.068 mmol), 3-(tetrahydropyran-2-yloxy)-pyrrolidine (58 mg, 0.34 mmol), and triethylamine (34 mg, 0.34 mmol) were dissolved in acetonitrile (5.0 ml), and the reaction mixture was stirred at 35° C. for 16 hours. The reaction mixture was concentrated in vacuo, and the residue was purified by preparative TLC (methylene chloride:methanol=20:1) to give Compound (BA-2) (51 mg, 96% yield from BA-1).

To solution of Compound (BA-2) in methanol (15 ml) was added 4 mol/L hydrochloric acid in dioxane (0.16 ml, 0.65 mmol) at 0° C., and the reaction mixture was stirred at room temperature for 3 days. The reaction mixture was concentrated in vacuo to give the title compound (13 mg, 36% yield).

$^1$H-NMR (DMSO-$d_6$, 400 MHz) δ: 8.47 (s, 1H), 8.17 (s, 1H), 7.55 (s, 1H), 7.11 (s, 1H), 7.03 (m, 1H), 4.43-4.39 (m, 3H), 3.83 (s, 3H), 3.33-3.27 (m, 2H), 3.14-3.04 (m, 4H), 1.87-1.78 (m, 2H).

Reference Example 72

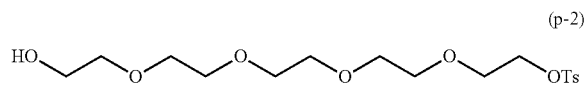 [SMILES: Cc1ccc(S(=O)(=O)OCCOCCOCCOCCOCCO)cc1]

To a solution of 3,6,9,12-tetraoxatetradecan-1,14-diol (0.50 g, 2.1 mmol), potassium iodide (69 mg, 0.42 mmol), and silver oxide (48 mg, 0.21 mmol) in methylene chloride (50 ml) was added p-toluenesulfonyl chloride (0.36 g, 1.9 mmol) at 0° C., and the reaction mixture was stirred at room temperature for 16 hours. The reaction mixture was purified by preparative TLC (methylene chloride:methanol=10:1) to give Compound (p-2) (0.31 g, 38% yield).

$^1$H-NMR (CDCl$_3$, 400 MHz) δ: 7.80 (d, J=8.4 Hz, 2H), 7.34 (d, J=8.4 Hz, 2H), 4.17-4.15 (m, 2H), 3.71-3.60 (m, 19H), 2.45 (s, 3H).

Reference Example 73

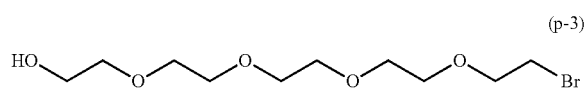 [SMILES: OCCOCCOCCOCCOCCBr]

A solution of Compound (p-2) (0.13 g, 0.32 mmol), potassium bromide (0.11 g, 0.95 mmol), and tetrabutylammonium bromide (0.10 g, 0.32 mmol) in acetone (10 ml) was stirred at 80° C. for 10 hours. The solvent was removed under reduced pressure, and the residue was purified by silica gel column chromatography (methylene chloride:methanol=20:1) to give Compound (p-3) (83 mg, 87% yield).

$^1$H-NMR (CDCl$_3$, 400 MHz) δ: 3.83-3.79 (m, 2H), 3.74-3.70 (m, 2H), 3.70-3.62 (m, 8H), 3.62-3.61 (m, 2H), 3.49-3.46 (m, 2H), 2.96 (br, 1H), 1.75 (s, 4H).

Reference Example 74

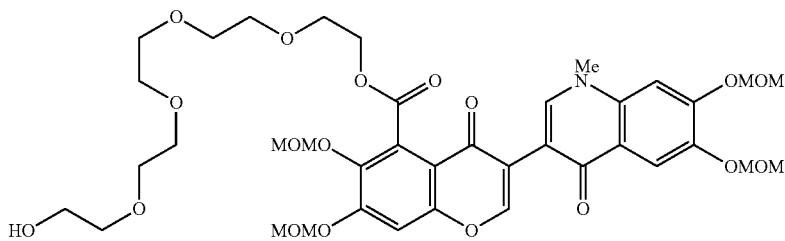

According to the method described in Reference example 56, the title compound (CA-1) (34 mg, 70% yield) was prepared from Compound (E-3') (50 mg, 0.060 mmol) and Compound (p-3) (91 mg, 0.30 mmol).

$^1$H-NMR (CDCl$_3$, 400 MHz) δ: 9.20 (s, 1H), 8.65 (s, 1H), 8.10 (s, 1H), 7.21 (s, 1H), 7.12 (s, 1H), 5.33 (s, 2H), 5.29 (s, 2H), 5.25 (s, 2H), 5.12 (s, 2H), 3.79 (s, 3H), 3.62-3.58 (m, 6H), 3.52-3.49 (m, 20H), 3.47 (s, 3H), 3.45 (s, 3H).

Example 29

14-Hydroxy-3,6,9,12-tetraoxatetradec-1-yl 3-(6,7-dihydroxy-1-methyl-4-oxo-1,4-dihydroquinolin-3-yl)-6,7-dihydroxy-4-oxo-4H-chromene-5-carboxylate

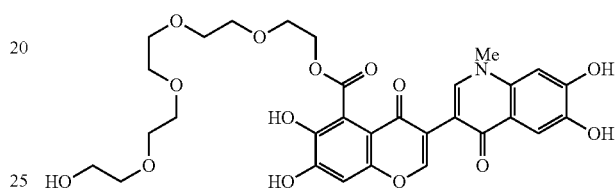

According to the method described in Example 23, the title compound (12 mg, 45% yield) was prepared from Compound (CA-1) (34 mg, 0.042 mmol).

$^1$H-NMR (DMSO-d$_6$, 400 MHz) δ: 8.58 (s, 1H), 8.16 (s, 1H), 7.57 (s, 1H), 7.01 (s, 1H), 6.95 (s, 1H), 4.31 (br, 2H), 3.77 (s, 3H), 3.68 (br, 2H), 3.51-3.36 (m, 16H).

Example 30

2-Amino-2-oxoethyl 3-(6,7-dihydroxy-1-methyl-4-oxo-1,4-dihydroquinolin-3-yl)-6,7-dihydroxy-4-oxo-4H-chromene-5-carboxylate

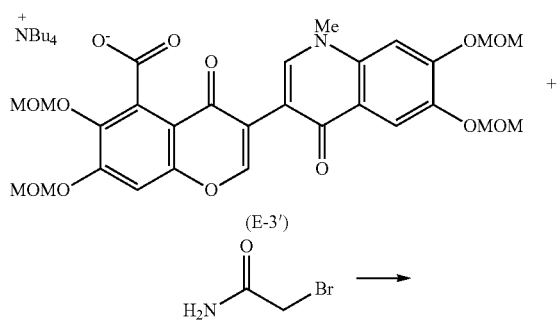

-continued

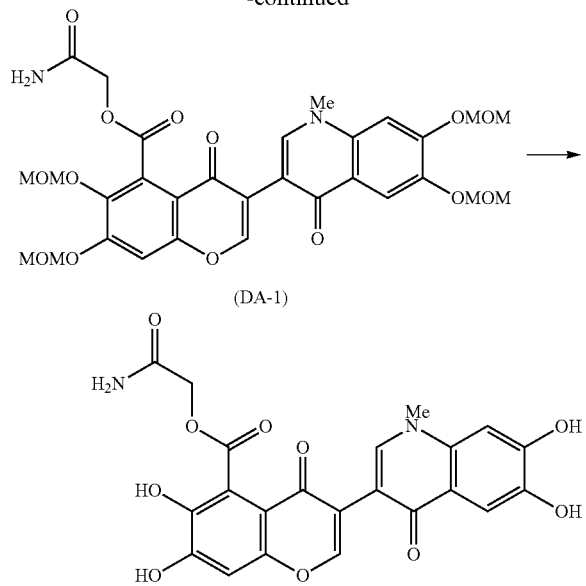

(DA-1)

According to the method described in Reference example 56, Compound (DA-1) (31 mg, 80% yield) was prepared from Compound (E-3') (50 mg, 0.060 mmol) and 2-bromo-acetamide (41 mg, 0.30 mmol).

According to the method described in Example 27, the title compound (22 mg, 92% yield) was prepared from Compound (DA-1) (31 mg, 1.8 mmol).

$^1$H-NMR (DMSO-$d_6$, 400 MHz) δ: 8.49 (s, 1H), 8.18-8.11 (m, 1H), 7.58 (s, 1H), 7.01 (s, 1H), 6.90 (s, 1H), 4.59-4.76 (m, 2H), 3.79 (s, 3H).

Example 31

2-(3-Methoxy-3-oxopropoxy)ethyl 3-(6,7-dihydroxy-1-methyl-4-oxo-1,4-dihydroquinolin-3-yl)-6,7-dihydroxy-4-oxo-4H-chromene-5-carboxylate

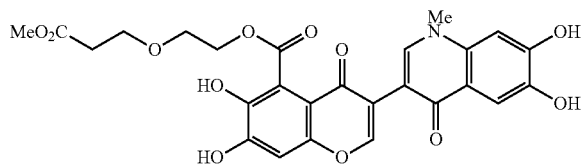 [SMILES: COC(=O)CCOCCOC(=O)c1c(O)c(O)cc2occ(-c3cn(C)c4cc(O)c(O)cc4c3=O)c(=O)c12]

To a solution of Compound (T-1) (32 mg, 0.040 mmol) in methanol (20 ml) was added 4 mol/L hydrogen chloride in dioxane (0.5 ml, 2.0 mmol) at 0° C., and the reaction mixture was stirred at room temperature for 4 days. The reaction mixture was concentrated in vacuo and the residue was purified with a preparative HPLC to give the title compound (10 mg, 42% yield).

$^1$H-NMR (DMSO-$d_6$, 400 MHz) δ: 8.40 (s, 1H), 8.10 (s, 1H), 7.58 (s, 1H), 7.01 (s, 1H), 6.84 (s, 1H), 4.31-4.26 (m, 2H), 3.79 (s, 3H), 3.70-3.59 (m, 4H), 3.52 (s, 4H), 2.51-2.49 (m, 2H).

(Test 1)
Inhibitory Activity for the Collapse Activity Caused by Sema3A 96 well-plate (SUMITOMO BAKELITE CO., LTD.) which was beforehand coated with polylysine was further coated with laminin (10 μL laminin, at room temperature, for 1 hour). To each well was added 100 μL of a medium (F12 medium containing 10% fetal bovine serum, 20 ng/mL NGF, 100 unit/mL penicillin, and 100 μg/mL streptomycin). Dorsal root ganglion harvested from 7-8 day-old chick embryo was inoculated thereto, and the culture medium was cultivated under the condition of 5% $CO_2$ and 37° C. for 16-20 hours. And then, each test compound in various concentrations was added to the medium, each test medium was cultivated for 30 minutes, 3 units/mL mouse semaphorin 3A (Sema3A) was added to each medium, and then each test medium was cultivated for more 30 minutes. Then, glutaraldehyde was added to the medium, in which the final concentration of glutaraldehyde was 1%. The medium was left to stand at room temperature for 15 minutes to make the tissue fragment fixed, and the ratio of the retracted growth cone was measured under a microscope. The following Table 1 shows the result of the collapse assay about each concentration of each compound in Test 1, i.e., residual ratio (%) of Sema3A activity. It means that the smaller the value is, the more potent the Sema3A inhibitory activity is. According to the result of the assessment, it has been found that all of the compound group shown in Table 1 have strong Sema3A inhibitory activity.

TABLE 1

| Example | 1 μM | 3 μM | 10 μM |
|---|---|---|---|
| 1 | 2.0 | 4.6 | — |
| 3 | 4.0 | — | — |
| 4 | 6.0 | — | — |
| 5 | 5.1 | 3.3 | — |
| 7 | — | <70 | <40 |
| 8 | 27.3 | 21.0 | — |
| 9 | 3.4 | 7.3 | — |
| 11 | 7.9 | — | — |
| 12 | 65.5 | — | — |
| 13 | — | — | <70 |
| 14 | 78.8 | 6.1 | — |
| 15 | 5.4 | 0.0 | — |
| 16 | 15.9 | 2.2 | — |
| 17 | 90.1 | 3.3 | — |
| 18 | 21.8 | 6.7 | — |
| 19 | 4.2 | 0.0 | — |
| 23 | <70 | <10 | — |
| 24 | <70 | <10 | — |
| 27 | <10 | <10 | — |
| 30 | — | <40 | — |

—: untested (Test 2)
Inhibitory Activity for the Neuropilin-Binding Activity Caused by Sema3A To each well of 96 well-plate (IWAKI) was seeded CHO cells stably-expressing mouse neuropilin, the cells were cultivated in F12 medium (10% fetal bovine serum, 100 units/mL penicillin, and 100 μg/mL streptomycin) under the condition of 5% $CO_2$ and 37° C. for 18 hours. And then, the culture medium was removed, and mouse Sema3A which included each test compound and alkaline phosphatase (AP) in various concentrations was added thereto, and the culture was reacted at room temperature for more one hour. Then, the reaction solution was removed, the residual cells were washed with HBSS solution (0.25% BSA) and dissolved in a solution (10 mM Tris including 1% Triton X-100) at 65° C. for one hour, and the AP activity thereof was measured. The following table 2 (Test 2) shows the result of inhibitory activity of each compound, i.e., residual ratio (%) of avidity. It means that the smaller the value is, the more potent the binding inhibitory activity. According to the result of the assessment, it has been found that all of the compound group shown in Table 2 have binding inhibitory activity for Sema3A.

TABLE 2

| Example | 100 μM |
|---------|--------|
| 20 | 56.5 |
| 21 | 58.5 |
| 22 | 62.1 |
| 25 | 90.5 |
| 26 | 97.8* |
| 28 | 87.1 |
| 29 | 49.3 |
| 31 | 69.4 |

—: untested
*it is the result when the concentration of the test compound is 10 μM.

(Test 3)
Drug Evaluation for Corneal Disorder in Dry Eye-Model Rat

A model rat whose exorbital lacrimal gland is excised is generally used as a model for evaluating the drug efficacy for corneal disorder caused by dry eye. As for corneal disorder of the rat, hyaluronic acid (HA) and diquafosol sodium (DQS) which are existing drugs, and the present compound (Example 3) were administered to the rat, and each efficacy thereof was evaluated.

Male SD rat was anesthetized with inhalational isoflurane, and the exorbital lacrimal gland thereof was excised to prepare a dry eye-model rat (the conditions to prepare the dry eye-model rat can be changed as necessary, for example, by combining the excision of exorbital lacrimal gland with the medication of streptozotocin or the like). Three weeks after the operation, each vehicle for eye drop (typically phosphate-buffered saline (PBS)), 0.3% HA ophthalmic solution, 3% DQS ophthalmic solution, and the ophthalmic solution of the present compound (Example 3) were administered to the rat in an awareness at 1 μL per shot, 6 times per day, for 4 weeks.

The site of corneal disorder was stained with a fluorescein (FITC) solution, and the extent of the disorder was evaluated with the score gained from the following method. First, the rat was anesthetized with inhalational isoflurane, and 1 μL of 0.5% FITC solution was dropped into the cornea of the rat. The extra FITC solution was washed with saline completely, and the site of corneal disorder was stained. Next, the staining of FITC in the rat's cornea was observed with a portable slit lamp, and evaluated with the following scores of 0-3 (*Atarashii Ganka* (*Journal of the Eye*); 21: 87-90 (2004)). (Evaluation Criteria)

0: no punctate stain (normal)
1: sparse punctate stain (punctate fluorescein-strains exist away each other)
2: middle (middle between 1 and 3)
3: dense punctate stain (punctate fluorescein strains exist closely each other)

The statistical significance for the drug effect was evaluated by nonparametric Tukey's multiple comparison test, in which the result of each test group was compared with that of the control (intact) group which was not operated by excising exorbital lacrimal gland.

The HA ophthalmic solution and the DQS ophthalmic solution exhibited only a little bit of the therapeutic effect for corneal disorder caused by dry eye. On the other hand, the compound of Example 3 exhibited a potent therapeutic effect for the corneal disorder, which suggests that the compound can normalize corneal disorder caused by dry eye. In a similar way, compared with the vehicle-administration group (PBS) in which the rat's exorbital lacrimal gland is excised, the compound of Example 3 exhibited a significant improvement (** denotes $p<0.01$), but neither the HA ophthalmic solution nor the DQS ophthalmic solution exhibited any significant improvement.

(Test 4)
Drug Evaluation for the Dysfunction of Corneal Nerves in Dry Eye Rat Model Male SD rat was anesthetized with inhalational isoflurane. The exorbital lacrimal gland thereof was excised, and at the same day, streptozotocin was administered intraperitoneally to the rat (55 mg/kg) to prepare a dry eye-model rat associated with the dysfunction of corneal nerves. Several weeks after the operation, 0.3% HA ophthalmic solution, 3% DQS ophthalmic solution, and 0.1% the ophthalmic solution of the present compound (Example 3) were administered to the rat in an awareness at 1 μL per shot, 6 times per day, for 4 weeks.

The cornea of the rat was softly held by hand. The drug effect for the dysfunction of corneal nerves was evaluated through blink reflex by contacting the cornea with the nylon filament of cochet-bonnet corneal esthesiometer. First, the tip of the nylon filament (length: 60 mm, diameter: 0.12 mm) was made to almost-vertically contact with the center of cornea, and the nylon filament was made to curve a little. And then, the experiment was continued while the nylon filament was shortened gradually, and the length of nylon string which the blink reflex of the rat was observed was identified as corneal perception (*Invest Ophthalmol Vis Sci.*; 53: 8067-74 (2012)).

The statistical significance for the drug effect was evaluated by confirming that P value is less than 5% in Student's t test between the intact group and the PBS group, and then carrying out Student's t test between the intact group and the present compound group. Lastly, Student's t tests between the intact group and the HA group, and between the intact group and the DQS group were carried out for the purpose of reference.

The HA ophthalmic solution and the DQS ophthalmic solution did not exhibit any therapeutic effect for the dysfunction of corneal nerves caused by dry eye at all. On the other hand, the compound of Example 3 exhibited a marked therapeutic effect for the dysfunction of corneal nerves, which suggests that the compound can normalize the dysfunction of nerves as clinical condition.

(Test 5)
Drug Evaluation for Corneal Disorder in Dry Eye Rat Model

For the corneal disorder in the model rat whose exorbital lacrimal gland is excised, the drug effect was evaluated about hyaluronic acid (HA) which is an existing drug, and the present compound.

Male SD rat was anesthetized with inhalational isoflurane, and the exorbital lacrimal gland thereof was excised to prepare a dry eye-model rat (the conditions to prepare the dry eye-model rat can be changed as necessary, for example, by combining the excision of exorbital lacrimal gland with the medication of streptozotocin or the like). Three weeks after the operation, each vehicle for eye drop (typically phosphate-buffered saline (PBS)), and 0.01%, 0.1%, and 1% the ophthalmic solutions of the present compound (Example 19) were administered to the rat in an awareness at 1 μL per shot, twice per day, for 4 weeks.

The scoring of disorder extent in the site of corneal disorder was evaluated with 4 grades of the evaluation criteria of 0-3 according to Test 3.

The statistical significance for the drug effect was evaluated by nonparametric Tukey's multiple comparison test, in which the result of each test group was compared with that of the vehicle-administration group (PBS) in which the rat's exorbital lacrimal gland is excised.

The compound of Example 19 (in the concentration of 0.01% to 1%) exhibited a marked improvement (** denotes p<0.01) for corneal disorder, which suggests that the compound can normalize corneal disorder caused by dry eye.

INDUSTRIAL APPLICABILITY

The compound of formula (1) or a pharmaceutically acceptable salt thereof of the present invention has a semaphorin inhibitory activity, and it is useful as a nerve regeneration promoter in peripheral or central nerve, or a medicament for treating or preventing neuropathic disease/neurodegenerative disease, a neurological disease associated with ischemic damage, and corneal disease, which includes the nerve regeneration promoter.

The invention claimed is:
1. A compound of formula (1):

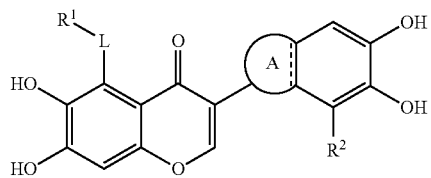

or a pharmaceutically acceptable salt thereof
wherein
$R^1$-L- is $R^1$—OC(O)— or $R^1$—NHC(O)—;
$R^1$ is
(i) hydrogen atom,
(ii) optionally-substituted $C_{1-6}$ alkyl group,
(iii) optionally-substituted $C_{2-6}$ alkenyl group,
(iv) optionally-substituted $C_{2-6}$ alkynyl group,
(v) optionally-substituted 3- to 8-membered cycloalkyl group,
(vi) optionally-substituted 4- to 8-membered cycloalkenyl group,
(vii) optionally-substituted 4- to 8-membered saturated aliphatic heterocyclyl group,
(viii) optionally-substituted 5- to 10-membered unsaturated aliphatic heterocyclyl group,
(ix) optionally-substituted 6- to 10-membered aryl group, or
(x) optionally-substituted 5- to 10-membered heteroaryl group;
$R^2$ is hydrogen atom, hydroxy group, or carboxyl group; and
Ring A is a group of formula (2) or (3):

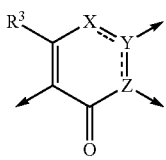

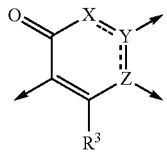

wherein $R^3$ is
(i) hydrogen atom,
(ii) optionally-substituted $C_{1-6}$ alkyl group,
(iii) optionally-substituted $C_{2-6}$ alkenyl group,
(iv) optionally-substituted $C_{2-6}$ alkynyl group,
(v) optionally-substituted 3- to 8-membered cycloalkyl group,
(vi) optionally-substituted 4- to 8-membered cycloalkenyl group,
(vii) optionally-substituted 4- to 8-membered saturated aliphatic heterocyclyl group,
(viii) optionally-substituted 5- to 10-membered unsaturated aliphatic heterocyclyl group,
(ix) optionally-substituted 6- to 10-membered aryl group, or
(x) optionally-substituted 5- to 10-membered heteroaryl group,
the part of X⋯Y⋯Z is X=Y—Z, X—Y=Z, or X—Y—Z,
X is nitrogen atom, $NR^4$, or oxygen atom, provided that X is not oxygen atom in the case of formula (2),
$R^4$ is
(i) hydrogen atom,
(ii) optionally-substituted $C_{1-6}$ alkyl group,
(iii) optionally-substituted $C_{2-6}$ alkenyl group,
(iv) optionally-substituted $C_{2-6}$ alkynyl group,
(v) optionally-substituted 3- to 8-membered cycloalkyl group,
(vi) optionally-substituted 4- to 8-membered cycloalkenyl group,
(vii) optionally-substituted 4- to 8-membered saturated aliphatic heterocyclyl group,
(viii) optionally-substituted 5- to 10-membered unsaturated aliphatic heterocyclyl group,
(ix) optionally-substituted 6- to 10-membered aryl group, or
(x) optionally-substituted 5- to 10-membered heteroaryl group,
Y is carbon atom or CH, and
Z is carbon atom, CH, or nitrogen atom, provided that the combination of X, Y, and Z should be any one of chemically-possible selections.
2. The compound of claim 1 or a pharmaceutically acceptable salt thereof, which is represented by formula (1'):

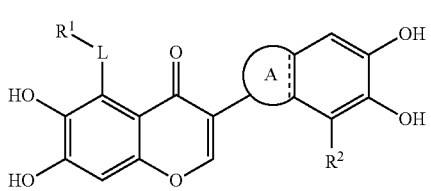

wherein
R¹-L- is R¹—OC(O)— or R¹—NHC(O)—;
R¹ is
(i) hydrogen atom,
(ii) optionally-substituted $C_{1-6}$ alkyl group,
(iii) optionally-substituted $C_{2-6}$ alkenyl group,
(iv) optionally-substituted $C_{2-6}$ alkynyl group,
(v) optionally-substituted 3- to 8-membered cycloalkyl group,
(vi) optionally-substituted 4- to 8-membered cycloalkenyl group,
(vii) optionally-substituted 4- to 8-membered saturated aliphatic heterocyclyl group,
(viii) optionally-substituted 5- to 10-membered unsaturated aliphatic heterocyclyl group,
(ix) optionally-substituted 6- to 10-membered aryl group, or
(x) optionally-substituted 5- to 10-membered heteroaryl group,
wherein the substituent(s) of the (ii) optionally-substituted $C_{1-6}$ alkyl group is one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, $C_{1-3}$ alkyl group, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and optionally-substituted 5- to 10-membered heteroaryl group (wherein the substituent(s) of said optionally-substituted 5- to 10-membered heteroaryl group is one or more substituents selected independently from the group consisting of amino group which may be substituted with one or two the same or different $C_{1-3}$ alkyl, $C_{1-3}$ alkyl group, hydroxy group, and carboxyl group), or
the (ii) optionally-substituted $C_{1-6}$ alkyl group may be any one of the following groups of formulae (4)-(6):
formula (4):

(4)

wherein m is 1, 2, 3, 4, or 5, $R^7$ is $C_{1-3}$ alkoxy group, amino acid group (which binds to C(O) at its N terminus), and peptide consisting of 2-3 amino acid residues (which binds to C(O) at its N terminus),
formula (5):

(5)

wherein q is 1, 2, 3, 4, or 5, $L^2$ is single bond or C(O), $R^8$ is hydroxy group, $C_{1-3}$ alkoxy group, amino group which may be substituted with one or two the same or different $C_{1-3}$ alkyl, amino acid group (which binds to $L^2$ at its N terminus), or peptide consisting of 2-3 amino acid residues (which binds to $L^2$ at its N terminus),
formula (6):

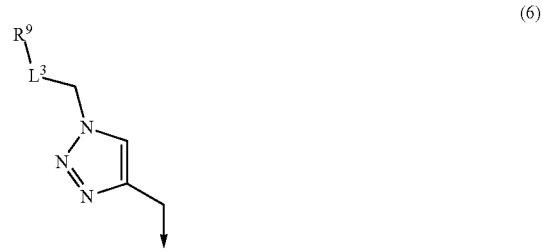

(6)

wherein $L^3$ is $CH_2$ or C(O), and $R^9$ is hydroxy group, $C_{1-3}$ alkoxy group, amino group which may be substituted with one or two the same or different $C_{1-3}$ alkyl, amino acid group (which binds to $L^3$ at its N terminus), or peptide consisting of 2-3 amino acid residues (which binds to $L^3$ at its N terminus),
the substituent(s) of the (iii) optionally-substituted $C_{2-6}$ alkenyl group, and the (iv) optionally-substituted $C_{2-6}$ alkynyl group are independently one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and 5- to 10-membered heteroaryl group,
the substituent(s) of the (v) optionally-substituted 3- to 8-membered cycloalkyl group, the (vi) optionally-substituted 4- to 8-membered cycloalkenyl group, the (vii) optionally-substituted 4- to 8-membered saturated aliphatic heterocyclyl group, the (viii) optionally-substituted 5- to 10-membered unsaturated aliphatic heterocyclyl group, the (ix) optionally-substituted 6- to 10-membered aryl group, and the (x) optionally-substituted 5- to 10-membered heteroaryl group are independently one or more substituents selected independently from the group consisting of hydroxy group, methoxy group, ethoxy group, amino group which may be substituted with one or two the same or different $C_{1-3}$ alkyl, and carboxyl group;

$R^2$ is hydrogen atom, hydroxy group, or carboxyl group; and

Ring A is a group of formula (2') or (3'):

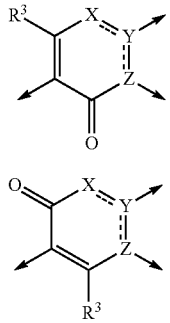

(2')

(3')

wherein $R^3$ is
(i) hydrogen atom,
(ii) optionally-substituted $C_{1-6}$ alkyl group,
(iii) optionally-substituted $C_{2-6}$ alkenyl group,
(iv) optionally-substituted $C_{2-6}$ alkynyl group,
(v) optionally-substituted 3- to 8-membered cycloalkyl group,
(vi) optionally-substituted 4- to 8-membered cycloalkenyl group,
(vii) optionally-substituted 4- to 8-membered saturated aliphatic heterocyclyl group,
(viii) optionally-substituted 5- to 10-membered unsaturated aliphatic heterocyclyl group,
(ix) optionally-substituted 6- to 10-membered aryl group, or
(x) optionally-substituted 5- to 10-membered heteroaryl group, wherein the substituent(s) of the (ii) optionally-substituted $C_{1-6}$ alkyl group, the (iii) optionally-substituted $C_{2-6}$ alkenyl group, the (iv) optionally-substituted $C_{2-6}$ alkynyl group, the (v) optionally-substituted 3- to 8-membered cycloalkyl group, the (vi) optionally-substituted 4- to 8-membered cycloalkenyl group, the (vii) optionally-substituted 4- to 8-membered saturated aliphatic heterocyclyl group, the (viii) optionally-substituted 5- to 10-membered unsaturated aliphatic heterocyclyl group, the (ix) optionally-substituted 6- to 10-membered aryl group, and the (x) optionally-substituted 5- to 10-membered heteroaryl group are independently one or more substituents selected independently from the group consisting of hydroxy group, methoxy group, ethoxy group, carboxyl group, carbamoyl group which may be substituted with one or two the same or different $C_{1-3}$ alkyl, and amino group which may be substituted with one or two the same or different $C_{1-3}$ alkyl, the part of X⸺Y⸺Z is X=Y—Z, X—Y=Z, or X—Y—Z, X is nitrogen atom, $NR^4$, or oxygen atom, provided that X is not oxygen atom in the case of formula (2'), $R^4$ is
(i) hydrogen atom,
(ii) optionally-substituted $C_{1-6}$ alkyl group,
(iii) optionally-substituted $C_{2-6}$ alkenyl group,
(iv) optionally-substituted $C_{2-6}$ alkynyl group,
(v) optionally-substituted 3- to 8-membered cycloalkyl group,
(vi) optionally-substituted 4- to 8-membered cycloalkenyl group,
(vii) optionally-substituted 4- to 8-membered saturated aliphatic heterocyclyl group,
(viii) optionally-substituted 5- to 10-membered unsaturated aliphatic heterocyclyl group,
(ix) optionally-substituted 6- to 10-membered aryl group, or
(x) optionally-substituted 5- to 10-membered heteroaryl group, wherein the substituent(s) of the (ii) optionally-substituted $C_{1-6}$ alkyl group, the (iii) optionally-substituted $C_{2-6}$ alkenyl group, the (iv) optionally-substituted $C_{2-6}$ alkynyl group, the (v) optionally-substituted 3- to 8-membered cycloalkyl group, the (vi) optionally-substituted 4- to 8-membered cycloalkenyl group, the (vii) optionally-substituted 4- to 8-membered saturated aliphatic heterocyclyl group, the (viii) optionally-substituted 5- to 10-membered unsaturated aliphatic heterocyclyl group, the (ix) optionally-substituted 6- to 10-membered aryl group, and the (x) optionally-substituted 5- to 10-membered heteroaryl group are independently one or more substituents selected independently from the group consisting of hydroxy group, methoxy group, ethoxy group, carboxyl group, carbamoyl group which may be substituted with one or two the same or different $C_{1-3}$ alkyl, and amino group which may be substituted with one or two the same or different $C_{1-3}$ alkyl, Y is carbon atom or CH, and Z is carbon atom, CH, or nitrogen atom, provided that the combination of X, Y, and Z should be any one of chemically-possible selections.

3. The compound of claim 2 or a pharmaceutically acceptable salt thereof, wherein $R^2$ is hydrogen atom.

4. The compound of claim 2 or a pharmaceutically acceptable salt thereof, wherein $R^3$ is (i) hydrogen atom, (ii) $C_{1-3}$ alkyl group, or (v) 3- to 6-membered cycloalkyl group.

5. The compound of claim 2 or a pharmaceutically acceptable salt thereof, wherein $R^4$ is (i) hydrogen atom, (ii) $C_{1-3}$ alkyl group, or (v) 3- to 6-membered cycloalkyl group.

6. The compound of claim 2 or a pharmaceutically acceptable salt thereof, wherein $R^1$ is (i) hydrogen atom, or (ii) optionally-substituted $C_{1-6}$ alkyl group, wherein the substituent(s) of the (ii) optionally-substituted $C_{1-6}$ alkyl group is one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, $C_{1-3}$ alkyl group, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and optionally-substituted 5- to 10-membered heteroaryl group (wherein the substituent(s) of said optionally-substituted 5- to 10-membered heteroaryl group is one or more substituents selected independently from the group consisting of amino group which may be substituted with one or two the same or different $C_{1-3}$ alkyl, $C_{1-3}$ alkyl group, hydroxy group, and carboxyl group), or the (ii) optionally-substituted $C_{1-6}$ alkyl group may be any one of the groups of formulae (4)-(6).

7. The compound of claim 2 or a pharmaceutically acceptable salt thereof, wherein
$R^1$ is
(i) hydrogen atom,
(ii) optionally-substituted $C_{1-3}$ alkyl group,
(iii) optionally-substituted $C_{2-4}$ alkenyl group,
(iv) optionally-substituted $C_{2-4}$ alkynyl group,
(v) optionally-substituted 3- to 6-membered cycloalkyl group,
(vi) optionally-substituted 4- to 6-membered cycloalkenyl group,
(vii) optionally-substituted 4- to 6-membered saturated aliphatic heterocyclyl group,
(viii) optionally-substituted 5- to 6-membered unsaturated aliphatic heterocyclyl group,
(ix) optionally-substituted 6- to 10-membered aryl group, or
(x) optionally-substituted 5- to 10-membered heteroaryl group,
wherein the substituent(s) of the (ii) optionally-substituted $C_{1-3}$ alkyl group is one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, $C_{1-3}$ alkyl group, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and optionally-substituted 5- to 10-membered heteroaryl group (wherein the substituent(s) of said optionally-substituted 5- to 10-membered heteroaryl group is one or more substituents selected independently from the group consisting of amino group which may be substituted with one or two the same or different $C_{1-3}$ alkyl, $C_{1-3}$ alkyl group, hydroxy group, and carboxyl group), or the (ii) optionally-substituted $C_{1-3}$ alkyl group may be any one of the groups of formulae (4)-(6),
in formula (4), m is 1, $R^7$ is amino acid group (which binds to C(O) at its N terminus),
in formula (5), q is 1, 2, 3, 4, or 5, $L^2$ is single bond or C(O), $R^8$ is hydroxy group or amino acid group (which binds to $L^2$ at its N terminus),
in formula (6), $L^3$ is C(O), $R^9$ is hydroxy group or amino acid group (which binds to $L^3$ at its N terminus),
the substituent(s) of the (iii) optionally-substituted $C_{2-4}$ alkenyl group, and the (iv) optionally-substituted $C_{2-4}$ alkynyl group are independently one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and 5- to 10-membered heteroaryl group,
the substituent(s) of the (v) optionally-substituted 3- to 6-membered cycloalkyl group, the (vi) optionally-substituted 4- to 6-membered cycloalkenyl group, the (vii) optionally-substituted 4- to 6-membered saturated aliphatic heterocyclyl group, the (viii) optionally-substituted 5- to 6-membered unsaturated aliphatic heterocyclyl group, the (ix) optionally-substituted 6- to 10-membered aryl group, and the (x) optionally-substituted 5- to 10-membered heteroaryl group are independently one or more substituents selected independently from the group consisting of hydroxy group, methoxy group, ethoxy group, amino group which may be substituted with one or two the same or different $C_{1-3}$ alkyl, and carboxyl group.

8. The compound of claim 2 or a pharmaceutically acceptable salt thereof, wherein
$R^1$ is (i) hydrogen atom, or (ii) optionally-substituted $C_{1-3}$ alkyl group,
wherein the substituent(s) of the (ii) optionally-substituted $C_{1-3}$ alkyl group is one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), optionally-substituted 3- to 6-membered cycloalkyl group (wherein the substituent(s) of said optionally-substituted 3- to 6-membered cycloalkyl group is one or more substituents selected independently from the group consisting of amino group which may be substituted with one or two the same or different $C_{1-3}$ alkyl, $C_{1-3}$ alkyl group, hydroxy group, and carboxyl group), optionally-substituted 4- to 6-membered saturated aliphatic heterocyclyl group (wherein the substituent(s) of said optionally-substituted 4- to 6-membered saturated aliphatic heterocyclyl group is one or more substituents selected independently from the group consisting of amino group which may be substituted with one or two the same or different $C_{1-3}$ alkyl, $C_{1-3}$ alkyl group, hydroxy group, and carboxyl group), and optionally-substituted 5- to 10-membered heteroaryl group (wherein the substituent(s) of said optionally-substituted 5- to 10-membered heteroaryl group is one or more substituents selected independently from the group consisting of amino group which may be substituted with one or two the same or different $C_{1-3}$ alkyl, $C_{1-3}$ alkyl group, hydroxy group, and carboxyl group), or the (ii) optionally-substituted $C_{1-3}$ alkyl group may be any one of the groups of formulae (4)-(6), in formula (4), m is 1, $R^7$ is amino acid group (which binds to C(O) at its N terminus), in formula (5), q is 1, 2, 3, 4, or 5, $L^2$ is single bond or C(O), $R^8$ is hydroxy group or amino acid group (which binds to $L^2$ at its N terminus), in formula (6), $L^3$ is C(O), $R^9$ is hydroxy group or amino acid group (which binds to $L^3$ at its N terminus).

9. The compound of claim 2 or a pharmaceutically acceptable salt thereof, wherein
$R^1$ is hydrogen atom, or the group of formula (6),
in formula (6), $L^3$ is C(O), $R^9$ is amino acid group (which binds to $L^3$ at its N terminus).

10. The compound of claim 2 or a pharmaceutically acceptable salt thereof, wherein Ring A is the group of formula (2').

11. The compound of claim 10 or a pharmaceutically acceptable salt thereof, wherein the part of x═══y═══z in formula (2') is N═C—CH, N═C—N, NR⁴—C═C, NR⁴—CH—N, or NR⁴—CH—CH.

12. The compound of claim 2 or a pharmaceutically acceptable salt thereof, wherein Ring A is the group of formula (3').

13. The compound of claim 12 or a pharmaceutically acceptable salt thereof, wherein the part of x═══y═══z in formula (3') is N═C—CH, N═C—N, NR⁴—C═C, NR⁴—CH—N, NR⁴—CH—CH, O—C═C, O—CH—N, or O—CH—CH.

14. The compound of claim 1 or a pharmaceutically acceptable salt thereof which is represented by formula (7):

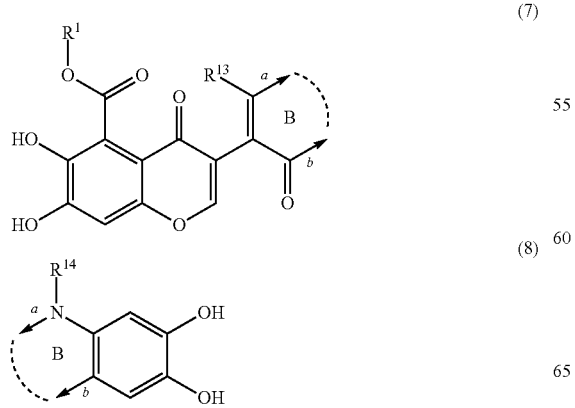

(7)

(8)

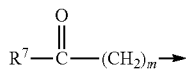

-continued

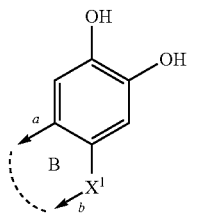

(9)

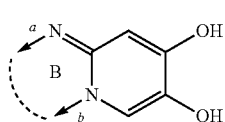

(10)

wherein
Ring B is a group of formula (8), (9), or (10);
$R^1$ is
(i) hydrogen atom,
(ii) $C_{1-3}$ alkyl group
which may be substituted with one or more substituents selected independently from the group consisting of hydroxy group, methoxy group, ethoxy group, carboxyl group, carbamoyl group (which may be substituted with one or two the same or different $C_{1-3}$ alkyl), $NR^5R^6$ (wherein $R^5$ and $R^6$ are independently hydrogen atom, $C_{1-3}$ alkyl group, carboxylmethyl group, 2-hydroxyethyl group, or 2-aminoethyl group), 3- to 6-membered cycloalkyl group (which may be substituted with one or more substituents selected independently from the group consisting of amino group which may be substituted with one or two the same or different $C_{1-3}$ alkyl, $C_{1-3}$ alkyl group, hydroxy group, and carboxyl group), 4- to 6-membered saturated aliphatic heterocyclyl group (which may be substituted with one or more substituents selected independently from the group consisting of amino group which may be substituted with one or two the same or different $C_{1-3}$ alkyl, $C_{1-3}$ alkyl group, hydroxy group, and carboxyl group), and 5- to 10-membered heteroaryl group (which may be substituted with one or more substituents selected independently from the group consisting of amino group which may be substituted with one or two the same or different $C_{1-3}$ alkyl, $C_{1-3}$ alkyl group, hydroxy group, and carboxyl group),
(iii) the group of formula (4):

(4)

wherein m is 1, 2, 3, 4, or 5, $R^7$ is $C_{1-3}$ alkoxy group, amino acid group (which binds to C(O) at its N terminus), and peptide consisting of 2-3 amino acid residues (which binds to C(O) at its N terminus),
(iv) the group of formula (5):

$R^8$-$L^2$-$(CH_2CH_2O)_q$$CH_2CH_2$→ (5)

wherein q is 1, 2, 3, 4, or 5, $L^2$ is single bond or C(O), $R^8$ is hydroxy group, $C_{1-3}$ alkoxy group, amino group which may be substituted with one or two the same or different $C_{1-3}$ alkyl, amino acid group (which binds to L² at its N terminus), or peptide consisting of 2-3 amino acid residues (which binds to L² at its N terminus), or
(v) the group of formula (6):

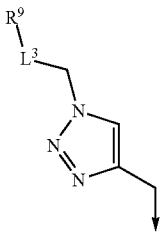

(6)

wherein L³ is CH₂ or C(O), and R⁹ is hydroxy group, $C_{1-3}$ alkoxy group, amino group which may be substituted with one or two the same or different $C_{1-3}$ alkyl, amino acid group (which binds to L³ at its N terminus), or peptide consisting of 2-3 amino acid residues (which binds to L³ at its N terminus);
X¹ is O or NR¹⁴; and
R¹³ and R¹⁴ are independently hydrogen atom, $C_{1-3}$ alkyl group, or 3- to 6-membered cycloalkyl group.

15. The compound of claim 14 or a pharmaceutically acceptable salt thereof, wherein Ring B is the group of formula (8).

16. The compound of claim 14 or a pharmaceutically acceptable salt thereof, wherein R¹ is the group of formula (4), (5), or (6).

17. The compound of claim 14 or a pharmaceutically acceptable salt thereof, wherein L² and L³ are C(O).

18. The compound of claim 14 or a pharmaceutically acceptable salt thereof wherein R⁷, R⁸, or R⁹ is amino acid group (which binds to C(O), L², or L³ at its N terminus).

19. The compound of claim 14 or a pharmaceutically acceptable salt thereof, wherein R⁷, R⁸, or R⁹ is L-glutamic acid (which binds to C(O), L², or L³ at its N terminus).

20. The compound of claim 1 or a pharmaceutically acceptable salt thereof, which is selected from the following compounds:
   3-(6,7-dihydroxy-1-methyl-4-oxo-1,4-dihydroquinolin-3-yl)-6,7-dihydroxy-4-oxo-4H-chromene-5-carboxylic acid,
   prop-2-yn-1-yl 3-(6,7-dihydroxy-1-methyl-4-oxo-1,4-dihydroquinolin-3-yl)-6,7-dihydroxy-4-oxo-4H-chromene-5-carboxylate,
   N-({4-[({[3-(6,7-dihydroxy-1-methyl-4-oxo-1,4-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid,
   N²-({4-[({[3-(6,7-dihydroxy-1-methyl-4-oxo-1,4-dihydroquinolin-3-yl)-6,7-dihydroxy-4-oxo-4H-chromen-5-yl]carbonyl}oxy)methyl]-1H-1,2,3-triazol-1-yl}acetyl)-L-arginine,
   N-{[3-(6,7-dihydroxy-1-methyl-4-oxo-1,4-dihydroquinolin-3-yl)-6,7-dihydroxy-4-oxo-4H-chromen-5-yl]carbonyl}-L-glutamic acid,
   3-(6,7-dihydroxy-1-methyl-4-oxo-1,4-dihydroquinolin-3-yl)-6,7-dihydroxy-4-oxo-N-(prop-2-yn-1-yl)-4H-chromene-5-carboxamide,
   3-(6,7-dihydroxy-1,2-dimethyl-4-oxo-1,4-dihydroquinolin-3-yl)-6,7-dihydroxy-4-oxo-4H-chromene-5-carboxylic acid,
   N-({4-[({[3-(6,7-dihydroxy-1,2-dimethyl-4-oxo-1,4-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid,
   6,6',7,7'-tetrahydroxy-2,4'-dioxo-2H,4'H-3,3'-bichromene-5'-carboxylic acid,
   prop-2-yn-1-yl 6,6',7,7'-tetrahydroxy-2,4'-dioxo-2H,4'H-3,3'-bichromene-5'-carboxylate,
   N-{[4-({[(6,6',7,7'-tetrahydroxy-2,4'-dioxo-2H,4'H-3,3'-bichromen-5'-yl)carbonyl]oxy}methyl)-1H-1,2,3-triazol-1-yl]acetyl}-L-glutamic acid,
   N²-{[4-({[(6,6',7,7'-tetrahydroxy-2,4'-dioxo-2H,4'H-3,3'-bichromen-5'-yl)carbonyl]oxy}methyl)-1H-1,2,3-triazol-1-yl]acetyl}-L-arginine,
   3-(6,7-dihydroxy-1-methyl-2-oxo-1,2-dihydroquinolin-3-yl)-6,7-dihydroxy-4-oxo-4H-chromene-5-carboxylic acid,
   N-({4-[({[3-(6,7-dihydroxy-1-methyl-2-oxo-1,2-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid,
   N-({4-[({[3-(6,7-dihydroxy-1,4-dimethyl-2-oxo-1,2-dihydroquinolin-3-yl)-6,7-dihydroxy-4-oxo-4H-chromen-5-yl]carbonyl}oxy)methyl]-1H-1,2,3-triazol-1-yl}acetyl)-L-glutamic acid,
   3-(7,8-dihydroxy-2-methyl-4-oxo-4H-pyrido[1,2-a]pyrimidin-3-yl)-6,7-dihydroxy-4-oxo-4H-chromene-5-carboxylic acid,
   N-({4-[({[3-(7,8-dihydroxy-2-methyl-4-oxo-4H-pyrido[1,2-a]pyrimidin-3-yl)-6,7-dihydroxy-4-oxo-4H-chromen-5-yl]carbonyl}oxy)methyl]-1H-1,2,3-triazol-1-yl}acetyl)-L-glutamic acid,
   N-[({[3-(7,8-dihydroxy-2-methyl-4-oxo-4H-pyrido[1,2-a]pyrimidin-3-yl)-6,7-dihydroxy-4-oxo-4H-chromen-5-yl]carbonyl}oxy)acetyl]-L-glutamic acid,
   N-[({[3-(6,7-dihydroxy-1-methyl-4-oxo-1,4-dihydroquinolin-3-yl)-6,7-dihydroxy-4-oxo-4H-chromen-5-yl]carbonyl}oxy)acetyl]-L-glutamic acid,
   3-[2-({[3-(6,7-dihydroxy-1-methyl-4-oxo-1,4-dihydroquinolin-3-yl)-6,7-dihydroxy-4-oxo-4H-chromen-5-yl]carbonyl}oxy)ethoxy]propanoic acid,
   N-{3-[2-({[3-(6,7-dihydroxy-1-methyl-4-oxo-1,4-dihydroquinolin-3-yl)-6,7-dihydroxy-4-oxo-4H-chromen-5-yl]carbonyl}oxy)ethoxy]propanoyl}-L-glutamic acid,
   2,2'-{[2-({[3-(6,7-dihydroxy-1-methyl-4-oxo-1,4-dihydroquinolin-3-yl)-6,7-dihydroxy-4-oxo-4H-chromen-5-yl]carbonyl}oxy)ethyl]imino}-diacetic acid,
   2,3-dihydroxypropyl 3-(6,7-dihydroxy-1-methyl-4-oxo-1,4-dihydroquinolin-3-yl)-6,7-dihydroxy-4-oxo-4H-chromene-5-carboxylate,
   (trans-4-aminocyclohexyl)methyl 3-(6,7-dihydroxy-1-methyl-4-oxo-1,4-dihydroquinolin-3-yl)-6,7-dihydroxy-4-oxo-4H-chromene-5-carboxylate,
   (1,4-dimethylpiperazin-2-yl)methyl 3-(6,7-dihydroxy-1-methyl-4-oxo-1,4-dihydroquinolin-3-yl)-6,7-dihydroxy-4-oxo-4H-chromene-5-carboxylate,
   (1-methyl-1H-imidazol-2-yl)methyl 3-(6,7-dihydroxy-1-methyl-4-oxo-1,4-dihydroquinolin-3-yl)-6,7-dihydroxy-4-oxo-4H-chromene-5-carboxylate,
   O-{[3-(6,7-dihydroxy-1-methyl-4-oxo-1,4-dihydroquinolin-3-yl)-6,7-dihydroxy-4-oxo-4H-chromen-5-yl]carbonyl}-L-homoserine,
   2-(3-hydroxypyrrolidin-1-yl)ethyl 3-(6,7-dihydroxy-1-methyl-4-oxo-1,4-dihydroquinolin-3-yl)-6,7-dihydroxy-4-oxo-4H-chromene-5-carboxylate,
   14-hydroxy-3,6,9,12-tetraoxatetradec-1-yl 3-(6,7-dihydroxy-1-methyl-4-oxo-1,4-dihydroquinolin-3-yl)-6,7-dihydroxy-4-oxo-4H-chromene-5-carboxylate, and 2-amino-2-oxoethyl 3-(6,7-dihydroxy-1-methyl-4-oxo-1,4-dihydroquinolin-3-yl)-6,7-dihydroxy-4-oxo-4H-chromene-5-carboxylate.

21. A pharmaceutical composition comprising the compound of claim 1 or a pharmaceutically acceptable salt thereof.

22. A semaphorin inhibitor comprising the compound of claim 1 or a pharmaceutically acceptable salt thereof as an active ingredient.

23. A nerve regeneration promoter comprising the compound of claim 1 or a pharmaceutically acceptable salt thereof as an active ingredient.

24. A medicament for treating and/or preventing a disease associated with neurodegeneration or neurological disorder, comprising the compound of claim 1 or a pharmaceutically acceptable salt thereof as an active ingredient.

25. A medicament for treating and/or preventing a neurological disease associated with ischemic damage, comprising the compound of claim 1 or a pharmaceutically acceptable salt thereof as an active ingredient.

26. A medicament for treating or preventing corneal disease, comprising the compound of claim 1 or a pharmaceutically acceptable salt thereof as an active ingredient.

27. The medicament of claim 26, wherein the corneal disease is dry eye.

28. The medicament of claim 26, wherein the corneal disease is a disease associated with neurodegeneration or neurological disorder.

* * * * *